US012630541B2

(12) United States Patent
Shi et al.

(10) Patent No.: US 12,630,541 B2
(45) Date of Patent: *May 19, 2026

(54) COMPOUNDS USEFUL AS INHIBITORS OF ALCAT 1

(71) Applicant: Perenna Pharmaceuticals, Inc., San Antonio, TX (US)

(72) Inventors: Yuguang Shi, San Antonio, TX (US); Daqing Che, Taizhou (CN); Jonathan Baell, Parkville (AU); Xiaoyu Liu, Wuhan (CN); Jiasheng Fu, Foster City, CA (US)

(73) Assignee: PERENNA PHARMACEUTICALS, INC., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/489,590

(22) Filed: Sep. 29, 2021

(65) Prior Publication Data

US 2022/0089582 A1 Mar. 24, 2022

Related U.S. Application Data

(63) Continuation of application No. 16/499,851, filed as application No. PCT/EP2018/058225 on Mar. 29, 2018, now Pat. No. 11,208,404.

(60) Provisional application No. 62/479,960, filed on Mar. 31, 2017.

(51) Int. Cl.

| | |
|---|---|
| ***C07D 413/04*** | (2006.01) |
| ***C07D 271/10*** | (2006.01) |
| ***C07D 271/113*** | (2006.01) |
| ***C07D 307/52*** | (2006.01) |
| ***C07D 307/56*** | (2006.01) |
| ***C07D 307/66*** | (2006.01) |
| ***C07D 307/68*** | (2006.01) |
| ***C07D 405/04*** | (2006.01) |
| ***C07D 413/06*** | (2006.01) |
| ***C07D 413/14*** | (2006.01) |
| ***C07D 417/04*** | (2006.01) |
| ***C07F 9/6558*** | (2006.01) |

(52) U.S. Cl.

CPC ......... *C07D 413/04* (2013.01); *C07D 271/10* (2013.01); *C07D 413/14* (2013.01); *C07D 417/04* (2013.01); *C07F 9/65586* (2013.01)

(58) Field of Classification Search

CPC .. C07D 413/04; C07D 271/10; C07D 413/14; C07D 417/04; C07D 271/113; C07D 307/52; C07D 307/56; C07D 307/66; C07D 307/68; C07D 405/04; C07D 413/06

See application file for complete search history.

(56) References Cited

U.S. PATENT DOCUMENTS

| | | | | |
|---|---|---|---|---|
| 7,629,340 | B2 | 12/2009 | Schmitz et al. | |
| 8,642,660 | B2 | 2/2014 | Goldfarb | |
| 8,680,137 | B2 | 3/2014 | Sun et al. | |
| 10,526,418 | B2 | 1/2020 | Shi | |
| 11,208,404 | B2 * | 12/2021 | Shi | C07D 307/52 |
| 2004/0176374 | A1 | 9/2004 | Wunberg et al. | |
| 2007/0265262 | A1 * | 11/2007 | Schmitz | C07D 413/12 514/254.01 |
| 2009/0105217 | A1 | 4/2009 | Coppo et al. | |
| 2009/0105240 | A1 | 4/2009 | Mustelin | |
| 2013/0161075 | A1 | 6/2013 | Lee et al. | |
| 2020/0109136 | A1 | 4/2020 | Shi et al. | |

FOREIGN PATENT DOCUMENTS

| | | | | |
|---|---|---|---|---|
| CN | 104302304 | A | 1/2015 | |
| JP | 2009519342 | A | 5/2009 | |
| JP | 2009538865 | A | 11/2009 | |
| JP | 2011507910 | A | 3/2011 | |
| JP | 2013513621 | A | 4/2013 | |
| KR | 20130074542 | A | 7/2013 | |
| WO | 2004098518 | A2 | 11/2004 | |
| WO | 2005040152 | A1 | 5/2005 | |
| WO | WO-2007070556 | A2 * | 6/2007 | C07D 207/16 |
| WO | 2013123305 | A1 | 8/2013 | |
| WO | 2014055644 | A2 | 4/2014 | |
| WO | 2014209905 | A2 | 12/2014 | |
| WO | 2014210319 | A2 | 12/2014 | |

OTHER PUBLICATIONS

CAS Registry No. 404836-52-8, which entered STN on Apr. 9, 2002 (Year: 2002).*

CAS Registry No. 885570-90-1, which entered STN on May 25, 2006 (Year: 2006).*

CAS Registry No. 1049481-93-7, which entered Registry on Sep. 14, 2008 (Year: 2008).*

CAS Registry No. 510717-63-2, which entered Registry on May 5, 2003 (Year: 2003).*

CAS Registry No. 380578-85-8, which entered Registry on Jan. 7, 2002 (Year: 2002).*

Frame et al. ACS Chem. Biol. 2015, 10, 775-783 and its supporting information (Year: 2015).*

CAS Registry No. 364737-34-8, which entered Registry on Oct. 26, 2001 (Year: 2001).*

(Continued)

*Primary Examiner* — Matthew P Coughlin

(74) *Attorney, Agent, or Firm* — MORRISON & FOERSTER LLP

(57) ABSTRACT

Inhibitors of ALCAT1 are described having the general formula: (I). These compounds offer a treatment for aging and age-related diseases.

(I)

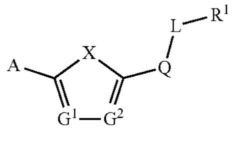

6 Claims, No Drawings

(56) References Cited

OTHER PUBLICATIONS

CAS Registry No. 518023-03-5, which entered Registry on May 21, 2003 (Year: 2003).*
CAS Registry No. 518023-02-4, which entered Registry on May 21, 2003 (Year: 2003).*
CAS Registry No. 1090445-17-2, which entered Registry on Dec. 26, 2008 (Year: 2008).*
Asgaonkar, K. D. et al. (Nov. 24, 2013). "QSAR And Molecular Docking Studies Of Oxadiazole-Ligated Pyrrole Derivatives As Enoyl-ACP (Coa) Reductase Inhibitors," Scientia Pharmaceutica 82(1):71-85.
Cao, J. et al. (Apr. 1, 2009). "ALCAT1 is a Polyglycerophospholipid Acyltransferase Potently Regulated by Adenine Nucleotide and Thyroid Status," AJP: Endocrinology And Metabolism 296(4):E647-E653.
CAS Registry No. 667435-03-2, which entered STN on Mar. 25, 2004, 1 page.
Gang, L. et al. (Oct. 13, 2016). "Design, Synthesis, and Pharmacological Evaluation of 2-(2,5-Dimethyl-5,6,7,8-tetrahydroquinolin-8-yl)-N-aryl Propanamides as Novel Smoothened (Smo) Antagonists", Journal of Medicinal Chemistry 59(24):11050-11068.
Gogoi, J. et al. (Apr. 21, 2015). "Microwave-Assisted Synthesis of Fused and Substituted 2-Aminopyridines from [beta]-Halo [alpha], [beta]-Unsaturated Aldehydes", Synthesis 47(13):1905-1912.
Harner, M.J. et al. (Oct. 14, 2014). "Fragment-Based Screening of the Bromodomain of ATAD2", Journal of Medicinal Chemistry 57(22):9687-9692.
International Preliminary Report on Patentability mailed Oct. 1, 2019, for PCT Patent Application No. PCT/ EP2018/058225, filed Mar. 29, 2018, 8 pages.
International Search Report mailed Jun. 10, 2018, for PCT Patent Application No. PCT/EP2018/058225, filed Mar. 29, 2018, 8 pages.
Lanier, M.C. et al. (Jan. 13, 2009). "N -[6-Amino-2-(heteroaryl)pyrimidin-4-yl]acetamides as A 2A Receptor Antagonists with Improved Drug Like Properties and in Vivo Efficacy," Journal Of Medicinal Chemistry 52(3):709-717.
Palakuti, R. et al. (Mar. 2017, e-pub. Apr. 7, 2016). "Identification Of Abelson Tyrosine Kinase Inhibitors As Potential Therapeutics For Alzheimer's Disease Using Multiple E-Pharmacophore Modeling And Molecular Dynamics," J. Biomol. Struct. Dyn. 35(4):883-896.
PubChem (May 28, 2009). "Schemb121866853," National Center for Biotechnology Information, PubChem Compound Summary for CID 29261281, 8 pages, as retrieved on Dec. 6, 2020 from https:// pubchem.ncbi .nlm. nih .gov/compound/Schembl21 866853.
Written Opinion of the International Searching Authority mailed Jun. 10, 2018, for PCT Patent Application No. PCT/EP2018/ 058225, filed Mar. 29, 2018, 8 pages.
Berge, S.M. et al. (Jan. 1977). "Pharmaceuticals Salts," J. Pharmaceutical Sciences 66(1):1-19.
CAS Registry No. 1030653-63-4 (Jun. 25, 2008). "3,5-Dibromo-2-ethoxy-N-[3-[5-(2-furanyl)-1,3,4-oxadiazol-2-yl] phenyl]benzamide," 1 page.
CAS Registry No. 1030657-86-3 (Jun. 25, 2008). "N-[3-[5-(2-Furanyl)-1,3,4-oxadiazol-2-yl]phenyl]-3-iodobenzamidE," 1 page.
CAS Registry No. 1030675-87-6 (Jun. 25, 2008). "Benzamide, 2-chloro-N-[3-[5-(2-furanyl)-1,3,4-oxadiazol-2-yl] phenyl]-," 1 page.
CAS Registry No. 1030677-21-4 (Jun. 25, 2008). "3,5-Dichloro-2-ethoxy-N-[3-[5-(2-furanyl)-1,3,4-oxadiazol-2-yl] phenyl]benzamide," 1 page.
CAS Registry No. 895954-04-8 (Jul. 25, 2006). "Benzamide, N-[3-[5-(2-furanyl)-1,3,4-oxadiazol-2-yl]phenyl]-3,4-dimethoxy-," 1 page.
CAS Registry No. 895954-12-8 (Jul. 25, 2006). "N-[3-[5-(2-Furanyl)-1,3,4-oxadiazol-2-yl]phenyl]-3,5-dimethoxybenzamide," 1 page.
CAS Registry No. 895954-20-8 (Jul. 25, 2006). "Benzamide, N-[3-[5-(2-furanyl)-1,3,4-oxadiazol-2-yl]phenyl]-3,4,5-trimethoxy-," 1 page.
CAS Registry No. 895956-97-5 (Jul. 25, 2006). "N-[3-[5-(2-Furanyl)-1,3,4-oxadiazol-2-yl]phenyl]-3-nitrobenzenesulfonamide," 1 page.
CAS Registry No. 898123-18-7 (Aug. 2, 2006). "3-Ethoxy-N-[3-[5-(2-furanyl)-1,3,4-oxadiazol-2-yl]phenyl] benzamide," 1 page.
Chen, H. et al. (Apr. 16, 2010). "Mitochondrial Fusion Is Required For Mtdna Stability In Skeletal Muscle And Tolerance Of Mtdna Mutations," Cell 141(2):280-289.
Joshi, N. et al. (Dec. 1996). "Synthesis and Antimicrobial Activity of Oxadiazole and Imidazolinone Derivatives Bearing a Trimethoxybenzamide Moiety," ChemInform 28(40):700-701.
Han, X. et al. (May 29, 2007). "Alterations In Myocardial Cardiolipin Content And Composition Occur At The Very Earliest Stages Of Diabetes: A Shotgun Lipidomics Study," Biochemistry 46(21):6417-6428, 24 pages.
Lee, H. J. et al. (Jan. 23, 2006). "Selective Remodeling Of Cardiolipin Fatty Acids In The Aged Rat Heart," Lipids In Health And Disease 5:1-4.
Li, J. et al. (Aug. 4, 2010). "Cardiolipin Remodeling By ALCAT1 Links Oxidative Stress And Mitochondrial Dysfunction To Obesity," Cell Metabolism 12(2):154-165.
Pachhamia, V. L. et al. (Apr. 1989). "Studies on 2, 5-Disubstituted 1, 3, 4-Oxadiazoles. Part 2. Preparation and Antimicrobial Activity of 2-Arylsulfonamido/α-Carbamylarylmethylamino-5-(4'-pyridyl)-1, 3, 4-oxadiazoles," J. Indian Chem. 66:250-251.
Paradies, G. et al. (2010, e-pub. Feb. 20, 2010). "Oxidative Stress, Mitochondrial Bioenergetics, And Cardiolipin In Aging," Free Radical Biology And Medicine 48(10):1286-1295.
Shi, Y. (2010). "Emerging Roles Of Cardiolipin Remodeling In Mitochondrial Dysfunction Associated With Diabetes, Obesity, And Cardiovascular Diseases," Journal Of Biomedical Research 24(1):6-15.
Sparagna, G. C. et al. (Apr. 2009). "Cardiolipin Remodeling In The Heart," Journal Of Cardiovascular Pharmacology 53(4):290-301.
CAS Registry No. 890981-91-6 (Jul. 7, 2006). "5-Bromo-N-[3-[5-(2-furanyl)-1,3,4-oxadiazol-2-yl]phenyl]-2-furancarboxamide," 1 page.
CAS Registry No. 899270-86-1 (Aug. 7, 2006). "3,5-Dichloro-4-ethoxy-N-[3-[5-(2-furanyl)-1,3,4-oxadiazol-2-yl]phenyl]benzamide," 1 page.
CAS Registry No. 890967-59-6 (Jul. 7, 2006). "N-[3-[5-(2-Furanyl)-1,3,4-oxadiazol-2-yl]phenyl]-2-benzofurancarboxamide," 1 page.
CAS Registry No. 899270-82-7 (Aug. 7, 2006). "3-Chloro-N-[3-[5-(2-furanyl)-1,3,4-oxadiazol-2-yl]phenyl]-4-methoxybenzamide," 1 page.
CAS Registry No. 1030527-86-6 (Jun. 25, 2008). "N-[3-[5-(1, 1-Dimethylethyl)-1,3,4-oxadiazol-2-yl]phenyl]-4-ethoxybenzamide," 1 page.
CAS Registry No. 1791106-12-1 (Jun. 29, 2015). "3,5-Dimethoxy-N-[3-(5-methyl-1,3,4-oxadiazol-2-yl)phenyl] benzamide," 1 page.
CAS Registry No. 1795566-61-8 (Jul. 6, 2015). "2-Fluoro-N-[3-(5-methyl-1,3,4-oxadiazol-2-yl)phenyl] benzamide," 1 page.
CAS Registry No. 337502-24-6 (May 23, 2001). "N-[3-[5-(2-Furanyl)-1,3,4-Oxadiazol-2-yl]phenyl]-2-thiophenecarboxamide," 1 page.
CAS Registry No. 354120-69-7 (Aug. 31, 2001). "2-Fluoro-N-[3-[5-(furan-2-yl)-1,3,4-oxadiazol-2-yl]phenyl] benzamide," 1 page.
CAS Registry No. 381206-04-8 (Jan. 9, 2002). "N-[3-[5-(2-Furanyl)-1,3,4-oxadiazol-2-yl]phenyl]-2-methylbenzamide," 1 page.
CAS Registry No. 444147-07-3 (Aug. 19, 2002). "N-[3-[5-(2-Furanyl)-1,3,4-oxadiazol-2-yl]phenyl]-2-nitrobenzamide," 1 page.
CAS Registry No. 496913-60-1 (Mar. 5, 2003). "N-[3-[5-(2-Furanyl)-1,3,4-oxadiazol-2-yl]phenyl]-3-methylbenzamide," 1 page.
CAS Registry No. 519147-45-6 (May 23, 2003). "N-[3-[5-(2-Furanyl)-1,3,4-oxadiazol-2-yl]phenyl]-4-methoxybenzamide," 1 page.
CAS Registry No. 578736-33-1 (Sep. 4, 2003). "N-[3-[5-(2-Furanyl)-1,3,4-oxadiazol-2-yl]phenyl]-2-iodobenzamide," 1 page.
CAS Registry No. 724747-39-1 (Aug. 10, 2004) "3-Bromo-N-[3-(5-furan-2-yl-[1,3,4]oxadiazol-2-yl)-phenyl]-benzamide," 1 page.
CAS Registry No. 831244-70-3 (Feb. 15, 2005). "3,4-Dichloro-N-[3-[5-(2-furanyl)-1,3,4-oxadiazol-2-yl]phenyl] benzamide," 1 page.
CAS Registry No. 890968-71-5 (Jul. 7, 2006). "2-Bromo-N-[3-(5-furan-2-yl-[1,3,4]oxadiazol-2-yl)-phenyl]-benzamide," 1 page.
CAS Registry No. 890974-19-3 (Jul. 7, 2006). "5-Bromo-2-ethoxy-N-[3-[5-(2-furanyl)-1,3,4-oxadiazol-2-yl]phenyl] benzamide," 1 page.
CAS Registry No. 895954-20-8 (Jul. 25, 2006). "N-[3-[5-(2-Furanyl)-1,3,4-oxadiazol-2-yl]phenyl]-3,4,5-trimethoxybenzamide," 1 page.
CAS Registry No. 899284-20-9 (Aug. 7, 2006). "N-[3-[5-(2-Furanyl)-1,3,4-oxadiazol-2-yl]phenyl]tetrahydro-2-furancarboxamide," 1 page.
CAS Registry No. 899296-70-9 (Aug. 7, 2006). "N-[3-[5-(2-Furanyl)-1,3,4-oxadiazol-2-yl]phenyl]-2-methyl-3-furancarboxamide," 1 page.

* cited by examiner

COMPOUNDS USEFUL AS INHIBITORS OF ALCAT 1

CROSS REFERENCE TO RELATED APPLICATIONS

This application is a continuation of U.S. patent application Ser. No. 16/499,851, which adopts the international filing date of Mar. 29, 2018, which is the U.S. national stage application under 35 U.S.C. § 371 of International Application No. PCT/EP2018/058225, filed internationally on Mar. 29, 2018, which claims priority benefit to U.S. Provisional Application No. 62/479,960, filed on Mar. 31, 2017, all of which are incorporated herein by reference for all purposes.

TECHNICAL FIELD

The present invention relates generally to compounds useful as inhibitors of ALCAT1. Such compounds are useful for the treatment of aging and age-related disorders.

BACKGROUND ART

Acyl-CoA:lysocardiolipin acyltransferase-1 (ALCAT1) is a polyglycerophospholipid acyltransferase of the endoplasmic reticulum which is primarily known for catalyzing the acylation of both monolysocardiolipin and dilysocardiolipin back into cardiolipin.

Recent research has evidenced a role of the enzyme ALCAT1 in the etiology of oxidative stress and various aging-related diseases, including type 2 diabetes, diabetic complications (nephropathy, retinopathy, and cardiomyopathy), cardiovascular diseases, neurological disorders (Parkinson's and Alzheimer's diseases). ALCAT1 is upregulated by oxidative stress and diet-induced obesity (DIO) and catalyses the remodeling of cardiolipin (CL) with fatty acyl chains that are highly sensitive to oxidative damage, leading to mitochondrial dysfunction, reactive oxygen species (ROS) production, and insulin resistance.

Dynamic networks are formed when mitochondria undergo a fusion event that causes the compartments of participating mitochondria to become continuous. The fusion event allows the constituents of each network to share solutes, metabolites, and proteins. Consequently, disruption of such networks causes oxidative stress and mitochondrial fragmentation, which has been implicated in the etiology of aging and age-related diseases.

In WO 2013/123305 (the disclosure of which is incorporated herein by reference in its entirety) a critical role of ALCAT1 in regulating mitochondrial biogenesis and mtDNA fidelity was demonstrated. ALCAT1 overexpression severely impaired mitochondrial fusion, leading to mitochondrial fragmentation and mtDNA depletion. Conversely, targeted inactivation of ALCAT1 in mice significantly increased mitochondrial mass and protected mitochondria from ROS-induced mitochondrial swelling and fragmentation. A role of ALCAT1 in regulating mtDNA fidelity was demonstrated, which is corroborated by previous studies that mitochondrial fusion is required to safeguard mtDNA integrity (Chen H et al., (2010) *Cell* 141(2):280-289).

WO 2013/123305 also provides evidence that ALCAT1 plays a key role in regulating MFN2 expression. MFN2 is required for mitochondrial and endoplasmic morphology and tethering ER and mitochondria as a functional bridge. ALCAT1 impairs mitochondrial fusion through MFN2 depletion, and links oxidative stress to mitochondrial fragmentation and MFN2 deficiency.

MFN2 deficiency has also been shown to cause skeletal muscle atrophy, which is consistent with the findings that ALCAT1 deficiency significantly increased skeletal muscle mass in ALCAT1 knockout mice (Li J et al., (2010) *Cell Metab* 12(2):154-165, Chen H et al. (2010) *Cell* 141(2):280-289).

WO 2013/123305 identified ALCAT1 as a missing link between mitochondrial fusion defects and reactive oxygen species (ROS) production in metabolic diseases. Cardiolipin (CL) remodeling by ALCAT1 significantly increased docosahexaenoic acid (DHA) content in CL, leading to proton leakage and oxidative stress. DHA content in the mitochondrial membrane inversely correlates with lifespan, and positively correlated with ROS production and lipid peroxidation index in mammals. Hence, increased DHA content in CL increases lipid peroxidation index and has been implicated in mitochondrial dysfunction in aging and age-related diseases (Han X, et al. (2007) Biochemistry 46(21):6417-6428: Sparagna GC & Lesnefoky E. J (2009) J Cardiovasc Pharmacol 53(4):290-301; Lee H-J, (2006) LzjJids Health & Dis. 5:2; Paradies G, et al., (2010) Free Radie Biol Med 4800):1286-1295; Shi Y (2010) J Biomed Res 24(1):6-15).

The onset of aging and age-related diseases is associated with oxidative stress and increased mtDNA mutation rate, which have been proposed as the primary causes of aging and age-related diseases. Additionally, MFN2 deficiency has been implicated in age-related metabolic diseases. Targeted inactivation of ALCAT1 prevents the onset of obesity, fatty liver diseases, and cardiomyopathy by preventing mitochondrial dysfunction. Therefore, it can be envisaged that the development of chemical inhibitors for ALCAT1 will provide a potential treatment for aging, age-related diseases, and other disorders caused by mitochondrial dysfunction, such as Barth syndrome.

WO 2013/123305 also showed that ALCAT1 plays a key role in regulating the onset of hypertrophic cardiomyopathy. The overexpression of ALCAT1 caused hypertrophic growth of H9c2 cells, whereas ablation of ALCAT1 prevented the onset of T4-induced cardiomyopathy and its related cardiac dysfunction, including ventricular hypertrophy, ventricular fibrosis, and elevated expression of collagen type I and III. CL remodeling by ALCAT1 caused depletion of tetralinoleoyl CL (TLCL), which has been identified as the primary cause of cardiomyopathy in Barth syndrome.

Ablation of ALCAT1 expression completely prevented cardiac lipid peroxidation caused by hyperthyroidism.

Ablation of ALCAT1 also prevents the onset of Barth syndrome by mitigating mitochondrial dysfunction. Development of inhibitors of ALCAT1 will provide a potential treatment for Barth syndrome, a lethal family inherited disease.

ALCAT1 is up-regulated by oxidative stress and by the onset of diabetes and obesity. Targeted inactivation of ALCAT1 prevents mitochondrial dysfunction and the onset of obesity which is a major causative factor for type 2 diabetes and cardiovascular diseases. Development of inhibitors of ALCAT1 will provide a potential treatment for cardiac hypertrophy and other heart diseases, the major cause of fatality in the developed countries.

Thus there is a need for compounds which act as inhibitors of ALCAT1, thereby offering a treatment for aging and age-related diseases. For example, such compounds could be useful in the treatment of diet-induced obesity, type-2 diabetes, diabetic complications (such as nephropathy, cardiomyopathy, retinopathy and erectile dysfunction), cardiovascular diseases, fatty liver diseases, neurodegenerative diseases such as Alzheimer's disease, and cancer. Such compounds could also be useful in the treatment of stroke, ischaemia, or reperfusion injury.

SUMMARY OF THE INVENTION

A first aspect of the invention is a compound according to formula (I) as described herein.

A second aspect of the invention is a composition comprising a compound according to formula (I) and a pharmaceutically acceptable carrier or diluent.

A third aspect of the invention is a compound according to formula (I) as described herein, for use in the treatment of the human or animal body by therapy.

A fourth aspect of the invention is a compound according to formula (I), for use in a method of inhibiting or down-regulating ALCAT1.

A fifth aspect of the invention is a compound as described herein, for use in the prevention or treatment of aging or age-related diseases.

A sixth aspect of the invention is the use of a compound according to formula (I), in the manufacture of a medicament for the prevention or treatment of aging or age-related diseases.

A seventh aspect of the invention is a method of inhibiting ALCAT1 comprising administering a therapeutically effective amount of a compound according to formula (I).

An eighth aspect of the invention is a method of treatment comprising administering to a patient in need of treatment a therapeutically effective amount of a compound, as described herein, preferably in the form of a pharmaceutical composition.

A ninth aspect of the invention is a method of treatment and/or prevention comprising administering to a subject in need of treatment and/or prevention a therapeutically-effective amount of an AS compound, as described herein, preferably in the form of a pharmaceutical composition.

A tenth aspect of the invention is a kit comprising (a) a compound according to formula (I), preferably provided as a pharmaceutical composition and in a suitable container and/or with suitable packaging; and (b) instructions for use, for example, written instructions on how to administer the compound.

Another aspect of the present invention is a compound obtainable by a method of synthesis as described herein, or a method comprising a method of synthesis as described herein.

Another aspect of the present invention is a compound obtained by a method of synthesis as described herein, or a method comprising a method of synthesis as described herein.

Another aspect of the present invention is a novel intermediates, as described herein, which is suitable for use in the methods of synthesis described herein.

Another aspect of the present invention is the use of such novel intermediates, as described herein, in the methods of synthesis described herein.

Another aspect of the present invention is a method of synthesising a compound described herein.

As will be appreciated by one of skill in the art, features and preferred embodiments of one aspect of the invention will also pertain to other aspect of the invention.

Any sub-titles herein are included for convenience only, and are not to be construed as limiting the disclosure in any way.

Compounds

A first aspect of the invention is a compound according to formula (I):

Formula (I)

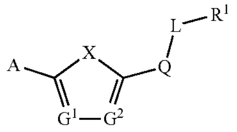

or a pharmaceutically acceptable salt, solvate or hydrate thereof, wherein:

X is selected from O and S;

$G^1$ and $G^2$ are each independently selected from N and CH;

A is selected from
- H,
- $C_{1-6}$ linear or branched alkyl or alkenyl optionally substituted with one or more groups $R^{A1}$,
- 5- or 6-membered heteroaryl groups containing 1 to 3 heteroatoms selected from N, O and S, optionally substituted with one or more groups $R^{B1}$,
- 4- to 6-membered heterocyclyl groups containing 1 to 3 heteroatoms selected from N, O and S, optionally substituted with one or more groups $R^{B2}$,
- —CN,
- —COOH, —COOR$^{C1}$, —COR$^{C2}$, —CONH$_2$, —CONHR$^{D1}$, —CON(R$^{D2}$)$_2$,
- —NH$_2$, —NHR$^{D4}$, —N(R$^{D3}$)$_2$, —NHCOOH, —NHCOOR$^{C1}$, —NHCOH, —NHCOR$^{C2}$, —NR$^{D6}$COOH—NR$^{D7}$COOR$^{C1}$, —NR$^{D5}$COR$^{C2}$, and
- —SR$^{E1}$;

L is a single bond, or is the group $L^A$, wherein $L^A$ is selected from
- —NR$^L$C(═O)—*, —C(═O)NR$^{L1}$—*,
- —NR$^L$C(═X$^L$)NR$^L$—*,
- —SO$_2$—NR$^L$—*, —NR$^L$—SO$_2$—*,
- —OC(═O)—NR$^L$—*, and —NR$^L$—C(═O)O—*;

wherein the asterisk (*) indicates the point of attachment to $R^1$;

$X^L$ is selected from O and S;

$R^L$ is selected from
- —H,
- —C(═O)(C$_{1-3}$alkyl),
- —P(═O)(OH)$_2$, and
- —S(═O)$_2$NH$_2$;

when L is a single bond, $R^1$ is $NH_2$;

when L is $L^A$, $R^1$ is $R^{1L}$, wherein $R^{1L}$ is selected from
- $C_{1-6}$ linear or branched unsubstituted alkyl;
- phenyl, optionally substituted with one to three groups $R^{PH}$,
- 5 or 6-membered cycloalkyl, optionally substituted with one or more groups $R^{B3}$,
- 5 or 6-membered heteroaryl or heterocyclyl containing 1-3 heteroatoms selected from N, O and S, optionally substituted with one or more groups $R^{B4}$, and
- 8 to 10-membered bicyclyl, or heterobicyclyl containing 1-3 heteroatoms selected from N, O and S, optionally substituted with one or more groups $R^{B5}$;

wherein each $R^{PH}$ is independently selected from
- $C_{1-6}$ linear or branched alkyl, alkenyl or alkynyl optionally substituted with one or more groups $R^{A2}$,
- phenyl, optionally substituted with one or more groups $R^{A3}$, naphthyl,
—F, —Cl, —Br, —I,
—COOH, —$COOR^{C1}$, —$COR^{C2}$, —$CONH_2$, —$COONH_2$, —$CONHR^{D1}$, —$CON(R^{D2})_2$,
—$NH_2$, —$NHR^{D4}$, —$NHR^{D8}$, —$N(R^{D3})_2$, —NHCOOH, —$NHCOOR^{C1}$, —NHCOH, —$NHCOR^{C2}$, —$NR^{D7}COOR^{C1}$, —$NR^{D5}COR^{C2}$, —$NHSO_2(C_{1-3}alkyl)$,
—$SO_2NH_2$, —$SO_2NHR^{D1}$, —$SO_2N(R^{D2})_2$, —$SO_2R^{E2}$, —$SR^{E1}$,
—$NO_2$,
—CN,
—OH, and —$OR^{PH4}$;

wherein $R^{PH4}$ is selected from
phenyl,
benzyl, and
$C_{1-6}$ linear or branched alkyl optionally substituted with one or more groups $R^{A5}$;

Q is selected from (Q1) and (Q2)

(Q1)

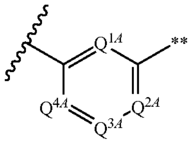

(Q2)

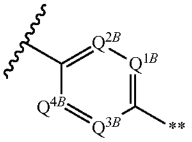

wherein the two asterisks (**) indicate the point of attachment to L;

two of $Q^{1A}$, $Q^{2A}$, $Q^{3A}$ and $Q^{4A}$ are CH;

the other two of $Q^{1A}$, $Q^{2A}$, $Q^{3A}$ and $Q^{4A}$ are independently selected from N, CH and $CR^{Q1}$;

two of $Q^{1B}$, $Q^{2B}$, $Q^{3B}$ and $Q^{4B}$ are CH;

the other two of $Q^{1B}$, $Q^{2B}$, $Q^{3B}$ and $Q^{4B}$ are independently selected from N, CH and $CR^{Q2}$;

each $R^{Q1}$ and each $R^{Q2}$ are independently selected from
—F, —Cl, —Br, —I,
$C_{1-6}$ linear or branched unsubstituted alkyl,
—OH, —$O(C_{1-6}alkyl)$,
—CN, and
$N(R^{D3})_2$;

$R^{C1}$ and $R^{C2}$ are each independently selected from
$C_{1-6}$ linear or branched alkyl, optionally substituted with one or more groups $R^{A6}$;
5-membered heteroaryl groups containing a single heteroatom selected from N, O and S, optionally substituted with one or two groups $R^{E3}$;

$R^{D1}$ to $R^{D7}$ are each independently selected from
$C_{1-6}$ linear or branched alkyl, optionally substituted with one or more groups $R^{A7}$,
—COOH, —$COOR^{C1}$, —$COR^{C2}$,
—$C(=NH)NH_2$,
or when two $R^{D2}$ or two $R^{D3}$ groups are attached to a single nitrogen atom they may, together with the nitrogen atom to which they are attached, form a 5 or 6-membered heterocyclic group containing 1-3 ring heteroatoms selected from N, O and S, optionally substituted with one or more groups $R^{D9}$;

wherein $R^{D9}$ is $C_{1-6}$ linear or branched alkyl, optionally substituted with one or more groups $R^{A8}$;

$R^{D}S$ is a $C_{5-6}$ heterocyclyl group containing one or two N atoms optionally substituted with one or more groups selected from
—SH, and
—$C(=O)OR^{D5A}$, wherein $R^{D5A}$ is a phenyl or benzyl group optionally substituted with an $NO_2$ group;

$R^{E1}$ and $R^{E2}$ are each independently selected from $C_{1-6}$ linear or branched unsubstituted alkyl, alkenyl or alkynyl;

$R^{E3}$ is independently selected from
—SH; and
—$C(=O)OR^{E4}$;

$R^{B1}$ to $R^{B5}$ are each independently selected from
$C_{1-6}$ linear or branched alkyl optionally substituted with one or more groups $R^{A9}$,
—F, —Cl, —Br,
—OH, —$O(C_{1-3}alkyl)$,
—CN,
—$NO_2$,
—COOH, —$COOR^{C1}$, —$COR^{C2}$, —$CONH_2$, —$CONHR^{D1}$, —$CON(R^{D2})_2$,
—$NH_2$, —$NHR^{D4}$, —$N(R^{D3})_2$, —NHCOOH, —$NHCOOR^{C1}$, —$NHCOR^{C2}$, —$NR^{D6}COOH$—$NR^{D7}COOR^{C1}$, and —$NR^{D5}COR^{C2}$;

$R^{E4}$ is independently selected from
phenyl or benzyl, optionally substituted with one or two groups $R^{A10}$;

$R^{A1}$ to $R^{A10}$ are each independently selected from
—F, —Cl, —Br,
—OH, —$OR^T$
—CN, —$NO_2$,
—$C(=O)R^T$, —COOH, —$COOR^T$, —$CON(R^G)_2$,
—$NH_2$, —$NHR^T$, —$N(R^T)_2$, —$NHC(=O)(R^F)$ and —$N(R^{D9})_2$;

$R^F$ is selected from
$C_{1-6}$ linear or branched unsubstituted alkyl, and
5 to 6-membered heteroaryl including one to three heteroatoms selected from N, O and S;

the group —$N(R^G)_2$ is selected from azetidino, imidazolidino, pyrazolidino, pyrrolidino, piperidino, piperazino, N—$C_{1-4}$alkyl-piperazino, morpholino, azepino or diazepino, optionally substituted with one or more groups selected from linear or branched $C_{1-4}$alkyl, phenyl or benzyl;

$R^T$ is $C_{1-6}$ linear or branched unsubstituted alkyl;

the two $R^{D9}$ groups together with the nitrogen atom to which they are attached form a group selected from
5-membered heteroaryl group containing one or two nitrogen atoms; and
6-membered heterocyclic group containing one or two heteroatoms each independently selected from N, O and S, with the proviso that the compound is not selected from any of the compounds (X1) to (X27):

(X1)

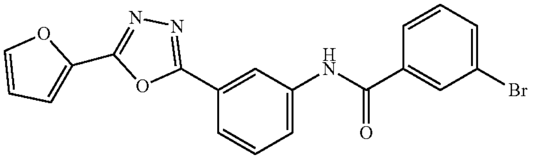

-continued
(X2)
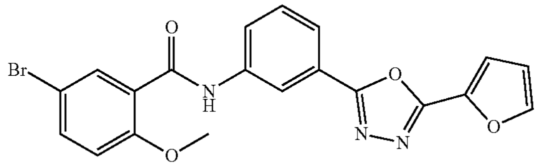
(X3)
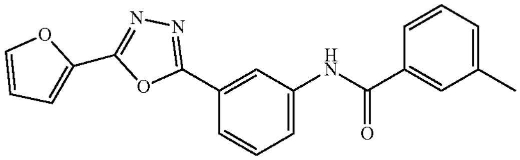
(X4)
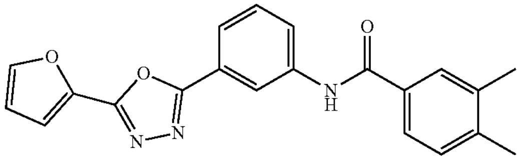
(X5)
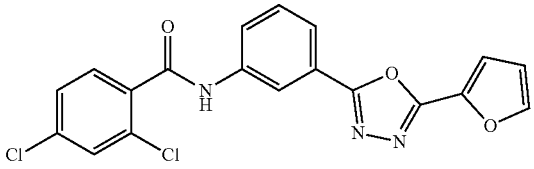
(X6)
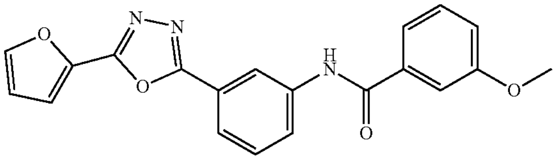
(X7)
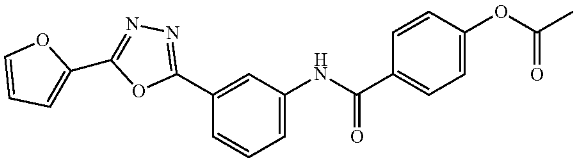
(X8)
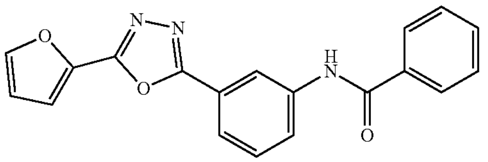
(X9)
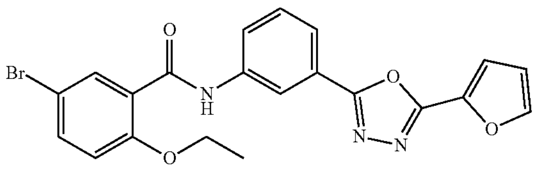
-continued
(X10)
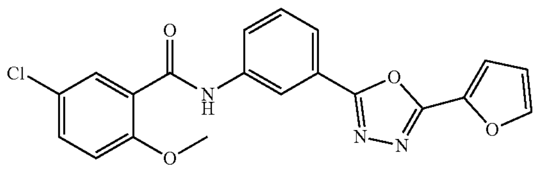
(X11)
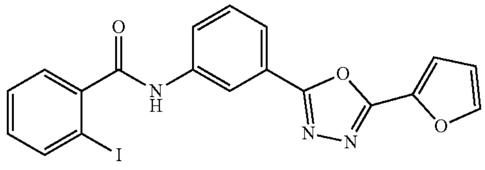
(X12)
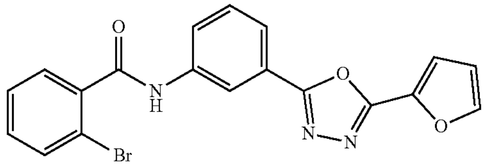
(X13)
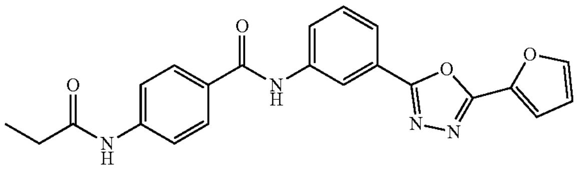
(X14)
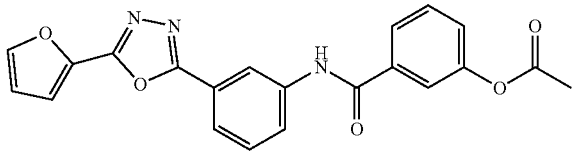
(X15)
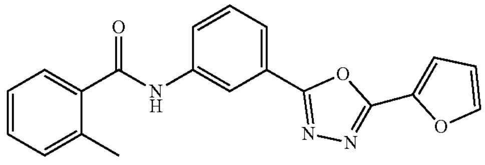
(X16)
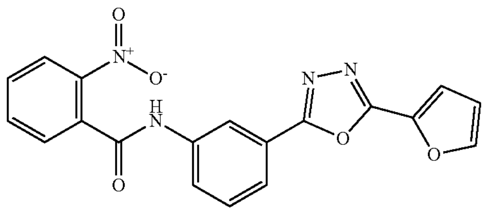
(X17)
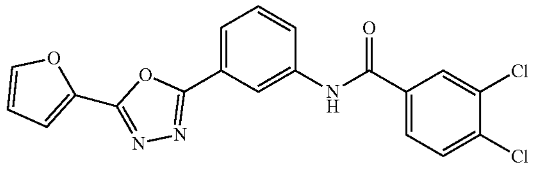

-continued (X18)

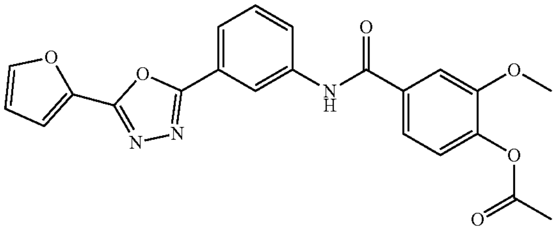

(X19)

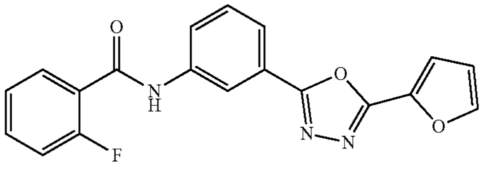

(X20)

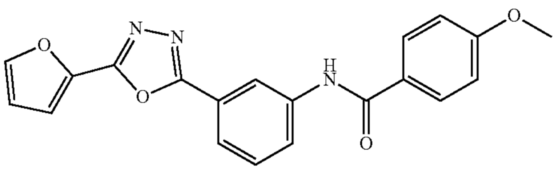

(X21)

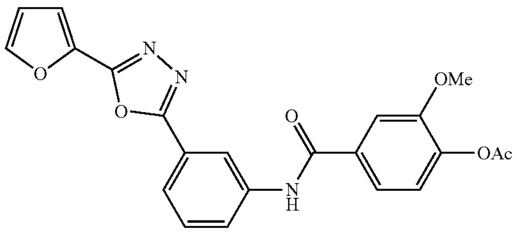

(X22)

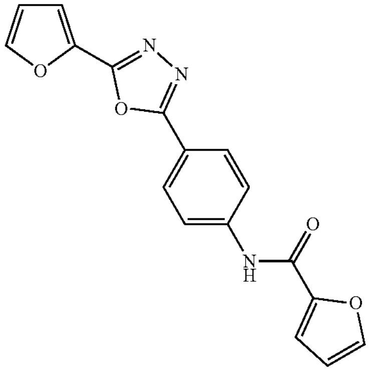

(X23)

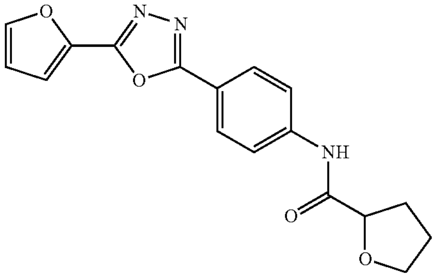

-continued (X24)

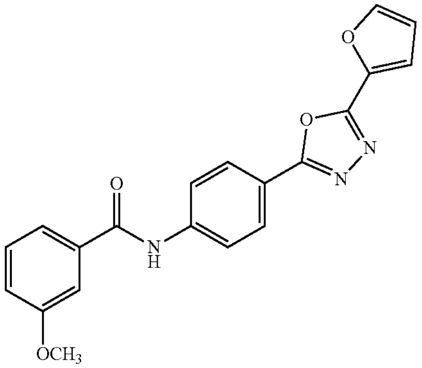

(X25)

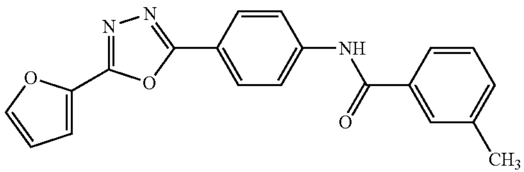

(X26)

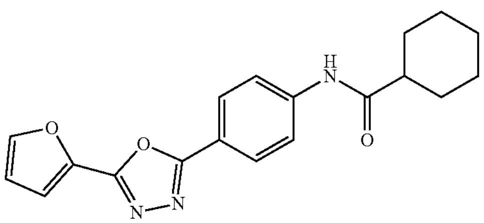

(X27)

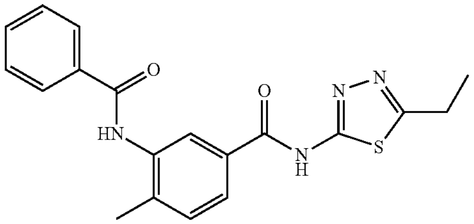

In some embodiments:

$R^L$ is selected from

—H, and —C(═O)($C_{1-3}$alkyl);

and in the group —N($R^{D9}$)$_2$, the two $R^{D9}$ groups together with the nitrogen atom to which they are attached form a 5-membered heteroaryl group containing one or two nitrogen atoms.

The Group X

In some embodiments, X is O.

In some embodiments, X is S.

The group $G^1$

In some embodiments, $G^1$ is N.

In some embodiments, $G^1$ is CH.

The group $G^2$

In some embodiments, $G^2$ is N.

In some embodiments, $G^2$ is CH.

The groups X, $G^1$ and $G^2$

In some embodiments, X is O, $G^1$ is N and $G^2$ is N.

In some embodiments, X is O, $G^1$ is N and $G^2$ is CH.

In some embodiments, X is O, $G^1$ is CH and $G^2$ is N.

In some embodiments, X is S, $G^1$ is N and $G^2$ is N.

In some embodiments, X is S, $G^1$ is CH and $G^2$ is N.

In some embodiments, X is O, $G^1$ is CH and $G^2$ is CH.

In some embodiments, X is O, one of $G^1$ and $G^2$ is selected from CH and N, and the other of $G^1$ and $G^2$ is N.

In some embodiments, X is S, one of $G^1$ and $G^2$ is selected from CH and N, and the other of $G^1$ and $G^2$ is N.

The group A

In some embodiments, A is —H.

In some embodiments, A is $C_{1-6}$ linear or branched alkyl or alkenyl optionally substituted with one or more groups $R^{A1}$.

In some embodiments, A is $C_{1-5}$ linear or branched alkyl or alkenyl optionally substituted with one or more groups $R^{A1}$.

In some embodiments, A is $C_{1-5}$ linear or branched alkyl optionally substituted with one or more groups $R^{A1}$.

In some embodiments, $R^{A1}$ is selected from

—OH, —$OR^T$

—C(=O)$R^T$, —COOH, —$COOR^T$,

—$NH_2$, —$NHR^T$, —$N(R^T)_2$, —NHC(=O)($R^F$) and —$N(R^{D9})_2$.

In some embodiments, $R^{A1}$ is selected from

—$OR^T$

—$NH_2$, —$NHR^T$, —$N(R^T)_2$, —NHC(=O)($R^F$) and —$N(R^{D9})_2$.

In some embodiments, -A is selected from methyl, ethyl, isopropyl,

—$CH_2NMe_2$, —$CH_2NHCOMe$, —$CH_2NHCO(R^F)$, —$CH_2N(R^{D3})_2$,

—$CH_2OMe$,

—$CH(NH_2)CH_3$ and —$CH(NH_2)CH_2CH(Me)_2$.

In some embodiments, -A is selected from 5- or 6-membered heteroaryl groups containing 1 to 3 heteroatoms selected from N, O and S, optionally substituted with one or more groups $R^{B1}$.

In some embodiments, -A is selected from 5-membered heteroaryl groups containing 1 to 3 heteroatoms selected from N, O and S, optionally substituted with one or more groups $R^{B1}$.

In some embodiments, -A is selected from 5-membered heteroaryl groups containing 1 or 2 heteroatoms selected from N, O and S, optionally substituted with one or more groups $R^{B1}$.

In some embodiments, -A is selected from 5-membered heteroaryl groups containing 1 heteroatom selected from N, O and S, optionally substituted with one or more groups $R^{B1}$.

In some embodiments, -A is selected from 5-membered unsubstituted heteroaryl groups containing 1 to 3 heteroatoms selected from N, O and S.

In some embodiments, -A is selected from 5-membered unsubstituted heteroaryl groups containing 1 or 2 heteroatoms selected from N, O and S.

In some embodiments, $R^{B1}$ is selected from $C_{1-3}$ linear or branched alkyl optionally substituted with one or more groups $R^{A9}$, —F, —Cl, —Br,

—CN,

—COOH, —$COOR^{C1}$, —$COR^{C2}$, —$CONH_2$, —$CONHR^{D1}$, —$CON(R^{D2})_2$,

—$NH_2$, —$NHR^{D4}$, —$N(R^{D3})_2$, —NHCOOH, —$NHCOOR^{C1}$, —$NHCOR^{C2}$, —$NR^{D6}$COOH $NR^{D7}COOR^{C1}$, and —$NR^{D5}COR^{C2}$.

In some embodiments, $R^{B1}$ is selected from $C_{1-3}$ linear or branched alkyl optionally substituted with one or more groups $R^{A9}$, —F, —Cl, —Br,

—CN,

—COOH, —$COOR^{C1}$, —$COR^{C2}$, —$CONH_2$, —$CONHR^{D1}$ and —$CON(R^{D2})_2$.

In some embodiments, $R^{B1}$ is selected from $C_{1-3}$ linear or branched alkyl optionally substituted with one or more groups $R^{A9}$, —F, —Cl, —Br,

—CN,

—$COR^{C2}$, —$CONH_2$, —$CONHR^{D1}$ and —$CON(R^{D2})_2$.

In some embodiments, $R^{B1}$ is selected from $C_{1-3}$ linear unsubstituted alkyl, —F, —Cl, —Br,

—CN,

—COOH, —$COOR^{C1}$, —$COR^{C2}$, —$CONH_2$, —$CONHR^{D1}$ and —$CON(R^{D2})_2$.

In some embodiments, $R^{B1}$ is selected from $C_{1-3}$ linear unsubstituted alkyl, —F, —Cl, —Br,

—CN,

—COOH, —$COOR^{C1}$ and —$COR^{C2}$.

In some embodiments, $R^{B1}$ is selected from methyl,

—$CH_2C_1$,

—F, —Cl, —Br,

—CN, and

—C(=O)Me.

In some embodiments, -A is selected from

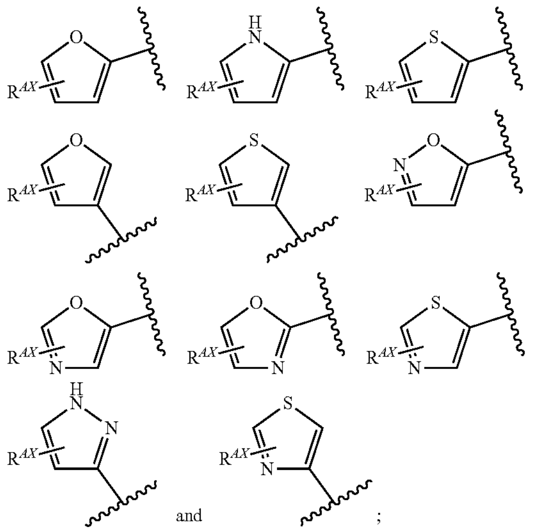

and ;

wherein $R^{AX}$ is a single optional ring substituent selected from $C_{1-3}$ linear or branched alkyl optionally substituted with one or more groups $R^{A9}$, —F, —Cl, —Br,

—CN,

—COOH, —$COOR^{C1}$, —$COR^{C2}$, —$CONH_2$, —$CONHR^{D1}$, —$CON(R^{D2})_2$,

—$NH_2$, —$NHR^{D4}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, $R^{AX}$ is a single optional ring substituent selected from $C_{1-3}$ linear unsubstituted alkyl, —F, —Cl, —Br,

—CN,

—COOH, —$COOR^{C1}$ and —$COR^{C2}$.

In some embodiments, $R^{AX}$ is absent, i.e. the ring is unsubstituted.

In some embodiments, -A is furan-2-yl, optionally substituted with one or more groups selected from $C_{1-3}$ linear or branched alkyl optionally substituted with one or more groups $R^{A9}$,
—F, —Cl, —Br,
—CN,
—COOH, —$COOR^{C1}$, —$COR^{C2}$, —$CONH_2$, —$CONHR^{D1}$, —$CON(R^{D2})_2$,
—$NH_2$, —$NHR^{D}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, -A is furan-2-yl, optionally substituted with one or more groups selected from $C_{1-3}$ linear unsubstituted alkyl,
—F, —Cl, —Br,
—CN,
—COOH, —$COOR^{C1}$ and —$COR^{C2}$.

In some embodiments, -A is furan-2-yl, optionally substituted with one group selected from $C_{1-3}$ linear unsubstituted alkyl,
—F, —Cl, —Br,
—CN,
—COOH, —$COOR^{C1}$ and —$COR^{C2}$.

In some embodiments, -A is unsubstituted furan-2-yl.

In some embodiments, -A is selected from 6-membered heteroaryl groups containing 1 to 3 heteroatoms selected from N, O and S, optionally substituted with one or more groups $R^{B1}$.

In some embodiments, -A is selected from 6-membered heteroaryl groups containing 1 or 2 heteroatoms selected from N, O and S, optionally substituted with one or more groups $R^{B1}$.

In some embodiments, -A is selected from 6-membered unsubstituted heteroaryl groups containing 1 or 2 heteroatoms selected from N, O and S. In some embodiments, -A is selected from 6-membered unsubstituted heteroaryl groups containing 1 or 2 heteroatoms selected from N.

In some embodiments, -A is selected from

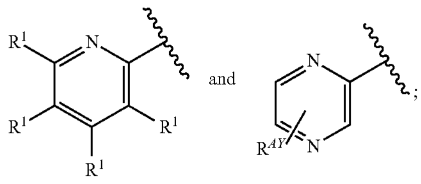

and ;

R1 = $R^{AY}$
R1 = 1 (ResIH)

wherein $R^{AY}$ is a single optional ring substituent selected from $C_{1-3}$ linear or branched alkyl optionally substituted with one or more groups $R^{A9}$,
—F, —Cl, —Br,
—CN,
—COOH, —$COOR^{C1}$, —$COR^{C2}$, —$CONH_2$, —$CONHR^{D1}$, —$CON(R^{D2})_2$,
—$NH_2$, —$NHR^{D4}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, $R^{AY}$ is absent, i.e. the ring is unsubstituted.

In some embodiments, -A is selected from 4- to 6-membered heterocyclyl groups containing 1 to 3 heteroatoms selected from N, O and S, optionally substituted with one or more groups $R^{B2}$.

In some embodiments, -A is selected from 4- and 5-membered heterocyclyl groups containing 1 or 2 heteroatoms selected from N, O and S, optionally substituted with one or more groups $R^{B2}$.

In some embodiments, -A is selected from 4- to 6-membered unsubstituted heterocyclyl groups containing 1 to 3 heteroatoms selected from N, O and S. In some embodiments, -A is selected from 4- to 6-membered unsubstituted heterocyclyl groups containing 1 or 2 heteroatoms selected from N, O and S. In some embodiments, -A is selected from 4- to 6-membered unsubstituted heterocyclyl groups containing 1 or 2 heteroatoms selected from N and O. In some embodiments, -A is selected from 4- to 6-membered unsubstituted heterocyclyl groups containing 1 heteroatom selected from N, O and S.

In some embodiments, -A is selected from

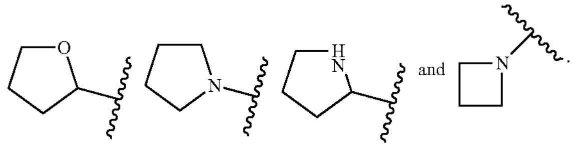

and .

In some embodiments, -A is —CN.

In some embodiments, -A is —COOH.

In some embodiments, -A is —$COOR^{C1}$. In some embodiments, $R^{C1}$ is selected from $C_{1-6}$ linear or branched unsubstituted alkyl. In some embodiments, $R^{C1}$ is selected from $C_{1-4}$ linear or branched unsubstituted alkyl. In some embodiments, $R^{C1}$ is selected from $C_{1-3}$ linear unsubstituted alkyl. In some embodiments, $R^{C1}$ is methyl.

In some embodiments, -A is —$COR^{C2}$. In some embodiments, $R^{C2}$ is selected from $C_{1-6}$ linear or branched unsubstituted alkyl. In some embodiments, $R^{C2}$ is selected from $C_{1-4}$ linear or branched unsubstituted alkyl. In some embodiments, $R^{C2}$ is selected from $C_{1-3}$ linear unsubstituted alkyl. In some embodiments, $R^{C2}$ is methyl.

In some embodiments, -A is —$CON(R^{D2})_2$. In some embodiments, each $R^{D2}$ is independently selected from $C_{1-6}$ linear or branched alkyl, optionally substituted with one or more groups $R^{A7}$. In some embodiments, each $R^{D2}$ is independently selected from unsubstituted $C_{1-6}$ linear or branched alkyl. In some embodiments, each $R^{D2}$ is independently selected from unsubstituted $C_{1-3}$ linear or branched alkyl. In some embodiments, each $R^{D2}$ is methyl.

In some embodiments, -A is —$NHCOR^{C2}$. In some embodiments, $R^{C2}$ is selected from $C_{1-6}$ linear or branched unsubstituted alkyl. In some embodiments, $R^{C2}$ is selected from $C_{1-4}$ linear or branched unsubstituted alkyl. In some embodiments, $R^{C2}$ is selected from $C_{1-3}$ linear unsubstituted alkyl. In some embodiments, $R^{C2}$ is methyl.

In some embodiments, -A is —$CONH_2$.

In some embodiments, -A is —$CONHR^{D1}$.

In some embodiments, -A is —$NH_2$.

In some embodiments, -A is —$NHR^{D4}$.

In some embodiments, -A is —$N(R^{D3})_2$.

In some embodiments, -A is —NHCOOH.

In some embodiments, -A is —$NHCOOR^{C1}$.

In some embodiments, -A is —NHCOH.

In some embodiments, -A is —$NR^{D6}$COOH.

In some embodiments, -A is —$NR^{D7}COOR^{C1}$.

In some embodiments, -A is —$NR^{D5}COR^{C2}$.

In some embodiments, -A is —$SR^{E1}$. In some embodiments, $R^{E1}$ is selected from $C_{2-6}$ linear or branched unsubstituted alkenyl. In some embodiments, $R^{E1}$ is selected from $C_{3-6}$ linear unsubstituted alkenyl. In some embodiments, $R^{E1}$ is allyl.

The group L

In some embodiments, L is a single bond. In some embodiments, L is the group $L^A$.

In some embodiments, L is $L^A$, and $L^A$ is selected from

—$NR^LC(=O)$—*, —$C(=O)NR^L$—*,

—$NR^LC(=X^L)NR^L$—*,

—$SO_2$—$NR^L$—*, —$NR^L$—$SO_2$—*,

—$OC(=O)$—$NR^L$—*, and —$NR^L$—$C(=O)O$—*;

wherein the asterisk (*) indicates the point of attachment to $R^1$.

In some embodiments, L is $L^A$, and $L^A$ is selected from —$NR^LC(=O)$—* and —$C(=O)NR^L$—*, wherein the asterisk (*) indicates the point of attachment to $R^1$.

In some embodiments, L is $L^A$, and $L^A$ is —$NR^L C(=O)$—*, wherein the asterisk (*) indicates the point of attachment to $R^1$.

In some embodiments, $R^L$ is —H. In some embodiments, $R^L$ is —$C(=O)(C_{1-3}alkyl)$. In some embodiments, $R^L$ is —$C(=O)Me$. In some embodiments, $R^L$ is —$P(=O)(OH)_2$. In some embodiments, $R^L$ is —$S(=O)_2NH_2$.

In some embodiments, $L^A$ is —$NHC(=O)$—* or —$C(=O)NH$—*. In some embodiments, $L^A$ is —$NHC(=O)$—*. In some embodiments, $L^A$ is —$NR^LC(=O)$—*, wherein $R^L$ is —$P(=O)(OH)_2$. In some embodiments, $L^A$ is —$NR^LC(=O)$—*, wherein $R^L$ is —$S(=O)_2NH_2$.

In some embodiments, L is $L^A$, and $L^A$ is —$NR^LC(=X^L)NR^L$—*. In some embodiments, L is $L^A$, and $L^A$ is —$SO_2$—$NR^L$—*. In some embodiments, L is $L^A$, and $L^A$ is —$NR^L$—$SO_2$—*. In some embodiments, L is $L^A$, and $L^A$ is —$OC(=O)$—$NR^L$—*. In some embodiments, L is $L^A$, and $L^A$ is —$NR^L$—$C(=O)O$—*.

In some embodiments, $X^L$ is O. In some embodiments, $X^L$ is S.

The Group $R^1$

When L is a single bond, $R^1$ is $NH_2$.

When L is $L^A$, $R^1$ is $R^{1L}$.

In some embodiments, $R^{1L}$ is selected from $C_{1-6}$ linear or branched unsubstituted alkyl. In some embodiments, $R^{1L}$ is methyl.

In some embodiments, $R^{1L}$ is phenyl, optionally substituted with one to three groups $R^{PH}$.

In some embodiments, $R^{1L}$ is phenyl, optionally substituted with one or two groups $R^{PH}$.

In some embodiments, $R^{1L}$ is phenyl, optionally substituted with one group $R^{PH}$. In some embodiments, $R^{1L}$ is phenyl, optionally substituted with two groups $R^{PH}$. In some embodiments, $R^{1L}$ is phenyl, optionally substituted with three groups $R^{PH}$.

In some embodiments, $R^{1L}$ is unsubstituted phenyl. In some embodiments, $R^{1L}$ is phenyl carrying a single substituent $R^{PH}$ which is in the ortho position. In some embodiments, $R^{1L}$ is phenyl carrying a single substituent $R^{PH}$ which is in the meta position. In some embodiments, $R^{1L}$ is phenyl carrying a single substituent $R^{PH}$ which is in the para position.

Herein, the term "in an ortho position" signifies the position on the ring relative to the L group, unless otherwise specified. The same applies to the terms "in a meta position" and "in a para position".

In some embodiments, $R^{1L}$ is phenyl carrying a single substituent $R^{PH}$ which is either in the ortho position or the para position.

In some embodiments, $R^{1L}$ is phenyl carrying two substituents $R^{PH}$ which are in the two meta positions. In some embodiments, $R^{1L}$ is phenyl carrying two substituents $R^{PH}$ which are in the two ortho positions.

In some embodiments, $R^{1L}$ is phenyl carrying two substituents $R^{PH}$, one in an ortho positon and one in a para position. In some embodiments, $R^{1L}$ is phenyl carrying two substituents $R^{PH}$, one in a meta positon and one in a para position. In some embodiments, $R^{1L}$ is phenyl carrying two substituents $R^{PH}$, a first of which is in an ortho position and a second of which is located para to the first. In some embodiments, $R^{1L}$ is phenyl carrying two substituents $R^{PH}$, a first of which is in an ortho position and a second of which is located in the meta position which is ortho to the first.

In some embodiments, $R^{1L}$ is phenyl carrying three substituents $R^{PH}$.

In some embodiments, $R^{1L}$ is phenyl carrying three substituents $R^{PH}$, wherein a first is in the para position and the second and third are in the two meta positions. In some embodiments, $R^{1L}$ is phenyl carrying three substituents $R^{PH}$, wherein a first is in an ortho position and the second and third are in the two meta positions. In some embodiments, $R^{1L}$ is phenyl carrying three substituents $R^{PH}$, wherein a first is in an ortho position, the second is in the para position and third is in the position para to the first.

In some embodiments, $R^{1L}$ is

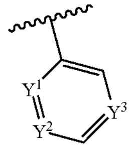

wherein one of $Y^1$, $Y^2$ and $Y^3$ is $CR^Y$; a second of $Y^1$, $Y^2$ and $Y^3$ is independently selected from $CR^Y$ and CH; and a third of $Y^1$, $Y^2$ and $Y^3$ is independently selected from $CR^Y$ and CH;

wherein each $R^Y$ is independently selected from linear or branched unsubstituted $C_{1-6}$ alkyl,

—$OR^{Y1}$;

—F, —Cl, —Br, —I,

—$CF_3$, —$CH_2F$, —$CF_2H$,

—$CH_2CF_3$, —$CH_2CH_2F$ and —$CH_2CF_2H$.

In some embodiments, one of $Y^1$, $Y^2$ and $Y^3$ is $CR^Y$; a second of $Y^1$, $Y^2$ and $Y^3$ is selected from $CR^Y$ and CH; and a third of $Y^1$, $Y^2$ and $Y^3$ is CH.

In some embodiments, $Y^1$ is $CR^Y$ and each of $Y^2$ and $Y^3$ are selected from CH and $CR^Y$.

In some embodiments, $Y^1$ is $CR^Y$ and $Y^2$ and $Y^3$ are both CH.

In some embodiments, $Y^1$ is $CR^Y$, one of $Y^2$ and $Y^3$ is CH and the other is $CR^Y$.

In some embodiments, $Y^1$ is $CR^Y$, $Y^2$ is CH and $Y^3$ is $CR^Y$.

In some embodiments, each of $Y^1$, $Y^2$ and $Y^3$ is $CR^Y$.

In some embodiments, $R^Y$ is independently selected from linear or branched unsubstituted $C_{1-6}$ alkyl, such as methyl, ethyl or n-propyl.

In some embodiments, $R^Y$ is independently selected from —$OR^{Y1}$, such as —OMe, —OEt, —$O^nPr$, —$OCF_3$, —$OCH_2F$, —$OCF_2H$, —$OCH_2CF_3$, —$OCH_2CH_2F$ or —$OCH_2CF_2H$.

In some embodiments, $R^Y$ is independently selected from —F, —Cl, —Br and —I. In some embodiments, $R^Y$ is independently selected from —F.

In some embodiments, $R^Y$ is independently selected from

—$CF_3$, —$CH_2F$, —$CF_2H$,

—$CH_2CF_3$, —$CH_2CH_2F$ and —$CH_2CF_2H$.

In some embodiments, $R^Y$ is —$CF_3$.

In some embodiments, $R^{Y1}$ is methyl. In some embodiments, $R^{Y1}$ is ethyl. In some embodiments, $R^{Y1}$ is n-propyl. In some embodiments, $R^{Y1}$ is —$CF_3$. In some embodiments, $R^{Y1}$ is —$CF_2H$. In some embodiments, $R^{Y1}$ is —$CFH_2$. In some embodiments, $R^{Y1}$ is —$CH_2CF_2H$. In some embodiments, $R^{Y1}$ is —$CH_2CFH_2$.

In some embodiments, each $R^{PH}$ is independently selected from

- $C_{1-6}$ linear or branched alkyl, alkenyl or alkynyl optionally substituted with one or more groups $R^{A2}$,
- phenyl, optionally substituted with one or more groups $R^{A3}$
- —F, —Cl, —Br, —I,
- —COOH, —$COOR^{C1}$, —$COR^{C2}$, —$CONH_2$, —$COONH_2$, —$CONHR^{D1}$, —$CON(R^{D2})_2$,
- —$NH_2$, —$NHR^{D4}$, —$NHR^{D8}$, —$N(R^{D3})_2$, —NHCOOH, —$NHCOOR^{C1}$, —NHCOH, —$NHCOR^{C2}$,
- —$NR^{D7}COOR^{C1}$, —$NR^{D5}COR^{C2}$, —$NHSO_2(C_{1-3}alkyl)$,
- —$SO_2NH_2$, —$SO_2NHR^{D1}$, —$SO_2N(R^{D2})_2$, —$SO_2R^{E2}$, —$SR^{E1}$,
- —$NO_2$,
- —CN,
- —OH, and —$OR^{PH4}$;

In some embodiments, each $R^{PH}$ is independently selected from

- $C_{1-4}$ linear or branched alkyl, alkenyl or alkynyl optionally substituted with one or more groups $R^{A2}$,
- unsubstituted phenyl,
- —F, —Cl, —Br, —I,
- —COOH, —$COOR^{C1}$, —$COR^{C2}$, —$CONH_2$, —$COONH_2$, —$CONHR^{D1}$, —$CON(R^{D2})_2$,
- —$NH_2$, —$NHR^{D4}$, —$NHR^{D8}$, —$N(R^{D3})_2$, —NHCOOH, —$NHCOOR^{C1}$, —NHCOH, —$NHCOR^{C2}$,
- —$NR^{D7}COOR^{C1}$, —$NR^{D5}COR^{C2}$, —$NHSO_2(C_{1-3}alkyl)$,
- —$SO_2NH_2$, —$SO_2NHR^{D1}$, —$SO_2N(R^{D2})_2$, —$SO_2R^{E2}$, —$SR^{E1}$,
- —$NO_2$,
- —CN,
- —OH, and —$OR^{PH4}$;

In some embodiments, each $R^{PH}$ is independently selected from

- $C_{1-4}$ linear or branched alkyl, alkenyl or alkynyl optionally substituted with one or more groups $R^{A2}$,
- —F, —Cl, —Br, —I,
- —OH, and —$OR^{PH4}$;

In some embodiments, each $R^{PH}$ is independently selected from

- $C_{1-6}$ linear alkyl optionally substituted with one or more groups $R^{A2}$,
- —F, —Cl, —Br, —I,
- —OH, and —$OR^{PH4}$;

In some embodiments, each $R^{PH}$ is independently selected from

- $C_{1-6}$ linear alkyl optionally substituted with one or more groups selected from —F, —Cl, —Br and —I,
- —F, —Cl, —Br, —I,
- —OH, and —$OR^{PH4}$ wherein $R^{PH4}$ is selected from $C_{1-6}$ linear or branched alkyl optionally substituted with one or more groups $R^{A5}$.

In some embodiments, $R^{1L}$ is phenyl carrying a first substituent $R^{PH}$ in the ortho position and a second substituent $R^{PH}$ in a position para to the first, wherein the $R^{PH}$ groups are each independently selected from

- $C_{1-6}$ linear alkyl optionally substituted with one or more groups $R^{A2}$,
- —F, —Cl, —Br, —I,
- —OH, and —$OR^{PH4}$;

In some embodiments, each $R^{PH}$ is independently selected from

- -Me, -Et, -$^t$Bu, —CH═CHMe, —CCH, —CCMe, -Ph,
- —OH, —OMe, —OEt, —O$^n$Pr, —O$^n$Pr, —O$^n$Bu, —O-sec-Bu, —O-iso-Bu, —OPh, —OBn,
- —$OCH_2CF_3$, —$OCF_3$, —$OCHF_2$, —$OCF_2H$, —$OCH_2CHF_2$, —$OCH_2CH_2F$,
- —$OCH_2C$(═O)OH, —$OCH_2C$(═O)OMe,
- —F, —Cl, —Br, —I,
- —$CF_3$, —$CHF_2$, —CN, —$CH_2CN$, —CH(Me)CN, —$CH_2OH$, —$CH_2OMe$, —$CH_2COOH$,
- —COOH, —COOMe, —$CONH_2$, —$CONMe_2$, —CONHMe, —C(═O)Me, —$COONH_2$,
- —$SO_2Me$, —$SO_2NH_2$, —SMe,
- —$NO_2$, —$NH_2$, —$NMe_2$, —NHMe, —NHC(═O)Me, —$NHSO_2Me$,

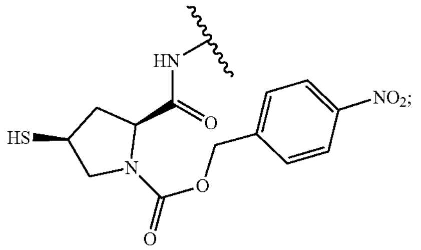

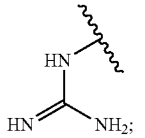

N-pyrrolidinyl, and N-piperidinyl.

In some embodiments, each $R^{PH}$ is independently selected from

- -Me, -Et, -$^t$Bu, —CH═CHMe, —CCH, —CCMe, -Ph,
- —OH, —OMe, —OEt, —O$^n$Pr, —O$^n$Bu, —O-sec-Bu, —O-iso-Bu, —OPh, —OBn,
- —$OCH_2CF_3$, —$OCF_3$, —$OCHF_2$, —$OCF_2H$, —$OCH_2CHF_2$, —$OCH_2CH_2F$,
- —$OCH_2C$(═O)OH, —$OCH_2C$(═O)OMe,
- —F, —Cl, —Br, —I,
- —$CF_3$, —$CHF_2$, —CN, —$CH_2CN$, —CH(Me)CN, —$CH_2OH$, —$CH_2OMe$, —$CH_2COOH$,
- —COOH, —COOMe, —$CONH_2$, —$CONMe_2$, —CONHMe, —C(═O)Me, —$COONH_2$,
- —$SO_2Me$, —$SO_2NH_2$, —SMe,
- —$NO_2$, —$NH_2$, —$NMe_2$, —NHMe, —NHC(═O)Me, —$NHSO_2Me$,

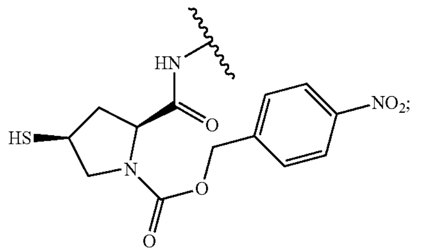

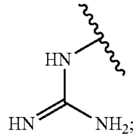

N-pyrrolidinyl, and N-piperidinyl.

In some embodiments, $R^{1L}$ is selected from

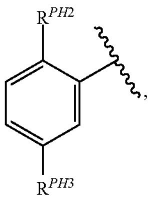,

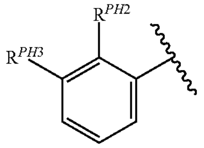 and

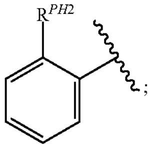;

wherein $R^{PH2}$ and $R^{PH3}$ are each independently selected from $C_{1-4}$ linear or branched alkyl, alkenyl or alkynyl optionally substituted with one or more groups $R^{A2}$, —F, —Cl, —Br, —I, —OH, and —$OR^{PH4}$.

In some embodiments, $R^{PH2}$ and $R^{PH3}$ are each independently selected from $C_{1-4}$ linear or branched alkyl optionally substituted with one or more groups $R^{A2}$, —F, —Cl, —Br, —I, —OH, and —$OR^{PH4}$.

In some embodiments, $R^{PH2}$ and $R^{PH3}$ are each independently selected from $C_{1-4}$ linear unsubstituted alkyl, —F, —Cl, —Br, —I, —OH, and —$OR^{PH4}$;

In some embodiments, $R^{PH2}$ and $R^{PH3}$ are each independently selected from $C_{1-4}$ linear unsubstituted alkyl, —F, —Cl, —Br, —OH, and —$OR^{PH4}$, wherein $R^{PH4}$ is independently selected from $C_{1-4}$ linear alkyl optionally substituted with one or more groups selected from —F, —Cl and —Br.

In some embodiments, $R^{PH2}$ and $R^{PH3}$ are each independently selected from $C_{1-4}$ linear unsubstituted alkyl, —F, —Cl, —Br, —OH, and —$OR^{PH4}$, wherein $R^{PH4}$ is independently selected from $C_{1-4}$ linear alkyl optionally substituted with one or more groups —F.

In some embodiments, each $R^{PH}$ group on $R^{1L}$ is identical. In other embodiments, each $R^{PH}$ group is different.

In some embodiments, $R^{1L}$ is 5 or 6-membered cycloalkyl, optionally substituted with one or more groups $R^{B3}$.

In some embodiments, $R^{1L}$ is 5 or 6-membered unsubstituted cycloalkyl.

In some embodiments, $R^{1L}$ is 5-membered cycloalkyl, optionally substituted with one or more groups $R^{B3}$. In some embodiments, $R^{1L}$ is 5-membered unsubstituted cycloalkyl.

In some embodiments, $R^{1L}$ is 6-membered cycloalkyl, optionally substituted with one or more groups $R^{B3}$. In some embodiments, $R^{1L}$ is 6-membered unsubstituted cycloalkyl.

In some embodiments, $R^{1L}$ is selected from unsubstituted cyclopentyl and unsubstituted cyclohexyl. In some embodiments, $R^{1L}$ is unsubstituted cyclohexyl.

In some embodiments, $R^{B3}$ is selected from $C_{1-4}$ linear or branched unsubstituted alkyl, —F, —Cl, —Br, —OH, —$O(C_{1-3}alkyl)$,

—CN,

—$NO_2$,

—COOH, —$COOR^{C1}$, —$COR^{C2}$, —$CONH_2$, —$CONHR^{D1}$, —$CON(R^{D2})_2$,

—$NH_2$, —$NHR^{D4}$, —$N(R^{D3})_2$, —NHCOOH, —NHCO-$OR^{C1}$, —$NHCOR^{C2}$, —$NR^{D6}COOH$—$NR^{D7}COOR^{C1}$, and —$NR^{D5}COR^{C2}$.

In some embodiments, $R^{B3}$ is selected from $C_{1-4}$ linear or branched unsubstituted alkyl, —F, —Cl, —Br, —OH, —$O(C_{1-3}alkyl)$,

—CN,

—COOH, —$COOR^{C1}$, —$COR^{C2}$, —$CONH_2$, —$CONHR^{D1}$, —$CON(R^{D2})_2$,

—$NH_2$, —$NHR^{D4}$ and —$N(R^{D3})_2$.

In some embodiments, $R^{B3}$ is selected from $C_{1-4}$ linear or branched unsubstituted alkyl, —F, —Cl, —Br, —OH and —$O(C_{1-3}alkyl)$.

In some embodiments, $R^{1L}$ is 5 or 6-membered heteroaryl or heterocyclyl containing 1-3 heteroatoms selected from N, O and S, optionally substituted with one or more groups $R^{B4}$.

In some embodiments, $R^{1L}$ is 5 or 6-membered heteroaryl containing 1-3 heteroatoms selected from N, O and S, optionally substituted with one or more groups $R^{B4}$.

In some embodiments, $R^{1L}$ is 5-membered heteroaryl or heterocyclyl containing 1-3 heteroatoms selected from N, O and S, optionally substituted with one or more groups $R^{B4}$. In some embodiments, $R^{1L}$ is 6-membered heteroaryl or heterocyclyl containing 1-3 heteroatoms selected from N, O and S, optionally substituted with one or more groups $R^{B4}$.

In some embodiments, $R^{1L}$ is 5 or 6-membered unsubstituted heteroaryl or heterocyclyl group containing 1-3 heteroatoms selected from N, O and S.

In some embodiments, $R^{1L}$ is 5 or 6-membered heteroaryl or heterocyclyl containing 1 or 2 heteroatoms selected from N, O and S, optionally substituted with one or more groups $R^{B4}$. In some embodiments, $R^{1L}$ is 5 or 6-membered heteroaryl or heterocyclyl containing 1 heteroatom selected from N, O and S, optionally substituted with one or more groups $R^{B4}$. In some embodiments, $R^{1L}$ is 5 or 6-membered heteroaryl or heterocyclyl containing 1 heteroatom selected from N, optionally substituted with one or more groups $R^{B4}$.

In some embodiments, $R^{1L}$ is a pyridinyl group, optionally substituted with one or more groups $R^{B4}$. In some embodiments, $R^{1L}$ is a pyridinyl group, optionally substituted with one or two groups independently selected from $R^{B4}$.

In some embodiments, $R^{1L}$ unsubstituted pyridinyl.

In some embodiments, $R^{1L}$ unsubstituted piperidinyl.

In some embodiments, $R^{1L}$ is 5-membered heteroaryl containing 1 or 2 heteroatoms selected from N, O and S, optionally substituted with one or more groups $R^{B4}$. In some embodiments, $R^{1L}$ is 5-membered heteroaryl containing 1 or 2 heteroatoms selected from N and O, optionally substituted with one or more groups $R^{B4}$. In some embodiments, $R^{1L}$ is 5-membered unsubstituted heteroaryl containing 1 or 2 heteroatoms selected from N and O.

In some embodiments, $R^{1L}$ is unsubstituted furanyl. In some embodiments, $R^{1L}$ is unsubstituted oxazolyl. In some embodiments, $R^{1L}$ is unsubstituted isoxazolyl.

In some embodiments, $R^{B4}$ is selected from $C_{1-4}$ linear or branched alkyl optionally substituted with one or more groups $R^{A9}$, —F, —Cl, —Br,
—OH, —O($C_{1-3}$alkyl),
—CN,
—$NO_2$,
—COOH, —$COOR^{C1}$, —$COR^{C2}$, —$CONH_2$, —$CONHR^{D1}$, —$CON(R^{D2})_2$,
—$NH_2$, —$NHR^{D4}$, —$N(R^{D3})_2$, —NHCOOH, —$NHCOOR^{C1}$, —$NHCOR^{C2}$, —$NR^{D6}$COOH
—$NR^{D7}COOR^{C1}$, and —$NR^{D5}COR^{C2}$.

In some embodiments, $R^{B4}$ is selected from $C_{1-6}$ linear alkyl optionally substituted with one or more groups $R^{A9}$,
—F, —Cl,
—OH, —O($C_{1-3}$alkyl),
—CN,
—$NO_2$,
—$NH_2$, —$NHR^{D4}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, $R^{B4}$ is selected from

—F, —Cl,
—OH, —O($C_{1-3}$alkyl),
—CN,
—$NO_2$,
—$NH_2$, —$NHR^{D4}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, $R^{B4}$ is selected from

—F, —Cl,
—O($C_{1-3}$alkyl),
—$NO_2$,
—$NH_2$, —$NHR^{D4}$, —$N(R^{D3})_2$, —NHCOOH, —$NHCOOR^{C1}$, —$NHCOR^{C2}$, —$NR^{D6}$COOH—$NR^{D7}COOR^{C1}$, and —$NR^{D5}COR^{C2}$.

In some embodiments, $R^{B4}$ is selected from

—F, —Cl,
—O($C_{1-3}$alkyl),
—$NO_2$,
—$NH_2$, and —$NHCOR^{C2}$.

In some embodiments, $R^{B4}$ is selected from

—F, —Cl, —OMe, —$NO_2$, —$NH_2$ and —NHC(=O)Me.

In some embodiments, $R^{1L}$ is 8 to 10-membered bicyclyl, or heterobicyclyl containing 1-3 heteroatoms selected from N, O and S, optionally substituted with one or more groups $R^{B5}$.

Herein, the term "bicyclyl" indicates a carbocyclic bicyclic ring system in which one, both or neither rings may be aromatic. The bicyclic ring system may be a fused system or a spiro system. Similarly, the term "heterobicyclyl" indicates a bicyclic ring system in which one, both or neither rings may be aromatic and in which the bicyclic system contains 1-3 heteroatoms selected from N, O and S. The heterobicyclic ring system may be a fused system or a spiro system.

In some embodiments, $R^{1L}$ is 8 to 10-membered bicyclyl, optionally substituted with one or more groups $R^{B5}$. In some embodiments, $R^{1L}$ is 8 to 10-membered heterobicyclyl containing 1-3 heteroatoms selected from N, O and S, optionally substituted with one or more groups $R^{B5}$.

In some embodiments, $R^{1L}$ is 9 or 10-membered bicyclyl, optionally substituted with one or more groups $R^{B5}$. In some embodiments, $R^{1L}$ is 8 to 10-membered unsubstituted bicyclyl. In some embodiments, $R^{1L}$ is 10-membered bicyclyl, optionally substituted with one or more groups $R^{B5}$. In some embodiments, $R^{1L}$ is 10-membered unsubstituted bicyclyl. In some embodiments, $R^{1L}$ is naphthyl, optionally substituted with one or more groups $R^{B5}$. In some embodiments, $R^{1L}$ is unsubstituted naphthyl.

In some embodiments, $R^{1L}$ is 9 or 10-membered heterobicyclyl containing 1 or 2 heteroatoms selected from N, O and S, optionally substituted with one or more groups $R^{B5}$. In some embodiments, $R^{1L}$ is 9 or 10-membered heterobicyclyl containing 1 or 2 heteroatoms selected from N and O, optionally substituted with one or more groups $R^{B5}$. In some embodiments, $R^{1L}$ is 9 or 10-membered heterobicyclyl containing 1 or 2 heteroatoms selected O, optionally substituted with one or more groups $R^{B5}$.

In some embodiments, $R^{1L}$ is 8 to 10-membered unsubstituted heterobicyclyl containing 1-3 heteroatoms selected from N, O and S. In some embodiments, $R^{1L}$ is 8 to 10-membered unsubstituted heterobicyclyl containing 1 or 2 heteroatoms selected from N, O and S. In some embodiments, $R^{1L}$ is 8 to 10-membered unsubstituted heterobicyclyl containing 1 or 2 heteroatoms selected from N and O. In some embodiments, $R^{1L}$ is 8 to 10-membered unsubstituted heterobicyclyl containing 1 or 2 heteroatoms selected from O.

In some embodiments, $R^{1L}$ is selected from

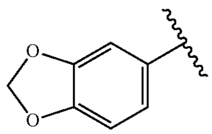
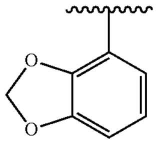
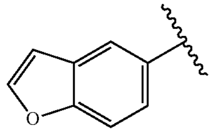
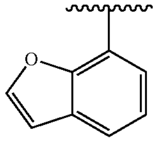
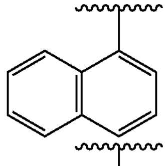
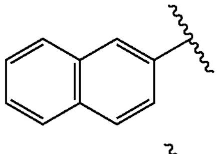
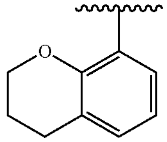
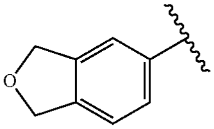
and
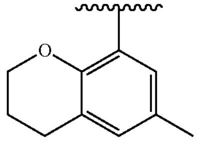
.

In some embodiments, the group —N($R^G$)$_2$ is piperazino, optionally substituted with one or more groups selected from linear or branched $C_{1-4}$alkyl, phenyl or benzyl. In some embodiments, the group —N($R^G$)$_2$ is piperazinyl substituted with one or more groups selected from linear or branched $C_{1-4}$alkyl. In some embodiments, the group —N($R^G$)$_2$ is piperazinyl substituted with one or more groups selected from linear $C_{1-4}$alkyl.

The group Q

In some embodiments, Q is the group (Q1):

(Q1)

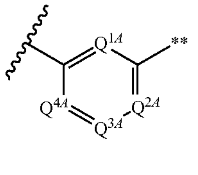

wherein the two asterisks (**) indicate the point of attachment to L;

two of $Q^{1A}$, $Q^{2A}$, $Q^{3A}$ and $Q^{4A}$ are CH; and the other two of $Q^{1A}$, $Q^{2A}$, $Q^{3A}$ and $Q^{4A}$ are independently selected from N, CH and $CR^{Q1}$.

In some embodiments, $Q^{1A}$, $Q^{3A}$ and $Q^{4A}$ are each CH and $Q^{2A}$ is selected from N, CH and $CR^{Q1}$. In some embodiments, $Q^{1A}$, $Q^{3A}$ and $Q^{4A}$ are each CH and $Q^{2A}$ is selected from CH and $CR^{Q1}$.

In some embodiments, $Q^{1A}$, $Q^{2A}$, $Q^{3A}$ and $Q^{4A}$ are each CH.

In some embodiments, one of $Q^{1A}$, $Q^{2A}$, $Q^{3A}$ and $Q^{4A}$ is $CR^{Q1}$ and the other three of $Q^{1A}$, $Q^{2A}$, $Q^{3A}$ and $Q^{4A}$ are each CH.

In some embodiments, $Q^{1A}$ and $Q^{3A}$ are CH, one of $Q^{2A}$ and $Q^{4A}$ is $CR^{Q1}$ and the other of $Q^{2A}$ and $Q^{4A}$ is CH.

In some embodiments, $Q^{2A}$, $Q^{3A}$ and $Q^{4A}$ are each CH and $Q^{1A}$ is $R^{Q1}$. In some embodiments, $Q^{1A}$, $Q^{3A}$ and $Q^{4A}$ are each CH and $Q^{2A}$ is $CR^{Q1}$. In some embodiments, $Q^{1A}$, $Q^{2A}$ and $Q^{4A}$ are each CH and $Q^{3A}$ is $CR^{Q1}$.

In some embodiments, one of $Q^{1A}$, $Q^{2A}$, $Q^{3A}$ and $Q^{4A}$ is CN and the other three of $Q^{1A}$, $Q^{2A}$, $Q^{3A}$ and $Q^{4A}$ are each CH.

In some embodiments, $Q^{2A}$, $Q^{3A}$ and $Q^{4A}$ are each CH and $Q^{1A}$ is CN. In some embodiments, $Q^{1A}$, $Q^{3A}$ and $Q^{4A}$ are each CH and $Q^{2A}$ is CN. In some embodiments, $Q^{1A}$, $Q^{2A}$ and $Q^{4A}$ are each CH and $Q^{3A}$ is CN. In some embodiments, $Q^{2A}$, $Q^{3A}$ and $Q^{4A}$ are each CH and $Q^{1A}$ is CN. In some embodiments, $Q^{1A}$, $Q^{2A}$ and $Q^{3A}$ are each CH and $Q^{4A}$ is CN.

In some embodiments, two of $Q^{1A}$, $Q^{2A}$, $Q^{3A}$ and $Q^{4A}$ are each independently $CR^{Q1}$ and the other two of $Q^{1A}$, $Q^{2A}$, $Q^{3A}$ and $Q^{4A}$ are each CH.

In some embodiments, $Q^{2A}$ and $Q^{4A}$ are each independently $CR^{Q1}$ and $Q^{1A}$ and $Q^{3A}$ are each CH.

In some embodiments, $Q^{1A}$ and $Q^{4A}$ are each independently $CR^{Q1}$ and $Q^{2A}$ and $Q^{3A}$ are each CH.

In some embodiments, two of $Q^{1A}$, $Q^{2A}$, $Q^{3A}$ and $Q^{4A}$ is CN and the other two of $Q^{1A}$, $Q^{2A}$, $Q^{3A}$ and $Q^{4A}$ are each CH.

In some embodiments, $Q^{1A}$ and $Q^{3A}$ are CH, one of $Q^{2A}$ and $Q^{4A}$ is CN and the other of $Q^{2A}$ and $Q^{4A}$ is CH.

In some embodiments, $Q^{2A}$ and $Q^{4A}$ are CH, one of $Q^{1A}$ and $Q^{3A}$ is CN and the other of $Q^{1A}$ and $Q^{3A}$ is CH.

In some embodiments, $Q^{1A}$ and $Q^{3A}$ are CH and each of $Q^{2A}$ and $Q^{4A}$ is independently selected from $CR^{Q1}$.

In some embodiments, $Q^{1A}$ is CN, one of $Q^{2A}$, $Q^{3A}$ and $Q^{4A}$ is CN and the other two of $Q^{2A}$, $Q^{3A}$ and $Q^{4A}$ are each CH.

In some embodiments, $Q^{1A}$ and $Q^{2A}$ are CN, and $Q^{3A}$ and $Q^{4A}$ are each CH.

In some embodiments, $R^{Q1}$ is selected from

—F, —Cl, —Br, —I, $C_{1-6}$ linear unsubstituted alkyl,

—OH, —O($C_{1-6}$alkyl),

—CN, and

—N($R^{D3}$)$_2$.

In some embodiments, $R^{Q1}$ is selected from

—F, —Cl, —Br, —I, $C_{1-3}$ linear unsubstituted alkyl,

—OH, —OMe, —OEt,

—CN, and

—$NMe_2$.

In some embodiments, $R^{Q1}$ is selected from —F, —Cl, —Br and —I. In some embodiments, $R^{Q1}$ is selected from —F, —C and —Br. In some embodiments, $R^{Q1}$ is —F.

In some embodiments, one of $Q^{1A}$, $Q^{2A}$, $Q^{3A}$ and $Q^{4A}$ is C(Hal) and the other three of $Q^{1A}$, $Q^{2A}$, $Q^{3A}$ and $Q^{4A}$ are each CH, wherein Hal is selected from F, Cl, Br and I. In some embodiments, one of $Q^{1A}$, $Q^{2A}$, $Q^{3A}$ and $Q^{4A}$ is CF and the other three of $Q^{1A}$, $Q^{2A}$, $Q^{3A}$ and $Q^{4A}$ are each CH.

In some embodiments, $Q^{1A}$, $Q^{3A}$ and $Q^{4A}$ are each CH and $Q^{2A}$ is CF.

In some embodiments, two of $Q^{1A}$, $Q^{2A}$, $Q^{3A}$ and $Q^{4A}$ are each independently C(Hal) and the other two of $Q^{1A}$, $Q^{2A}$, $Q^{3A}$ and $Q^{4A}$ are each CH, wherein Hal is selected from F, Cl, Br and I. In some embodiments, two of $Q^{1A}$, $Q^{2A}$, $Q^{3A}$ and $Q^{4A}$ are each CF and the other two of $Q^{1A}$, $Q^{2A}$, $Q^{3A}$ and $Q^{4A}$ are each CH.

In some embodiments, Q is selected from

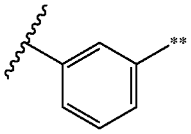

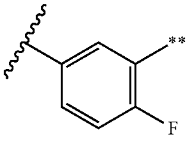

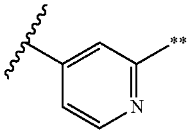

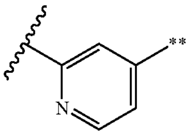

and

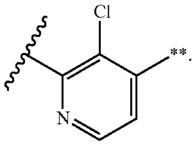

In some embodiments, Q is the group (Q2):

(Q2)

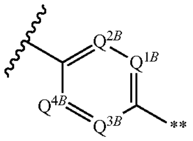

wherein the two asterisks (**) indicate the point of attachment to L;

two of $Q^{1B}$, $Q^{2B}$, $Q^{3B}$ and $Q^{4B}$ are CH; and the other two of $Q^{1B}$, $Q^{2B}$, $Q^{3B}$ and $Q^{4B}$ are independently selected from N, CH and $CR^{Q2}$.

In some embodiments, $Q^{1B}$, $Q^{2B}$, $Q^{3B}$ and $Q^{4B}$ are each CH.

In some embodiments, Q is selected from (Q1) and (Q2), wherein the two asterisks (**) indicate the point of attachment to L; two of $Q^{1A}$, $Q^{2A}$, $Q^{3A}$ and $Q^{4A}$ are CH; the other two of $Q^{1A}$, $Q^{2A}$, $Q^{3A}$ and $Q^{4A}$ are independently selected from N, CH and $CR^{Q1}$; and each of $Q^{1B}$, $Q^{2B}$, $Q^{3B}$ and $Q^{4B}$ are CH.

Compounds of Formula IA

In some embodiments, the compound is a compound according to Formula IA:

Formula (IA)

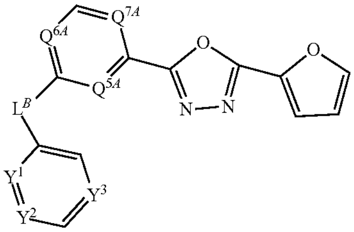

or a pharmaceutically acceptable salt, solvate or hydrate thereof, wherein $L^B$ is selected from

—$NR^{L1}C(=O)$—*, —$C(=O)NR^{L1}$—*

—$NR^{L1}C(=X^{L1})NR^{L1}$—*

—$SO_2$—$NR^{L1}$—*, —$NR^{L1}$—$SO_2$—*,

—OC(=O)—$NR^{L1}$—*, and —$NR^{L1}$—C(=O)O—*;

wherein the asterisk (*) indicates the point of attachment to the terminal phenyl group;

$X^{L1}$ is selected from O and S;

$R^{L1}$ is selected from

—H,

—$C(=O)(C_{1-3}alkyl)$,

—$P(=O)(OH)_2$ and

—$S(=O)_2NH_2$;

one of $Y^1$, $Y^2$ and $Y^3$ is $CR^Y$;

a second of $Y^1$, $Y^2$ and $Y^3$ is independently selected from $CR^Y$ and CH; and a third of $Y^1$, $Y^2$ and $Y^3$ is independently selected from $CR^Y$ and CH;

one of $Q^{5A}$, $Q^{6A}$ and $Q^{7A}$ is selected from N and CH; and the other two of $Q^{5A}$, $Q^{6A}$ and $Q^{7A}$ are each independently selected from CH and $CR^{Q3}$;

wherein each $R^Y$ is independently selected from linear or branched unsubstituted $C_{1-6}$ alkyl,

—$OR^{Y1}$;

—F, —Cl, —Br, —I,

—$CF_3$, —$CH_2F$, —$CF_2H$,

—$(CH_2)_nN(R^{N1})_2$,

—$CH_2CF_3$, —$CH_2CH_2F$ and —$CH_2CF_2H$;

wherein, in the group —$N(R^{N1})_2$, the N atom and the two $R^{N1}$ groups to which it is attached form a 6-membered heterocyclic group containing one or two heteroatoms each independently selected from N, O and S;

n is an integer selected from 1, 2 or 3;

wherein $R^{Y1}$ is selected from linear or branched unsubstituted $C_{1-6}$ alkyl,

—$CF_3$, —$CH_2F$, —$CF_2H$,

—$(CH_2)_mN(R^{N2})_2$,

—$CH_2CF_3$, —$CH_2CH_2F$ and —$CH_2CF_2H$;

wherein, in the group —$N(R^{N2})_2$, the N atom and the two $R^{N2}$ groups to which it is attached form a 6-membered heterocyclic group containing one or two heteroatoms each independently selected from N, O and S;

m is an integer selected from 1, 2 and 3;

$R^{Q3}$ is selected from

—F, —Cl, —Br, —I, $C_{1-6}$ linear or branched unsubstituted alkyl,

—OH, —$O(C_{1-6}alkyl)$, and

—CN.

In some embodiments:

$R^{L1}$ is selected from —H and —$C(=O)(C_{1-3}alkyl)$;

each $R^Y$ is independently selected from linear or branched unsubstituted $C_{1-6}$ alkyl,

—$OR^{Y1}$;

—F, —Cl, —Br, —I,

—$CF_3$, —$CH_2F$, —$CF_2H$,

—$CH_2CF_3$, —$CH_2CH_2F$ and —$CH_2CF_2H$; and $R^{Y1}$ is selected from linear or branched unsubstituted $C_{1-6}$ alkyl,

—$CF_3$, —$CH_2F$, —$CF_2H$,

—$CH_2CF_3$, —$CH_2CH_2F$ and —$CH_2CF_2H$.

The Group $L^B$

In some embodiments, $L^B$ is selected from —$NR^{L1}C(=O)$—* and —$C(=O)NR^{L1}$—*, wherein the asterisk (*) indicates the point of attachment to the terminal phenyl group.

In some embodiments, $L^B$ is —$NR^{L1}C(=O)$—*, wherein the asterisk (*) indicates the point of attachment to the terminal phenyl group.

In some embodiments, $R^{L1}$ is —H. In some embodiments, $R^{L1}$ is —$C(=O)(C_{1-3}alkyl)$. In some embodiments, $R^{L1}$ is —C(=O)Me.

In some embodiments, $L^B$ is —NHC(=O)—*, wherein the asterisk (*) indicates the point of attachment to the terminal phenyl group.

In some embodiments, $L^B$ is —NHC(=O)—* or —C(=O)NH—*. In some embodiments, $L^B$ is —NHC(=O)—*.

In some embodiments, $L^B$ is —$NR^LC(=O)$—*, wherein $R^L$ is —$P(=O)(OH)_2$. In some embodiments, $L^B$ is —$NR^LC(=O)$—*, wherein $R^L$ is —$S(=O)_2NH_2$.

In some embodiments, $L^B$ is —$NR^{L1}C(=X^{L1})NR^L$—*. In some embodiments, $L^B$ is —$SO_2$—$NR^{L1}$—*. In some embodiments, $L^B$ is —$NR^L$—S—$O_2$—*. In some embodiments, $L^B$ is —OC(=O)—$NR^{L1}$—*. In some embodiments, $L^A$ is —$NR^{L1}$—C(=O)O—*.

In some embodiments, $X^{L1}$ is O. In some embodiments, $X^{L1}$ is S.

The Groups $Y^1$, $Y^2$ and $Y^3$

One of $Y^1$, $Y^2$ and $Y^3$ is $CR^Y$; a second of $Y^1$, $Y^2$ and $Y^3$ is independently selected from $CR^Y$ and CH; and a third of $Y^1$, $Y^2$ and $Y^3$ is independently selected from $CR^Y$ and CH.

In some embodiments, one of $Y^1$, $Y^2$ and $Y^3$ is $CR^Y$; a second of $Y^1$, $Y^2$ and $Y^3$ is selected from $CR^Y$ and CH; and a third of $Y^1$, $Y^2$ and $Y^3$ is CH.

In some embodiments, $Y^1$ is $CR^Y$ and each of $Y^2$ and $Y^3$ are selected from CH and $CR^Y$.

In some embodiments, $Y^1$ is $CR^Y$ and $Y^2$ and $Y^3$ are both CH.

In some embodiments, $Y^1$ is $CR^Y$, one of $Y^2$ and $Y^3$ is CH and the other is $CR^Y$.

In some embodiments, $Y^1$ is $CR^Y$, $Y^2$ is CH and $Y^3$ is $CR^Y$.

In some embodiments, each of $Y^1$, $Y^2$ and $Y^3$ is $CR^Y$.

In some embodiments, $R^Y$ is independently selected from linear or branched unsubstituted $C_{1-6}$ alkyl, such as methyl, ethyl or n-propyl.

In some embodiments, $R^Y$ is independently selected from —$OR^{Y1}$, such as —OMe, —OEt, —$O^nPr$, —$OCF_3$, —$OCH_2F$, —$OCF_2H$, —$OCH_2CF_3$, —$OCH_2CH_2F$ or —$OCH_2CF_2H$.

In some embodiments, $R^Y$ is independently selected from —F, —Cl, —Br and —I. In some embodiments, $R^Y$ is independently selected from —F.

In some embodiments, $R^Y$ is independently selected from —$CF_3$, —$CH_2F$, —$CF_2H$,
—$CH_2CF_3$, —$CH_2CH_2F$ and —$CH_2CF_2H$.

In some embodiments, $R^Y$ is —$CF_3$.

In some embodiments, $R^Y$ is —$(CH_2)_nN(R^{N1})_2$. In some embodiments, n is 3. In some embodiments, the group —$N(R^{N1})_2$ is a 6-membered heterocyclic group selected from morpholino and piperidinyl. In some embodiments, n is 3 and the group —$N(R^{N1})_2$ is a 6-membered heterocyclic group selected from morpholino and piperidinyl.

In some embodiments, $R^{Y1}$ is methyl. In some embodiments, $R^{Y1}$ is ethyl. In some embodiments, $R^{Y1}$ is n-propyl. In some embodiments, $R^{Y1}$ is —$CF_3$. In some embodiments, $R^{Y1}$ is —$CF_2H$. In some embodiments, $R^{Y1}$ is —$CFH_2$. In some embodiments, $R^{Y1}$ is —$CH_2CF_2H$. In some embodiments, $R^{Y1}$ is —$CH_2CFH_2$.

In some embodiments, $R^{Y1}$ is —$(CH_2)_mN(R^{N2})_2$. In some embodiments, m is 2. In some embodiments, the group —$N(R^{N2})_2$ is a 6-membered heterocyclic group selected from morpholino and piperidinyl. In some embodiments, m is 2 and the group —$N(R^{N2})_2$ is a 6-membered heterocyclic group selected from morpholino and piperidinyl.

The Groups $Q^{5A}$, $Q^{6A}$ and $Q^{7A}$

One of $Q^{5A}$, $Q^{6A}$ and $Q^{7A}$ is selected from N and CH; and the other two of $Q^{5A}$, $Q^{6A}$ and $Q^{7A}$ are each independently selected from CH and $CR^{Q3}$.

In some embodiments, $Q^{5A}$, $Q^{6A}$ and $Q^{7A}$ are each CH. In some embodiments, one of $Q^{5A}$ and $Q^{6A}$ is $CR^{Q3}$, the other is CH and $Q^{7A}$ is CH. In some embodiments, one of $Q^{6A}$ and $Q^{7A}$ is N, the other is CH and $Q^{5A}$ is CH.

In some embodiments, $Q^{6A}$ is $CR^{Q3}$ and each of $Q^{5A}$ and $Q^{7A}$ are CH.

In some embodiments, $R^{Q3}$ is selected from —F, —Cl, —Br and —I. In some embodiments, $R^{Q3}$ is —F. In some embodiments, $Q^{6A}$ is CF and each of $Q^{5A}$ and $Q^{7A}$ are CH.

In some embodiments, $L^B$ is —NHC(═O)—*, wherein the asterisk (*) indicates the point of attachment to the terminal phenyl group; $Y^2$ is CH; one of $Y^1$ and $Y^3$ is $CR^Y$; a second of $Y^1$ and $Y^3$ is selected from $CR^Y$ and CH; $Q^{5A}$ and $Q^{7A}$ are each CH; and $Q^{6A}$ is selected from N, CH and $CR^{Q3}$;

wherein each $R^Y$ is independently selected from
- linear or branched unsubstituted $C_{1-6}$ alkyl,
- —$OR^{Y1}$;
- —F, —Cl, —Br, —I,
- —$CF_3$, —$CH_2F$, —$CF_2H$,
- —$CH_2CF_3$, —$CH_2CH_2F$ and —$CH_2CF_2H$;

$R^{Y1}$ is selected from
- linear or branched unsubstituted $C_{1-6}$ alkyl,
- —$CF_3$, —$CH_2F$, —$CF_2H$,
- —$CH_2CF_3$, —$CH_2CH_2F$ and —$CH_2CF_2H$;

and $R^{Q3}$ is selected from
- —F, —Cl, —Br, —I,
- $C_{1-6}$ linear or branched unsubstituted alkyl,
- —OH, —O($C_{1-6}$alkyl), and
- —CN.

Compounds of Formula (IB)

In some embodiments, the compound is a compound according to Formula IB:

Formula (IB)

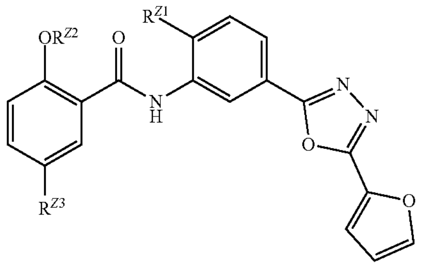

wherein $R^{Z1}$ is selected from
- —H,
- —F, —Cl, —Br and —I;

and $R^{Z3}$ is selected from
- —H,
- $C_{1-6}$ linear alkyl, optionally substituted with one, two or three substituents each independently selected from —F, —Cl, and —Br,
- —F, —Cl, —Br, —I, and
- —$OR^{Z5}$;

wherein $R^{Z2}$ and $R^{Z5}$ are each independently selected from $C_{1-6}$ linear alkyl, optionally substituted with one, two or three substituents each independently selected from —F, —Cl, and —Br.

The Group $R^{Z1}$

In some embodiments, $R^{Z1}$ is selected from —F, —Cl and —Br. In some embodiments, $R^{Z1}$ is selected from —F and —Cl. In some embodiments, $R^{Z1}$ is —F.

The Group $R^{Z2}$

In some embodiments, $R^{Z2}$ is selected from $C_{1-6}$ linear unsubstituted alkyl. In some embodiments, $R^{Z2}$ is selected from $C_{1-4}$ linear unsubstituted alkyl. In some embodiments, $R^{Z2}$ is selected from methyl, ethyl or n-propyl.

In some embodiments, $R^{Z2}$ is selected from $C_{1-6}$ linear alkyl, substituted with one, two or three substituents each independently selected from —F, —Cl, and —Br. In some embodiments, $R^{Z2}$ is selected from $C_{1-4}$ linear alkyl, substituted with one, two or three substituents each independently selected from —F, —Cl, and —Br. In some embodiments, $R^{Z2}$ is selected from methyl or ethyl, substituted with one, two or three substituents each independently selected from —F, —Cl, and —Br.

In some embodiments, $R^{Z2}$ is selected from methyl or ethyl, substituted with one, two or three —F substituents.

In some embodiments, $R^{Z2}$ is selected from
—$CH_2CHF_2$, —$CH_2CH_2F$, —$CH_2CF_3$,
—$CHF_2$, —$CH_2F$ and —$CF_3$.

The Group $R^{Z3}$

In some embodiments, $R^{Z3}$ is —H. In some embodiments, $R^{Z3}$ is $C_{1-6}$ linear unsubstituted alkyl. In some embodiments, $R^{Z3}$ is $C_{1-4}$ linear unsubstituted alkyl. In some embodiments, $R^{Z3}$ is selected from methyl, ethyl or n-propyl.

In some embodiments, $R^{Z3}$ is selected from $C_{1-6}$ linear alkyl, substituted with one, two or three substituents each independently selected from —F, —Cl, and —Br. In some embodiments, $R^{Z3}$ is selected from $C_{1-6}$ linear alkyl, substituted with one, two or three F substituents. In some embodiments, $R^{Z3}$ is selected from $C_{1-3}$ linear alkyl, substituted with one, two or three substituents each independently selected from —F, —Cl, and —Br. In some embodiments, $R^{Z3}$ is selected from $C_{1-3}$ linear alkyl, substituted with one, two or three F substituents. In some embodiments, $R^{Z3}$ is selected from $C_{1-3}$ linear alkyl, substituted with three F substituents. In some embodiments, $R^{Z3}$ is —$CF_3$.

In some embodiments, $R^{Z3}$ is selected from —F, —Cl, —Br and —I. In some embodiments, $R^{Z3}$ is selected from —F, —Cl and —Br.

In some embodiments, $R^{Z3}$ is —$OR^{Z5}$—.

The Group $R^{Z5}$

In some embodiments, $R^{Z5}$ is selected from $C_{1-6}$ linear alkyl, substituted with one, two or three substituents each independently selected from —F, —Cl, and —Br. In some embodiments, $R^{Z5}$ is selected from $C_{1-4}$ linear alkyl, substituted with one, two or three substituents each independently selected from —F, —Cl, and —Br. In some embodiments, $R^{Z5}$ is selected from methyl or ethyl, substituted with one, two or three substituents each independently selected from —F, —Cl, and —Br.

In some embodiments, $R^{Z5}$ is selected from methyl or ethyl, substituted with one, two or three —F substituents. In some embodiments, $R^{Z5}$ is methyl, substituted with one, two or three —F substituents. In some embodiments, $R^{Z5}$ is —$CF_3$.

In some embodiments, $R^{Z1}$ is selected from —H and —F;

$R^{Z3}$ is selected from —H, -Me, -Et, —$^{n}$Pr, —F, —Cl, —Br and —$OR^{Z5}$; and $R^{Z2}$ and $R^{Z5}$ are each independently selected from $C_{1-6}$ linear alkyl, optionally substituted with one, two or three —F substituents.

In some embodiments, $R^{Z1}$ is —F;

$R^{Z3}$ is selected from -Me, -Et, —$^{n}$Pr, —F, —Cl, —Br and —$OR^{Z5}$; and $R^{Z2}$ and $R^{Z5}$ are each independently selected from $C_{1-6}$ linear alkyl, optionally substituted with one, two or three —F substituents.

In some embodiments, $R^{Z1}$ is —F;

$R^{Z3}$ is selected from -Me, -Et, —$^{n}$ Pr, —F, —Cl, —Br and —$OR^{Z5}$; and $R^{Z2}$ and $R^{Z5}$ are each independently selected from $C_{1-6}$ linear unsubstituted alkyl.

In some embodiments, $R^{Z1}$ is —F;

$R^{Z3}$ is selected from -Me, -Et, —$^{n}$ Pr, —F, —Cl, —Br and —$OR^{Z5}$; and $R^{Z2}$ and $R^{Z5}$ are each independently selected from $C_{1-3}$ linear unsubstituted alkyl.

It is believed that the following compounds (X1) to (X27) are known:

(X1)

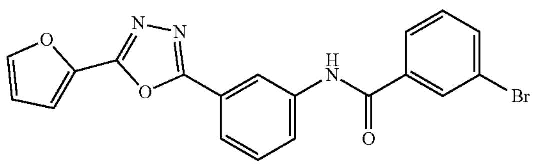

(X2)

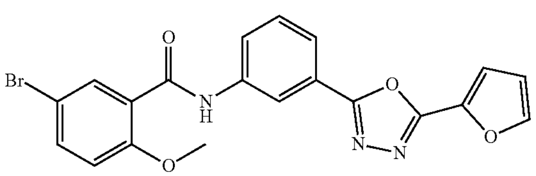

-continued (X3)

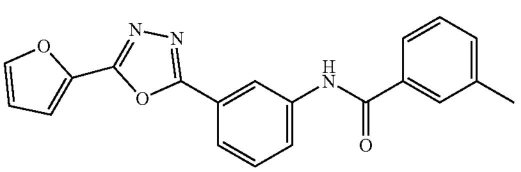

(X4)

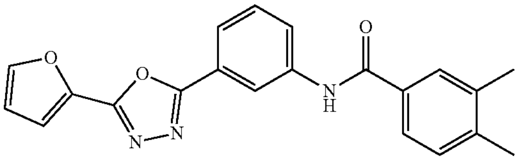

(X5)

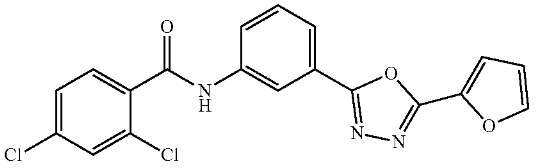

(X6)

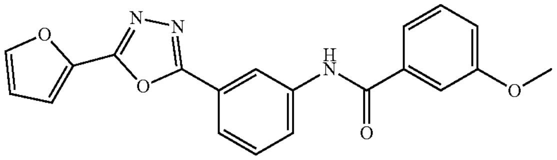

(X7)

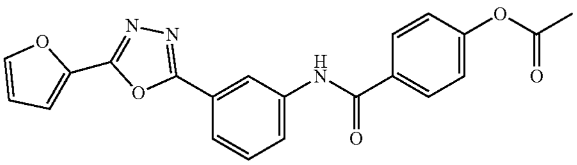

(X8)

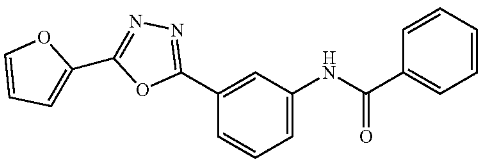

(X9)

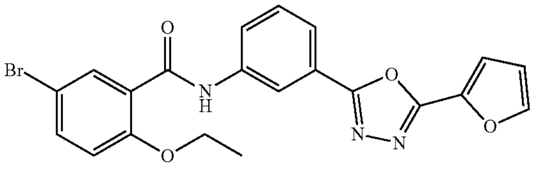

(X10)

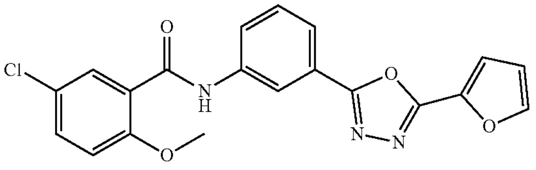

-continued
(X11)
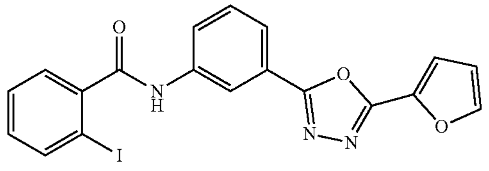
(X12)
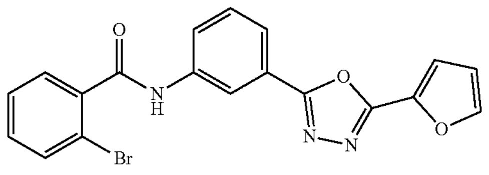
(X13)
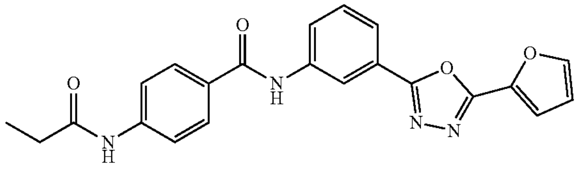
(X14)
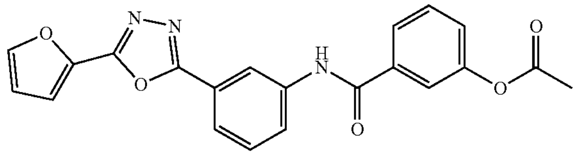
(X15)
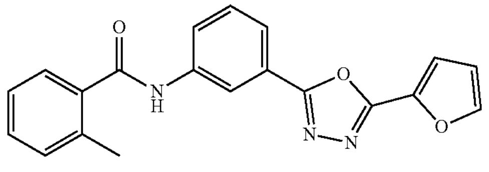
(X16)
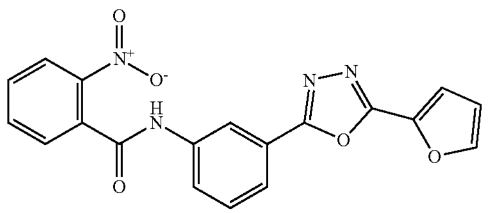
(X17)
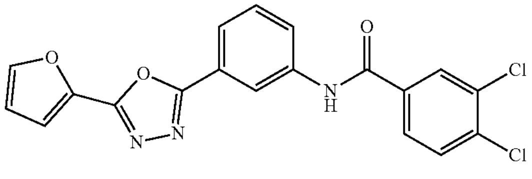
-continued
(X18)
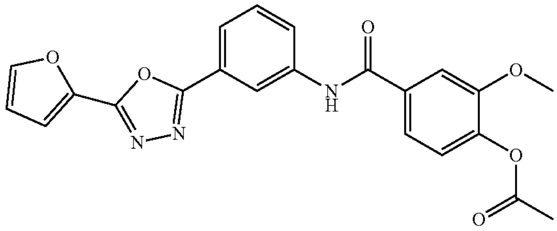
(X19)
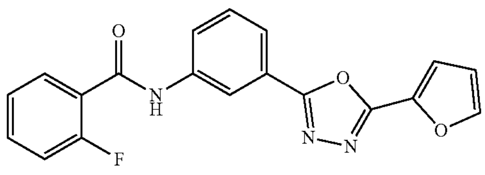
(X20)
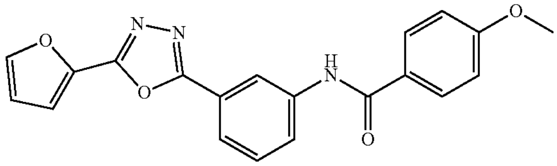
(X21)
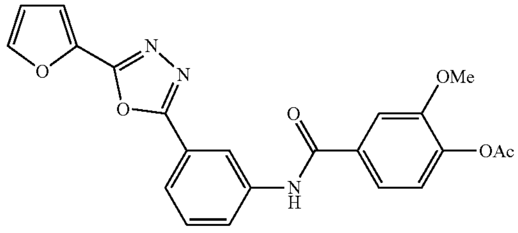
(X22)
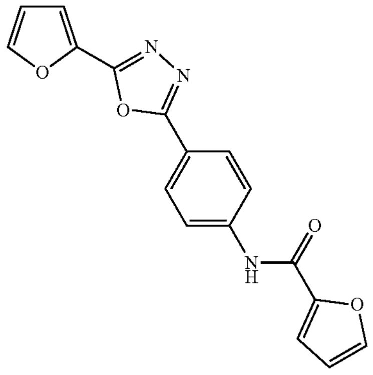
(X23)
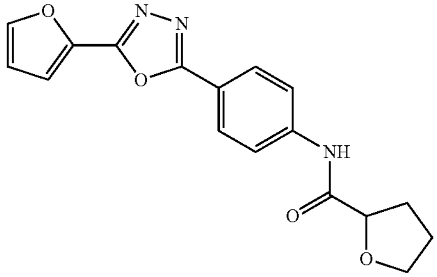

-continued (X24)

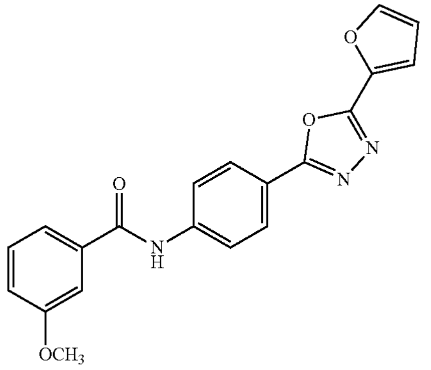

(X25)

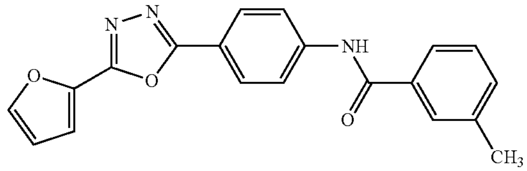

(X26)

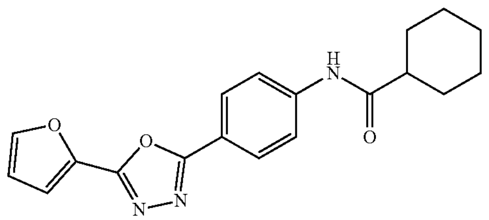

(X27)

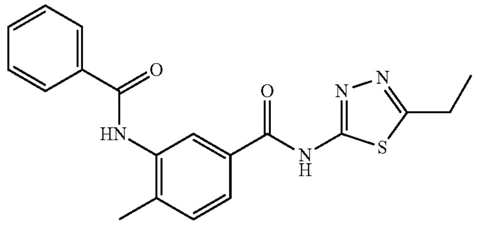

Therefore, compounds according to the first aspect are not selected from any of the compounds (X1) to (X27).

Nevertheless, in other aspects described herein the compounds may be selected from a compound (X1) to (X27). In particular, in some embodiments compounds for use in treatment of diseases as described herein may be selected from a compound selected from (X1) to (X27). Similarly, in some embodiments methods of treatment of diseases as described herein may involve the use of a compound selected from (X1) to (X27).

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by the variables (e.g., X, $G^1$, $G^2$, A, $R^{A1}$-$R^{A10}$, $R^{B1}$-$R^{B5}$, $R^{C1}$, $R^{C2}$, $R^{D1}$-$R^{D9}$, $R^{E1}$-$R^{E4}$, $R^F$, $R^T$, Q, $Q^{1A}$-$Q^{4A}$, $Q^{1B}$-$Q^{4B}$, L, $L^A$, $R^1$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested for biological activity). In addition, all sub-combinations of the chemical groups listed in the embodiments describing such variables are also specifically embraced by the present invention and are disclosed herein just as if each and every such sub-combination of chemical groups was individually and explicitly disclosed herein.

SPECIFIC EMBODIMENTS

In some embodiments, the compound is selected from a compound in Table 1:

TABLE 1

| Compound Number | Structure |
|---|---|
| 1 | 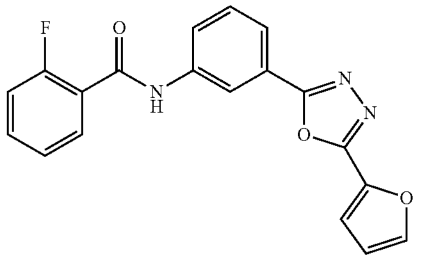 |

TABLE 1-continued
| Compound Number | Structure |
| --- | --- |
| 2 | 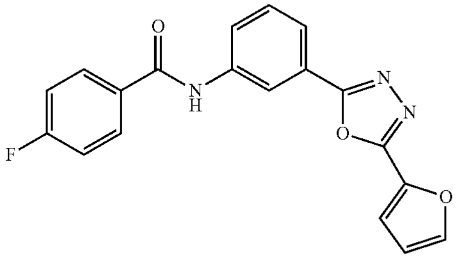 |
| 3 | 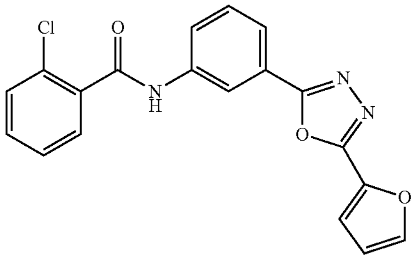 |
| 4 | 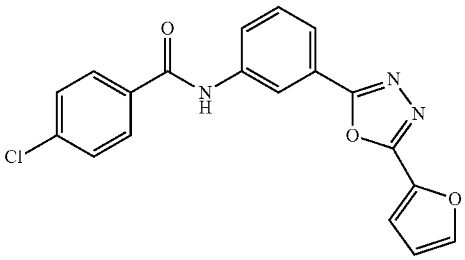 [SMILES: O=C(Nc1cccc(-c2nnc(-c3ccco3)o2)c1)c1ccc(Cl)cc1] |
| 5 | 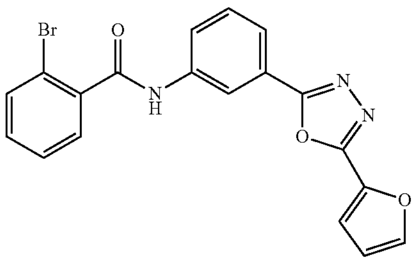 [SMILES: O=C(Nc1cccc(-c2nnc(-c3ccco3)o2)c1)c1ccccc1Br] |
| 6 | 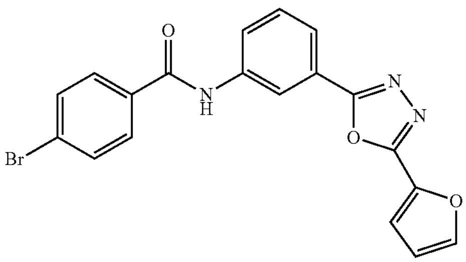 |
| 7 | 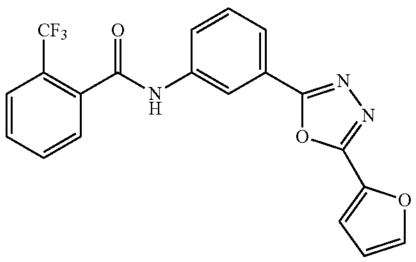 |

TABLE 1-continued
| Compound Number | Structure |
|---|---|
| 8 | 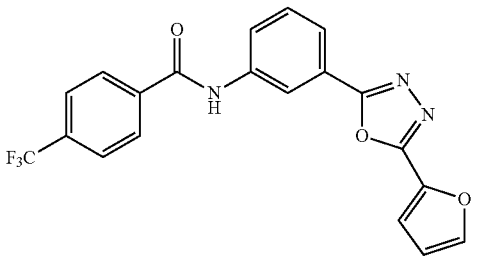 [SMILES: O=C(Nc1cccc(-c2nnc(-c3ccco3)o2)c1)c1ccc(C(F)(F)F)cc1] |
| 9 | 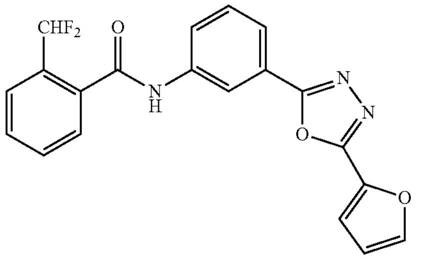 |
| 10 | 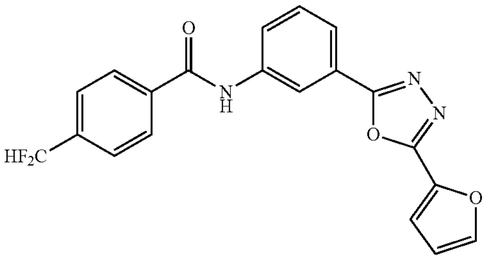 |
| 11 | 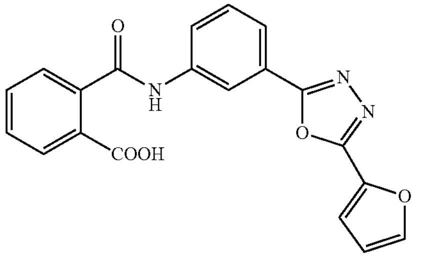 [SMILES: O=C(O)c1ccccc1C(=O)Nc1cccc(-c2nnc(-c3ccco3)o2)c1] |
| 12 | 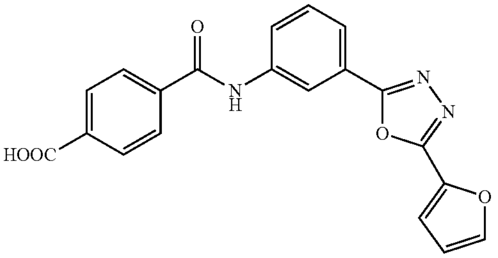 |

TABLE 1-continued
| Compound Number | Structure |
|---|---|
| 13 | 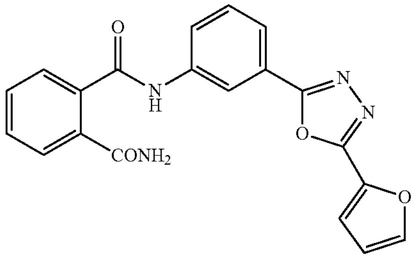 [SMILES: NC(=O)c1ccccc1C(=O)Nc1cccc(-c2nnc(-c3ccco3)o2)c1] |
| 14 | 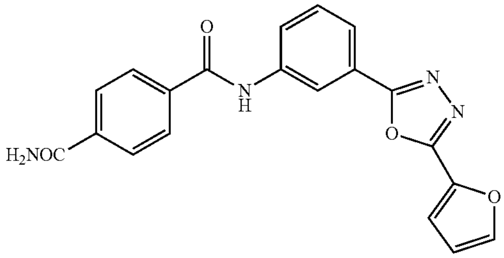 [SMILES: NC(=O)c1ccc(C(=O)Nc2cccc(-c3nnc(-c4ccco4)o3)c2)cc1] |
| 15 | 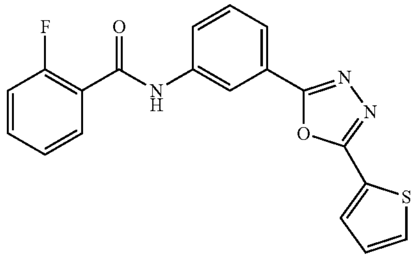 |
| 16 | 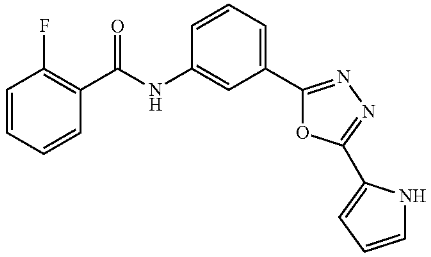 [SMILES: O=C(Nc1cccc(-c2nnc(-c3ccc[nH]3)o2)c1)c1ccccc1F] |
| 17 | 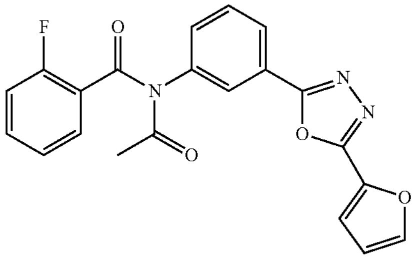 [SMILES: CC(=O)N(C(=O)c1ccccc1F)c1cccc(-c2nnc(-c3ccco3)o2)c1] |

TABLE 1-continued
| Compound Number | Structure |
| --- | --- |
| 18 | 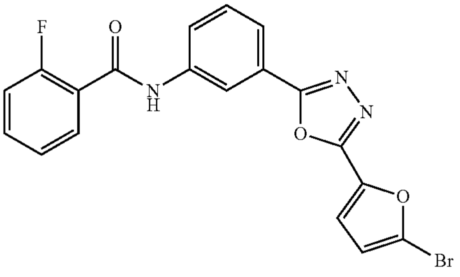 [SMILES: O=C(Nc1cccc(-c2nnc(-c3ccc(Br)o3)o2)c1)c1ccccc1F] |
| 19 | 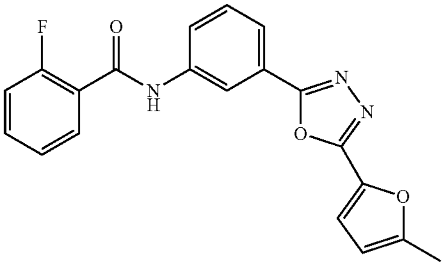 [SMILES: Cc1ccc(-c2nnc(-c3cccc(NC(=O)c4ccccc4F)c3)o2)o1] |
| 20 | 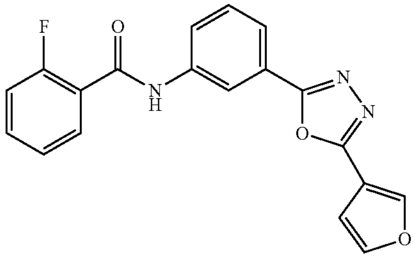 |
| 21 | 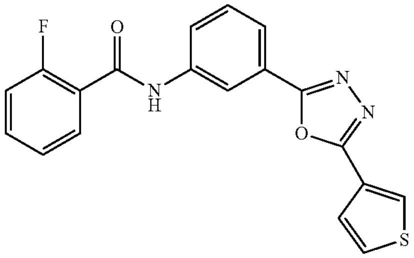 [SMILES: O=C(Nc1cccc(-c2nnc(-c3ccoc3)o2)c1)c1ccccc1F] |
| 22 | 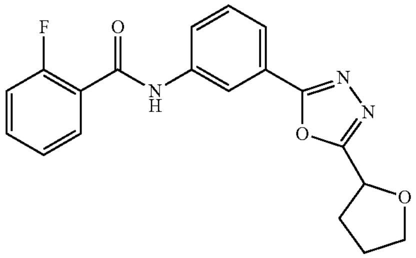 [SMILES: O=C(Nc1cccc(-c2nnc(C3CCCO3)o2)c1)c1ccccc1F] |

TABLE 1-continued
| Compound Number | Structure |
|---|---|
| 23 | 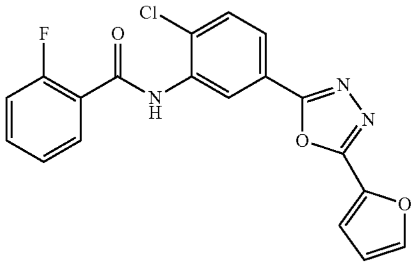 |
| 24 | 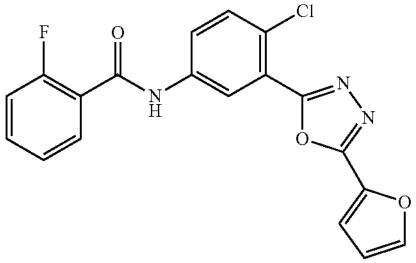 [SMILES: O=C(Nc1ccc(Cl)c(-c2nnc(-c3ccco3)o2)c1)c1ccccc1F] |
| 25 | 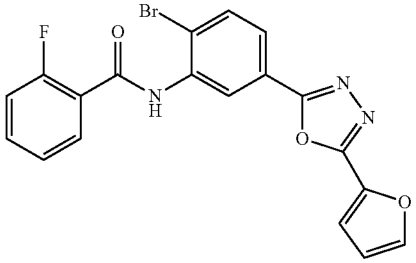 [SMILES: O=C(Nc1cc(-c2nnc(-c3ccco3)o2)ccc1Br)c1ccccc1F] |
| 26 | 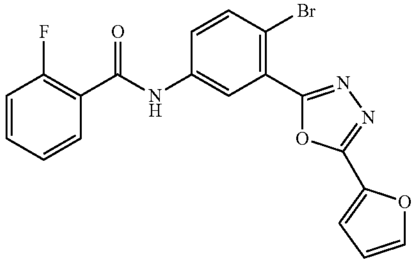 [SMILES: O=C(Nc1ccc(Br)c(-c2nnc(-c3ccco3)o2)c1)c1ccccc1F] |
| 27 | 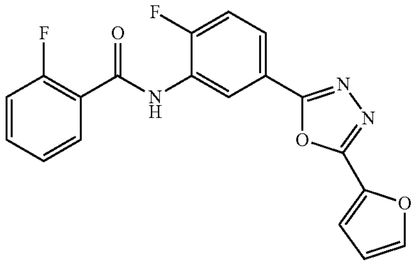 |

TABLE 1-continued
| Compound Number | Structure |
|---|---|
| 28 | 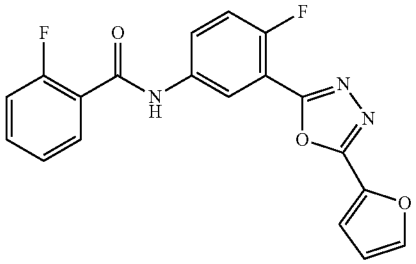 [SMILES: O=C(Nc1ccc(F)c(-c2nnc(-c3ccco3)o2)c1)c1ccccc1F] |
| 29 | 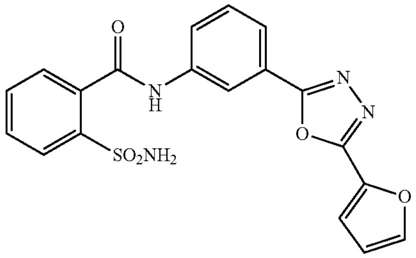 [SMILES: NS(=O)(=O)c1ccccc1C(=O)Nc1cccc(-c2nnc(-c3ccco3)o2)c1] |
| 30 | 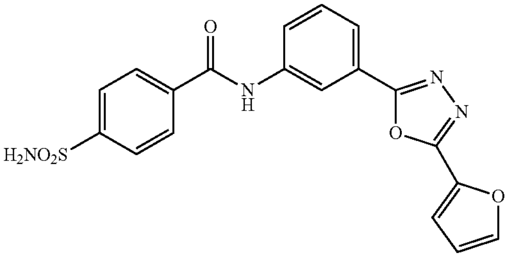 [SMILES: NS(=O)(=O)c1ccc(C(=O)Nc2cccc(-c3nnc(-c4ccco4)o3)c2)cc1] |
| 31 | 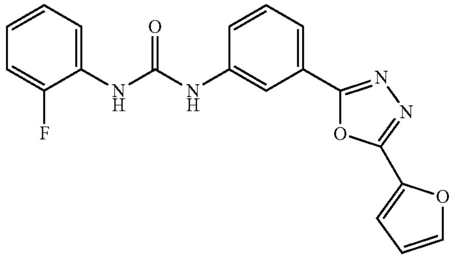 [SMILES: O=C(Nc1cccc(-c2nnc(-c3ccco3)o2)c1)Nc1ccccc1F] |
| 32 | 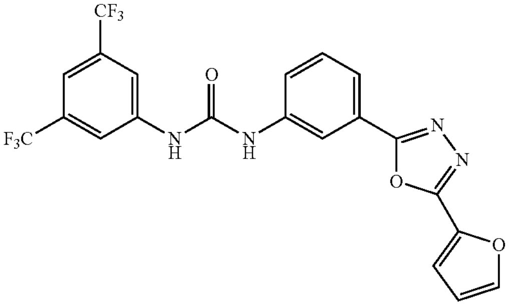 [SMILES: O=C(Nc1cccc(-c2nnc(-c3ccco3)o2)c1)Nc1cc(C(F)(F)F)cc(C(F)(F)F)c1] |
| 33 | 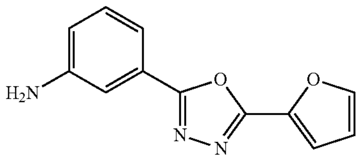 [SMILES: Nc1cccc(-c2nnc(-c3ccco3)o2)c1] |

TABLE 1-continued
| Compound Number | Structure |
|---|---|
| 34 | 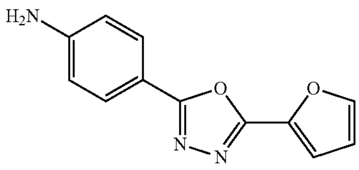 [SMILES: Nc1ccc(-c2nnc(-c3ccco3)o2)cc1] |
| 35 | 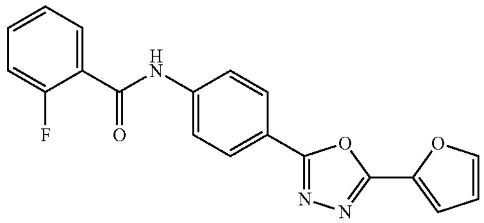 [SMILES: O=C(Nc1ccc(-c2nnc(-c3ccco3)o2)cc1)c1ccccc1F] |
| 36 | 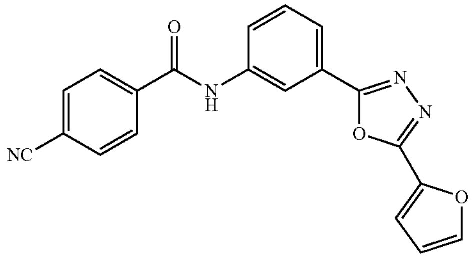 [SMILES: N#Cc1ccc(C(=O)Nc2cccc(-c3nnc(-c4ccco4)o3)c2)cc1] |
| 37 | 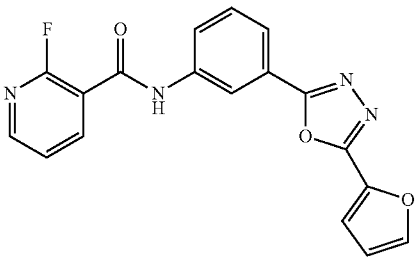 [SMILES: O=C(Nc1cccc(-c2nnc(-c3ccco3)o2)c1)c1cccnc1F] |
| 38 | 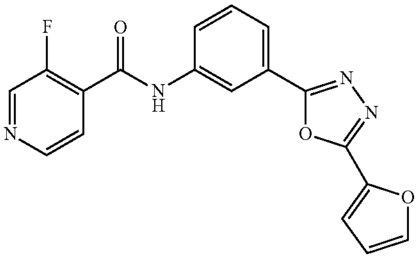 [SMILES: O=C(Nc1cccc(-c2nnc(-c3ccco3)o2)c1)c1ccncc1F] |
| 39 | 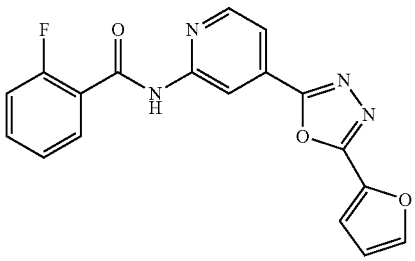 |

TABLE 1-continued
| Compound Number | Structure |
|---|---|
| 40 | 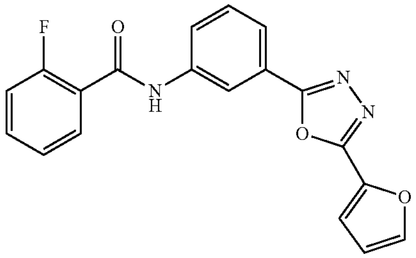 |
| 41 | 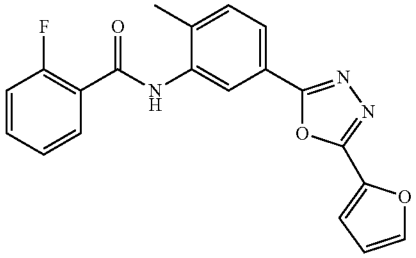 [SMILES: Cc1ccc(-c2nnc(-c3ccco3)o2)cc1NC(=O)c1ccccc1F] |
| 42 | 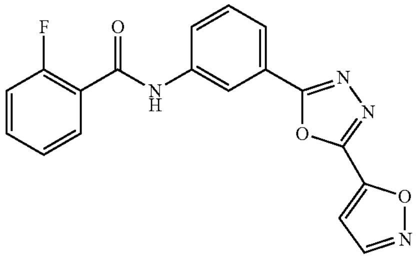 [SMILES: O=C(Nc1cccc(-c2nnc(-c3ccno3)o2)c1)c1ccccc1F] |
| 43 | 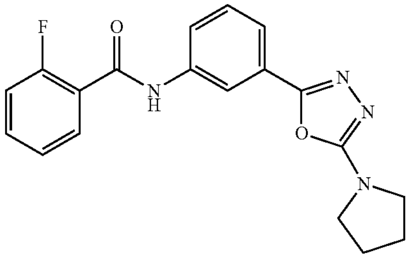 [SMILES: O=C(Nc1cccc(-c2nnc(N3CCCC3)o2)c1)c1ccccc1F] |
| 44 | 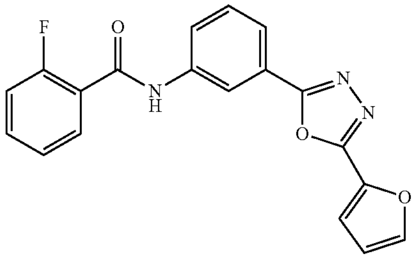 |
| 45 | 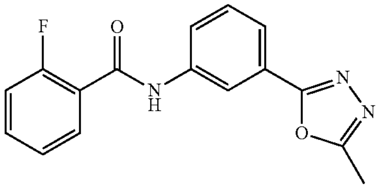 [SMILES: Cc1nnc(-c2cccc(NC(=O)c3ccccc3F)c2)o1] |

TABLE 1-continued
| Compound Number | Structure |
|---|---|
| 46 | 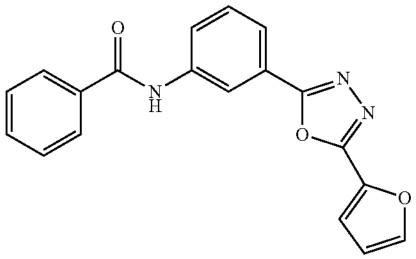 [SMILES: O=C(Nc1cccc(-c2nnc(-c3ccco3)o2)c1)c1ccccc1] |
| 47 | 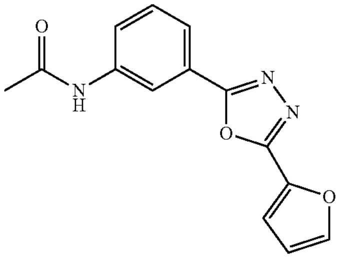 [SMILES: CC(=O)Nc1cccc(-c2nnc(-c3ccco3)o2)c1] |
| 48 | 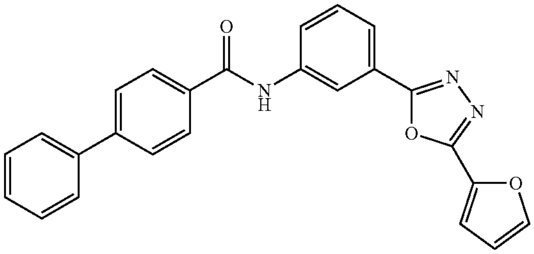 [SMILES: O=C(Nc1cccc(-c2nnc(-c3ccco3)o2)c1)c1ccc(-c2ccccc2)cc1] |
| 49 | 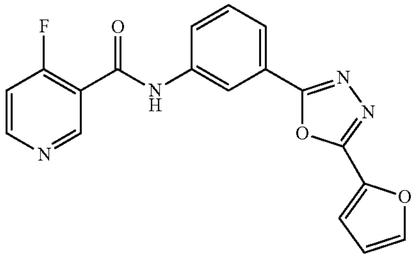 [SMILES: O=C(Nc1cccc(-c2nnc(-c3ccco3)o2)c1)c1cnccc1F] |
| 50 | 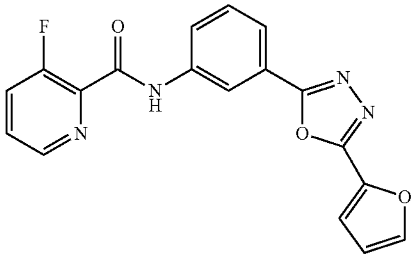 [SMILES: O=C(Nc1cccc(-c2nnc(-c3ccco3)o2)c1)c1ncccc1F] |

TABLE 1-continued
| Compound Number | Structure |
|---|---|
| 51 | 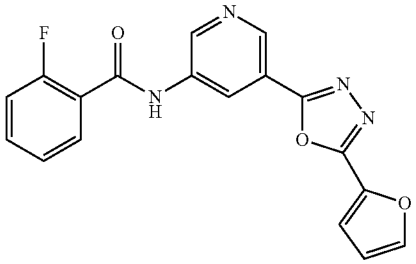 [SMILES: O=C(Nc1cncc(-c2nnc(-c3ccco3)o2)c1)c1ccccc1F] |
| 52 | 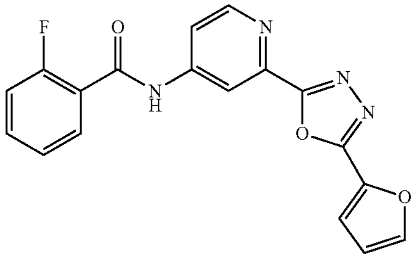 [SMILES: O=C(Nc1ccnc(-c2nnc(-c3ccco3)o2)c1)c1ccccc1F] |
| 53 | 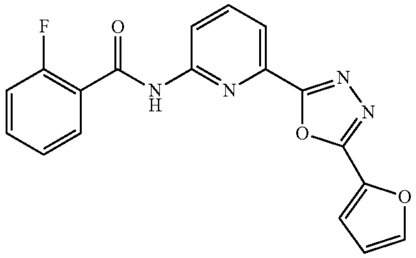 [SMILES: O=C(Nc1cccc(-c2nnc(-c3ccco3)o2)n1)c1ccccc1F] |
| 54 | 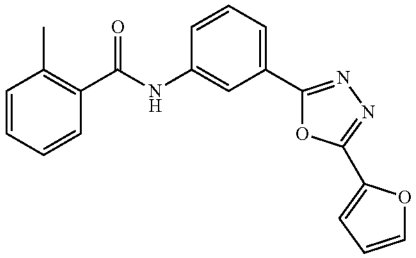 [SMILES: Cc1ccccc1C(=O)Nc1cccc(-c2nnc(-c3ccco3)o2)c1] |
| 55 | 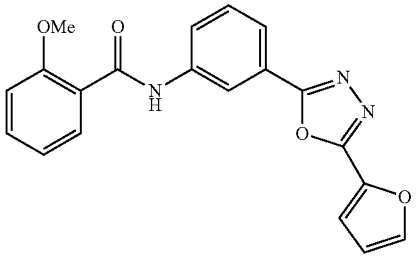 [SMILES: COc1ccccc1C(=O)Nc1cccc(-c2nnc(-c3ccco3)o2)c1] |

TABLE 1-continued
| Compound Number | Structure |
|---|---|
| 56 | 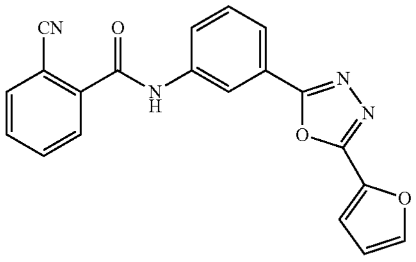 [SMILES: N#Cc1ccccc1C(=O)Nc1cccc(-c2nnc(-c3ccco3)o2)c1] |
| 57 | 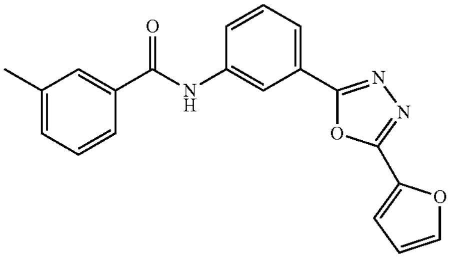 [SMILES: Cc1cccc(C(=O)Nc2cccc(-c3nnc(-c4ccco4)o3)c2)c1] |
| 58 | 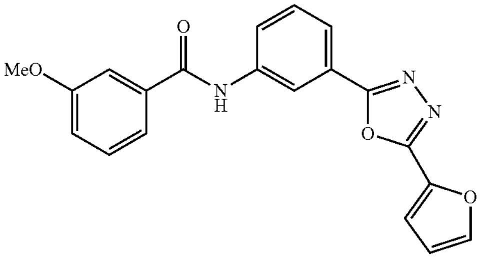 [SMILES: COc1cccc(C(=O)Nc2cccc(-c3nnc(-c4ccco4)o3)c2)c1] |
| 59 | 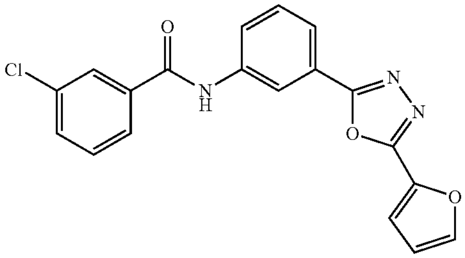 [SMILES: O=C(Nc1cccc(-c2nnc(-c3ccco3)o2)c1)c1cccc(Cl)c1] |
| 60 | 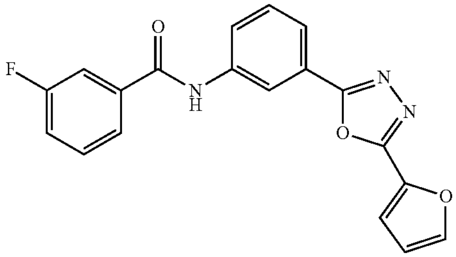 [SMILES: O=C(Nc1cccc(-c2nnc(-c3ccco3)o2)c1)c1cccc(F)c1] |

TABLE 1-continued
| Compound Number | Structure |
| --- | --- |
| 61 | 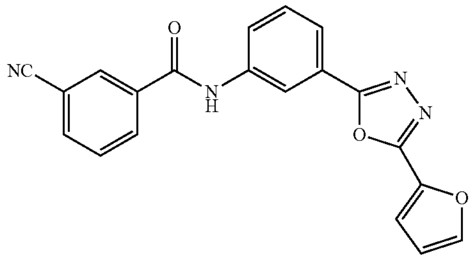 |
| 62 | 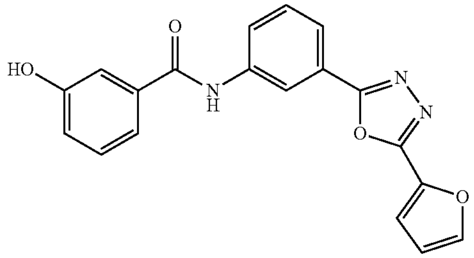 [SMILES: N#Cc1cccc(C(=O)Nc2cccc(-c3nnc(-c4ccco4)o3)c2)c1] |
| 63 | 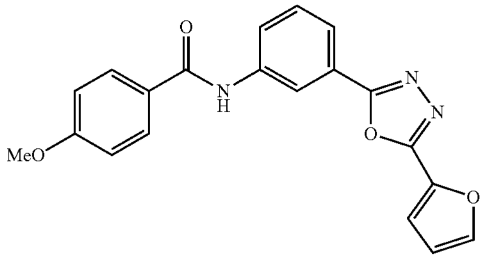 [SMILES: COc1ccc(C(=O)Nc2cccc(-c3nnc(-c4ccco4)o3)c2)cc1] |
| 64 | 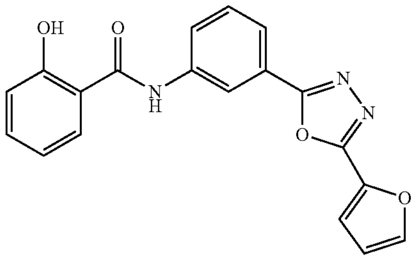 [SMILES: O=C(Nc1cccc(-c2nnc(-c3ccco3)o2)c1)c1ccccc1O] |
| 65 | 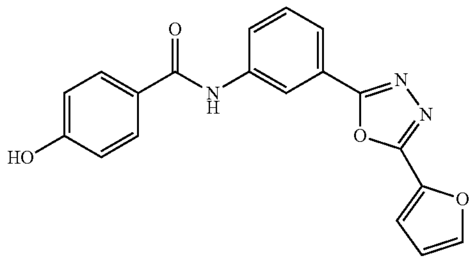 |

TABLE 1-continued
| Compound Number | Structure |
|---|---|
| 66 | 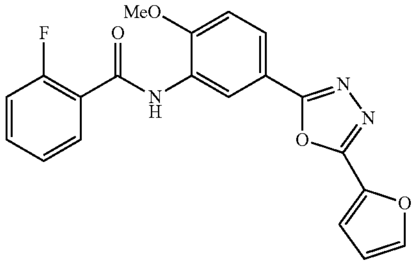 [SMILES: COc1ccc(-c2nnc(-c3ccco3)o2)cc1NC(=O)c1ccccc1F] |
| 67 | 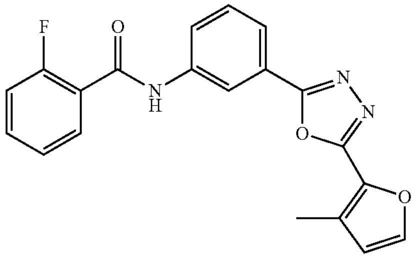 [SMILES: Cc1ccoc1-c1nnc(-c2cccc(NC(=O)c3ccccc3F)c2)o1] |
| 68 | 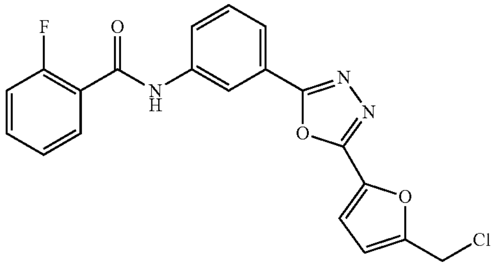 [SMILES: O=C(Nc1cccc(-c2nnc(-c3ccc(CCl)o3)o2)c1)c1ccccc1F] |
| 69 | 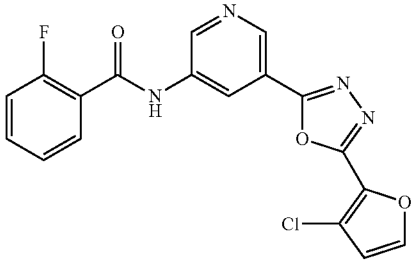 [SMILES: O=C(Nc1cncc(-c2nnc(-c3occc3Cl)o2)c1)c1ccccc1F] |
| 70 | 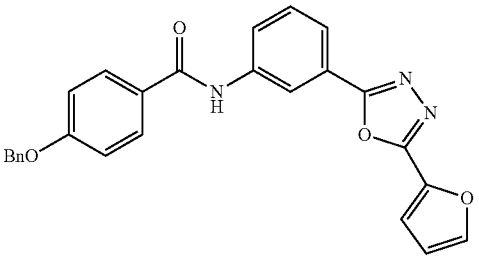 |

TABLE 1-continued
| Compound Number | Structure |
|---|---|
| 71 | 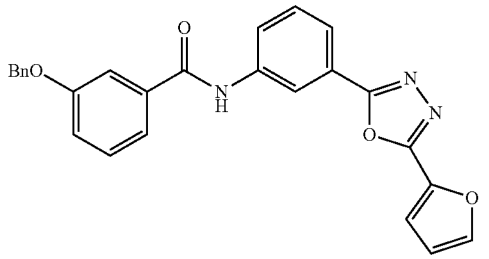 |
| 72 | 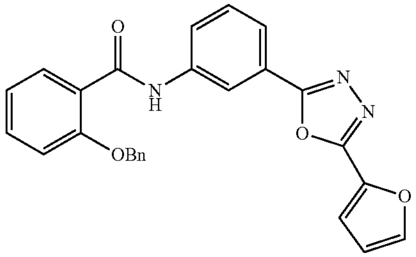 [SMILES: O=C(Nc1cccc(-c2nnc(-c3ccco3)o2)c1)c1ccccc1OCc1ccccc1] |
| 73 | 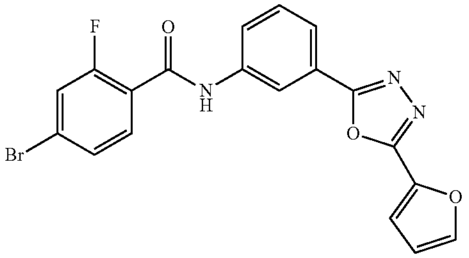 |
| 74 | 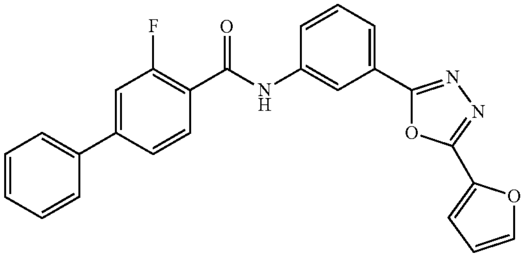 [SMILES: O=C(Nc1cccc(-c2nnc(-c3ccco3)o2)c1)c1ccc(-c2ccccc2)cc1F] |
| 75 | 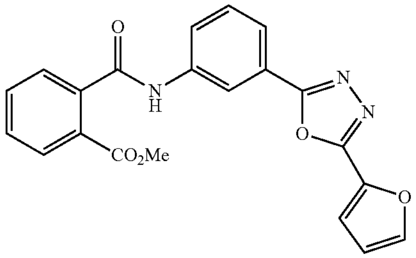 [SMILES: COC(=O)c1ccccc1C(=O)Nc1cccc(-c2nnc(-c3ccco3)o2)c1] |

TABLE 1-continued
| Compound Number | Structure |
|---|---|
| 76 | 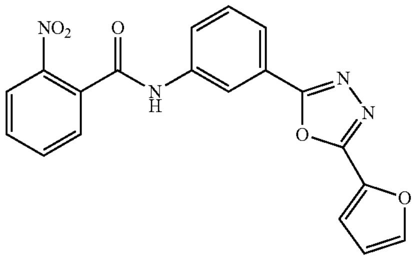 [SMILES: O=C(Nc1cccc(-c2nnc(-c3ccco3)o2)c1)c1ccccc1[N+](=O)[O-]] |
| 77 | 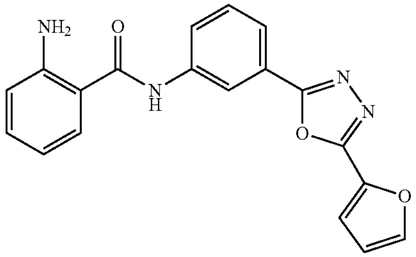 |
| 78 | 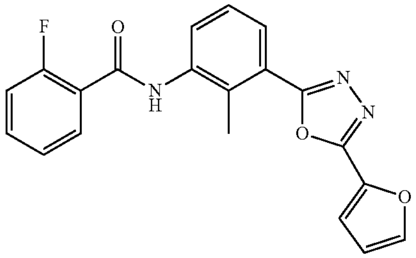 [SMILES: Cc1c(NC(=O)c2ccccc2F)cccc1-c1nnc(-c2ccco2)o1] |
| 79 | 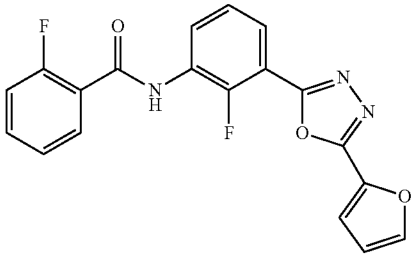 [SMILES: O=C(Nc1cccc(-c2nnc(-c3ccco3)o2)c1F)c1ccccc1F] |
| 80 | 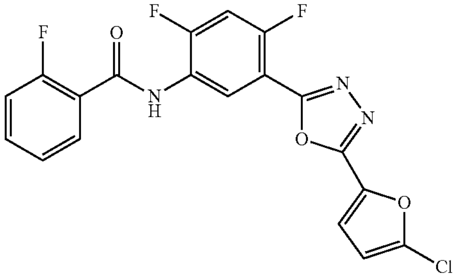 [SMILES: O=C(Nc1cc(-c2nnc(-c3ccc(Cl)o3)o2)c(F)cc1F)c1ccccc1F] |

TABLE 1-continued
| Compound Number | Structure |
|---|---|
| 81 | 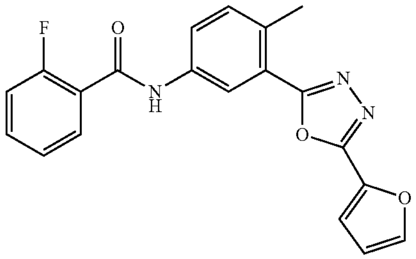 [SMILES: Cc1ccc(NC(=O)c2ccccc2F)cc1-c1nnc(-c2ccco2)o1] |
| 82 | 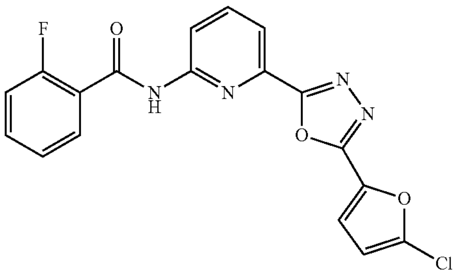 [SMILES: O=C(Nc1cccc(-c2nnc(-c3ccc(Cl)o3)o2)n1)c1ccccc1F] |
| 83 | 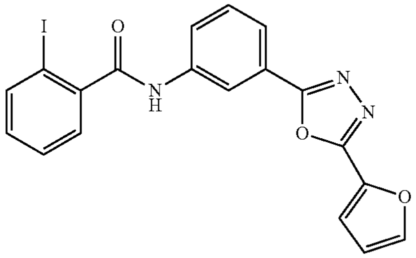 [SMILES: O=C(Nc1cccc(-c2nnc(-c3ccco3)o2)c1)c1ccccc1I] |
| 84 | 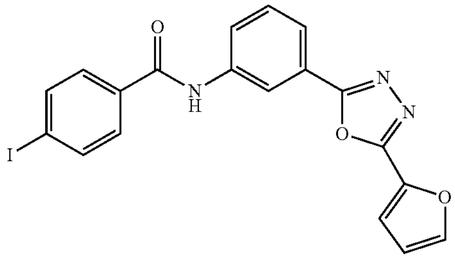 [SMILES: O=C(Nc1cccc(-c2nnc(-c3ccco3)o2)c1)c1ccc(I)cc1] |
| 85 | 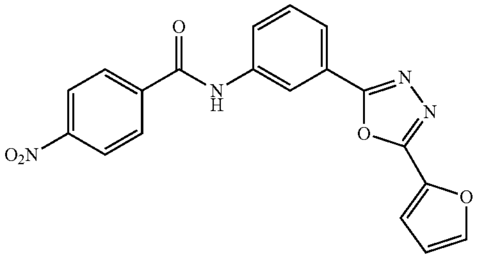 |

TABLE 1-continued
| Compound Number | Structure |
|---|---|
| 86 | 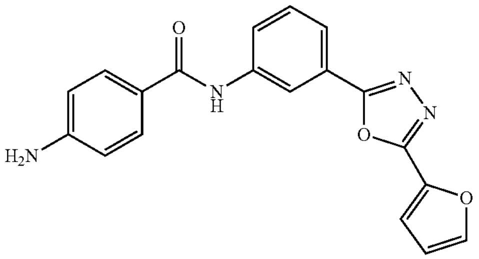 [SMILES: O=C(Nc1cccc(-c2nnc(-c3ccco3)o2)c1)c1ccc([N+](=O)[O-])cc1] |
| 87 | 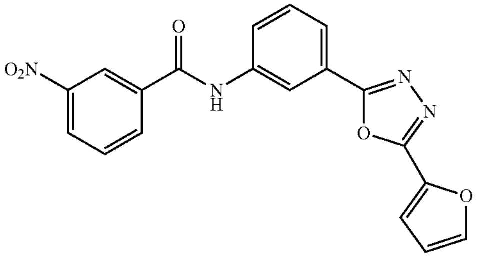 [SMILES: O=C(Nc1cccc(-c2nnc(-c3ccco3)o2)c1)c1cccc([N+](=O)[O-])c1] |
| 88 | 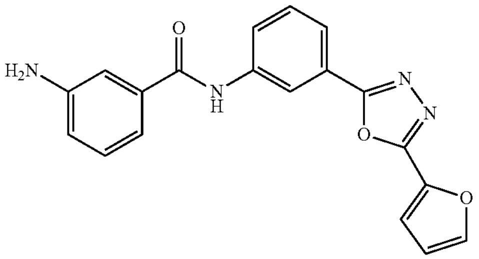 |
| 89 | 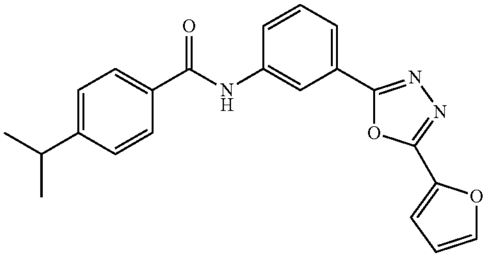 [SMILES: CC(C)c1ccc(C(=O)Nc2cccc(-c3nnc(-c4ccco4)o3)c2)cc1] |
| 90 | 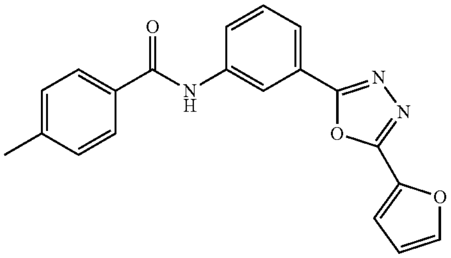 [SMILES: Cc1ccc(C(=O)Nc2cccc(-c3nnc(-c4ccco4)o3)c2)cc1] |

TABLE 1-continued
| Compound Number | Structure |
|---|---|
| 91 | 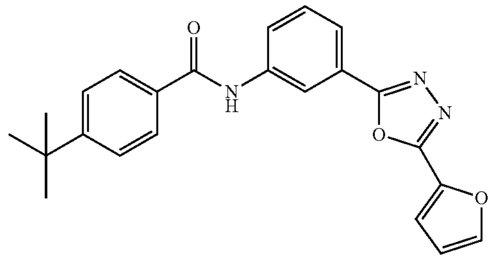 [SMILES: CC(C)(C)c1ccc(C(=O)Nc2cccc(-c3nnc(-c4ccco4)o3)c2)cc1] |
| 92 | 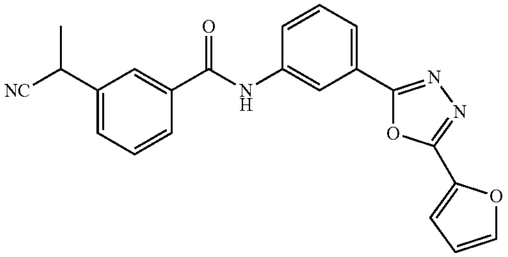 [SMILES: CC(C#N)c1cccc(C(=O)Nc2cccc(-c3nnc(-c4ccco4)o3)c2)c1] |
| 93 | 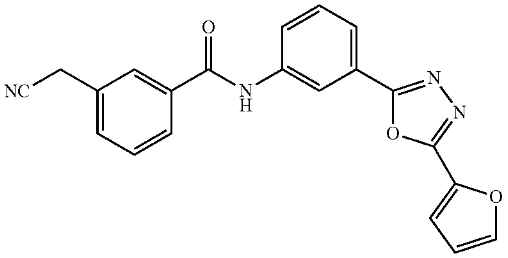 [SMILES: N#CCc1cccc(C(=O)Nc2cccc(-c3nnc(-c4ccco4)o3)c2)c1] |
| 94 | 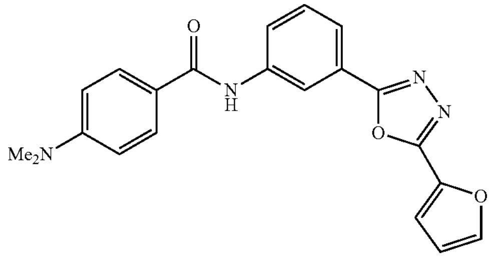 |
| 95 | 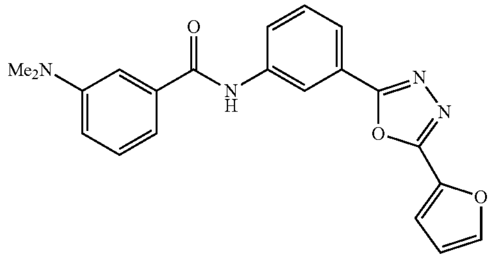 |

TABLE 1-continued
| Compound Number | Structure |
| --- | --- |
| 96 | 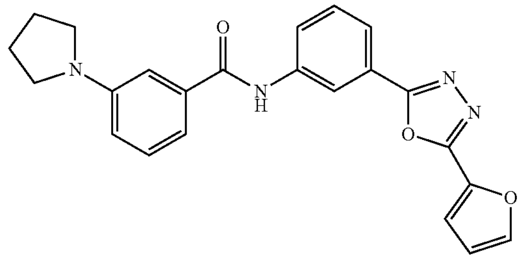 [SMILES: O=C(Nc1cccc(-c2nnc(-c3ccco3)o2)c1)c1cccc(N2CCCC2)c1] |
| 97 | 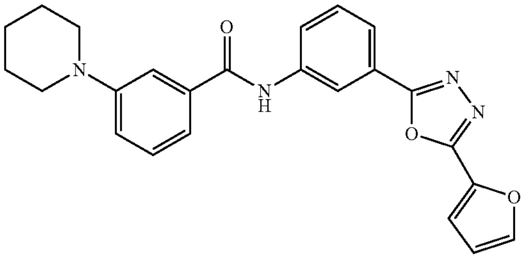 [SMILES: O=C(Nc1cccc(-c2nnc(-c3ccco3)o2)c1)c1cccc(N2CCCCC2)c1] |
| 98 | 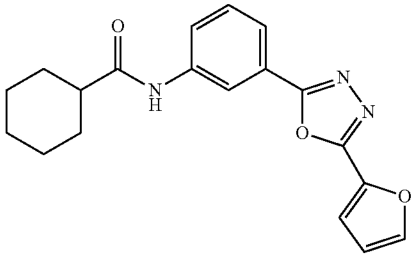 [SMILES: O=C(Nc1cccc(-c2nnc(-c3ccco3)o2)c1)C1CCCCC1] |
| 99 | 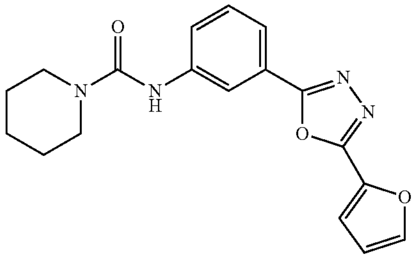 [SMILES: O=C(Nc1cccc(-c2nnc(-c3ccco3)o2)c1)N1CCCCC1] |
| 100 | 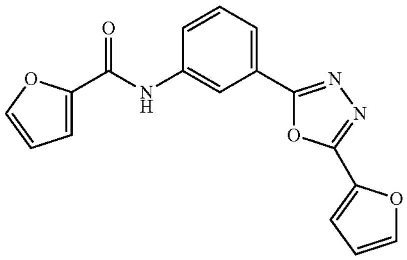 [SMILES: O=C(Nc1cccc(-c2nnc(-c3ccco3)o2)c1)c1ccco1] |

TABLE 1-continued
| Compound Number | Structure |
|---|---|
| 101 | 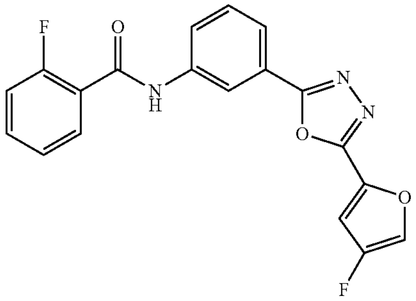 [SMILES: O=C(Nc1cccc(-c2nnc(-c3cc(F)co3)o2)c1)c1ccccc1F] |
| 102 | 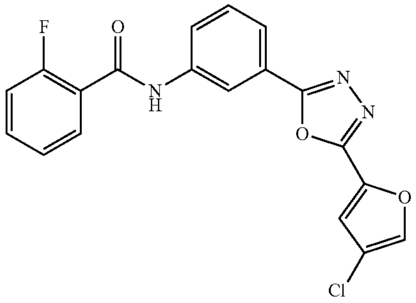 [SMILES: O=C(Nc1cccc(-c2nnc(-c3cc(Cl)co3)o2)c1)c1ccccc1F] |
| 103 | 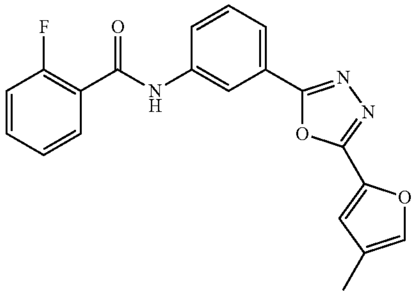 [SMILES: Cc1coc(-c2nnc(-c3cccc(NC(=O)c4ccccc4F)c3)o2)c1] |
| 104 | 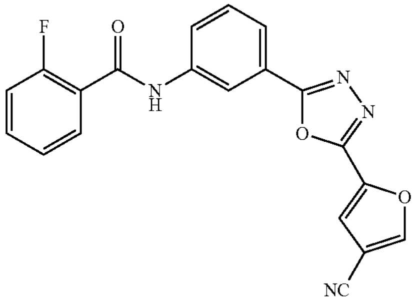 |
| 105 | 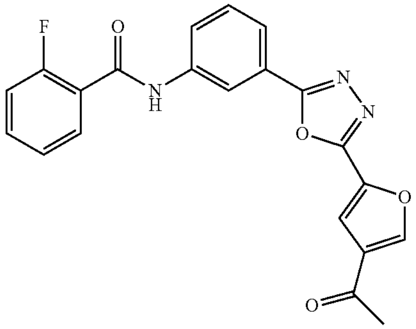 [SMILES: CC(=O)c1coc(-c2nnc(-c3cccc(NC(=O)c4ccccc4F)c3)o2)c1] |

TABLE 1-continued
| Compound Number | Structure |
|---|---|
| 106 | 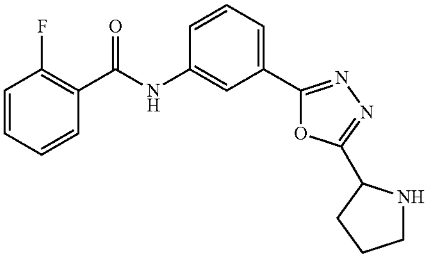 [SMILES: O=C(Nc1cccc(-c2nnc(C3CCCN3)o2)c1)c1ccccc1F] |
| 107 | 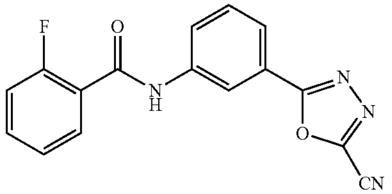 [SMILES: N#Cc1nnc(-c2cccc(NC(=O)c3ccccc3F)c2)o1] |
| 108 | 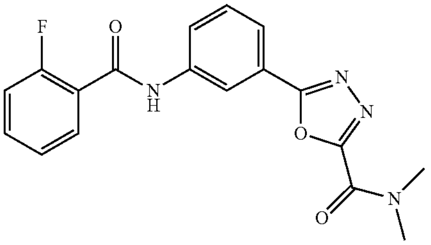 [SMILES: CN(C)C(=O)c1nnc(-c2cccc(NC(=O)c3ccccc3F)c2)o1] |
| 109 | 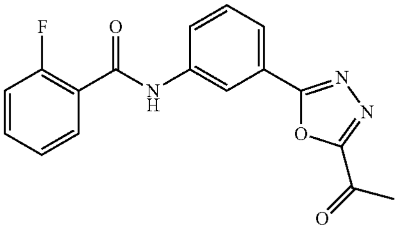 [SMILES: CC(=O)c1nnc(-c2cccc(NC(=O)c3ccccc3F)c2)o1] |
| 110 | 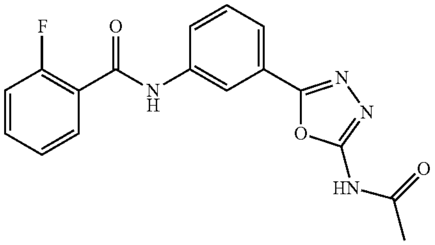 [SMILES: CC(=O)Nc1nnc(-c2cccc(NC(=O)c3ccccc3F)c2)o1] |
| 111 | 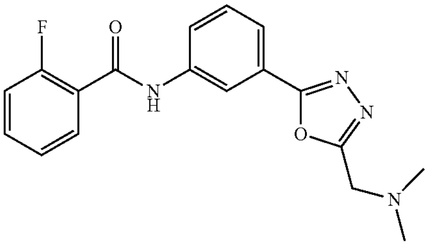 [SMILES: CN(C)Cc1nnc(-c2cccc(NC(=O)c3ccccc3F)c2)o1] |

TABLE 1-continued
| Compound Number | Structure |
|---|---|
| 112 | 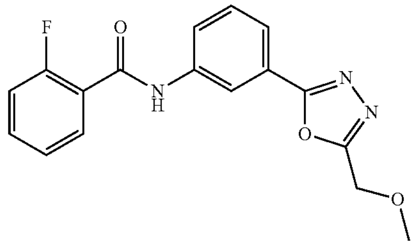 [SMILES: COCc1nnc(-c2cccc(NC(=O)c3ccccc3F)c2)o1] |
| 113 | 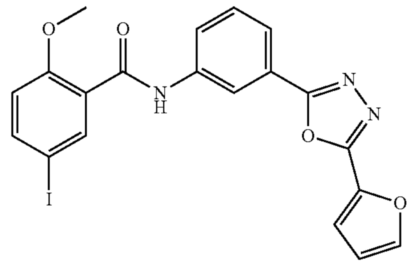 [SMILES: COc1ccc(I)cc1C(=O)Nc1cccc(-c2nnc(-c3ccco3)o2)c1] |
| 114 | 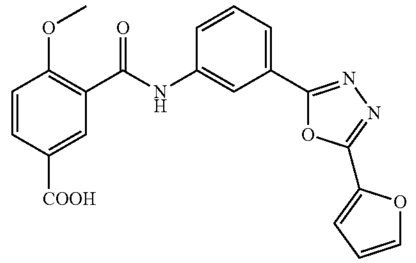 [SMILES: COc1ccc(C(=O)O)cc1C(=O)Nc1cccc(-c2nnc(-c3ccco3)o2)c1] |
| 115 | 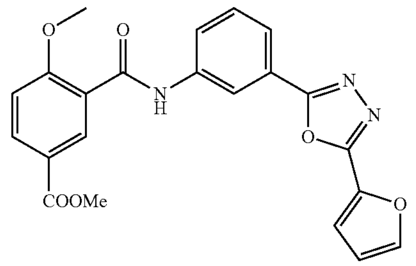 [SMILES: COC(=O)c1ccc(OC)c(C(=O)Nc2cccc(-c3nnc(-c4ccco4)o3)c2)c1] |
| 116 | 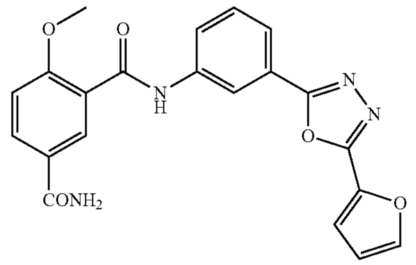 [SMILES: COc1ccc(C(N)=O)cc1C(=O)Nc1cccc(-c2nnc(-c3ccco3)o2)c1] |

TABLE 1-continued
| Compound Number | Structure |
|---|---|
| 117 | 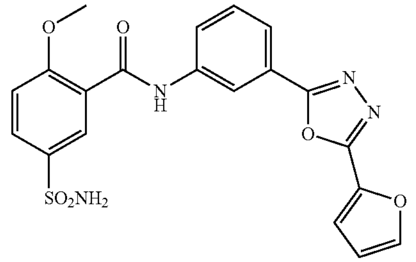 [SMILES: COc1ccc(S(N)(=O)=O)cc1C(=O)Nc1cccc(-c2nnc(-c3ccco3)o2)c1] |
| 118 | 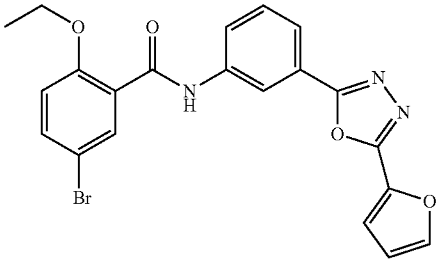 |
| 119 | 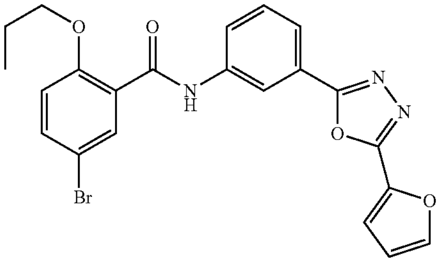 [SMILES: CCCOc1ccc(Br)cc1C(=O)Nc1cccc(-c2nnc(-c3ccco3)o2)c1] |
| 120 | 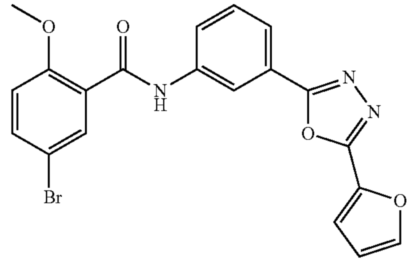 [SMILES: COc1ccc(Br)cc1C(=O)Nc1cccc(-c2nnc(-c3ccco3)o2)c1] |
| 121 | 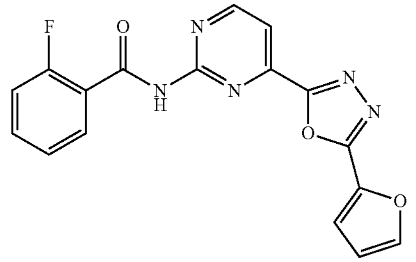 |

TABLE 1-continued
| Compound Number | Structure |
|---|---|
| 122 | 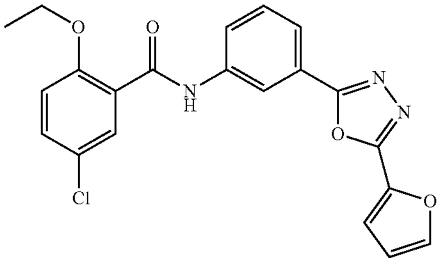 |
| 123 | 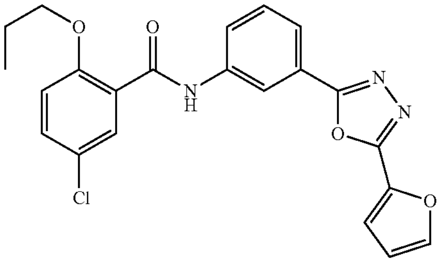 [SMILES: CCCOc1ccc(Cl)cc1C(=O)Nc1cccc(-c2nnc(-c3ccco3)o2)c1] |
| 124 | 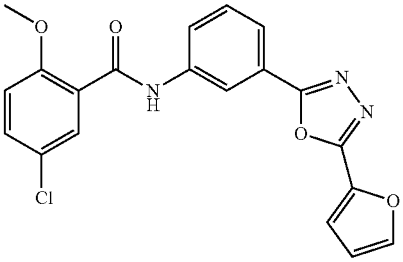 [SMILES: COc1ccc(Cl)cc1C(=O)Nc1cccc(-c2nnc(-c3ccco3)o2)c1] |
| 125 | 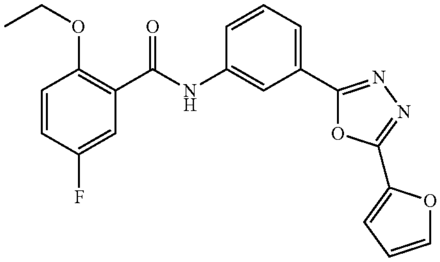 |
| 126 | 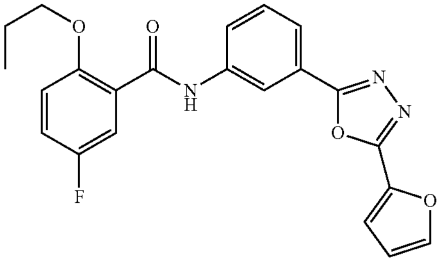 [SMILES: CCCOc1ccc(F)cc1C(=O)Nc1cccc(-c2nnc(-c3ccco3)o2)c1] |

TABLE 1-continued
| Compound Number | Structure |
|---|---|
| 127 | 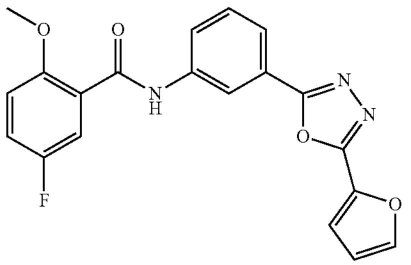 [SMILES: COc1ccc(F)cc1C(=O)Nc1cccc(-c2nnc(-c3ccco3)o2)c1] |
| 128 | 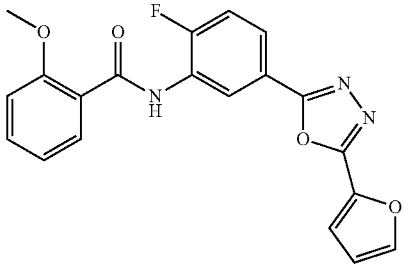 [SMILES: COc1ccccc1C(=O)Nc1cc(-c2nnc(-c3ccco3)o2)ccc1F] |
| 129 | 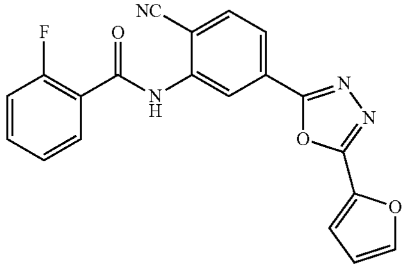 [SMILES: N#Cc1ccc(-c2nnc(-c3ccco3)o2)cc1NC(=O)c1ccccc1F] |
| 130 | 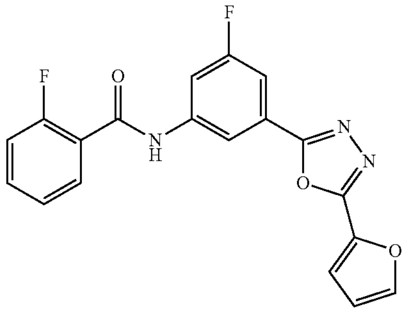 [SMILES: O=C(Nc1cc(F)cc(-c2nnc(-c3ccco3)o2)c1)c1ccccc1F] |
| 131 | 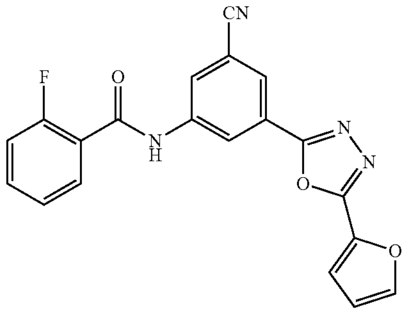 [SMILES: N#Cc1cc(NC(=O)c2ccccc2F)cc(-c2nnc(-c3ccco3)o2)c1] |

TABLE 1-continued
| Compound Number | Structure |
| --- | --- |
| 132 | 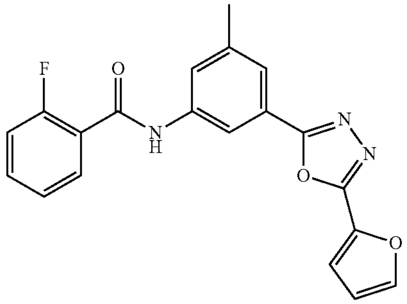 [SMILES: Cc1cc(NC(=O)c2ccccc2F)cc(-c2nnc(-c3ccco3)o2)c1] |
| 133 | 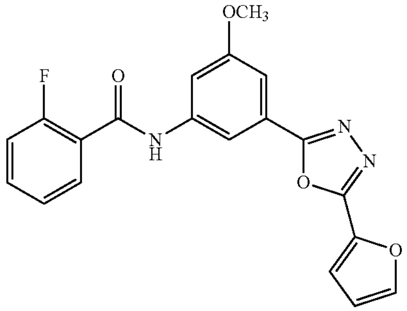 [SMILES: COc1cc(NC(=O)c2ccccc2F)cc(-c2nnc(-c3ccco3)o2)c1] |
| 134 | 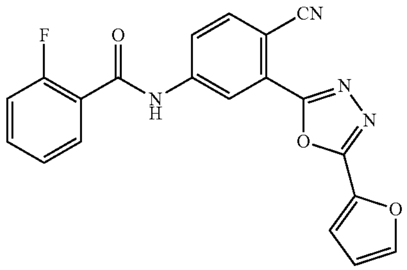 [SMILES: N#Cc1ccc(NC(=O)c2ccccc2F)cc1-c1nnc(-c2ccco2)o1] |
| 135 | 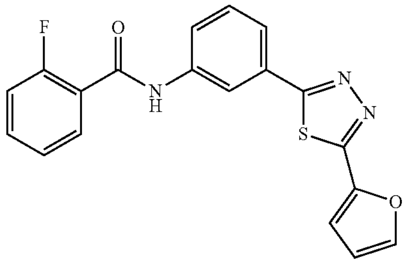 [SMILES: O=C(Nc1cccc(-c2nnc(-c3ccco3)s2)c1)c1ccccc1F] |
| 136 | 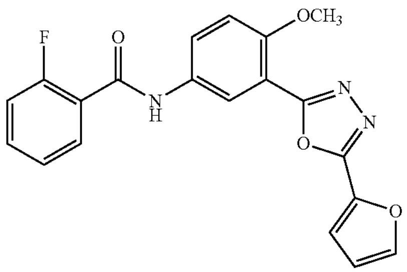 [SMILES: COc1ccc(NC(=O)c2ccccc2F)cc1-c1nnc(-c2ccco2)o1] |

TABLE 1-continued
| Compound Number | Structure |
|---|---|
| 137 | 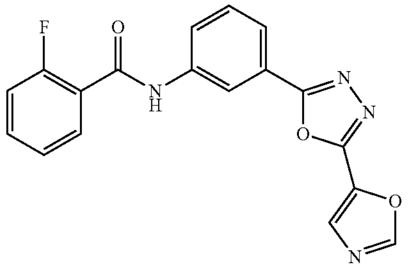 [SMILES: O=C(Nc1cccc(-c2nnc(-c3cnco3)o2)c1)c1ccccc1F] |
| 138 | 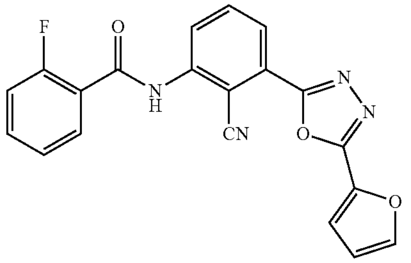 [SMILES: N#Cc1c(NC(=O)c2ccccc2F)cccc1-c1nnc(-c2ccco2)o1] |
| 139 | 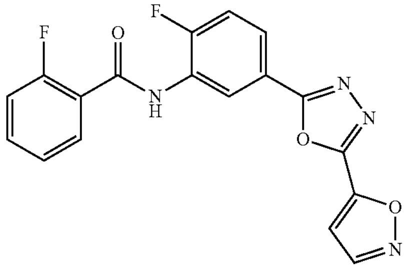 [SMILES: O=C(Nc1cc(-c2nnc(-c3ccno3)o2)ccc1F)c1ccccc1F] |
| 140 | 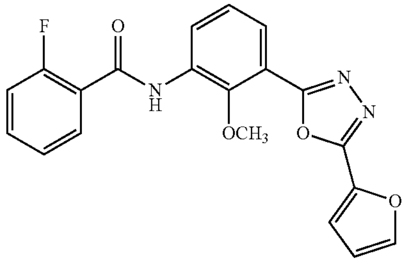 [SMILES: COc1c(NC(=O)c2ccccc2F)cccc1-c1nnc(-c2ccco2)o1] |
| 141 | 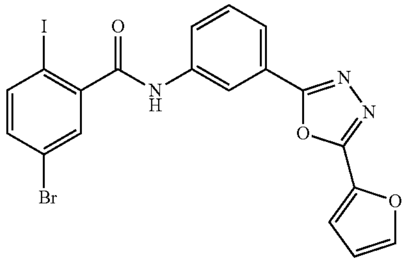 [SMILES: O=C(Nc1cccc(-c2nnc(-c3ccco3)o2)c1)c1cc(Br)ccc1I] |

TABLE 1-continued
| Compound Number | Structure |
|---|---|
| 142 | 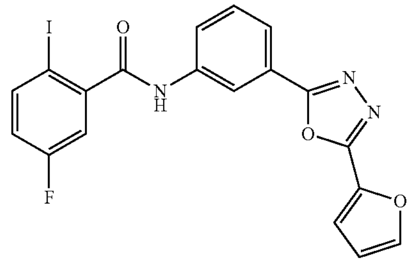 [SMILES: O=C(Nc1cccc(-c2nnc(-c3ccco3)o2)c1)c1cc(F)ccc1I] |
| 143 | 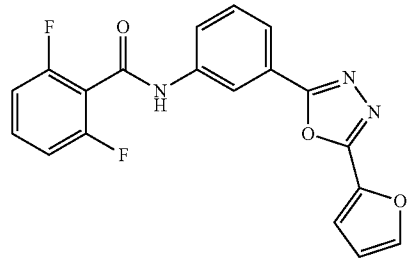 [SMILES: O=C(Nc1cccc(-c2nnc(-c3ccco3)o2)c1)c1c(F)cccc1F] |
| 144 | 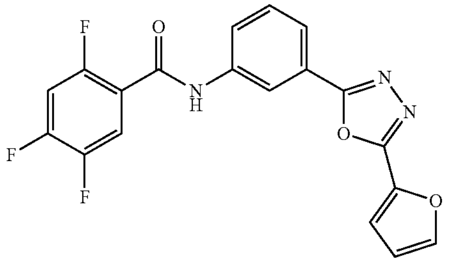 [SMILES: O=C(Nc1cccc(-c2nnc(-c3ccco3)o2)c1)c1cc(F)c(F)cc1F] |
| 145 | 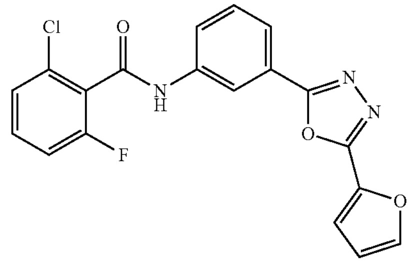 [SMILES: O=C(Nc1cccc(-c2nnc(-c3ccco3)o2)c1)c1c(F)cccc1Cl] |
| 146 | 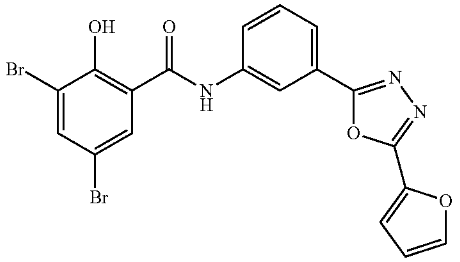 [SMILES: O=C(Nc1cccc(-c2nnc(-c3ccco3)o2)c1)c1cc(Br)cc(Br)c1O] |

TABLE 1-continued
| Compound Number | Structure |
| --- | --- |
| 147 | 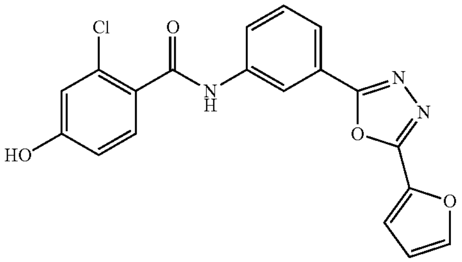 [SMILES: O=C(Nc1cccc(-c2nnc(-c3ccco3)o2)c1)c1ccc(O)cc1Cl] |
| 148 | 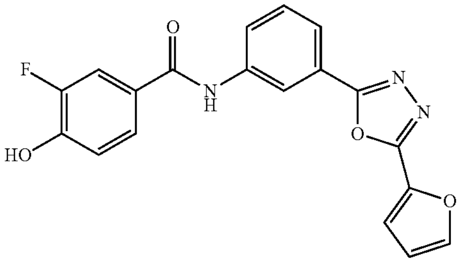 [SMILES: O=C(Nc1cccc(-c2nnc(-c3ccco3)o2)c1)c1ccc(O)c(F)c1] |
| 149 | 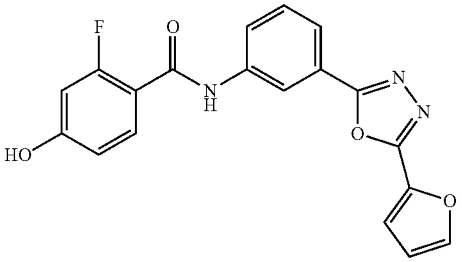 [SMILES: O=C(Nc1cccc(-c2nnc(-c3ccco3)o2)c1)c1ccc(O)cc1F] |
| 150 | 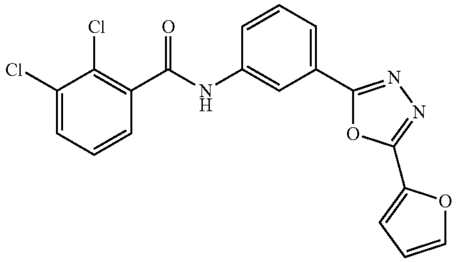 [SMILES: O=C(Nc1cccc(-c2nnc(-c3ccco3)o2)c1)c1cccc(Cl)c1Cl] |
| 151 | 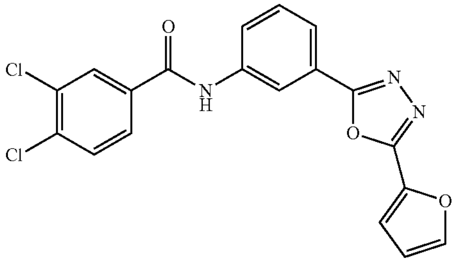 [SMILES: O=C(Nc1cccc(-c2nnc(-c3ccco3)o2)c1)c1ccc(Cl)c(Cl)c1] |

TABLE 1-continued
| Compound Number | Structure |
|---|---|
| 152 | 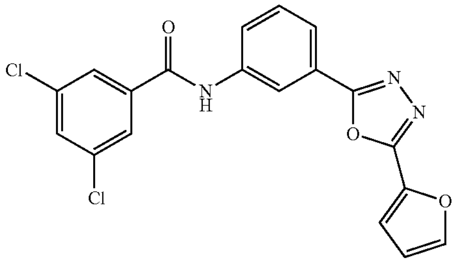 [SMILES: O=C(Nc1cccc(-c2nnc(-c3ccco3)o2)c1)c1cc(Cl)cc(Cl)c1] |
| 153 | 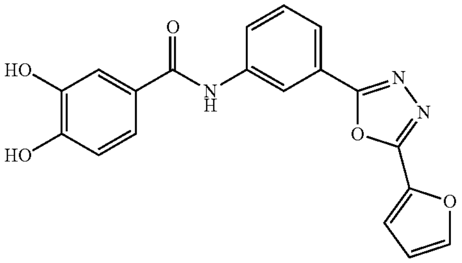 [SMILES: O=C(Nc1cccc(-c2nnc(-c3ccco3)o2)c1)c1ccc(O)c(O)c1] |
| 154 | 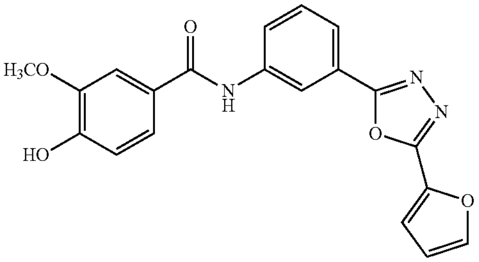 [SMILES: COc1cc(C(=O)Nc2cccc(-c3nnc(-c4ccco4)o3)c2)ccc1O] |
| 155 | 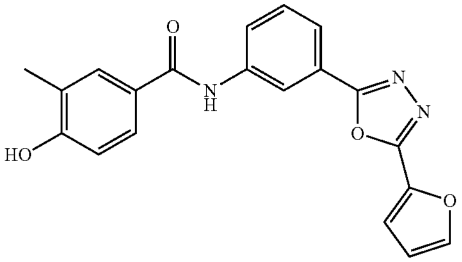 [SMILES: Cc1cc(C(=O)Nc2cccc(-c3nnc(-c4ccco4)o3)c2)ccc1O] |
| 156 | 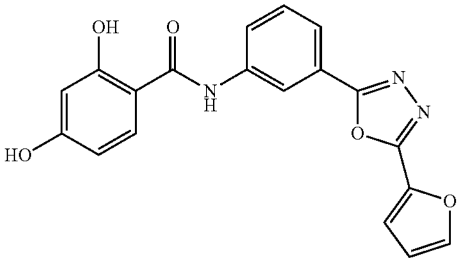 [SMILES: O=C(Nc1cccc(-c2nnc(-c3ccco3)o2)c1)c1ccc(O)cc1O] |

TABLE 1-continued
| Compound Number | Structure |
| --- | --- |
| 157 | 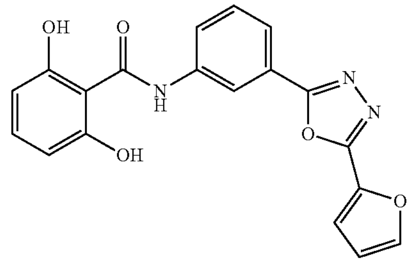 [SMILES: O=C(Nc1cccc(-c2nnc(-c3ccco3)o2)c1)c1c(O)cccc1O] |
| 158 | 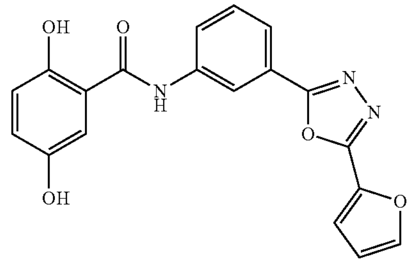 [SMILES: O=C(Nc1cccc(-c2nnc(-c3ccco3)o2)c1)c1cc(O)ccc1O] |
| 159 | 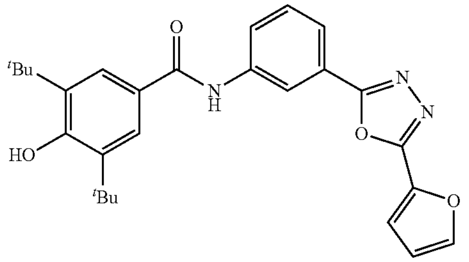 |
| 160 | 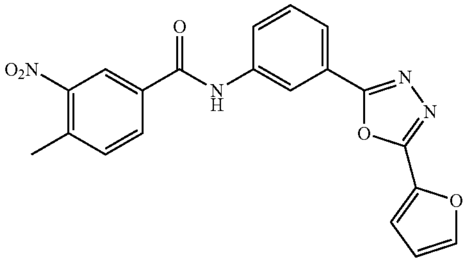 [SMILES: Cc1ccc(C(=O)Nc2cccc(-c3nnc(-c4ccco4)o3)c2)cc1[N+](=O)[O-]] |
| 161 | 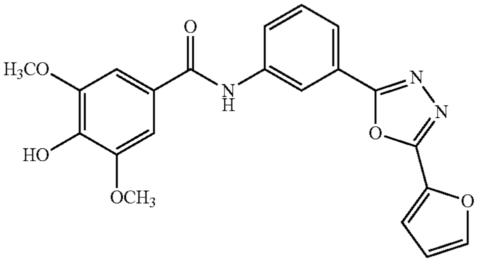 [SMILES: COc1cc(C(=O)Nc2cccc(-c3nnc(-c4ccco4)o3)c2)cc(OC)c1O] |

TABLE 1-continued
| Compound Number | Structure |
| --- | --- |
| 162 | 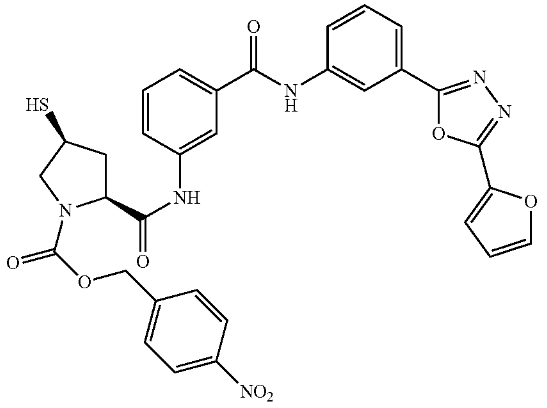 [SMILES: O=C(Nc1cccc(-c2nnc(-c3ccco3)o2)c1)c1cccc(NC(=O)[C@@H]2C[C@H](S)CN2C(=O)OCc2ccc([N+](=O)[O-])cc2)c1] |
| 163 | 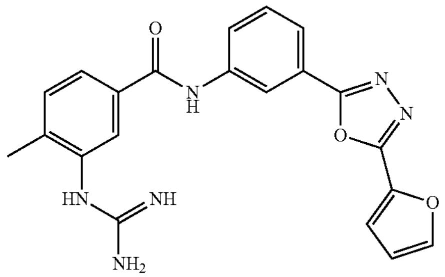 [SMILES: Cc1ccc(C(=O)Nc2cccc(-c3nnc(-c4ccco4)o3)c2)cc1NC(=N)N] |
| 164 | 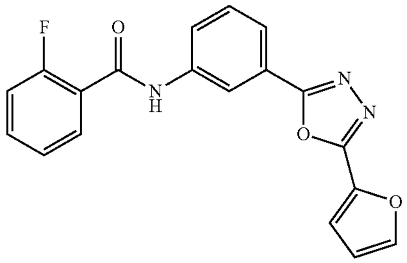 [SMILES: O=C(Nc1cccc(-c2nnc(-c3ccco3)o2)c1)c1ccccc1F] |
| 165 | 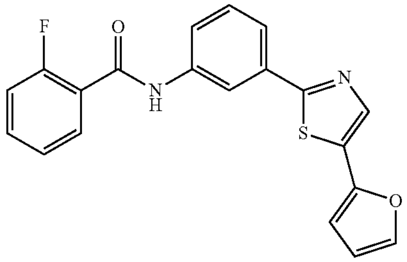 [SMILES: O=C(Nc1cccc(-c2ncc(-c3ccco3)s2)c1)c1ccccc1F] |
| 166 | 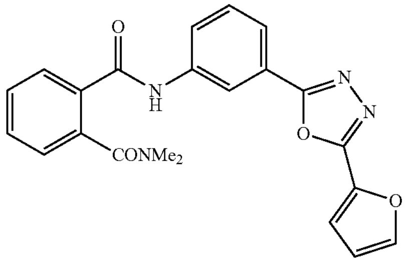 |

TABLE 1-continued
| Compound Number | Structure |
|---|---|
| 167 | 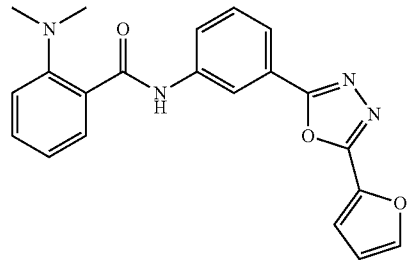 [SMILES: CN(C)c1ccccc1C(=O)Nc1cccc(-c2nnc(-c3ccco3)o2)c1] |
| 168 | 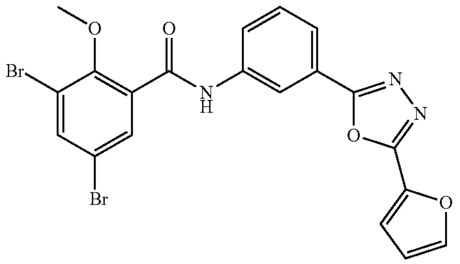 [SMILES: COc1c(Br)cc(Br)cc1C(=O)Nc1cccc(-c2nnc(-c3ccco3)o2)c1] |
| 169 | 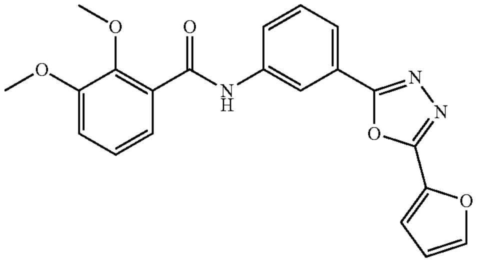 [SMILES: COc1cccc(C(=O)Nc2cccc(-c3nnc(-c4ccco4)o3)c2)c1OC] |
| 170 | 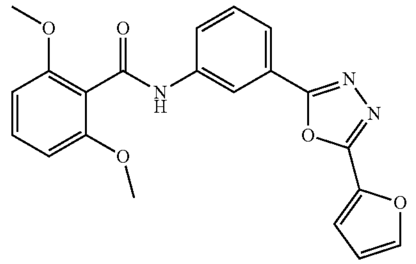 [SMILES: COc1cccc(OC)c1C(=O)Nc1cccc(-c2nnc(-c3ccco3)o2)c1] |
| 171 | 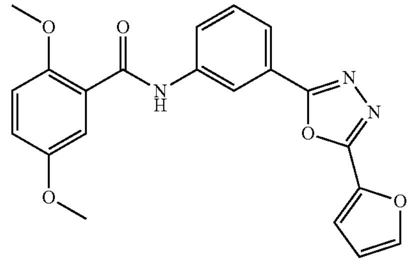 [SMILES: COc1ccc(OC)c(C(=O)Nc2cccc(-c3nnc(-c4ccco4)o3)c2)c1] |

TABLE 1-continued
| Compound Number | Structure |
|---|---|
| 172 | 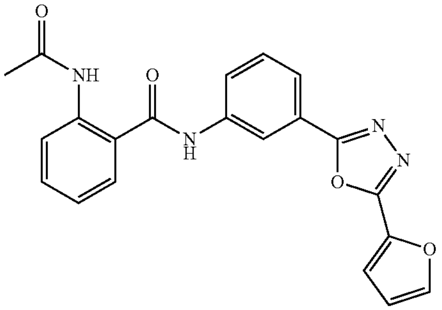 [SMILES: CC(=O)Nc1ccccc1C(=O)Nc1cccc(-c2nnc(-c3ccco3)o2)c1] |
| 173 | 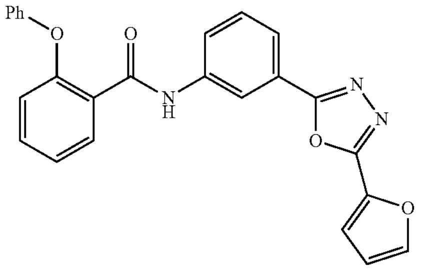 [SMILES: O=C(Nc1cccc(-c2nnc(-c3ccco3)o2)c1)c1ccccc1Oc1ccccc1] |
| 174 | 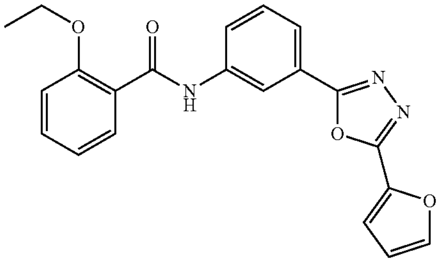 |
| 175 | 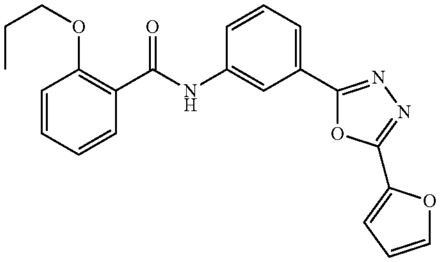 [SMILES: CCCOc1ccccc1C(=O)Nc1cccc(-c2nnc(-c3ccco3)o2)c1] |
| 176 | 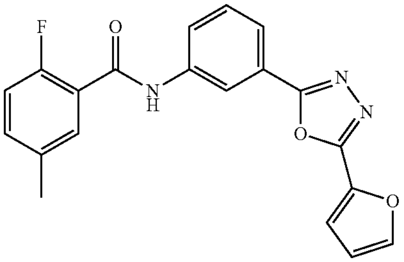 [SMILES: Cc1ccc(F)c(C(=O)Nc2cccc(-c3nnc(-c4ccco4)o3)c2)c1] |

TABLE 1-continued
| Compound Number | Structure |
|---|---|
| 177 | 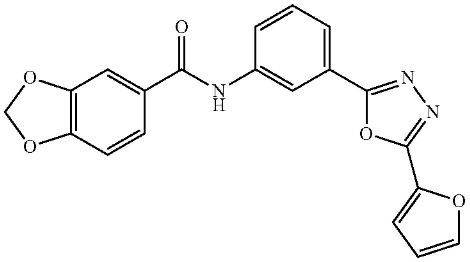 [SMILES: O=C(Nc1cccc(-c2nnc(-c3ccco3)o2)c1)c1ccc2c(c1)OCO2] |
| 178 | 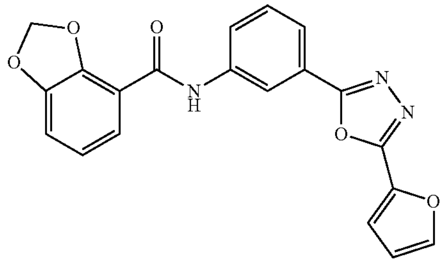 [SMILES: O=C(Nc1cccc(-c2nnc(-c3ccco3)o2)c1)c1cccc2c1OCO2] |
| 179 | 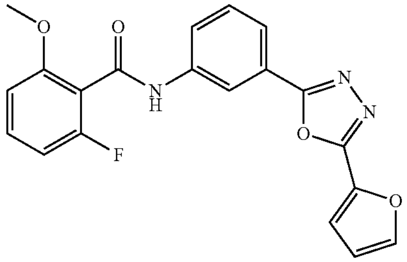 [SMILES: COc1cccc(F)c1C(=O)Nc1cccc(-c2nnc(-c3ccco3)o2)c1] |
| 180 | 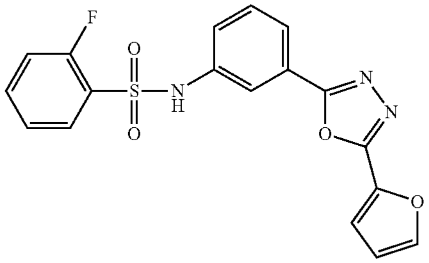 [SMILES: O=S(=O)(Nc1cccc(-c2nnc(-c3ccco3)o2)c1)c1ccccc1F] |
| 181 | 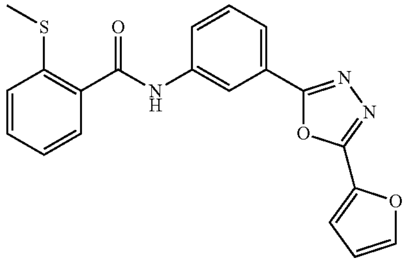 |

TABLE 1-continued
| Compound Number | Structure |
| --- | --- |
| 182 | 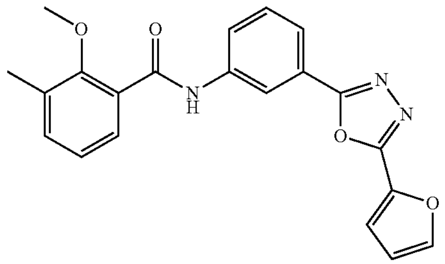 [SMILES: COc1c(C)cccc1C(=O)Nc1cccc(-c2nnc(-c3ccco3)o2)c1] |
| 183 | 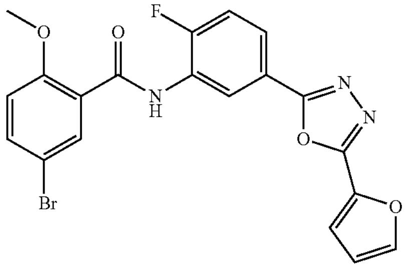 |
| 184 | 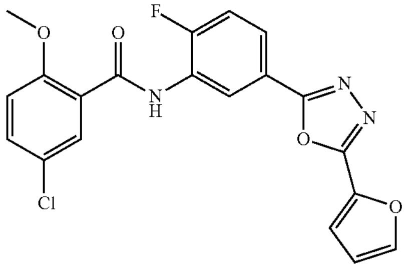 |
| 185 | 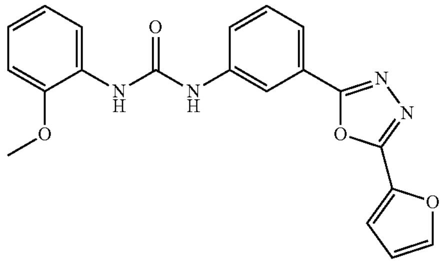 [SMILES: COc1ccccc1NC(=O)Nc1cccc(-c2nnc(-c3ccco3)o2)c1] |
| 186 | 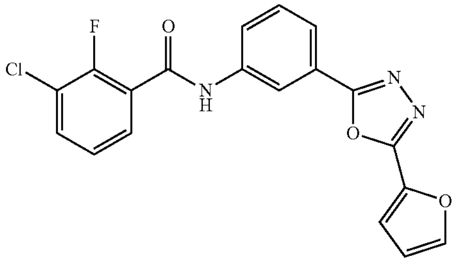 [SMILES: O=C(Nc1cccc(-c2nnc(-c3ccco3)o2)c1)c1cccc(Cl)c1F] |

TABLE 1-continued
| Compound Number | Structure |
| --- | --- |
| 187 | 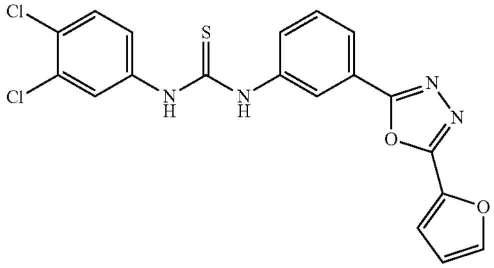 [SMILES: S=C(Nc1cccc(-c2nnc(-c3ccco3)o2)c1)Nc1ccc(Cl)c(Cl)c1] |
| 188 | 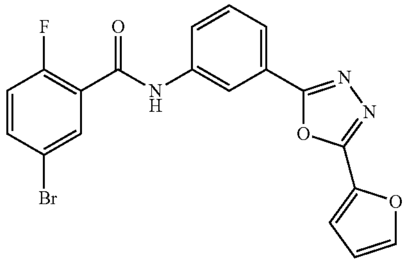 |
| 189 | 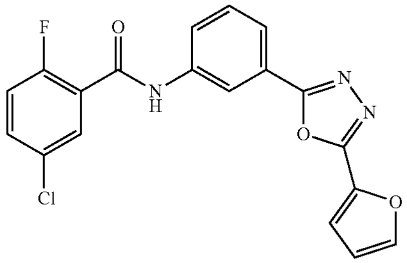 |
| 190 | 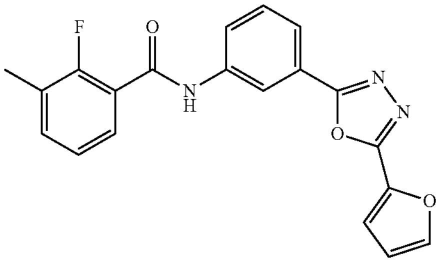 [SMILES: Cc1cccc(C(=O)Nc2cccc(-c3nnc(-c4ccco4)o3)c2)c1F] |
| 191 | 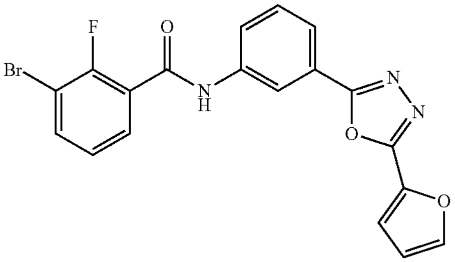 |

TABLE 1-continued
| Compound Number | Structure |
|---|---|
| 192 | 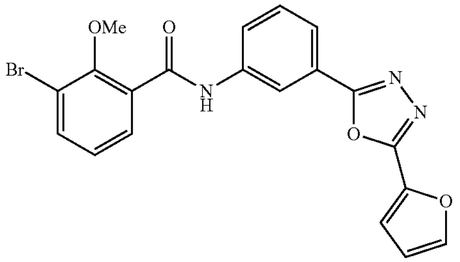 |
| 193 | 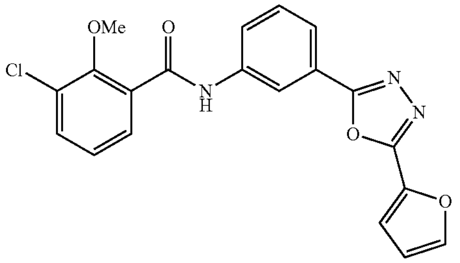 [SMILES: COc1c(Cl)cccc1C(=O)Nc1cccc(-c2nnc(-c3ccco3)o2)c1] |
| 194 | 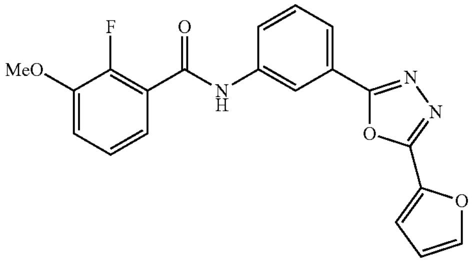 [SMILES: COc1cccc(C(=O)Nc2cccc(-c3nnc(-c4ccco4)o3)c2)c1F] |
| 195 | 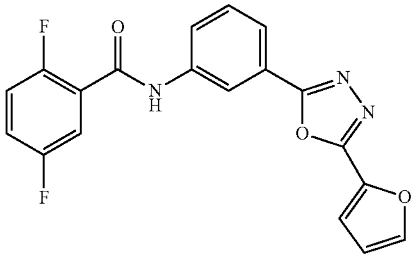 |
| 196 | 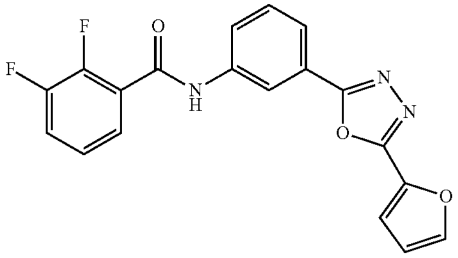 [SMILES: O=C(Nc1cccc(-c2nnc(-c3ccco3)o2)c1)c1cccc(F)c1F] |

TABLE 1-continued
| Compound Number | Structure |
|---|---|
| 197 | 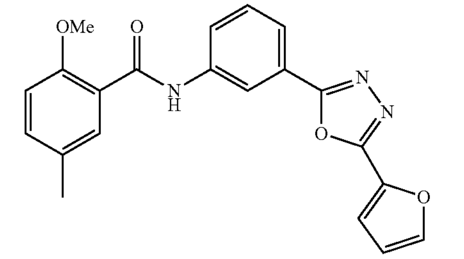 [SMILES: COc1ccc(C)cc1C(=O)Nc1cccc(-c2nnc(-c3ccco3)o2)c1] |
| 198 | 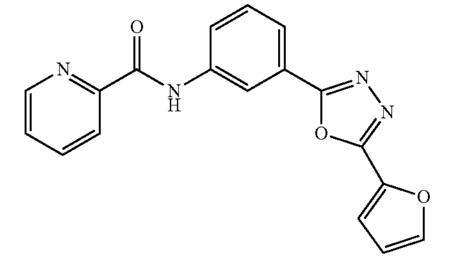 |
| 199 | 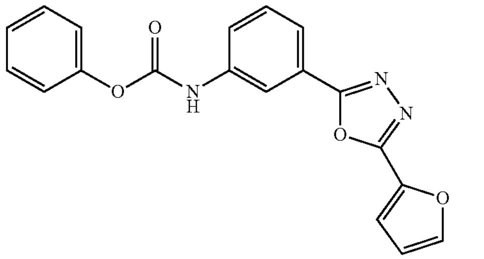 [SMILES: O=C(Nc1cccc(-c2nnc(-c3ccco3)o2)c1)Oc1ccccc1] |
| 200 | 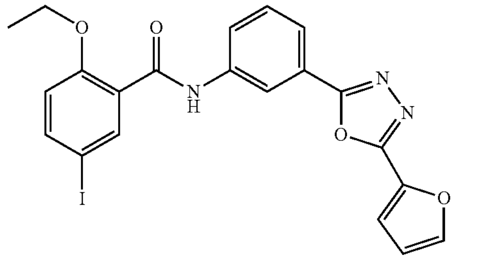 [SMILES: CCOc1ccc(I)cc1C(=O)Nc1cccc(-c2nnc(-c3ccco3)o2)c1] |
| 201 | 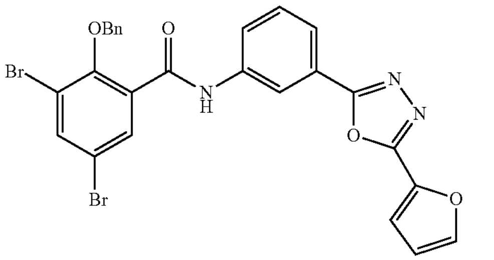 [SMILES: O=C(Nc1cccc(-c2nnc(-c3ccco3)o2)c1)c1cc(Br)cc(Br)c1OCc1ccccc1] |
| 202 | 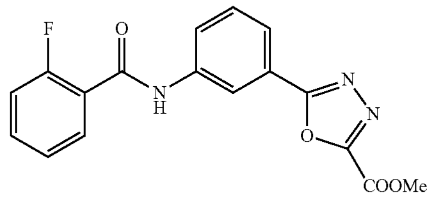 [SMILES: COC(=O)c1nnc(-c2cccc(NC(=O)c3ccccc3F)c2)o1] |

TABLE 1-continued
| Compound Number | Structure |
|---|---|
| 203 | 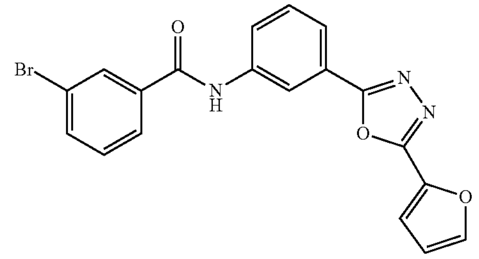 [SMILES: O=C(Nc1cccc(-c2nnc(-c3ccco3)o2)c1)c1cccc(Br)c1] |
| 204 | 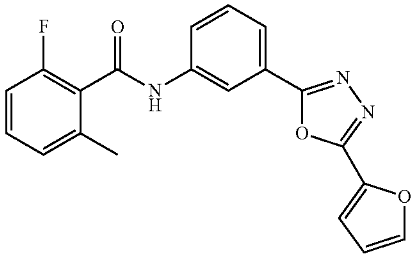 [SMILES: Cc1cccc(F)c1C(=O)Nc1cccc(-c2nnc(-c3ccco3)o2)c1] |
| 205 | 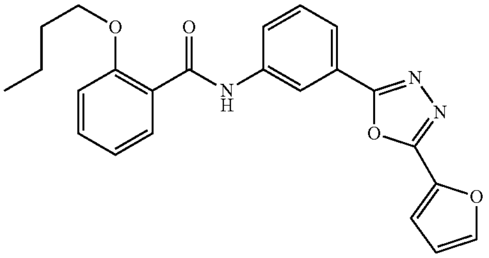 [SMILES: CCCCOc1ccccc1C(=O)Nc1cccc(-c2nnc(-c3ccco3)o2)c1] |
| 206 | 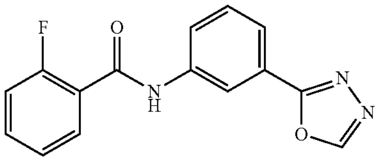 [SMILES: O=C(Nc1cccc(-c2nnco2)c1)c1ccccc1F] |
| 207 | 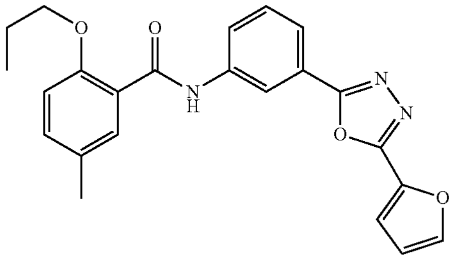 [SMILES: CCCOc1ccc(C)cc1C(=O)Nc1cccc(-c2nnc(-c3ccco3)o2)c1] |
| 208 | 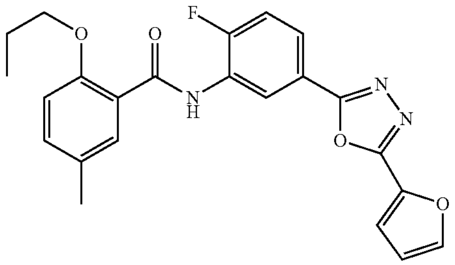 [SMILES: CCCOc1ccc(C)cc1C(=O)Nc1cc(-c2nnc(-c3ccco3)o2)ccc1F] |

TABLE 1-continued
| Compound Number | Structure |
| --- | --- |
| 209 | 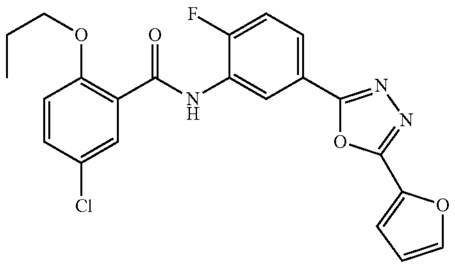 [SMILES: CCCOc1ccc(Cl)cc1C(=O)Nc1cc(-c2nnc(-c3ccco3)o2)ccc1F] |
| 210 | 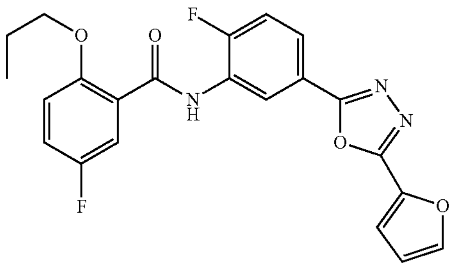 [SMILES: CCCOc1ccc(F)cc1C(=O)Nc1cc(-c2nnc(-c3ccco3)o2)ccc1F] |
| 211 | 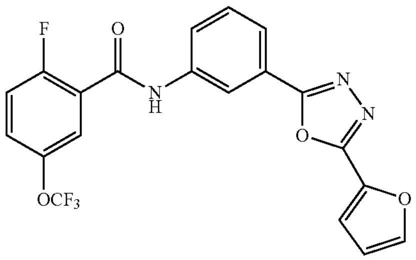 [SMILES: O=C(Nc1cccc(-c2nnc(-c3ccco3)o2)c1)c1cc(OC(F)(F)F)ccc1F] |
| 212 | 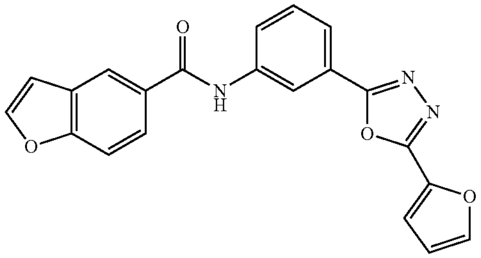 [SMILES: O=C(Nc1cccc(-c2nnc(-c3ccco3)o2)c1)c1ccc2occc2c1] |
| 213 | 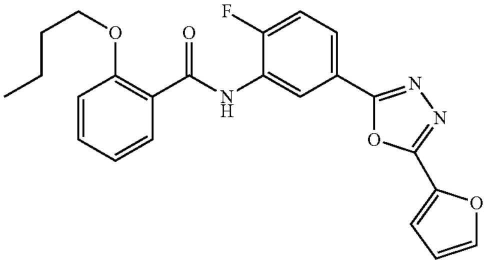 [SMILES: CCCCOc1ccccc1C(=O)Nc1cc(-c2nnc(-c3ccco3)o2)ccc1F] |

TABLE 1-continued
| Compound Number | Structure |
|---|---|
| 214 | 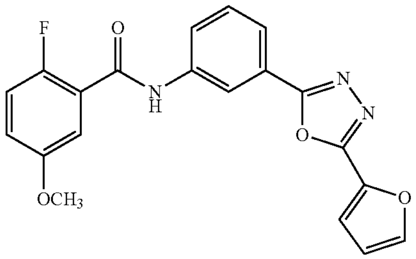 |
| 215 | 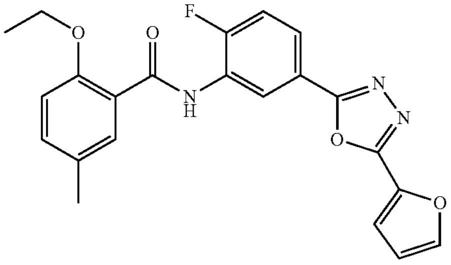 [SMILES: CCOc1ccc(C)cc1C(=O)Nc1cc(-c2nnc(-c3ccco3)o2)ccc1F] |
| 216 | 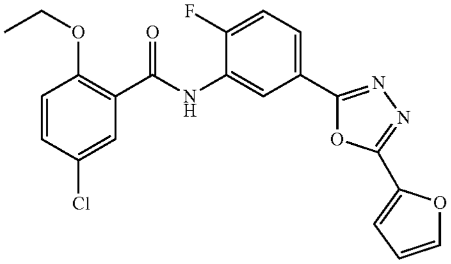 [SMILES: CCOc1ccc(Cl)cc1C(=O)Nc1cc(-c2nnc(-c3ccco3)o2)ccc1F] |
| 217 | 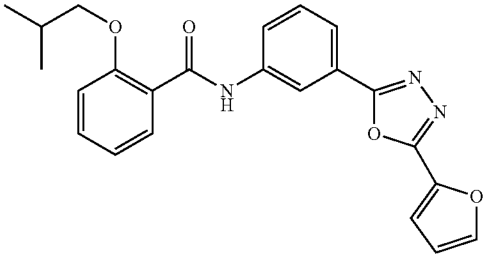 [SMILES: CC(C)COc1ccccc1C(=O)Nc1cccc(-c2nnc(-c3ccco3)o2)c1] |
| 218 | 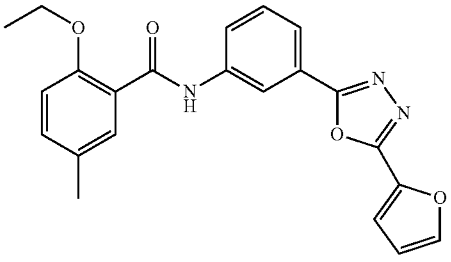 [SMILES: CCOc1ccc(C)cc1C(=O)Nc1cccc(-c2nnc(-c3ccco3)o2)c1] |

TABLE 1-continued
| Compound Number | Structure |
|---|---|
| 219 | 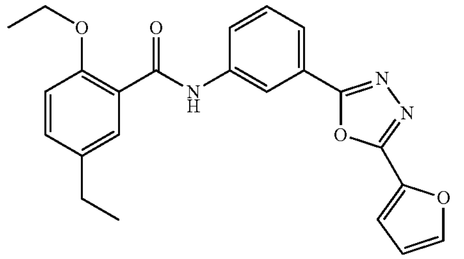 [SMILES: CCOc1ccc(CC)cc1C(=O)Nc1cccc(-c2nnc(-c3ccco3)o2)c1] |
| 220 | 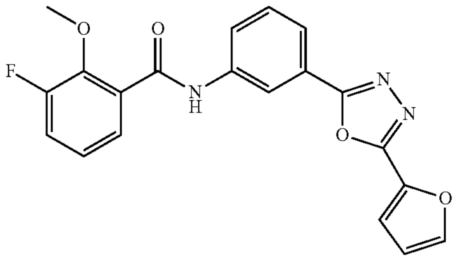 [SMILES: COc1c(F)cccc1C(=O)Nc1cccc(-c2nnc(-c3ccco3)o2)c1] |
| 221 | 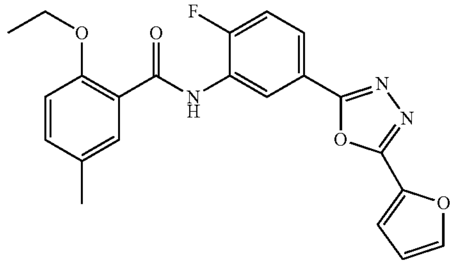 [SMILES: CCOc1ccc(C)cc1C(=O)Nc1cc(-c2nnc(-c3ccco3)o2)ccc1F] |
| 222 | 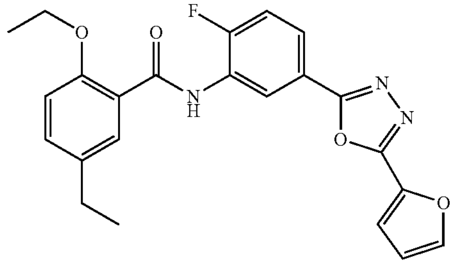 [SMILES: CCOc1ccc(CC)cc1C(=O)Nc1cc(-c2nnc(-c3ccco3)o2)ccc1F] |
| 223 | 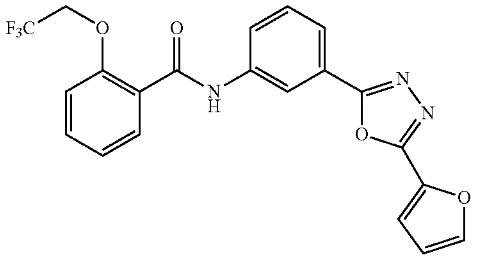 [SMILES: O=C(Nc1cccc(-c2nnc(-c3ccco3)o2)c1)c1ccccc1OCC(F)(F)F] |

TABLE 1-continued
| Compound Number | Structure |
|---|---|
| 224 | 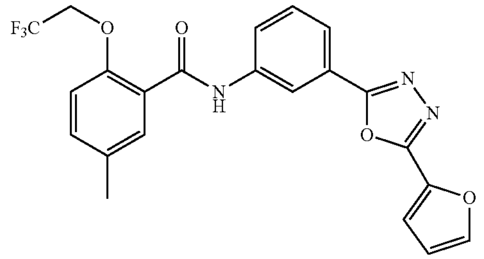 [SMILES: Cc1ccc(OCC(F)(F)F)c(C(=O)Nc2cccc(-c3nnc(-c4ccco4)o3)c2)c1] |
| 225 | 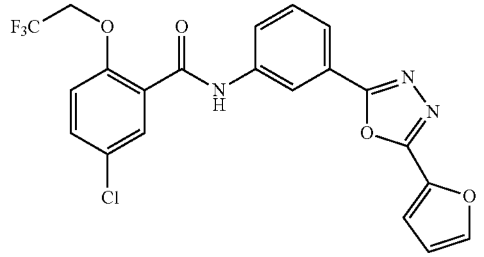 |
| 226 | 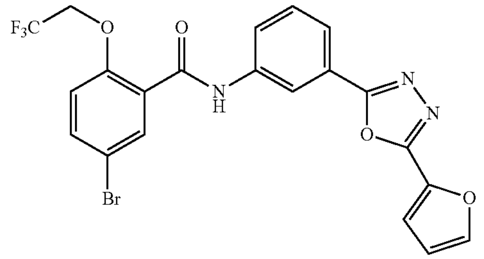 [SMILES: O=C(Nc1cccc(-c2nnc(-c3ccco3)o2)c1)c1cc(Br)ccc1OCC(F)(F)F] |
| 227 | 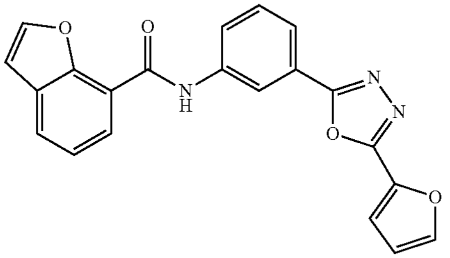 [SMILES: O=C(Nc1cccc(-c2nnc(-c3ccco3)o2)c1)c1cccc2ccoc12] |
| 228 | 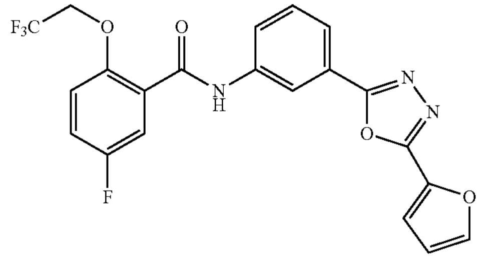 [SMILES: O=C(Nc1cccc(-c2nnc(-c3ccco3)o2)c1)c1cc(F)ccc1OCC(F)(F)F] |

TABLE 1-continued
| Compound Number | Structure |
|---|---|
| 229 | 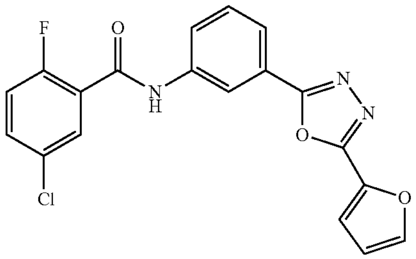 |
| 230 | 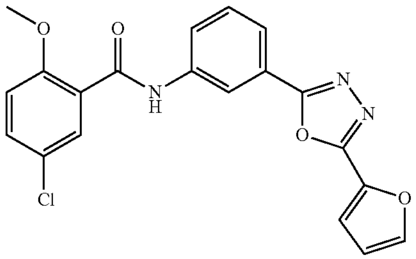 |
| 231 | 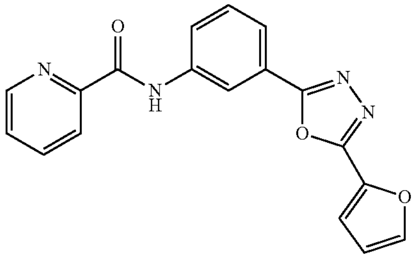 [SMILES: O=C(Nc1cccc(-c2nnc(-c3ccco3)o2)c1)c1ccccn1] |
| 232 | 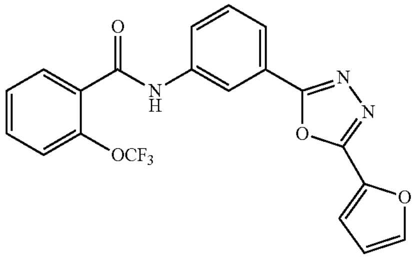 |
| 233 | 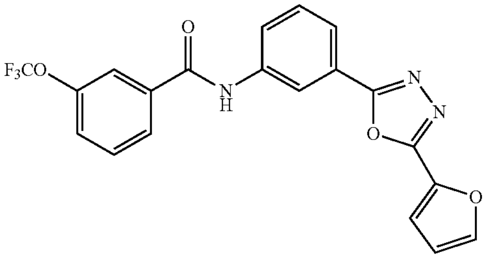 [SMILES: O=C(Nc1cccc(-c2nnc(-c3ccco3)o2)c1)c1cccc(OC(F)(F)F)c1] |

TABLE 1-continued
| Compound Number | Structure |
|---|---|
| 234 | 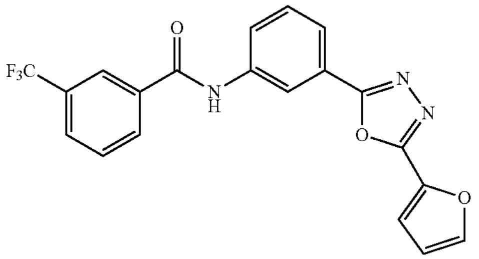 |
| 235 | 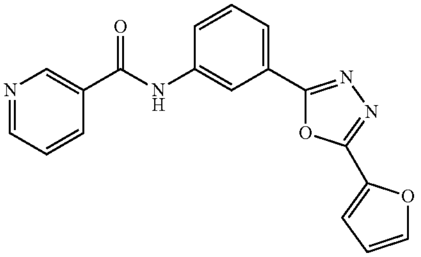 [SMILES: O=C(Nc1cccc(-c2nnc(-c3ccco3)o2)c1)c1cccnc1] |
| 236 | 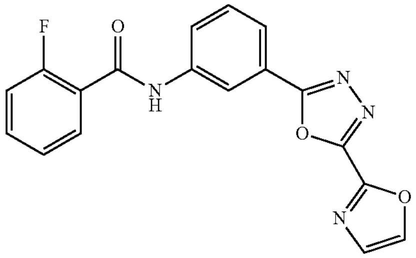 |
| 237 | 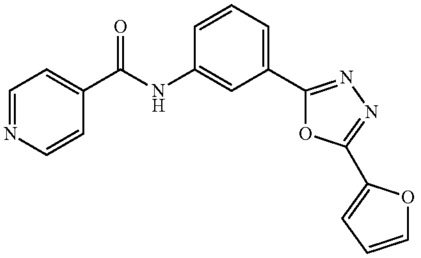 [SMILES: O=C(Nc1cccc(-c2nnc(-c3ccco3)o2)c1)c1ccncc1] |
| 238 | 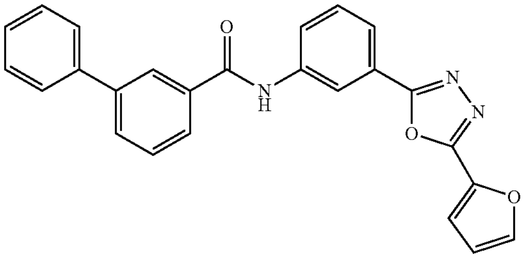 [SMILES: O=C(Nc1cccc(-c2nnc(-c3ccco3)o2)c1)c1cccc(-c2ccccc2)c1] |

TABLE 1-continued
| Compound Number | Structure |
| --- | --- |
| 239 | 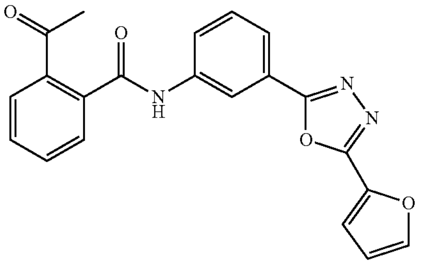 [SMILES: CC(=O)c1ccccc1C(=O)Nc1cccc(-c2nnc(-c3ccco3)o2)c1] |
| 240 | 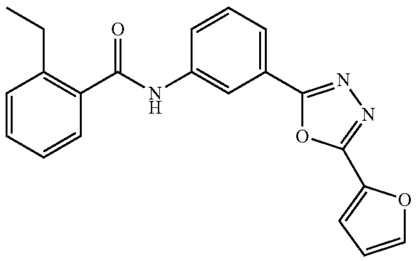 [SMILES: CCc1ccccc1C(=O)Nc1cccc(-c2nnc(-c3ccco3)o2)c1] |
| 241 | 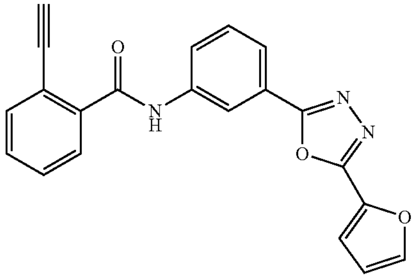 [SMILES: C#Cc1ccccc1C(=O)Nc1cccc(-c2nnc(-c3ccco3)o2)c1] |
| 242 | 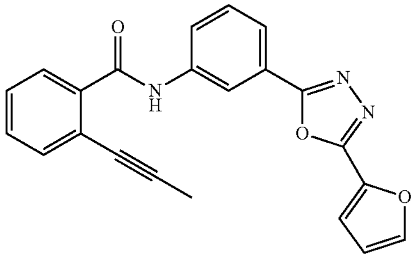 [SMILES: CC#Cc1ccccc1C(=O)Nc1cccc(-c2nnc(-c3ccco3)o2)c1] |
| 243 | 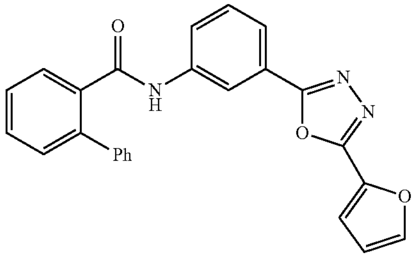 [SMILES: O=C(Nc1cccc(-c2nnc(-c3ccco3)o2)c1)c1ccccc1-c1ccccc1] |

TABLE 1-continued
| Compound Number | Structure |
|---|---|
| 244 | 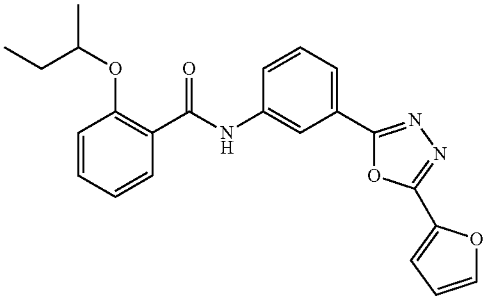 [SMILES: CCC(C)Oc1ccccc1C(=O)Nc1cccc(-c2nnc(-c3ccco3)o2)c1] |
| 245 | 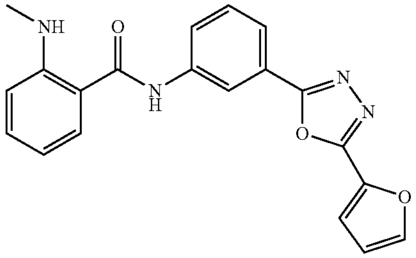 [SMILES: CNc1ccccc1C(=O)Nc1cccc(-c2nnc(-c3ccco3)o2)c1] |
| 246 | 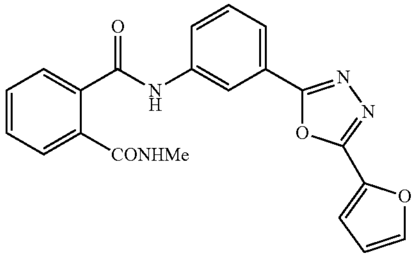 |
| 247 | 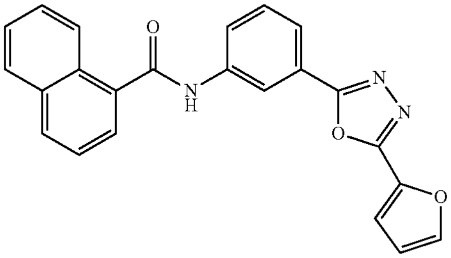 [SMILES: O=C(Nc1cccc(-c2nnc(-c3ccco3)o2)c1)c1cccc2ccccc12] |
| 248 | 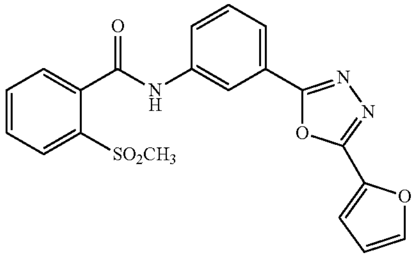 [SMILES: CS(=O)(=O)c1ccccc1C(=O)Nc1cccc(-c2nnc(-c3ccco3)o2)c1] |

TABLE 1-continued
| Compound Number | Structure |
|---|---|
| 249 | 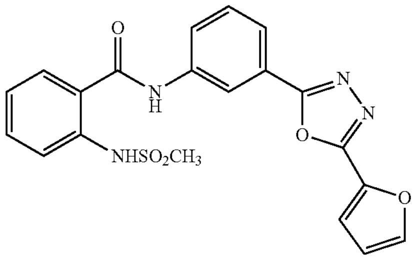 |
| 250 | 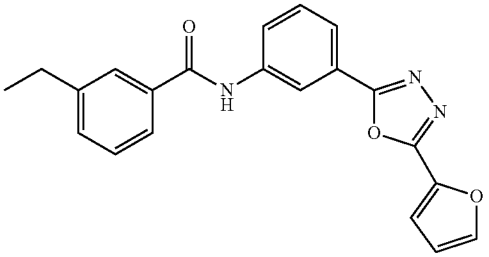 [SMILES: CCc1cccc(C(=O)Nc2cccc(-c3nnc(-c4ccco4)o3)c2)c1] |
| 251 | 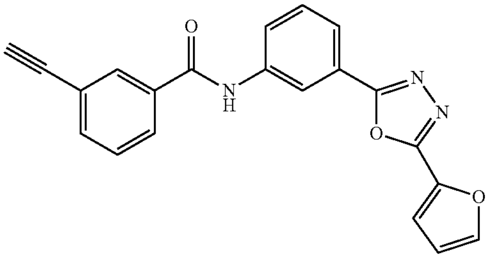 [SMILES: C#Cc1cccc(C(=O)Nc2cccc(-c3nnc(-c4ccco4)o3)c2)c1] |
| 252 | 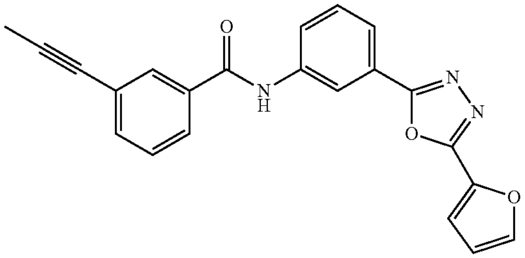 [SMILES: CC#Cc1cccc(C(=O)Nc2cccc(-c3nnc(-c4ccco4)o3)c2)c1] |
| 253 | 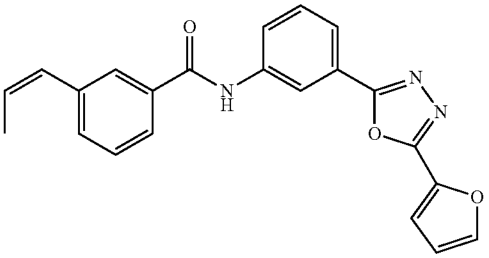 [SMILES: C/C=C\c1cccc(C(=O)Nc2cccc(-c3nnc(-c4ccco4)o3)c2)c1] |

TABLE 1-continued
| Compound Number | Structure |
|---|---|
| 254 | 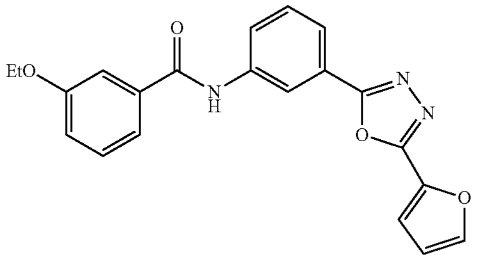 |
| 255 | 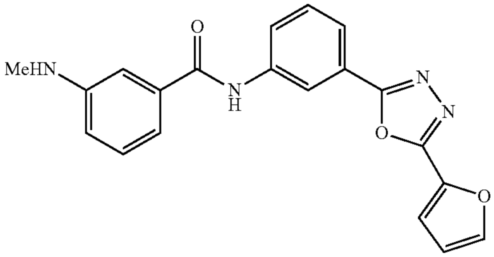 [SMILES: CNc1cccc(C(=O)Nc2cccc(-c3nnc(-c4ccco4)o3)c2)c1] |
| 256 | 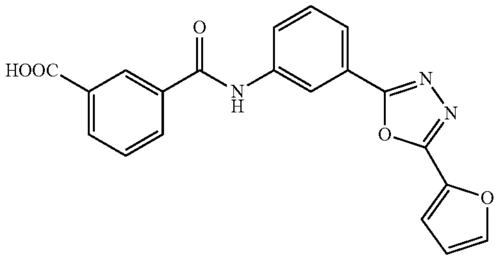 [SMILES: O=C(O)c1cccc(C(=O)Nc2cccc(-c3nnc(-c4ccco4)o3)c2)c1] |
| 257 | 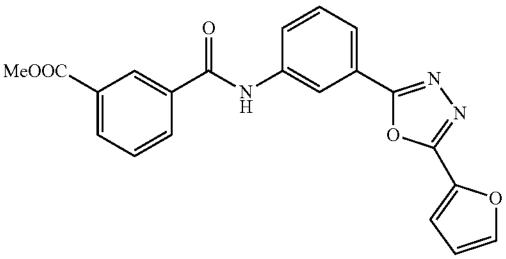 [SMILES: COC(=O)c1cccc(C(=O)Nc2cccc(-c3nnc(-c4ccco4)o3)c2)c1] |
| 258 | 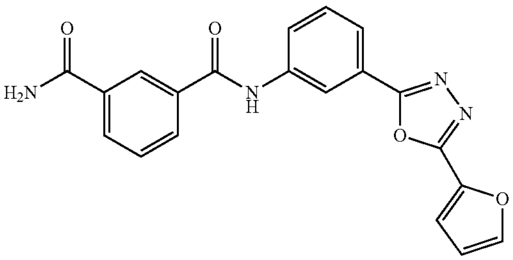 [SMILES: NC(=O)c1cccc(C(=O)Nc2cccc(-c3nnc(-c4ccco4)o3)c2)c1] |

TABLE 1-continued
| Compound Number | Structure |
|---|---|
| 259 | 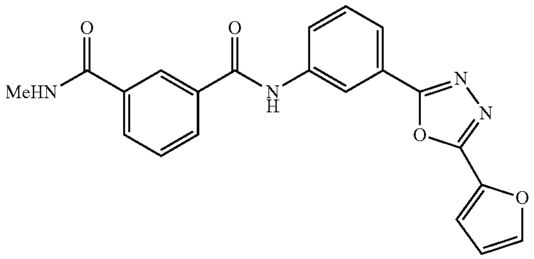 [SMILES: CNC(=O)c1cccc(C(=O)Nc2cccc(-c3nnc(-c4ccco4)o3)c2)c1] |
| 260 | 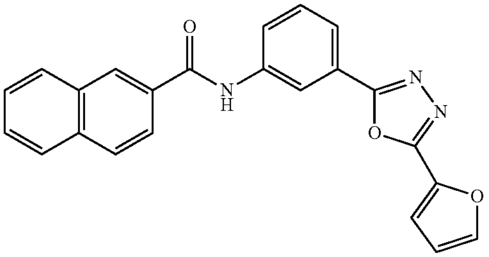 [SMILES: O=C(Nc1cccc(-c2nnc(-c3ccco3)o2)c1)c1ccc2ccccc2c1] |
| 261 | 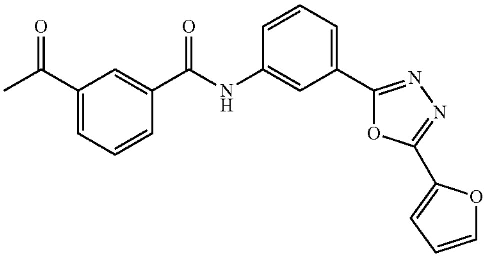 [SMILES: CC(=O)c1cccc(C(=O)Nc2cccc(-c3nnc(-c4ccco4)o3)c2)c1] |
| 262 | 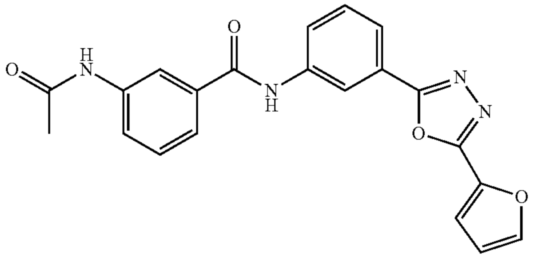 [SMILES: CC(=O)Nc1cccc(C(=O)Nc2cccc(-c3nnc(-c4ccco4)o3)c2)c1] |
| 263 | 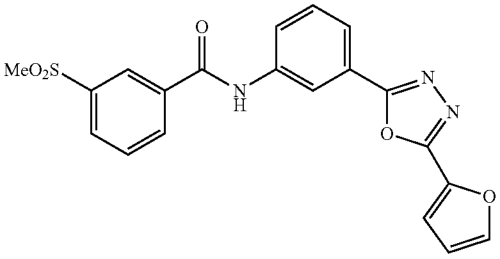 [SMILES: CS(=O)(=O)c1cccc(C(=O)Nc2cccc(-c3nnc(-c4ccco4)o3)c2)c1] |

TABLE 1-continued
| Compound Number | Structure |
| --- | --- |
| 264 | 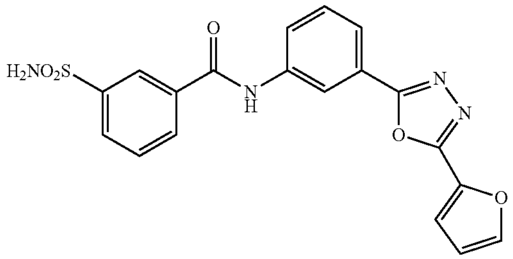 [SMILES: NS(=O)(=O)c1cccc(C(=O)Nc2cccc(-c3nnc(-c4ccco4)o3)c2)c1] |
| 265 | 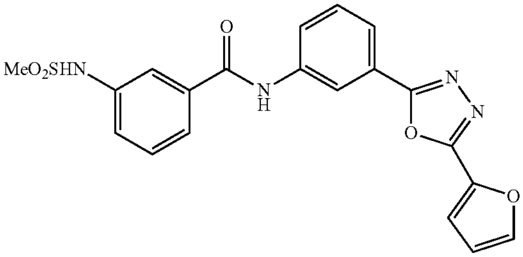 |
| 266 | 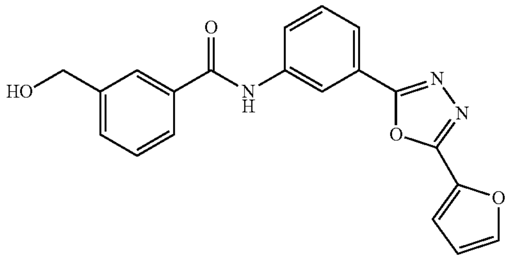 |
| 267 | 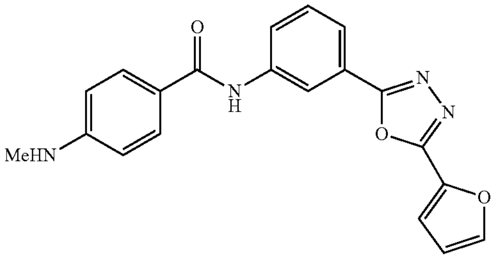 [SMILES: CNc1ccc(C(=O)Nc2cccc(-c3nnc(-c4ccco4)o3)c2)cc1] |
| 268 | 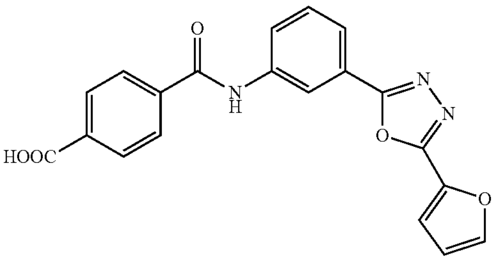 [SMILES: O=C(O)c1ccc(C(=O)Nc2cccc(-c3nnc(-c4ccco4)o3)c2)cc1] |

TABLE 1-continued
| Compound Number | Structure |
|---|---|
| 269 | 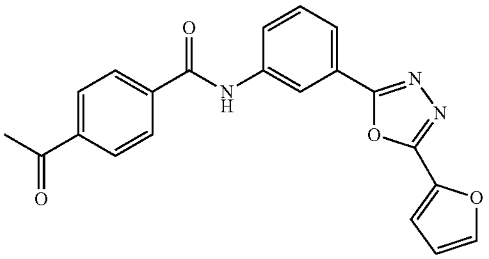 [SMILES: CC(=O)c1ccc(C(=O)Nc2cccc(-c3nnc(-c4ccco4)o3)c2)cc1] |
| 270 | 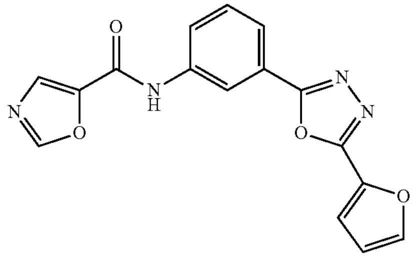 [SMILES: O=C(Nc1cccc(-c2nnc(-c3ccco3)o2)c1)c1cnco1] |
| 271 | 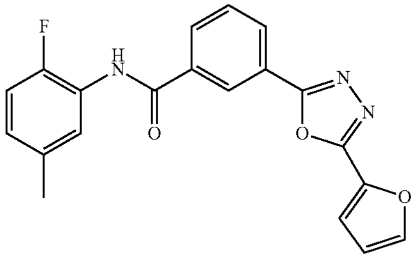 [SMILES: Cc1ccc(F)c(NC(=O)c2cccc(-c3nnc(-c4ccco4)o3)c2)c1] |
| 272 | 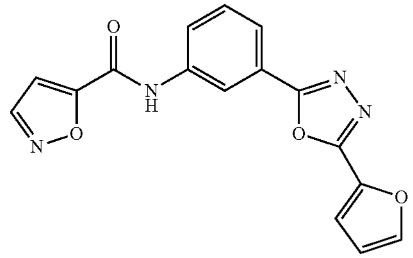 [SMILES: O=C(Nc1cccc(-c2nnc(-c3ccco3)o2)c1)c1ccno1] |
| 273 | 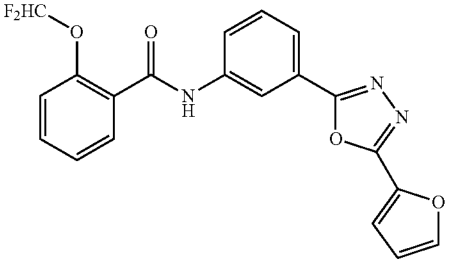 [SMILES: O=C(Nc1cccc(-c2nnc(-c3ccco3)o2)c1)c1ccccc1OC(F)F] |

TABLE 1-continued
| Compound Number | Structure |
| --- | --- |
| 274 | 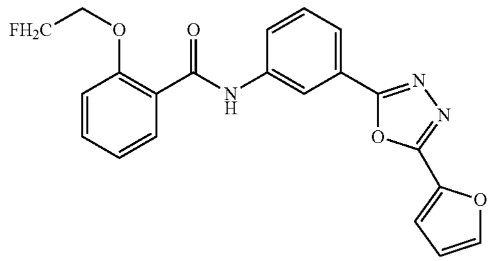 |
| 275 | 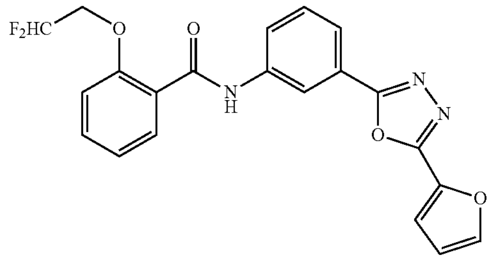 [SMILES: O=C(Nc1cccc(-c2nnc(-c3ccco3)o2)c1)c1ccccc1OCC(F)F] |
| 276 | 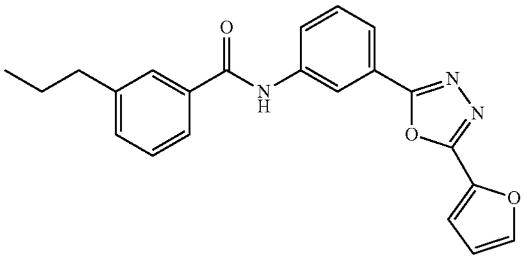 [SMILES: CCCc1cccc(C(=O)Nc2cccc(-c3nnc(-c4ccco4)o3)c2)c1] |
| 277 | 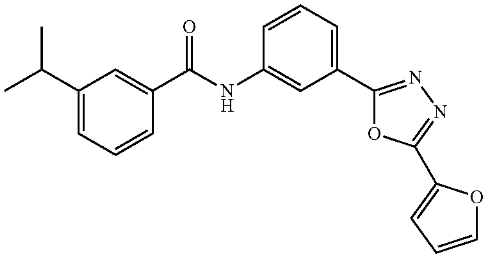 [SMILES: CC(C)c1cccc(C(=O)Nc2cccc(-c3nnc(-c4ccco4)o3)c2)c1] |
| 278 | 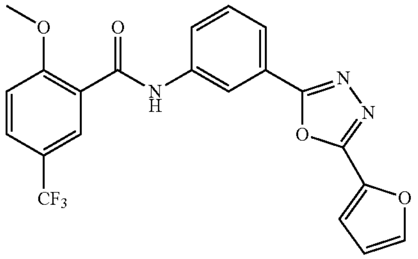 |

TABLE 1-continued
| Compound Number | Structure |
|---|---|
| 279 | 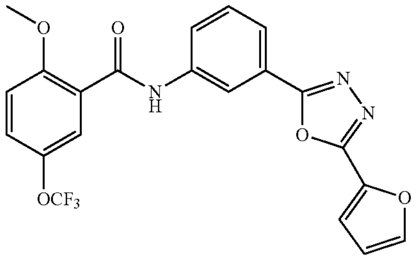 |
| 280 | 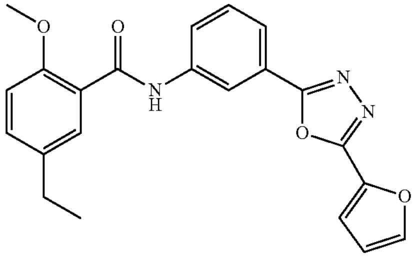 [SMILES: CCc1ccc(OC)c(C(=O)Nc2cccc(-c3nnc(-c4ccco4)o3)c2)c1] |
| 281 | 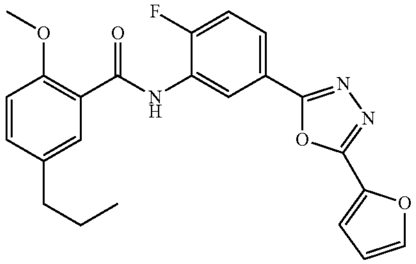 [SMILES: CCCc1ccc(OC)c(C(=O)Nc2cc(-c3nnc(-c4ccco4)o3)ccc2F)c1] |
| 282 | 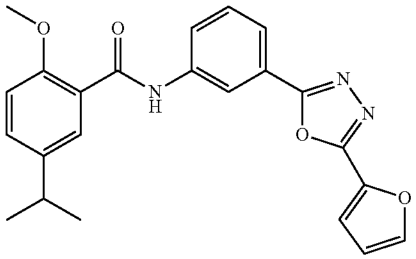 [SMILES: COc1ccc(C(C)C)cc1C(=O)Nc1cccc(-c2nnc(-c3ccco3)o2)c1] |
| 283 | 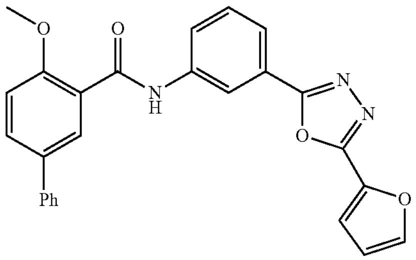 |

TABLE 1-continued
| Compound Number | Structure |
| --- | --- |
| 284 | 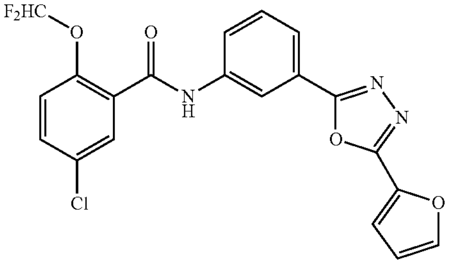 [SMILES: O=C(Nc1cccc(-c2nnc(-c3ccco3)o2)c1)c1cc(Cl)ccc1OC(F)F] |
| 285 | 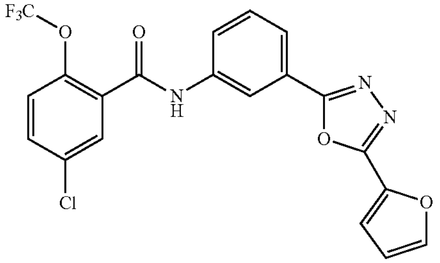 [SMILES: O=C(Nc1cccc(-c2nnc(-c3ccco3)o2)c1)c1cc(Cl)ccc1OC(F)(F)F] |
| 286 | 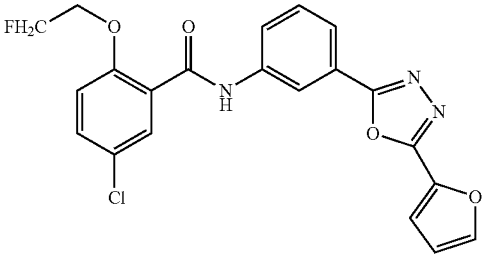 |
| 287 | 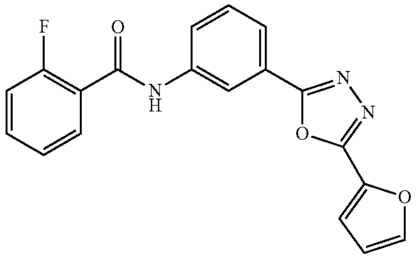 |
| 288 | 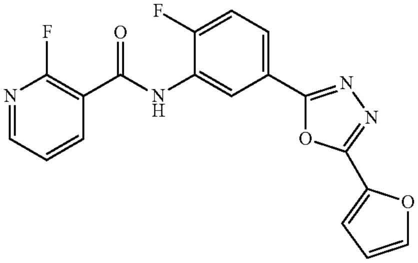 [SMILES: O=C(Nc1cc(-c2nnc(-c3ccco3)o2)ccc1F)c1cccnc1F] |
| 289 | 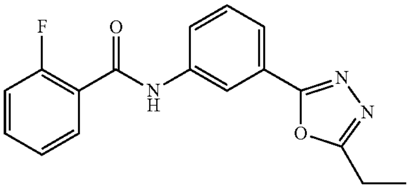 [SMILES: CCc1nnc(-c2cccc(NC(=O)c3ccccc3F)c2)o1] |

TABLE 1-continued
| Compound Number | Structure |
|---|---|
| 290 | 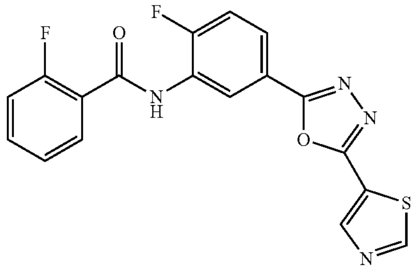 [SMILES: O=C(Nc1cc(-c2nnc(-c3cnco3)o2)ccc1F)c1ccccc1F] |
| 291 | 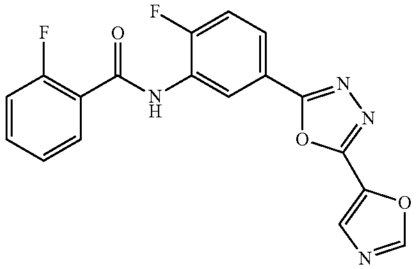 |
| 292 | 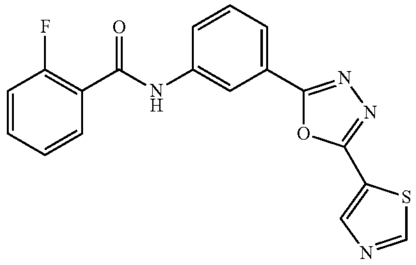 [SMILES: O=C(Nc1cccc(-c2nnc(-c3cncs3)o2)c1)c1ccccc1F] |
| 293 | 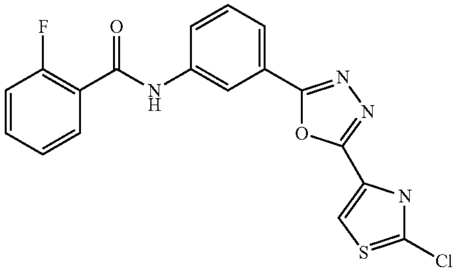 |
| 294 | 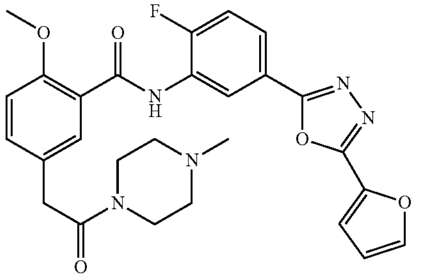 [SMILES: COc1ccc(CC(=O)N2CCN(C)CC2)cc1C(=O)Nc1cc(-c2nnc(-c3ccco3)o2)ccc1F] |

TABLE 1-continued
| Compound Number | Structure |
|---|---|
| 295 | 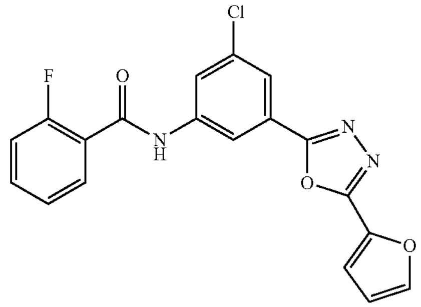 [SMILES: O=C(Nc1cc(Cl)cc(-c2nnc(-c3ccco3)o2)c1)c1ccccc1F] |
| 296 | 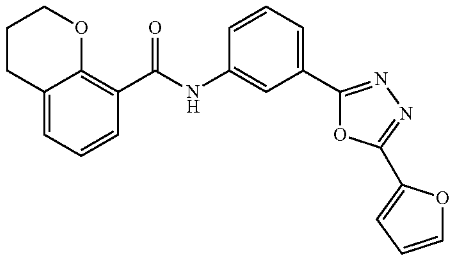 [SMILES: O=C(Nc1cccc(-c2nnc(-c3ccco3)o2)c1)c1cccc2c1OCCC2] |
| 297 | 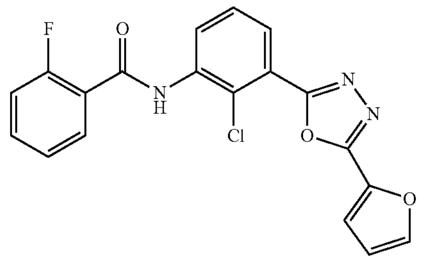 |
| 298 | 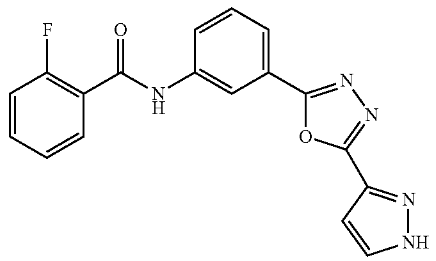 [SMILES: O=C(Nc1cccc(-c2nnc(-c3cc[nH]n3)o2)c1)c1ccccc1F] |
| 299 | 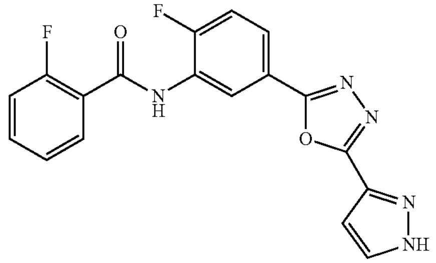 [SMILES: O=C(Nc1cc(-c2nnc(-c3cc[nH]n3)o2)ccc1F)c1ccccc1F] |

TABLE 1-continued
| Compound Number | Structure |
|---|---|
| 300 | 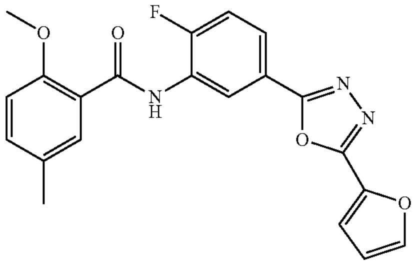 [SMILES: COc1ccc(C)cc1C(=O)Nc1cc(-c2nnc(-c3ccco3)o2)ccc1F] |
| 301 | 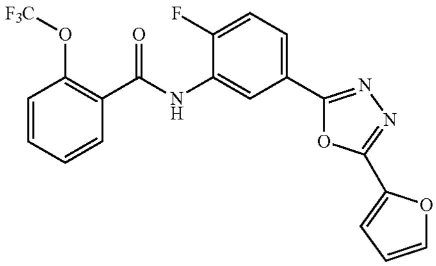 [SMILES: O=C(Nc1cc(-c2nnc(-c3ccco3)o2)ccc1F)c1ccccc1OC(F)(F)F] |
| 302 | 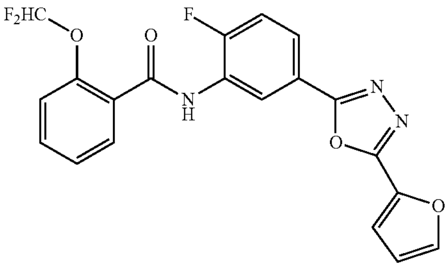 [SMILES: O=C(Nc1cc(-c2nnc(-c3ccco3)o2)ccc1F)c1ccccc1OC(F)F] |
| 303 | 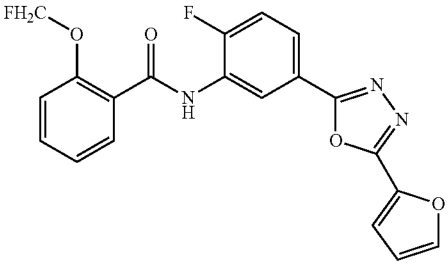 |
| 304 | 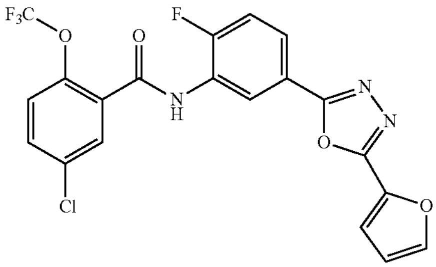 [SMILES: O=C(Nc1cc(-c2nnc(-c3ccco3)o2)ccc1F)c1cc(Cl)ccc1OC(F)(F)F] |

TABLE 1-continued
| Compound Number | Structure |
|---|---|
| 305 | 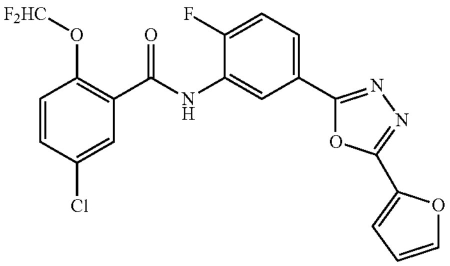 [SMILES: O=C(Nc1cc(-c2nnc(-c3ccco3)o2)ccc1F)c1cc(Cl)ccc1OC(F)F] |
| 306 | 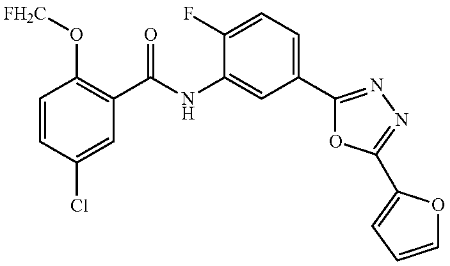 |
| 307 | 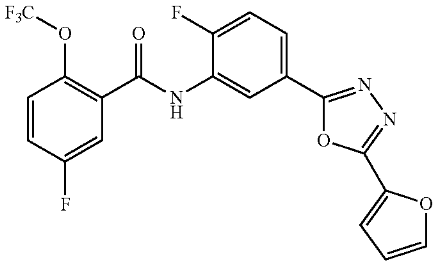 [SMILES: O=C(Nc1cc(-c2nnc(-c3ccco3)o2)ccc1F)c1cc(F)ccc1OC(F)(F)F] |
| 308 | 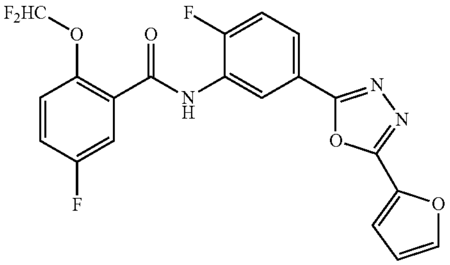 [SMILES: O=C(Nc1cc(-c2nnc(-c3ccco3)o2)ccc1F)c1cc(F)ccc1OC(F)F] |
| 309 | 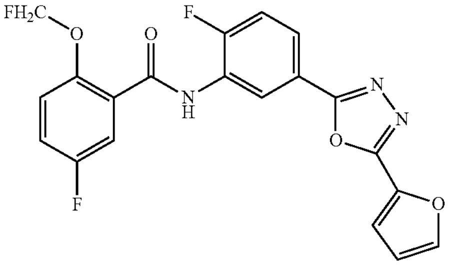 |

TABLE 1-continued
| Compound Number | Structure |
| --- | --- |
| 310 | 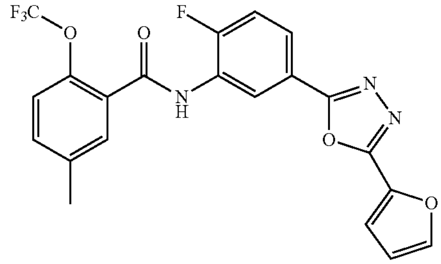 [SMILES: Cc1ccc(OC(F)(F)F)c(C(=O)Nc2cc(-c3nnc(-c4ccco4)o3)ccc2F)c1] |
| 311 | 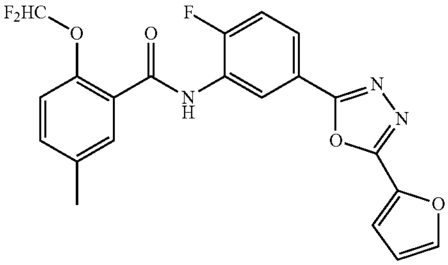 [SMILES: Cc1ccc(OC(F)F)c(C(=O)Nc2cc(-c3nnc(-c4ccco4)o3)ccc2F)c1] |
| 312 | 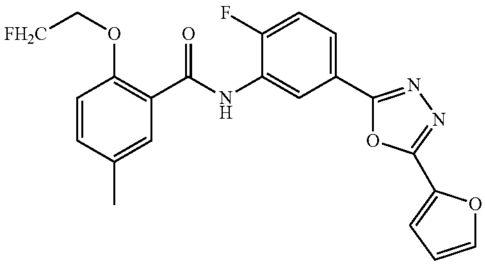 |
| 313 | 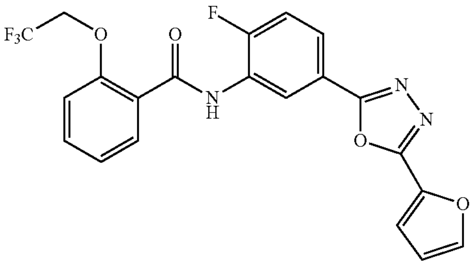 [SMILES: O=C(Nc1cc(-c2nnc(-c3ccco3)o2)ccc1F)c1ccccc1OCC(F)(F)F] |
| 314 | 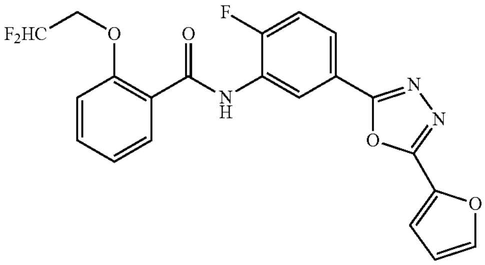 [SMILES: O=C(Nc1cc(-c2nnc(-c3ccco3)o2)ccc1F)c1ccccc1OCC(F)F] |

TABLE 1-continued
| Compound Number | Structure |
|---|---|
| 315 | 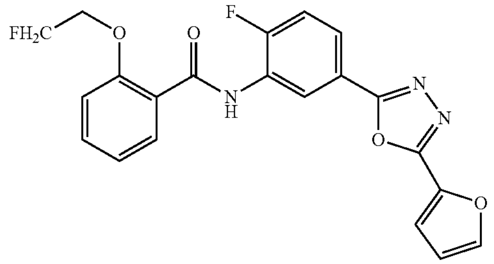 |
| 316 | 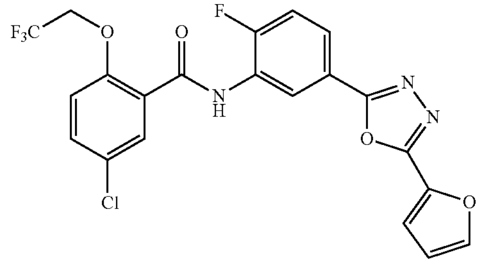 [SMILES: O=C(Nc1cc(-c2nnc(-c3ccco3)o2)ccc1F)c1cc(Cl)ccc1OCC(F)(F)F] |
| 317 | 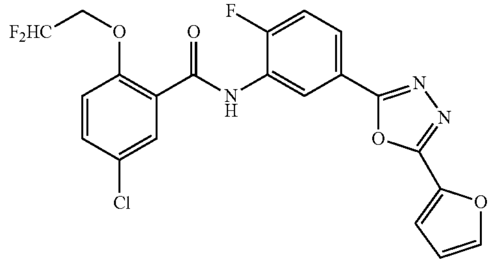 [SMILES: O=C(Nc1cc(-c2nnc(-c3ccco3)o2)ccc1F)c1cc(Cl)ccc1OCC(F)F] |
| 318 | 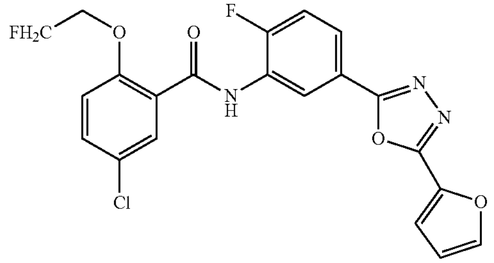 |
| 319 | 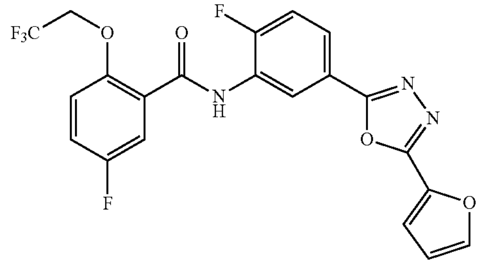 [SMILES: O=C(Nc1cc(-c2nnc(-c3ccco3)o2)ccc1F)c1cc(F)ccc1OCC(F)(F)F] |

TABLE 1-continued
| Compound Number | Structure |
| --- | --- |
| 320 | 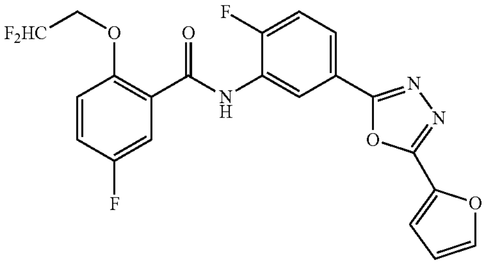 [SMILES: O=C(Nc1cc(-c2nnc(-c3ccco3)o2)ccc1F)c1cc(F)ccc1OCC(F)F] |
| 321 | 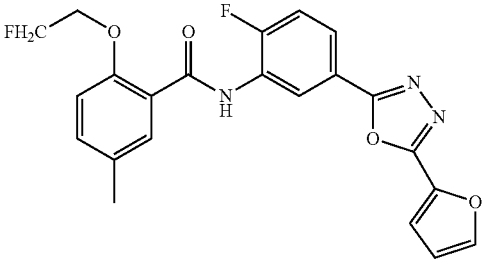 |
| 322 | 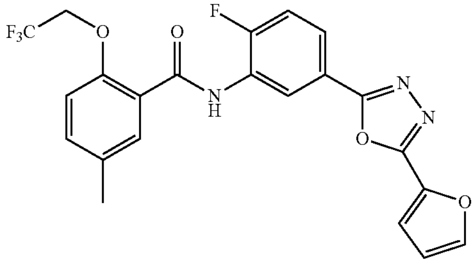 [SMILES: Cc1ccc(OCC(F)(F)F)c(C(=O)Nc2cc(-c3nnc(-c4ccco4)o3)ccc2F)c1] |
| 323 | 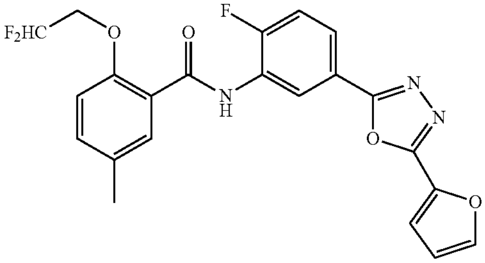 [SMILES: Cc1ccc(OCC(F)F)c(C(=O)Nc2cc(-c3nnc(-c4ccco4)o3)ccc2F)c1] |
| 324 | 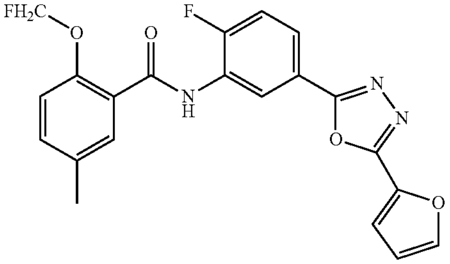 |

TABLE 1-continued
| Compound Number | Structure |
|---|---|
| 325 | 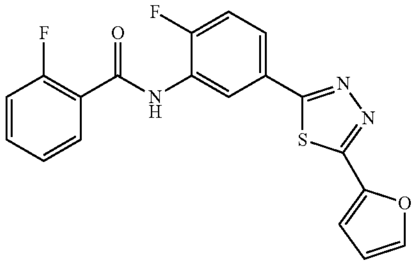 |
| 326 | 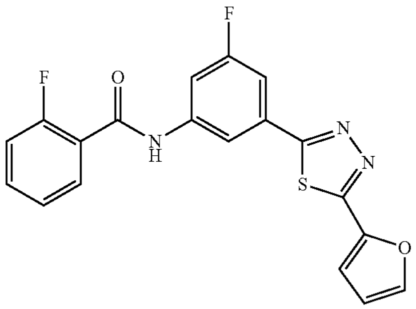 [SMILES: O=C(Nc1cc(F)cc(-c2nnc(-c3ccco3)s2)c1)c1ccccc1F] |
| 327 | 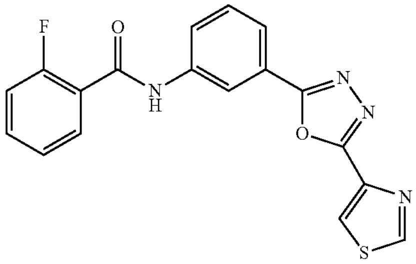 [SMILES: O=C(Nc1cccc(-c2nnc(-c3cscn3)o2)c1)c1ccccc1F] |
| 328 | 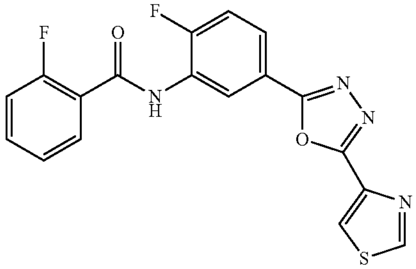 [SMILES: O=C(Nc1cc(-c2nnc(-c3cscn3)o2)ccc1F)c1ccccc1F] |
| 329 | 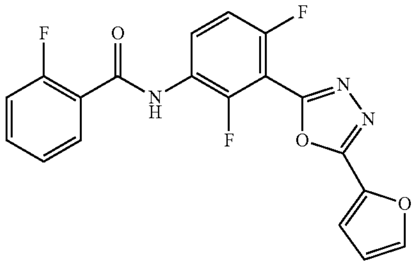 [SMILES: O=C(Nc1ccc(F)c(-c2nnc(-c3ccco3)o2)c1F)c1ccccc1F] |

TABLE 1-continued
| Compound Number | Structure |
|---|---|
| 330 | 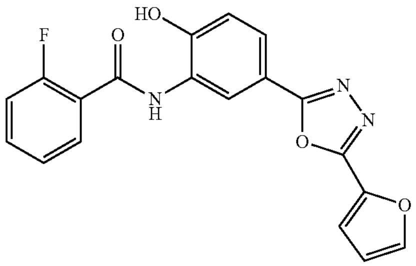 [SMILES: O=C(Nc1cc(-c2nnc(-c3ccco3)o2)ccc1O)c1ccccc1F] |
| 331 | 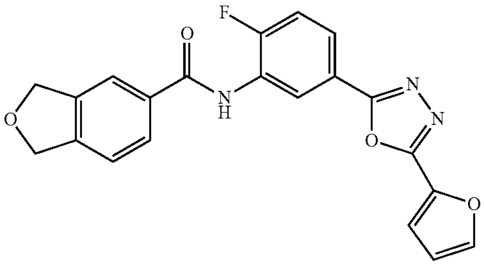 [SMILES: O=C(Nc1cc(-c2nnc(-c3ccco3)o2)ccc1F)c1ccc2c(c1)COC2] |
| 332 | 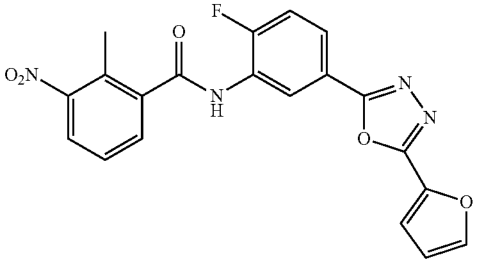 |
| 333 | 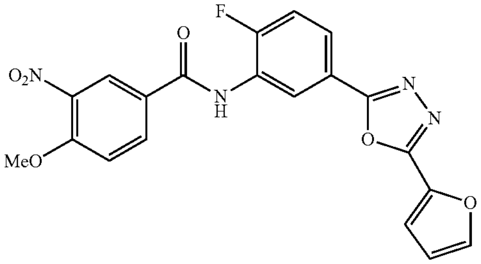 [SMILES: COc1ccc(C(=O)Nc2cc(-c3nnc(-c4ccco4)o3)ccc2F)cc1[N+](=O)[O-]] |
| 334 | 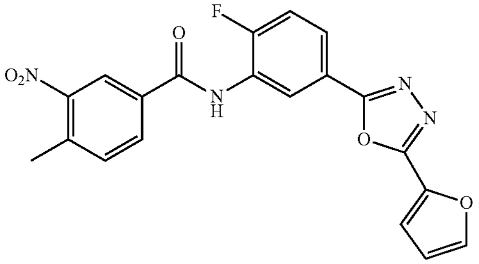 [SMILES: Cc1ccc(C(=O)Nc2cc(-c3nnc(-c4ccco4)o3)ccc2F)cc1[N+](=O)[O-]] |

TABLE 1-continued
| Compound Number | Structure |
|---|---|
| 335 | 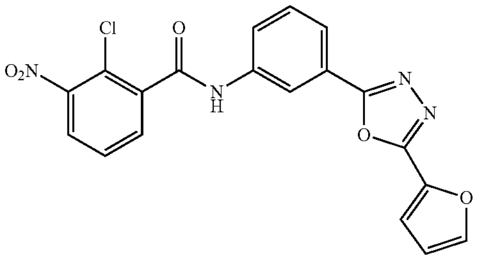 [SMILES: O=C(Nc1cccc(-c2nnc(-c3ccco3)o2)c1)c1cccc([N+](=O)[O-])c1Cl] |
| 336 | 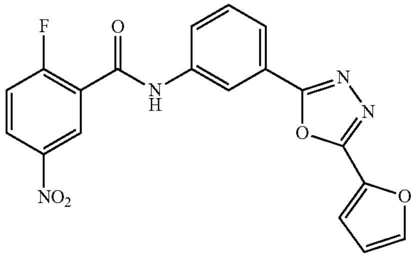 [SMILES: O=C(Nc1cccc(-c2nnc(-c3ccco3)o2)c1)c1cc([N+](=O)[O-])ccc1F] |
| 337 | 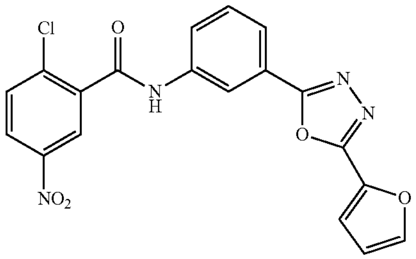 [SMILES: O=C(Nc1cccc(-c2nnc(-c3ccco3)o2)c1)c1cc([N+](=O)[O-])ccc1Cl] |
| 338 | 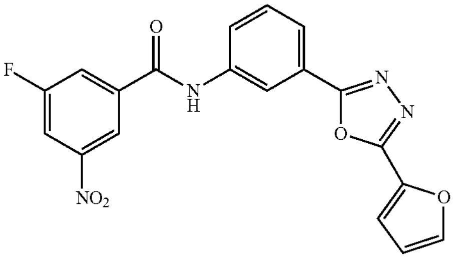 [SMILES: O=C(Nc1cccc(-c2nnc(-c3ccco3)o2)c1)c1cc(F)cc([N+](=O)[O-])c1] |
| 339 | 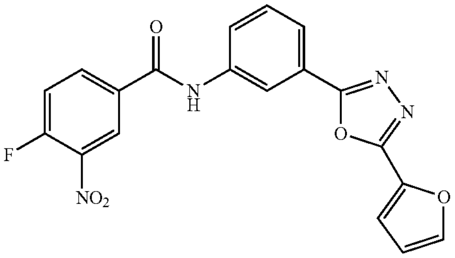 [SMILES: O=C(Nc1cccc(-c2nnc(-c3ccco3)o2)c1)c1ccc(F)c([N+](=O)[O-])c1] |

TABLE 1-continued
| Compound Number | Structure |
|---|---|
| 340 | 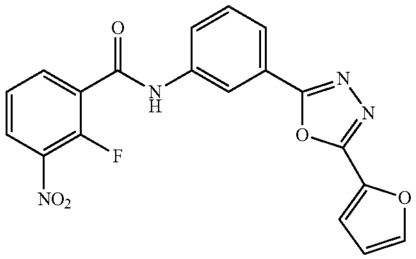 [SMILES: O=C(Nc1cccc(-c2nnc(-c3ccco3)o2)c1)c1cccc([N+](=O)[O-])c1F] |
| 341 | 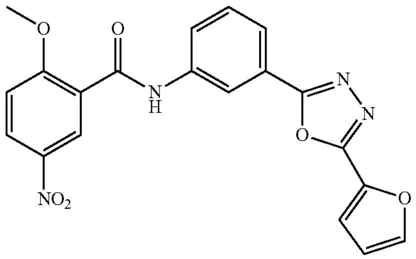 [SMILES: COc1ccc([N+](=O)[O-])cc1C(=O)Nc1cccc(-c2nnc(-c3ccco3)o2)c1] |
| 342 | 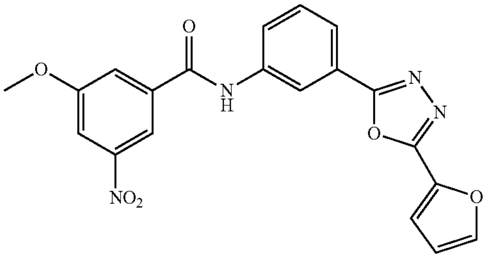 [SMILES: COc1cc(C(=O)Nc2cccc(-c3nnc(-c4ccco4)o3)c2)cc([N+](=O)[O-])c1] |
| 343 | 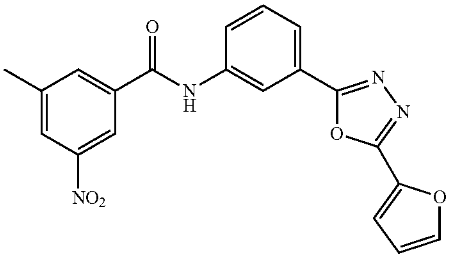 [SMILES: Cc1cc(C(=O)Nc2cccc(-c3nnc(-c4ccco4)o3)c2)cc([N+](=O)[O-])c1] |
| 344 | 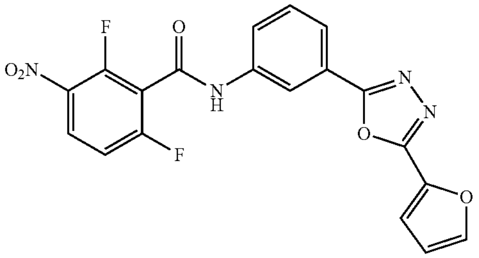 [SMILES: O=C(Nc1cccc(-c2nnc(-c3ccco3)o2)c1)c1c(F)ccc([N+](=O)[O-])c1F] |

TABLE 1-continued
| Compound Number | Structure |
| --- | --- |
| 345 | 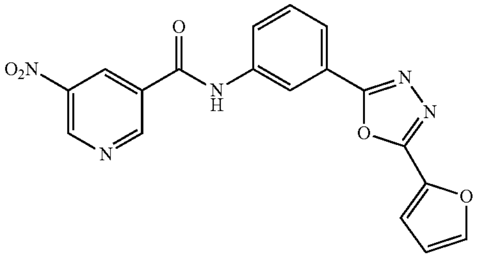 [SMILES: O=C(Nc1cccc(-c2nnc(-c3ccco3)o2)c1)c1cncc([N+](=O)[O-])c1] |
| 346 | 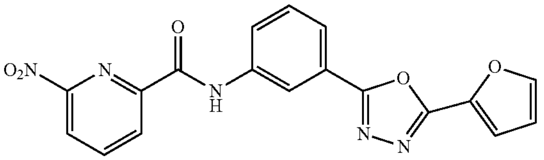 [SMILES: O=C(Nc1cccc(-c2nnc(-c3ccco3)o2)c1)c1cccc([N+](=O)[O-])n1] |
| 347 | 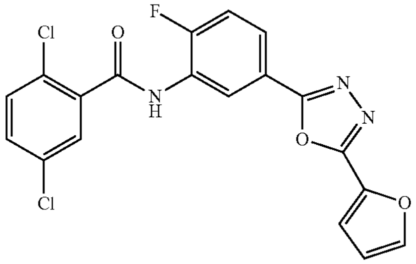 [SMILES: O=C(Nc1cc(-c2nnc(-c3ccco3)o2)ccc1F)c1cc(Cl)ccc1Cl] |
| 348 | 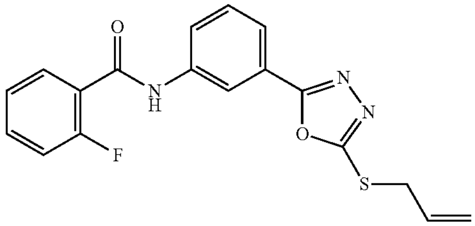 [SMILES: C=CCSc1nnc(-c2cccc(NC(=O)c3ccccc3F)c2)o1] |
| 349 | 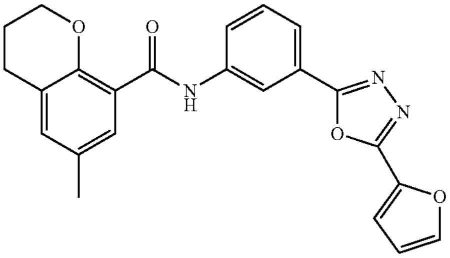 [SMILES: Cc1cc2c(c(C(=O)Nc3cccc(-c4nnc(-c5ccco5)o4)c3)c1)OCCC2] |
| 350 | 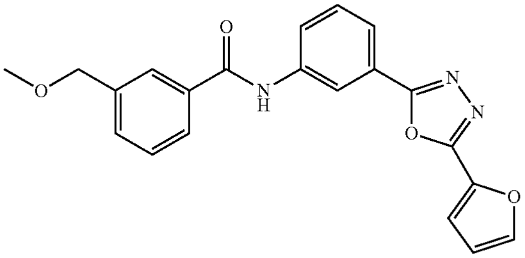 |

TABLE 1-continued
| Compound Number | Structure |
|---|---|
| 351 | 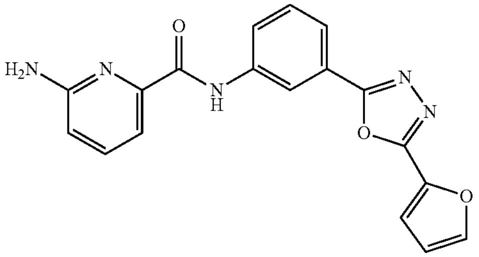 [SMILES: Nc1cccc(C(=O)Nc2cccc(-c3nnc(-c4ccco4)o3)c2)n1] |
| 352 | 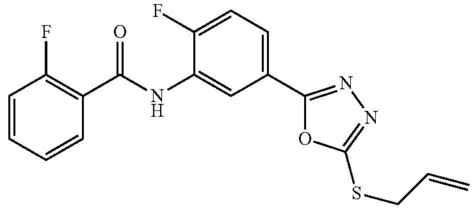 [SMILES: C=CCSc1nnc(-c2ccc(F)c(NC(=O)c3ccccc3F)c2)o1] |
| 353 | 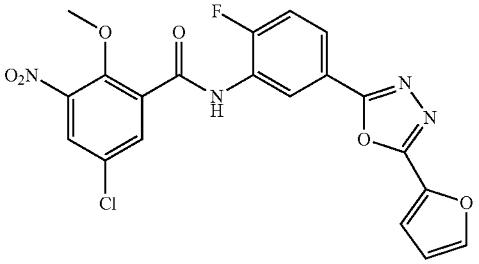 |
| 354 | 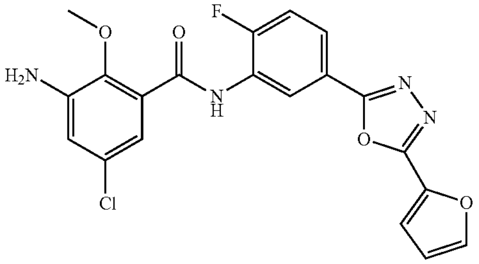 [SMILES: COc1c(C(=O)Nc2cc(-c3nnc(-c4ccco4)o3)ccc2F)cc(Cl)cc1[N+](=O)[O-]] |
| 355 | 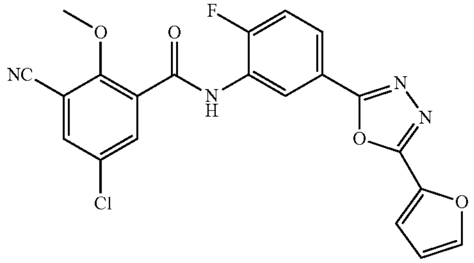 [SMILES: COc1c(C#N)cc(Cl)cc1C(=O)Nc1cc(-c2nnc(-c3ccco3)o2)ccc1F] |
| 356 | 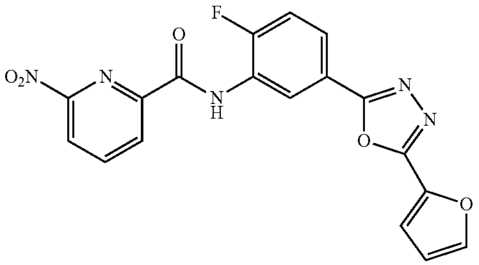 [SMILES: O=C(Nc1cc(-c2nnc(-c3ccco3)o2)ccc1F)c1cccc([N+](=O)[O-])n1] |

TABLE 1-continued
| Compound Number | Structure |
|---|---|
| 357 | 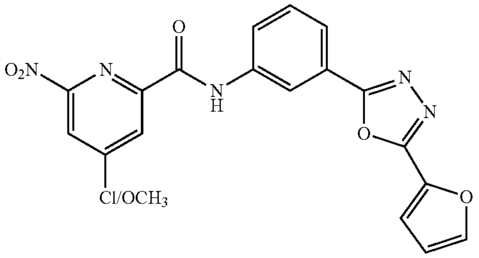 |
| 358 | 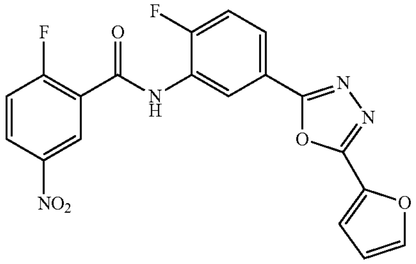 [SMILES: O=C(Nc1cc(-c2nnc(-c3ccco3)o2)ccc1F)c1cc([N+](=O)[O-])ccc1F] |
| 359 | 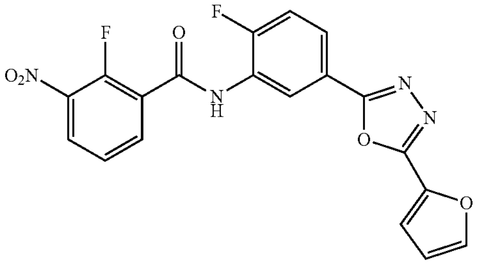 [SMILES: O=C(Nc1cc(-c2nnc(-c3ccco3)o2)ccc1F)c1cccc([N+](=O)[O-])c1F] |
| 360 | 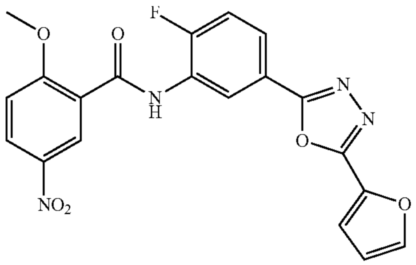 [SMILES: COc1ccc([N+](=O)[O-])cc1C(=O)Nc1cc(-c2nnc(-c3ccco3)o2)ccc1F] |
| 361 | 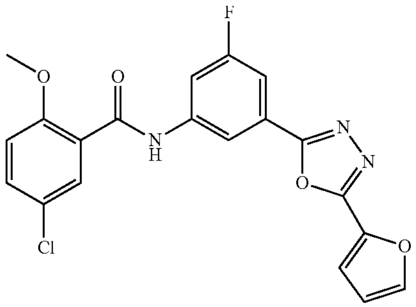 [SMILES: COc1ccc(Cl)cc1C(=O)Nc1cc(F)cc(-c2nnc(-c3ccco3)o2)c1] |

TABLE 1-continued
| Compound Number | Structure |
|---|---|
| 362 | 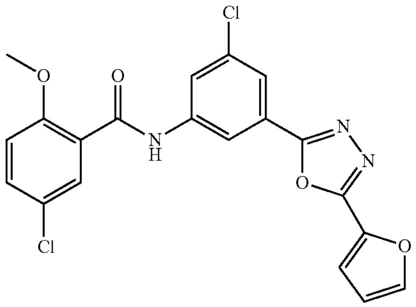 |
| 363 | 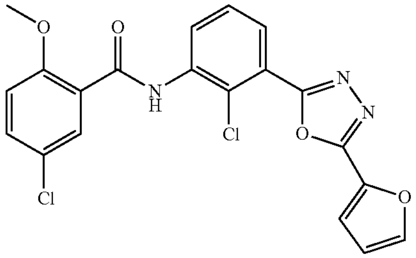 [SMILES: COc1ccc(Cl)cc1C(=O)Nc1cccc(-c2nnc(-c3ccco3)o2)c1Cl] |
| 364 | 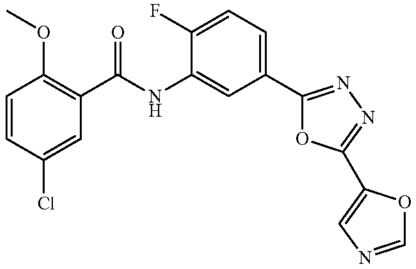 [SMILES: COc1ccc(Cl)cc1C(=O)Nc1cc(-c2nnc(-c3cnco3)o2)ccc1F] |
| 365 | 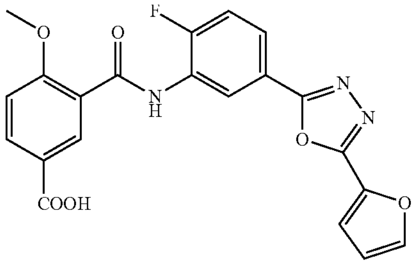 [SMILES: COc1ccc(C(=O)O)cc1C(=O)Nc1cc(-c2nnc(-c3ccco3)o2)ccc1F] |
| 366 | 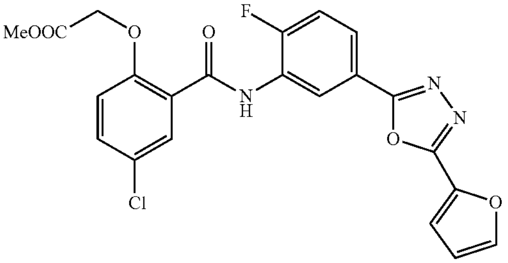 [SMILES: COC(=O)COc1ccc(Cl)cc1C(=O)Nc1cc(-c2nnc(-c3ccco3)o2)ccc1F] |

TABLE 1-continued
| Compound Number | Structure |
|---|---|
| 367 | 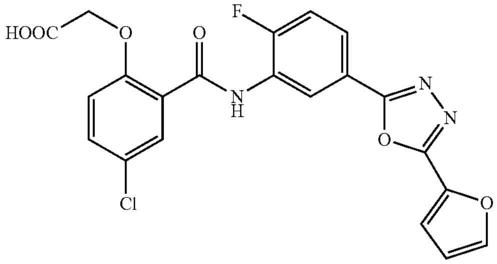 [SMILES: O=C(O)COc1ccc(Cl)cc1C(=O)Nc1cc(-c2nnc(-c3ccco3)o2)ccc1F] |
| 368 | 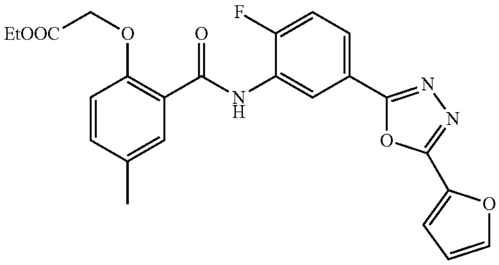 [SMILES: CCOC(=O)COc1ccc(C)cc1C(=O)Nc1cc(-c2nnc(-c3ccco3)o2)ccc1F] |
| 369 | 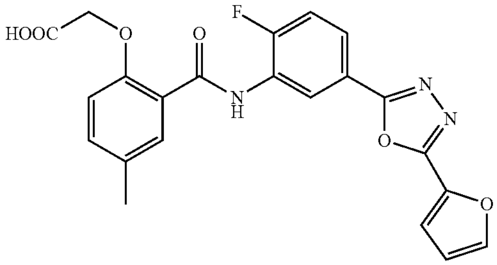 [SMILES: Cc1ccc(OCC(=O)O)c(C(=O)Nc2cc(-c3nnc(-c4ccco4)o3)ccc2F)c1] |
| 370 | 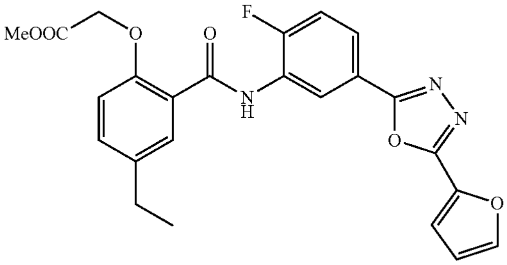 [SMILES: CCc1ccc(OCC(=O)OC)c(C(=O)Nc2cc(-c3nnc(-c4ccco4)o3)ccc2F)c1] |
| 371 | 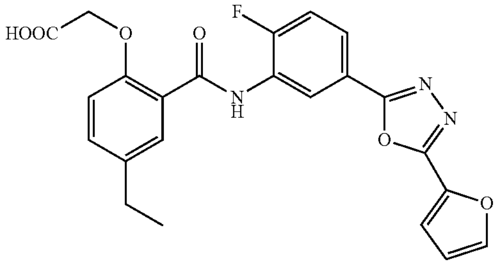 [SMILES: CCc1ccc(OCC(=O)O)c(C(=O)Nc2cc(-c3nnc(-c4ccco4)o3)ccc2F)c1] |

TABLE 1-continued
| Compound Number | Structure |
|---|---|
| 372 | 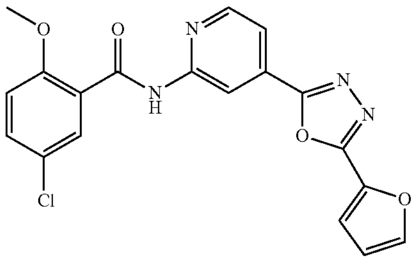 [SMILES: COc1ccc(Cl)cc1C(=O)Nc1cc(-c2nnc(-c3ccco3)o2)ccn1] |
| 373 | 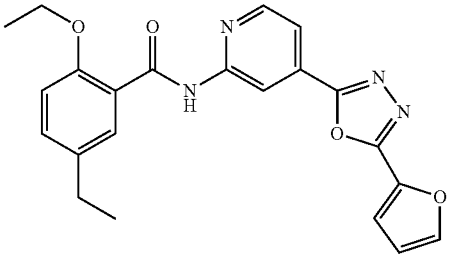 |
| 374 | 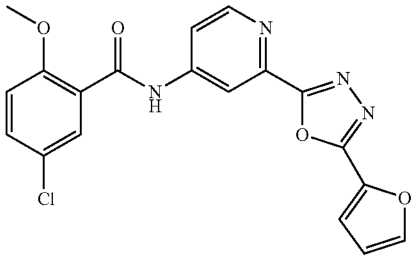 [SMILES: COc1ccc(Cl)cc1C(=O)Nc1ccnc(-c2nnc(-c3ccco3)o2)c1] |
| 375 | 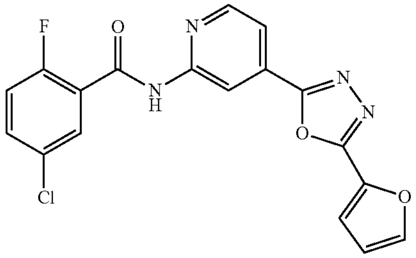 [SMILES: O=C(Nc1cc(-c2nnc(-c3ccco3)o2)ccn1)c1cc(Cl)ccc1F] |
| 376 | 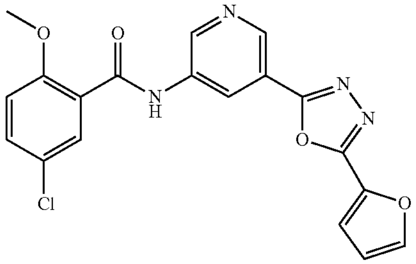 [SMILES: COc1ccc(Cl)cc1C(=O)Nc1cncc(-c2nnc(-c3ccco3)o2)c1] |

TABLE 1-continued
| Compound Number | Structure |
|---|---|
| 377 | 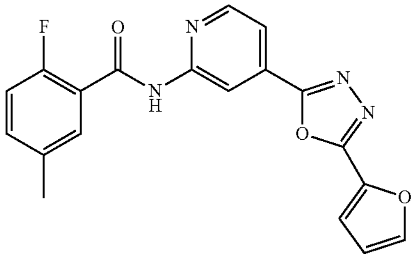 [SMILES: Cc1ccc(F)c(C(=O)Nc2cc(-c3nnc(-c4ccco4)o3)ccn2)c1] |
| 378 | 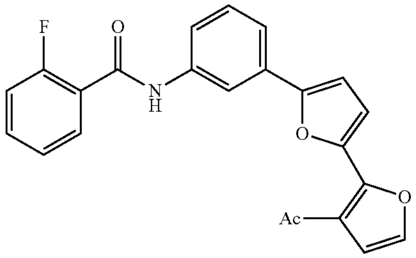 [SMILES: CC(=O)c1ccoc1-c1ccc(-c2cccc(NC(=O)c3ccccc3F)c2)o1] |
| 379 | 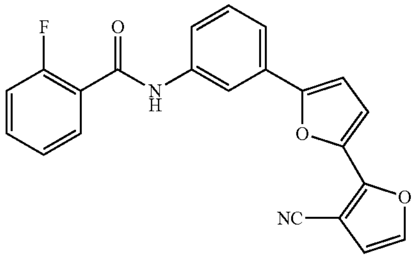 [SMILES: N#Cc1ccoc1-c1ccc(-c2cccc(NC(=O)c3ccccc3F)c2)o1] |
| 380 | 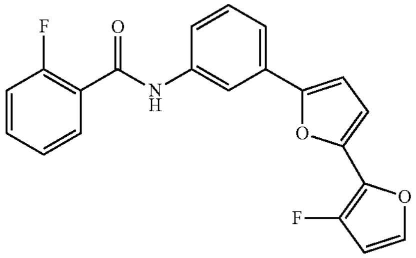 [SMILES: O=C(Nc1cccc(-c2ccc(-c3occc3F)o2)c1)c1ccccc1F] |
| 381 | 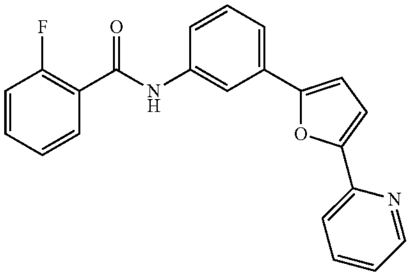 [SMILES: O=C(Nc1cccc(-c2ccc(-c3ccccn3)o2)c1)c1ccccc1F] |

TABLE 1-continued
| Compound Number | Structure |
|---|---|
| 382 | 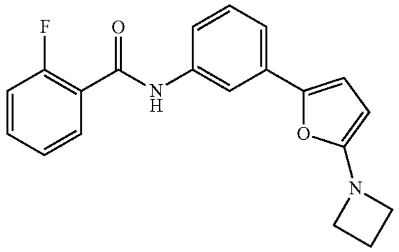 [SMILES: O=C(Nc1cccc(-c2ccc(N3CCC3)o2)c1)c1ccccc1F] |
| 383 | 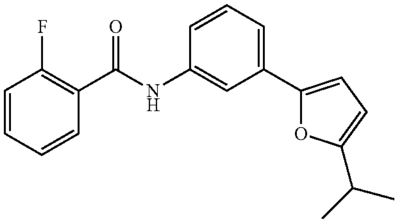 [SMILES: CC(C)c1ccc(-c2cccc(NC(=O)c3ccccc3F)c2)o1] |
| 384 | 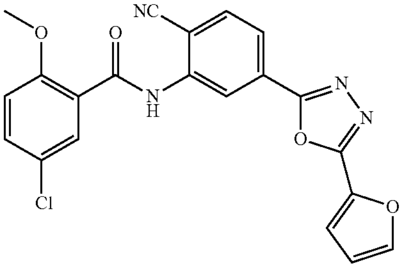 [SMILES: COc1ccc(Cl)cc1C(=O)Nc1cc(-c2nnc(-c3ccco3)o2)ccc1C#N] |
| 385 | 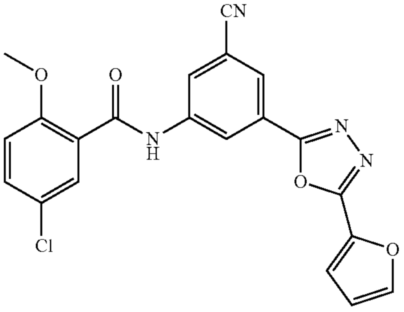 [SMILES: COc1ccc(Cl)cc1C(=O)Nc1cc(C#N)cc(-c2nnc(-c3ccco3)o2)c1] |
| 386 | 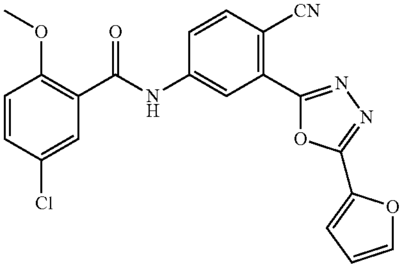 [SMILES: COc1ccc(Cl)cc1C(=O)Nc1ccc(C#N)c(-c2nnc(-c3ccco3)o2)c1] |

TABLE 1-continued
| Compound Number | Structure |
|---|---|
| 387 | 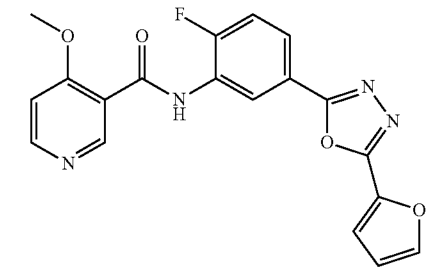 |
| 388 | 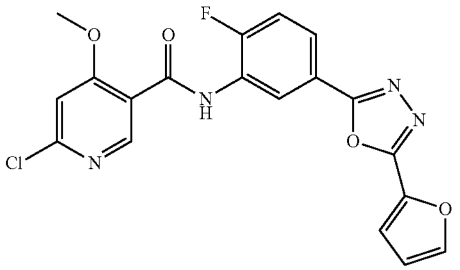 [SMILES: COc1cc(Cl)ncc1C(=O)Nc1cc(-c2nnc(-c3ccco3)o2)ccc1F] |
| 389 | 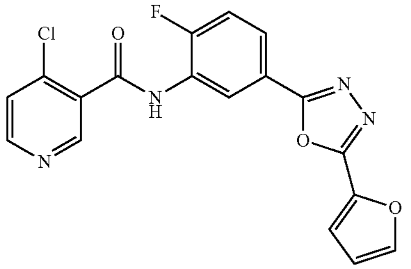 [SMILES: O=C(Nc1cc(-c2nnc(-c3ccco3)o2)ccc1F)c1cnccc1Cl] |
| 390 | 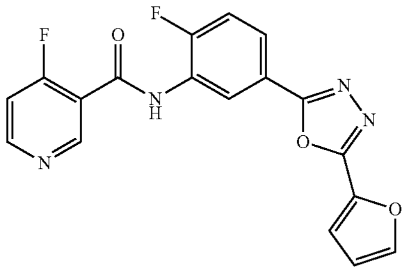 [SMILES: O=C(Nc1cc(-c2nnc(-c3ccco3)o2)ccc1F)c1cnccc1F] |
| 391 | 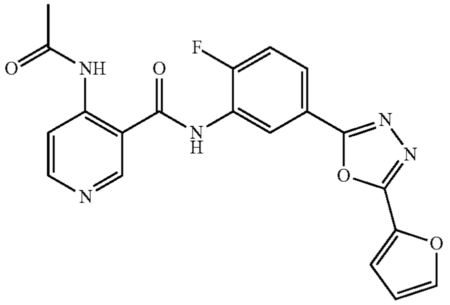 [SMILES: CC(=O)Nc1ccncc1C(=O)Nc1cc(-c2nnc(-c3ccco3)o2)ccc1F] |

TABLE 1-continued
| Compound Number | Structure |
| --- | --- |
| 392 | 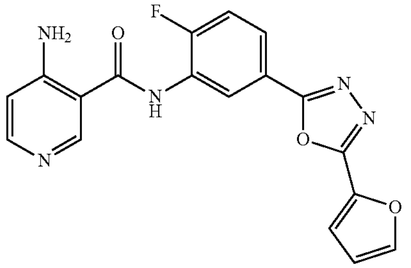 [SMILES: Nc1ccncc1C(=O)Nc1cc(-c2nnc(-c3ccco3)o2)ccc1F] |
| 393 | 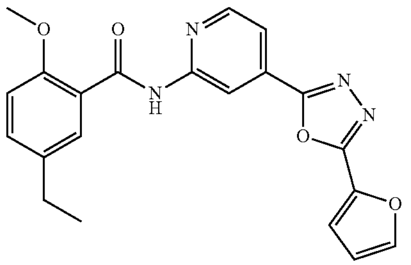 [SMILES: CCc1ccc(OC)c(C(=O)Nc2cc(-c3nnc(-c4ccco4)o3)ccn2)c1] |
| 394 | 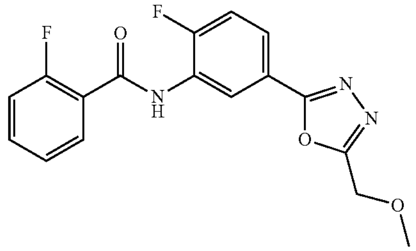 [SMILES: COCc1nnc(-c2ccc(F)c(NC(=O)c3ccccc3F)c2)o1] |
| 395 | 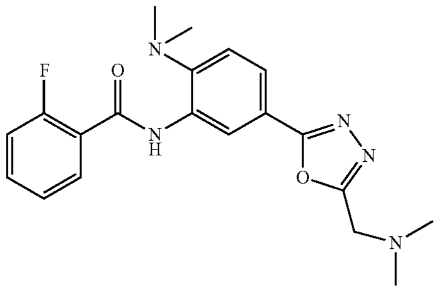 [SMILES: CN(C)Cc1nnc(-c2ccc(N(C)C)c(NC(=O)c3ccccc3F)c2)o1] |
| 396 | 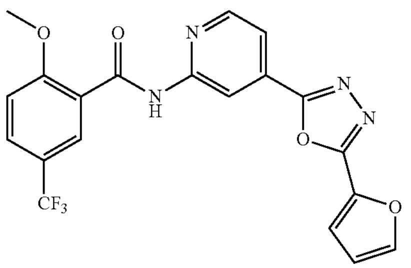 |

TABLE 1-continued
| Compound Number | Structure |
|---|---|
| 397 | 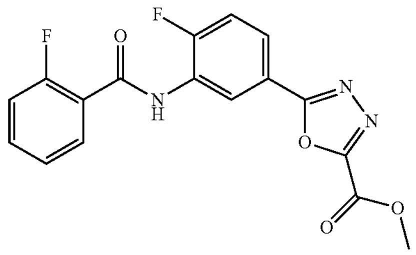 [SMILES: COC(=O)c1nnc(-c2ccc(F)c(NC(=O)c3ccccc3F)c2)o1] |
| 398 | 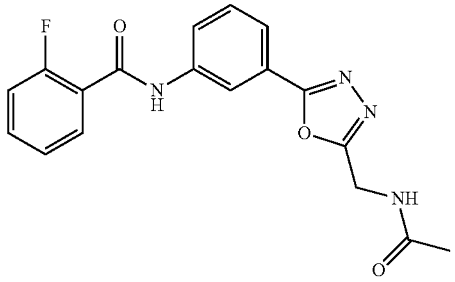 [SMILES: CC(=O)NCc1nnc(-c2cccc(NC(=O)c3ccccc3F)c2)o1] |
| 399 | 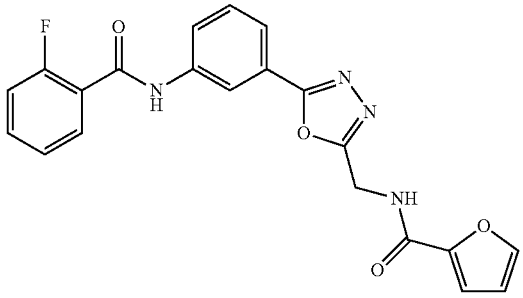 [SMILES: O=C(NCc1nnc(-c2cccc(NC(=O)c3ccccc3F)c2)o1)c1ccco1] |
| 400 | 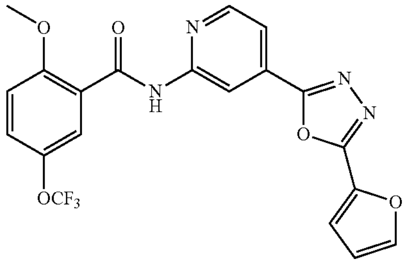 [SMILES: COc1ccc(OC(F)(F)F)cc1C(=O)Nc1cc(-c2nnc(-c3ccco3)o2)ccn1] |
| 401 | 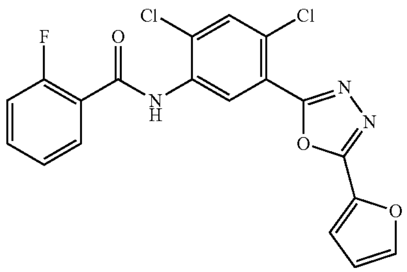 [SMILES: O=C(Nc1cc(-c2nnc(-c3ccco3)o2)c(Cl)cc1Cl)c1ccccc1F] |

TABLE 1-continued
| Compound Number | Structure |
|---|---|
| 402 | 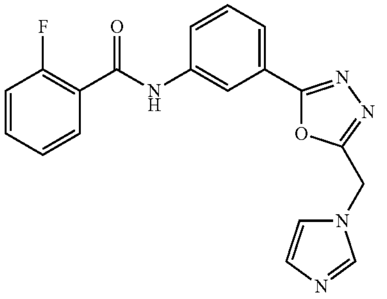 [SMILES: O=C(Nc1cccc(-c2nnc(Cn3ccnc3)o2)c1)c1ccccc1F] |
| 403 | 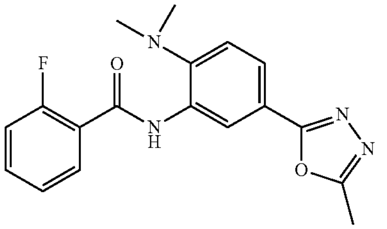 [SMILES: Cc1nnc(-c2ccc(N(C)C)c(NC(=O)c3ccccc3F)c2)o1] |
| 404 | 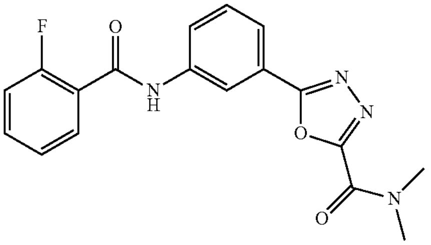 [SMILES: CN(C)C(=O)c1nnc(-c2cccc(NC(=O)c3ccccc3F)c2)o1] |
| 405 | 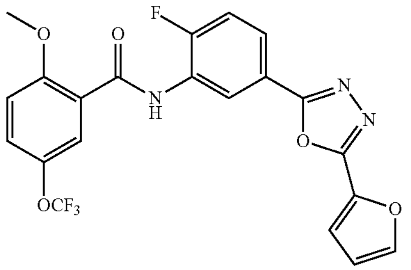 |
| 406 | 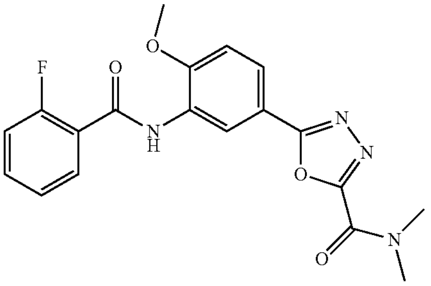 [SMILES: COc1ccc(-c2nnc(C(=O)N(C)C)o2)cc1NC(=O)c1ccccc1F] |
| 407 | 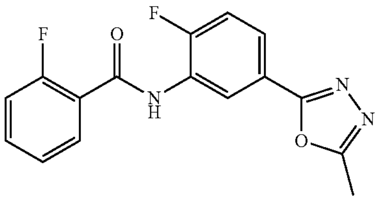 [SMILES: Cc1nnc(-c2ccc(F)c(NC(=O)c3ccccc3F)c2)o1] |

TABLE 1-continued
| Compound Number | Structure |
|---|---|
| 408 | 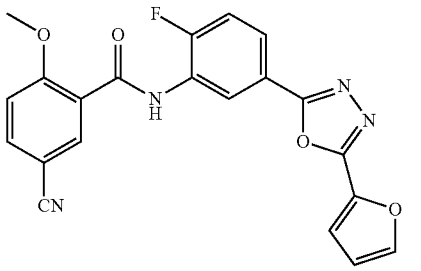 [SMILES: COc1ccc(C#N)cc1C(=O)Nc1cc(-c2nnc(-c3ccco3)o2)ccc1F] |
| 409 | 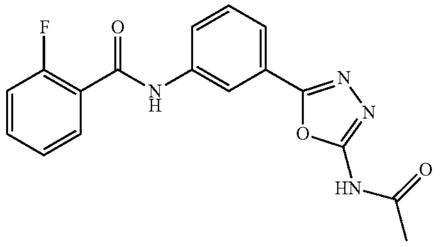 [SMILES: CC(=O)Nc1nnc(-c2cccc(NC(=O)c3ccccc3F)c2)o1] |
| 410 | 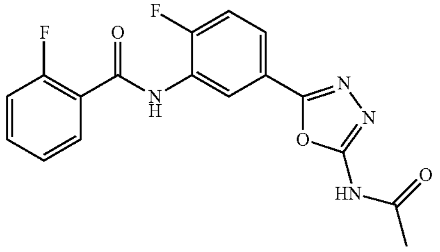 [SMILES: CC(=O)Nc1nnc(-c2ccc(F)c(NC(=O)c3ccccc3F)c2)o1] |
| 411 | 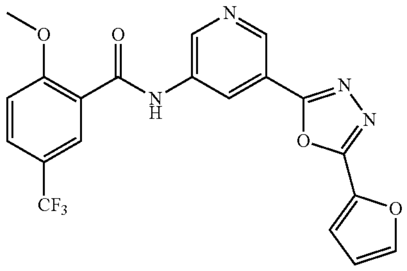 [SMILES: COc1ccc(C(F)(F)F)cc1C(=O)Nc1cncc(-c2nnc(-c3ccco3)o2)c1] |
| 412 | 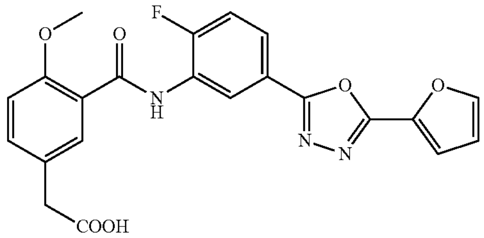 [SMILES: COc1ccc(CC(=O)O)cc1C(=O)Nc1cc(-c2nnc(-c3ccco3)o2)ccc1F] |
| 413 | 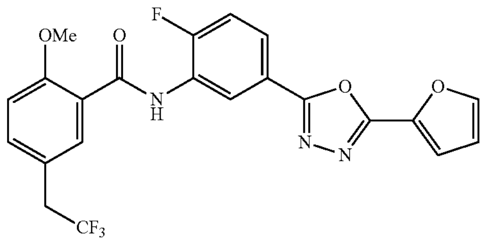 [SMILES: COc1ccc(CC(F)(F)F)cc1C(=O)Nc1cc(-c2nnc(-c3ccco3)o2)ccc1F] |

TABLE 1-continued
| Compound Number | Structure |
|---|---|
| 414 | 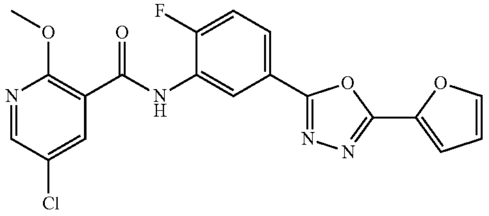 [SMILES: COc1ncc(Cl)cc1C(=O)Nc1cc(-c2nnc(-c3ccco3)o2)ccc1F] |
| 415 | 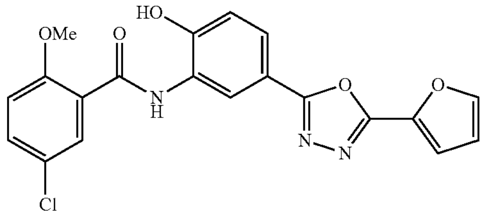 [SMILES: COc1ccc(Cl)cc1C(=O)Nc1cc(-c2nnc(-c3ccco3)o2)ccc1O] |
| 416 | 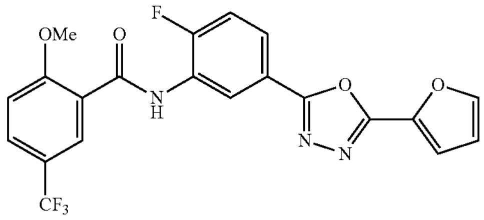 [SMILES: COc1ccc(C(F)(F)F)cc1C(=O)Nc1cc(-c2nnc(-c3ccco3)o2)ccc1F] |
| 417 | 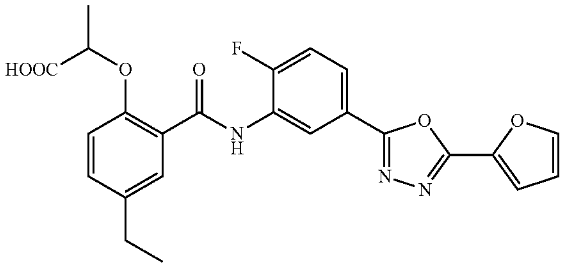 [SMILES: CCc1ccc(OC(C)C(=O)O)c(C(=O)Nc2cc(-c3nnc(-c4ccco4)o3)ccc2F)c1] |
| 418 | 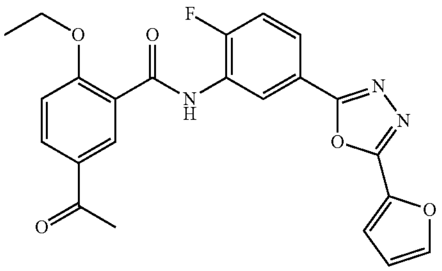 [SMILES: CCOc1ccc(C(C)=O)cc1C(=O)Nc1cc(-c2nnc(-c3ccco3)o2)ccc1F] |
| 419 | 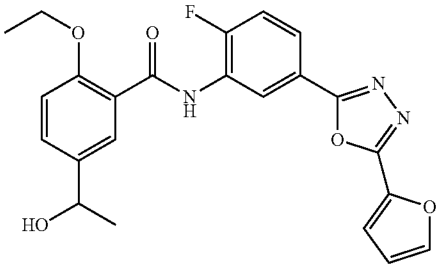 [SMILES: CCOc1ccc(C(C)O)cc1C(=O)Nc1cc(-c2nnc(-c3ccco3)o2)ccc1F] |

TABLE 1-continued
| Compound Number | Structure |
|---|---|
| 420 | 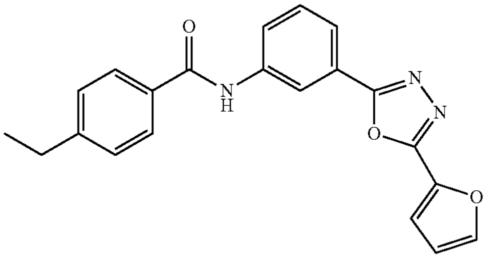 [SMILES: CCc1ccc(C(=O)Nc2cccc(-c3nnc(-c4ccco4)o3)c2)cc1] |
| 421 | 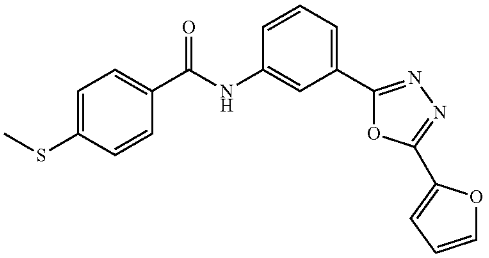 [SMILES: CSc1ccc(C(=O)Nc2cccc(-c3nnc(-c4ccco4)o3)c2)cc1] |
| 422 | 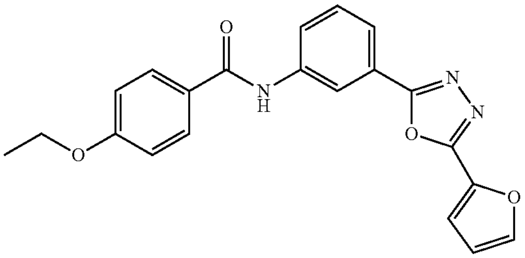 [SMILES: CCOc1ccc(C(=O)Nc2cccc(-c3nnc(-c4ccco4)o3)c2)cc1] |
| 423 | 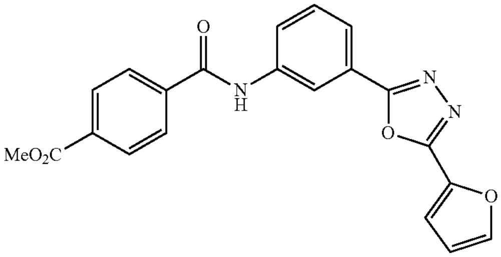 [SMILES: CS(=O)(=O)c1ccc(C(=O)Nc2cccc(-c3nnc(-c4ccco4)o3)c2)cc1] |
| 424 | 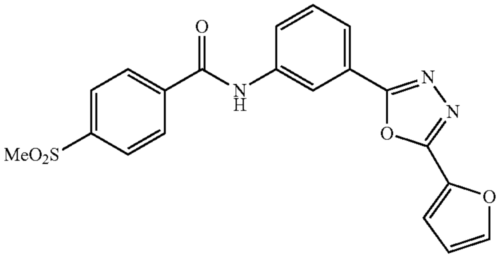 |
| 425 | 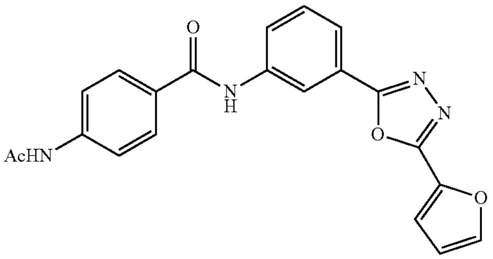 [SMILES: CC(=O)Nc1ccc(C(=O)Nc2cccc(-c3nnc(-c4ccco4)o3)c2)cc1] |

TABLE 1-continued
| Compound Number | Structure |
| --- | --- |
| 426 | 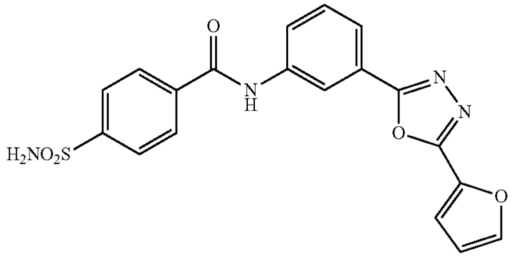 |
| 427 | 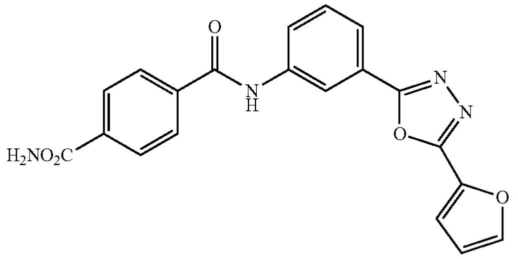 [SMILES: NS(=O)(=O)c1ccc(C(=O)Nc2cccc(-c3nnc(-c4ccco4)o3)c2)cc1] |
| 428 | 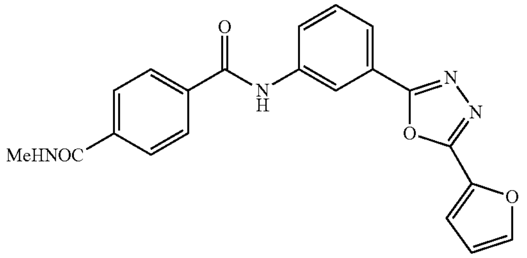 |
| 429 | 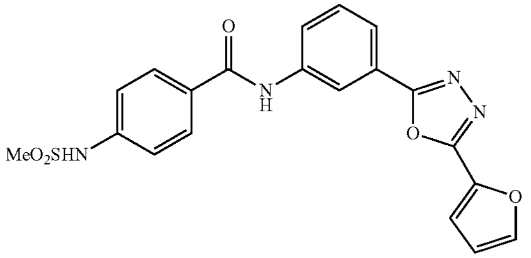 |
| 430 | 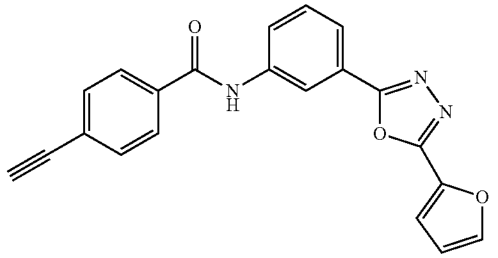 [SMILES: C#Cc1ccc(C(=O)Nc2cccc(-c3nnc(-c4ccco4)o3)c2)cc1] |

TABLE 1-continued
| Compound Number | Structure |
|---|---|
| 431 | 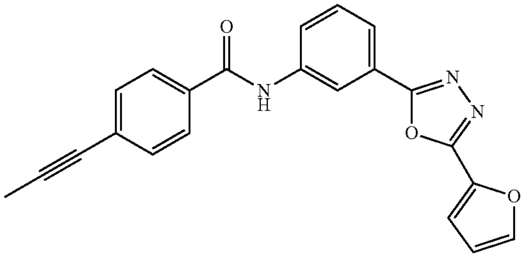 [SMILES: CC#Cc1ccc(C(=O)Nc2cccc(-c3nnc(-c4ccco4)o3)c2)cc1] |
| 432 | 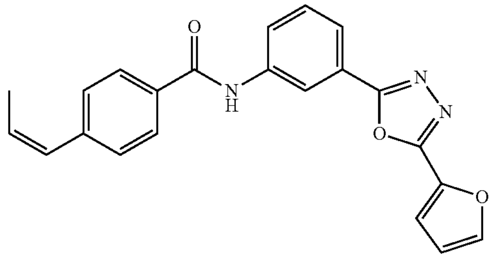 [SMILES: C/C=C\c1ccc(C(=O)Nc2cccc(-c3nnc(-c4ccco4)o3)c2)cc1] |
| 433 | 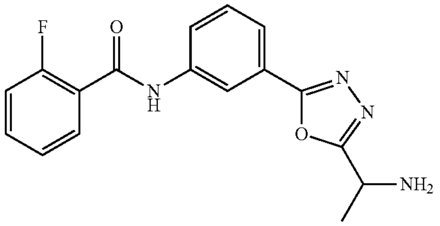 [SMILES: CC(N)c1nnc(-c2cccc(NC(=O)c3ccccc3F)c2)o1] |
| 434 | 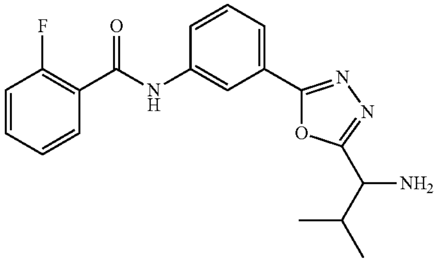 [SMILES: CC(C)C(N)c1nnc(-c2cccc(NC(=O)c3ccccc3F)c2)o1] |
| 435 | 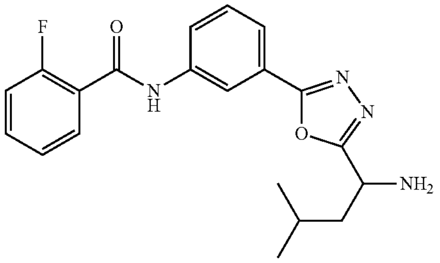 [SMILES: CC(C)CC(N)c1nnc(-c2cccc(NC(=O)c3ccccc3F)c2)o1] |
| 436 | 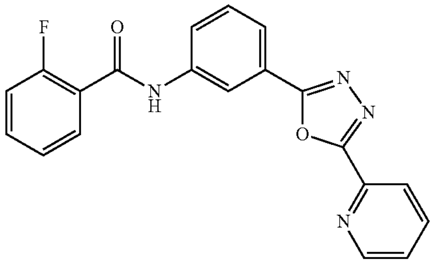 [SMILES: O=C(Nc1cccc(-c2nnc(-c3ccccn3)o2)c1)c1ccccc1F] |

TABLE 1-continued
| Compound Number | Structure |
| --- | --- |
| 437 | 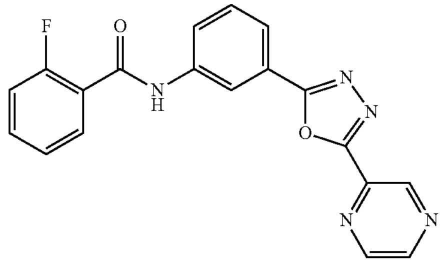 [SMILES: O=C(Nc1cccc(-c2nnc(-c3cnccn3)o2)c1)c1ccccc1F] |
| 438 | 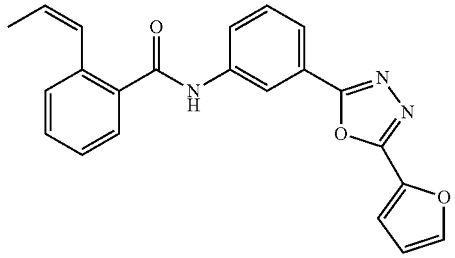 [SMILES: C/C=C\c1ccccc1C(=O)Nc1cccc(-c2nnc(-c3ccco3)o2)c1] |
| 439 | 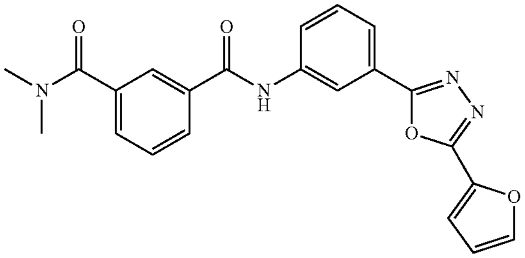 [SMILES: CN(C)C(=O)c1cccc(C(=O)Nc2cccc(-c3nnc(-c4ccco4)o3)c2)c1] |
| 440 | 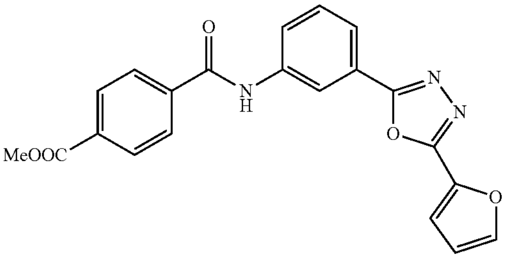 [SMILES: COC(=O)c1ccc(C(=O)Nc2cccc(-c3nnc(-c4ccco4)o3)c2)cc1] |
| 441 | 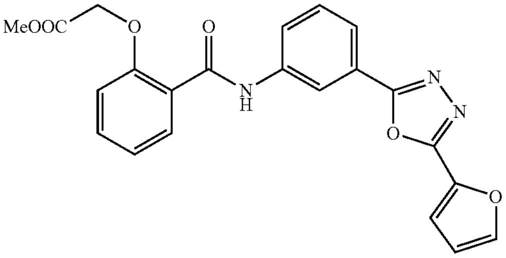 [SMILES: COC(=O)COc1ccccc1C(=O)Nc1cccc(-c2nnc(-c3ccco3)o2)c1] |

TABLE 1-continued
| Compound Number | Structure |
| --- | --- |
| 442 | 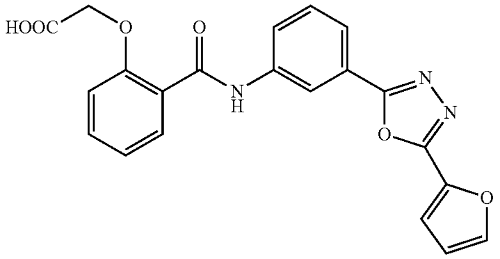 [SMILES: O=C(O)COc1ccccc1C(=O)Nc1cccc(-c2nnc(-c3ccco3)o2)c1] |
| 443 | 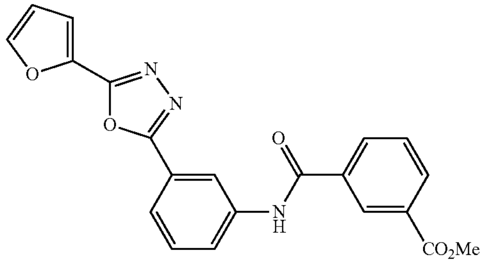 [SMILES: COC(=O)c1cccc(C(=O)Nc2cccc(-c3nnc(-c4ccco4)o3)c2)c1] |
| 444 | 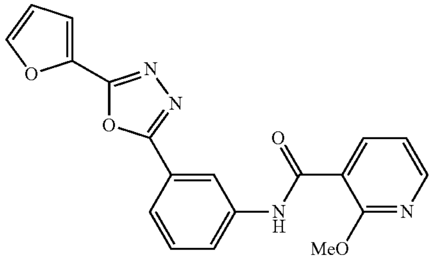 [SMILES: COc1ncccc1C(=O)Nc1cccc(-c2nnc(-c3ccco3)o2)c1] |
| 445 | 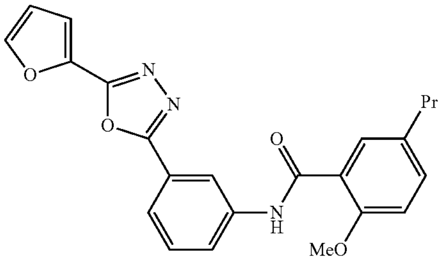 |
| 446 | 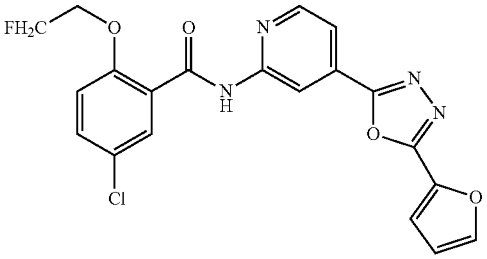 |

TABLE 1-continued
| Compound Number | Structure |
|---|---|
| 447 | 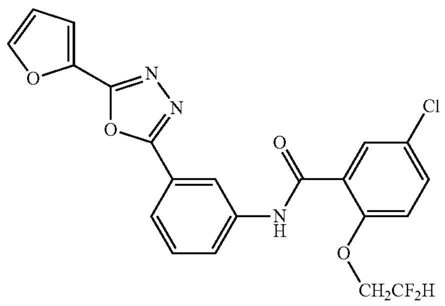 |
| 448 | 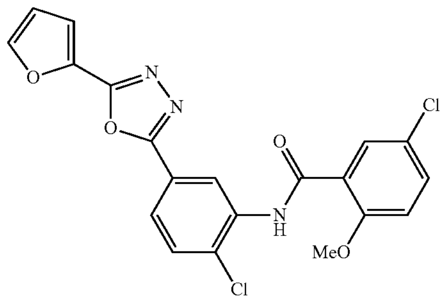 [SMILES: COc1ccc(Cl)cc1C(=O)Nc1cc(-c2nnc(-c3ccco3)o2)ccc1Cl] |
| 449 | 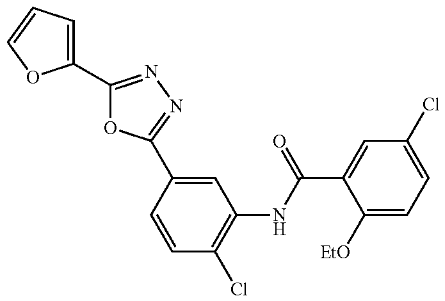 [SMILES: CCOc1ccc(Cl)cc1C(=O)Nc1cc(-c2nnc(-c3ccco3)o2)ccc1Cl] |
| 450 | 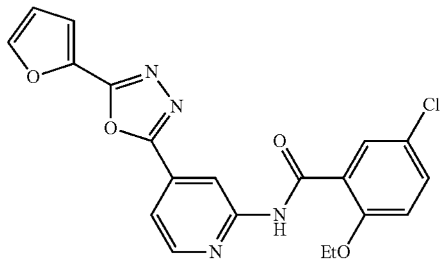 [SMILES: CCOc1ccc(Cl)cc1C(=O)Nc1cc(-c2nnc(-c3ccco3)o2)ccn1] |
| 451 | 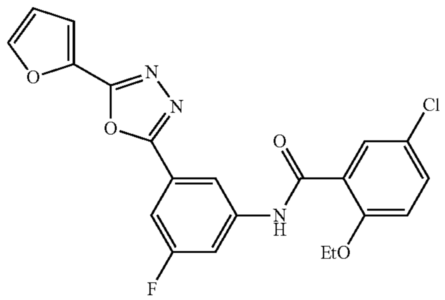 [SMILES: CCOc1ccc(Cl)cc1C(=O)Nc1cc(F)cc(-c2nnc(-c3ccco3)o2)c1] |

TABLE 1-continued
| Compound Number | Structure |
|---|---|
| 452 | 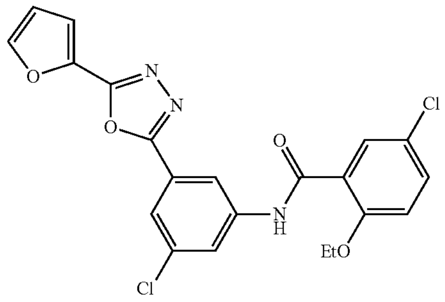 [SMILES: CCOc1ccc(Cl)cc1C(=O)Nc1cc(Cl)cc(-c2nnc(-c3ccco3)o2)c1] |
| 453 | 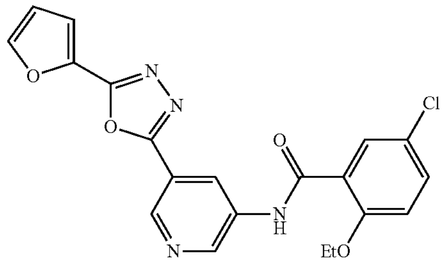 [SMILES: CCOc1ccc(Cl)cc1C(=O)Nc1cncc(-c2nnc(-c3ccco3)o2)c1] |
| 454 | 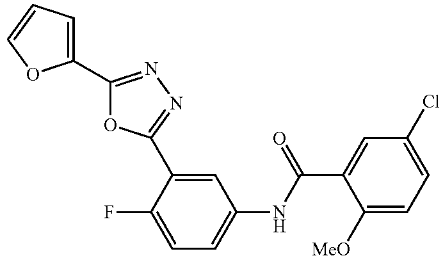 [SMILES: COc1ccc(Cl)cc1C(=O)Nc1ccc(F)c(-c2nnc(-c3ccco3)o2)c1] |
| 455 | 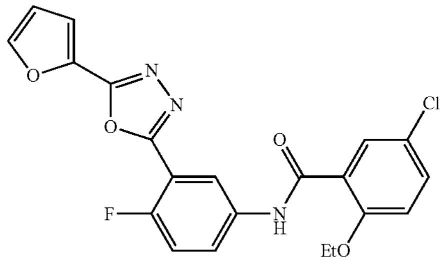 [SMILES: CCOc1ccc(Cl)cc1C(=O)Nc1ccc(F)c(-c2nnc(-c3ccco3)o2)c1] |
| 456 | 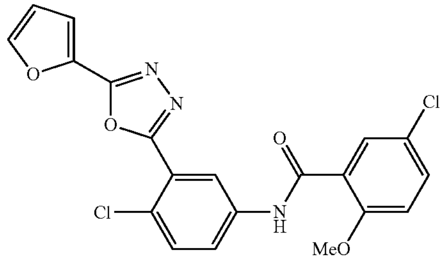 [SMILES: COc1ccc(Cl)cc1C(=O)Nc1ccc(Cl)c(-c2nnc(-c3ccco3)o2)c1] |

TABLE 1-continued
| Compound Number | Structure |
|---|---|
| 457 | 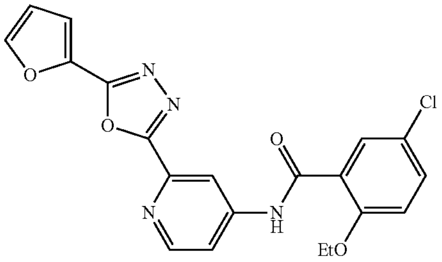 [SMILES: CCOc1ccc(Cl)cc1C(=O)Nc1ccnc(-c2nnc(-c3ccco3)o2)c1] |
| 458 | 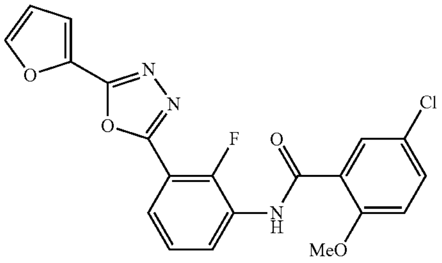 [SMILES: COc1ccc(Cl)cc1C(=O)Nc1cccc(-c2nnc(-c3ccco3)o2)c1F] |
| 459 | 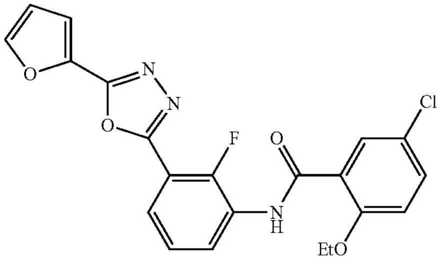 [SMILES: CCOc1ccc(Cl)cc1C(=O)Nc1cccc(-c2nnc(-c3ccco3)o2)c1F] |
| 460 | 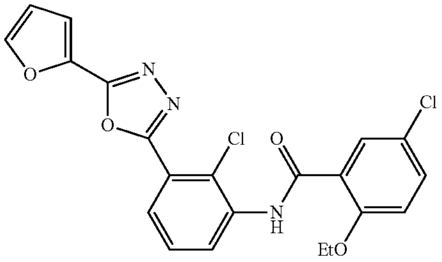 [SMILES: CCOc1ccc(Cl)cc1C(=O)Nc1cccc(-c2nnc(-c3ccco3)o2)c1Cl] |
| 461 | 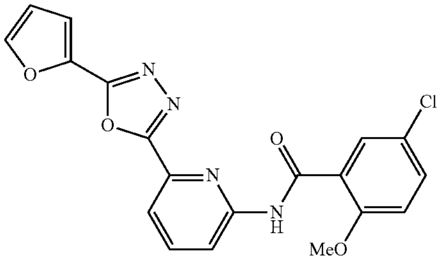 [SMILES: COc1ccc(Cl)cc1C(=O)Nc1cccc(-c2nnc(-c3ccco3)o2)n1] |

TABLE 1-continued
| Compound Number | Structure |
| --- | --- |
| 462 | 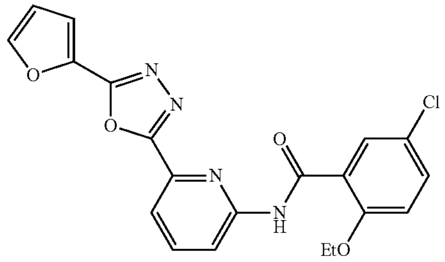 [SMILES: CCOc1ccc(Cl)cc1C(=O)Nc1cccc(-c2nnc(-c3ccco3)o2)n1] |
| 463 | 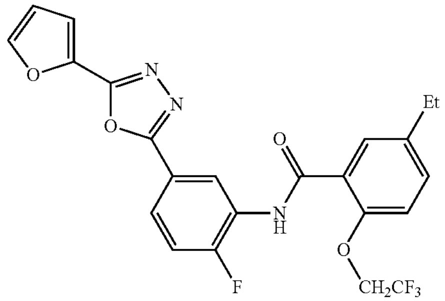 |
| 464 | 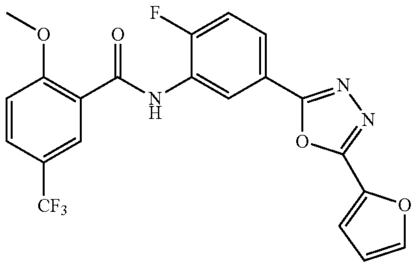 |
| 465 | 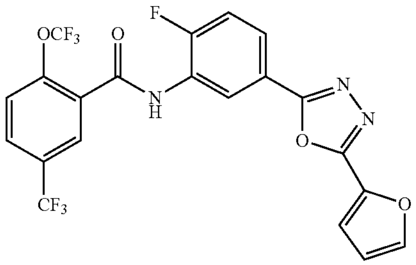 [SMILES: O=C(Nc1cc(-c2nnc(-c3ccco3)o2)ccc1F)c1cc(C(F)(F)F)ccc1OC(F)(F)F] |
| 466 | 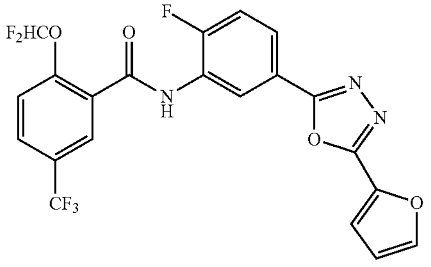 [SMILES: O=C(Nc1cc(-c2nnc(-c3ccco3)o2)ccc1F)c1cc(C(F)(F)F)ccc1OC(F)F] |

TABLE 1-continued
| Compound Number | Structure |
|---|---|
| 467 | 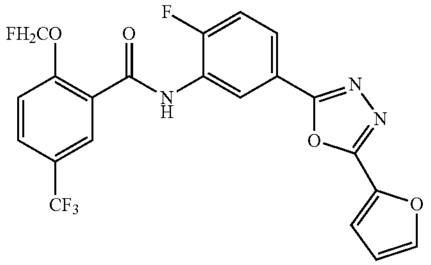 |
| 468 | 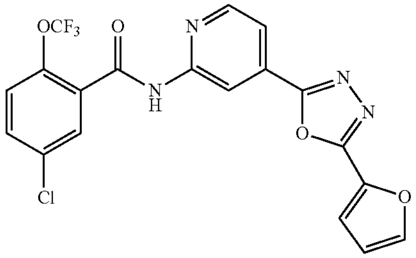 [SMILES: O=C(Nc1cc(-c2nnc(-c3ccco3)o2)ccn1)c1cc(Cl)ccc1OC(F)(F)F] |
| 469 | 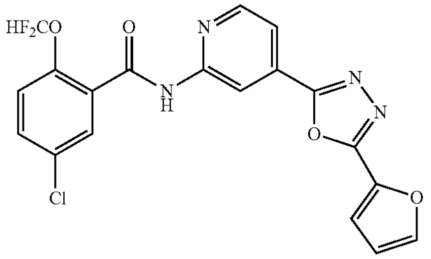 |
| 470 | 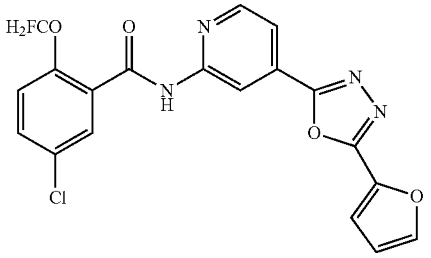 |
| 471 | 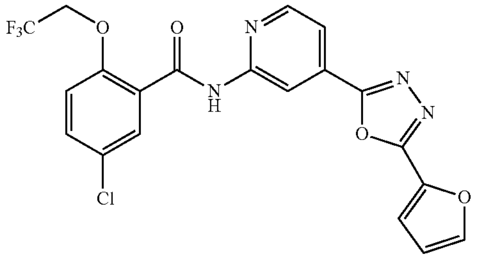 [SMILES: O=C(Nc1cc(-c2nnc(-c3ccco3)o2)ccn1)c1cc(Cl)ccc1OCC(F)(F)F] |

TABLE 1-continued
| Compound Number | Structure |
|---|---|
| 472 | 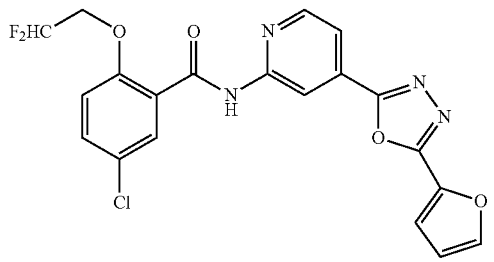 [SMILES: O=C(Nc1cc(-c2nnc(-c3ccco3)o2)ccn1)c1cc(Cl)ccc1OCC(F)F] |
| 473 | 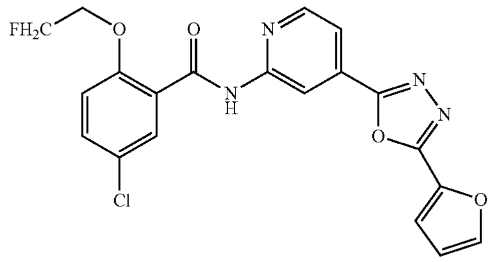 |
| 474 | 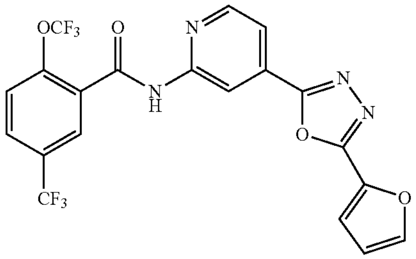 |
| 475 | 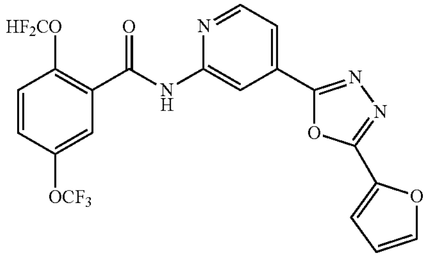 |
| 476 | 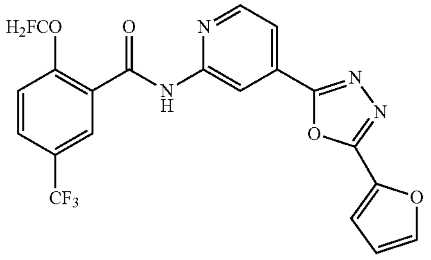 |

TABLE 1-continued
| Compound Number | Structure |
|---|---|
| 477 | 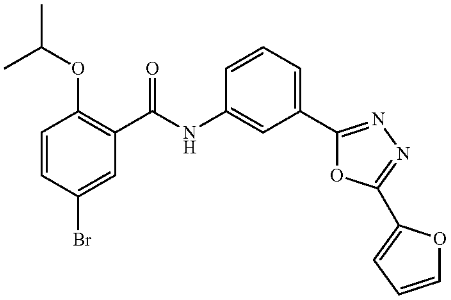 |
| 478 | 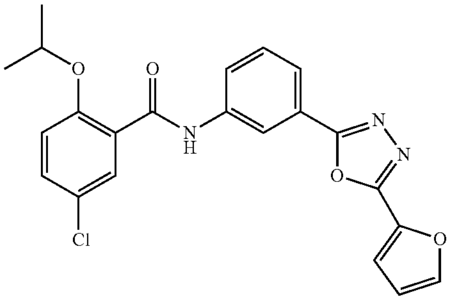 [SMILES: CC(C)Oc1ccc(Cl)cc1C(=O)Nc1cccc(-c2nnc(-c3ccco3)o2)c1] |
| 479 | 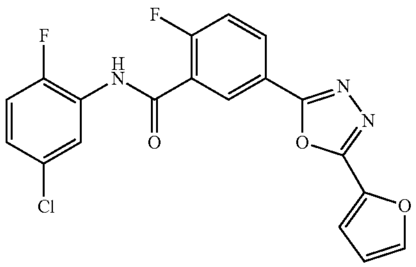 [SMILES: O=C(Nc1cc(Cl)ccc1F)c1cc(-c2nnc(-c3ccco3)o2)ccc1F] |
| 480 | 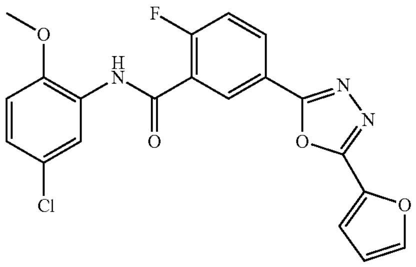 [SMILES: COc1ccc(Cl)cc1NC(=O)c1cc(-c2nnc(-c3ccco3)o2)ccc1F] |
| 481 | 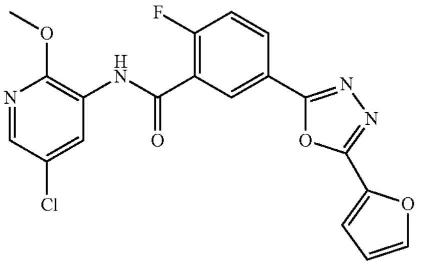 [SMILES: COc1ncc(Cl)cc1NC(=O)c1cc(-c2nnc(-c3ccco3)o2)ccc1F] |

TABLE 1-continued
| Compound Number | Structure |
|---|---|
| 482 | 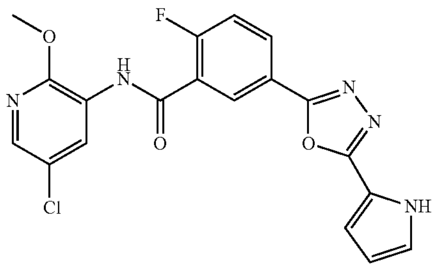 [SMILES: COc1ncc(Cl)cc1NC(=O)c1cc(-c2nnc(-c3ccc[nH]3)o2)ccc1F] |
| 483 | 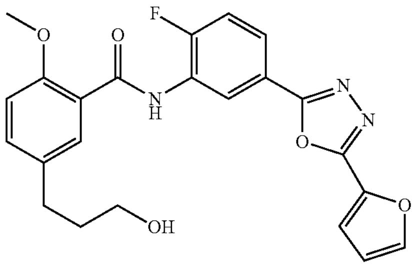 [SMILES: COc1ccc(CCCO)cc1C(=O)Nc1cc(-c2nnc(-c3ccco3)o2)ccc1F] |
| 484 | 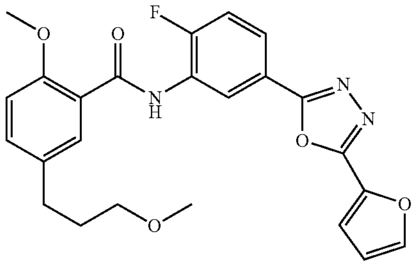 [SMILES: COCCCc1ccc(OC)c(C(=O)Nc2cc(-c3nnc(-c4ccco4)o3)ccc2F)c1] |
| 485 | 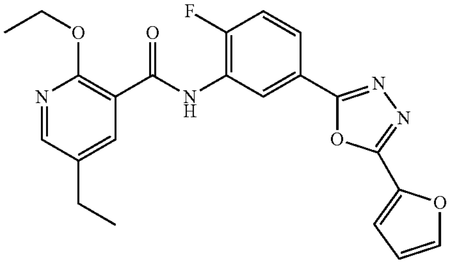 [SMILES: CCOc1ncc(CC)cc1C(=O)Nc1cc(-c2nnc(-c3ccco3)o2)ccc1F] |
| 486 | 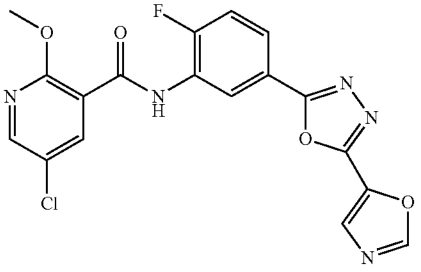 [SMILES: COc1ncc(Cl)cc1C(=O)Nc1cc(-c2nnc(-c3cnco3)o2)ccc1F] |

TABLE 1-continued
| Compound Number | Structure |
|---|---|
| 487 | 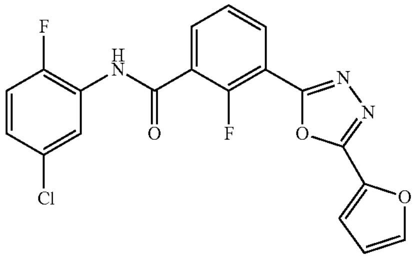 [SMILES: O=C(Nc1cc(Cl)ccc1F)c1cccc(-c2nnc(-c3ccco3)o2)c1F] |
| 488 | 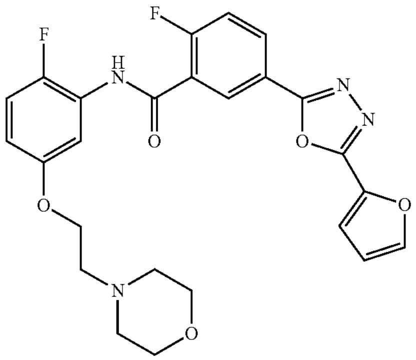 [SMILES: O=C(Nc1cc(OCCN2CCOCC2)ccc1F)c1cc(-c2nnc(-c3ccco3)o2)ccc1F] |
| 489 | 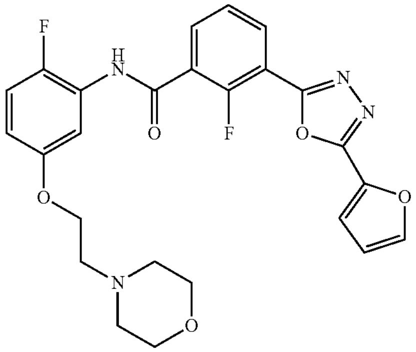 [SMILES: O=C(Nc1cc(OCCN2CCOCC2)ccc1F)c1cccc(-c2nnc(-c3ccco3)o2)c1F] |
| 490 | 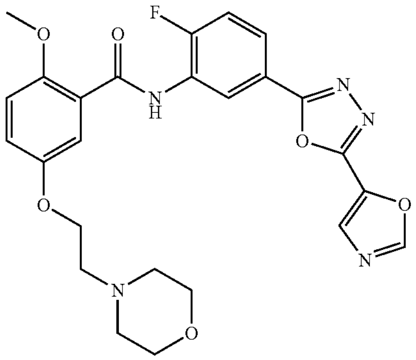 [SMILES: COc1ccc(OCCN2CCOCC2)cc1C(=O)Nc1cc(-c2nnc(-c3cnco3)o2)ccc1F] |

TABLE 1-continued
| Compound Number | Structure |
|---|---|
| 491 | 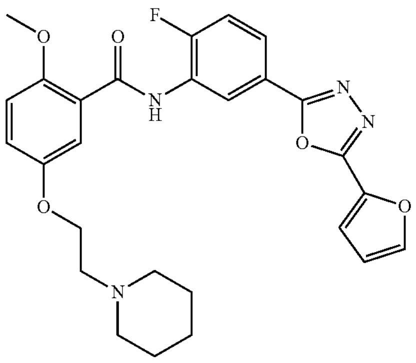 [SMILES: COc1ccc(OCCN2CCCCC2)cc1C(=O)Nc1cc(-c2nnc(-c3ccco3)o2)ccc1F] |
| 492 | 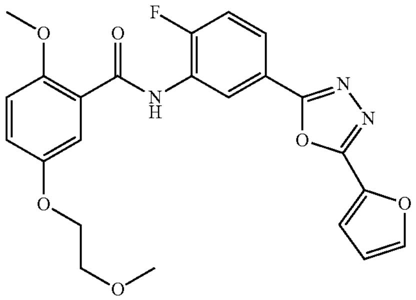 [SMILES: COCCOc1ccc(OC)c(C(=O)Nc2cc(-c3nnc(-c4ccco4)o3)ccc2F)c1] |
| 493 | 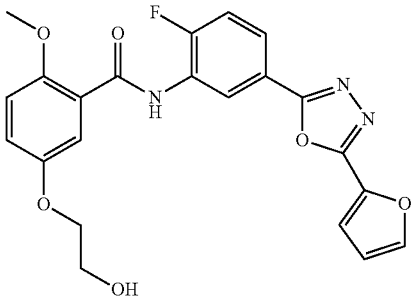 [SMILES: COc1ccc(OCCO)cc1C(=O)Nc1cc(-c2nnc(-c3ccco3)o2)ccc1F] |
| 494 | 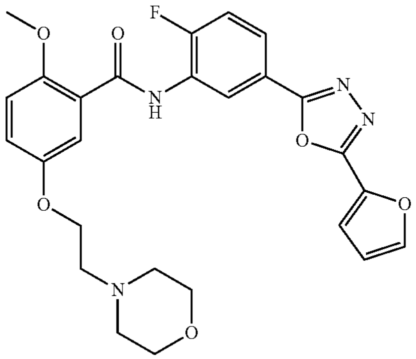 [SMILES: COc1ccc(OCCN2CCOCC2)cc1C(=O)Nc1cc(-c2nnc(-c3ccco3)o2)ccc1F] |

In some embodiments, the compound is selected from a compound in Table 2:
TABLE 2
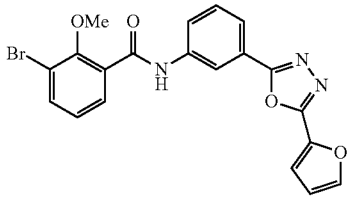 [SMILES: COc1c(Br)cccc1C(=O)Nc1cccc(-c2nnc(-c3ccco3)o2)c1]
Compound 192
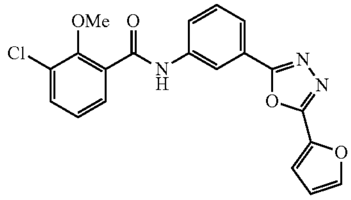 [SMILES: COc1c(Cl)cccc1C(=O)Nc1cccc(-c2nnc(-c3ccco3)o2)c1]
Compound 193
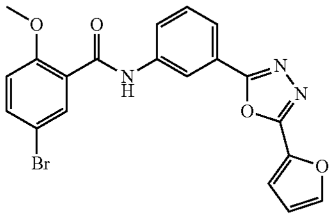
Compound 120
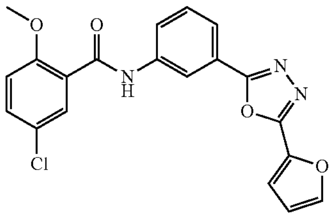 [SMILES: COc1ccc(Cl)cc1C(=O)Nc1cccc(-c2nnc(-c3ccco3)o2)c1]
Compound 124
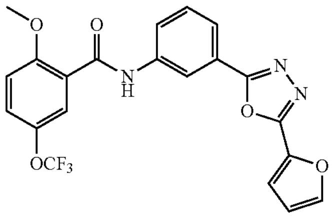 [SMILES: COc1ccc(OC(F)(F)F)cc1C(=O)Nc1cccc(-c2nnc(-c3ccco3)o2)c1]
Compound 279
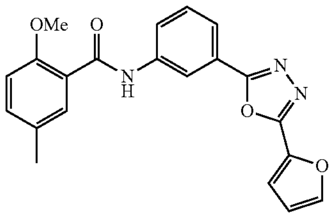 [SMILES: COc1ccc(C)cc1C(=O)Nc1cccc(-c2nnc(-c3ccco3)o2)c1]
Compound 197
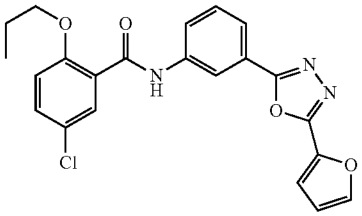
Compound 123
TABLE 2-continued
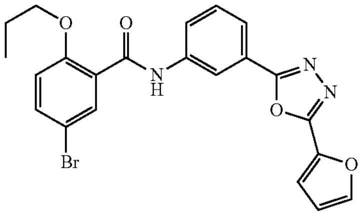 [SMILES: CCCOc1ccc(Cl)cc1C(=O)Nc1cccc(-c2nnc(-c3ccco3)o2)c1]
Compound 119
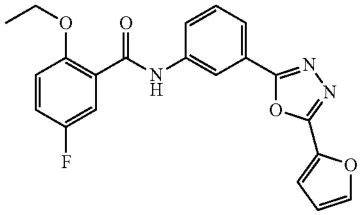
Compound 125
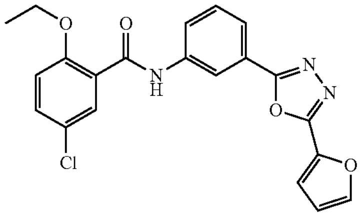
Compound 122
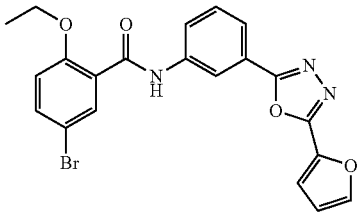
Compound 118
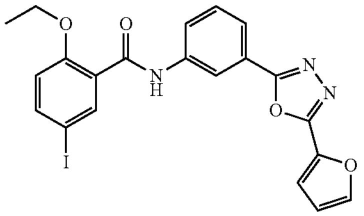 [SMILES: CCOc1ccc(F)cc1C(=O)Nc1cccc(-c2nnc(-c3ccco3)o2)c1]
Compound 200
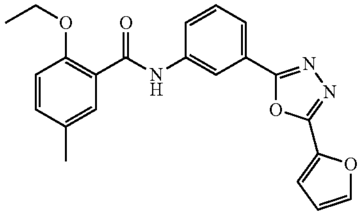
Compound 218
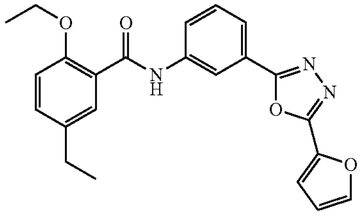 [SMILES: CCOc1ccc(CC)cc1C(=O)Nc1cccc(-c2nnc(-c3ccco3)o2)c1]
Compound 219

TABLE 2-continued
Compound 211
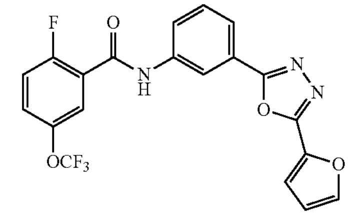 [SMILES: O=C(Nc1cccc(-c2nnc(-c3ccco3)o2)c1)c1cc(OC(F)(F)F)ccc1F]
Compound 228
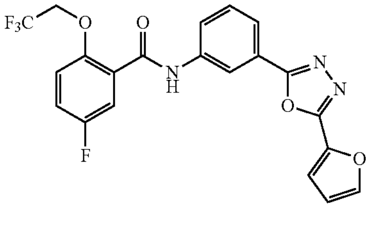 [SMILES: O=C(Nc1cccc(-c2nnc(-c3ccco3)o2)c1)c1cc(F)ccc1OCC(F)(F)F]
Compound 225
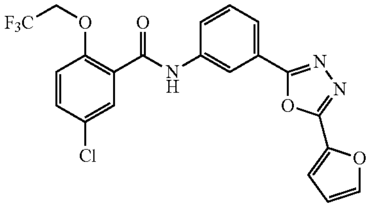 [SMILES: O=C(Nc1cccc(-c2nnc(-c3ccco3)o2)c1)c1cc(Cl)ccc1OCC(F)(F)F]
Compound 226
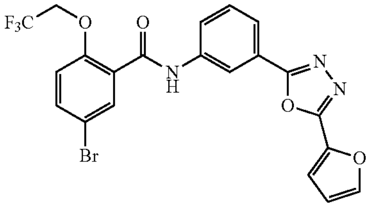
Compound 184
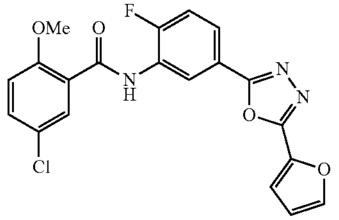 [SMILES: COc1ccc(Cl)cc1C(=O)Nc1cc(-c2nnc(-c3ccco3)o2)ccc1F]
Compound 216
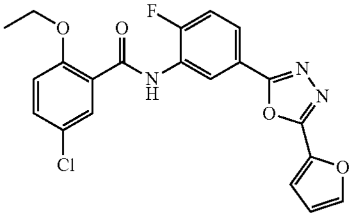 [SMILES: CCOc1ccc(Cl)cc1C(=O)Nc1cc(-c2nnc(-c3ccco3)o2)ccc1F]
Compound 128
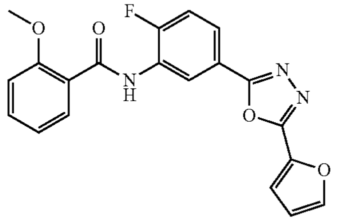 [SMILES: COc1ccccc1C(=O)Nc1cc(-c2nnc(-c3ccco3)o2)ccc1F]
TABLE 2-continued
Compound 39
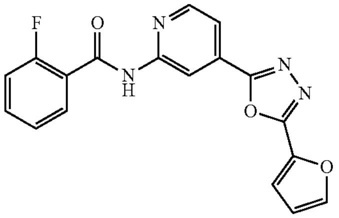 [SMILES: O=C(Nc1cc(-c2nnc(-c3ccco3)o2)ccn1)c1ccccc1F]
Compound 183
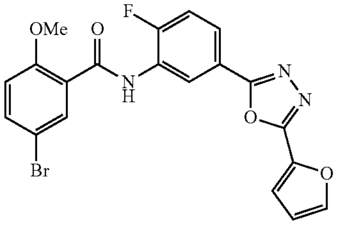
Compound 300
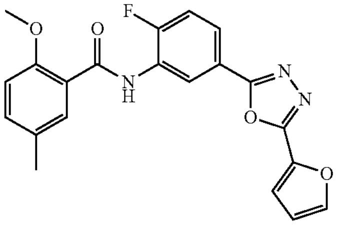 [SMILES: COc1ccc(C)cc1C(=O)Nc1cc(-c2nnc(-c3ccco3)o2)ccc1F]
Compound 215
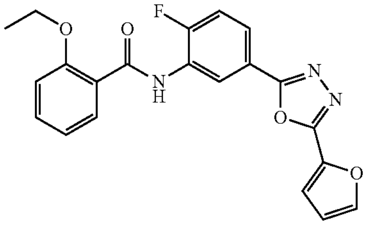 [SMILES: CCOc1ccccc1C(=O)Nc1cc(-c2nnc(-c3ccco3)o2)ccc1F]
Compound 313
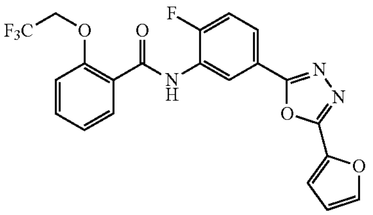 [SMILES: O=C(Nc1cc(-c2nnc(-c3ccco3)o2)ccc1F)c1ccccc1OCC(F)(F)F]
Compound 314
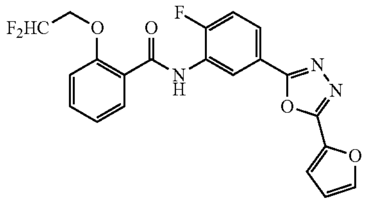 [SMILES: O=C(Nc1cc(-c2nnc(-c3ccco3)o2)ccc1F)c1ccccc1OCC(F)F]
Compound 315
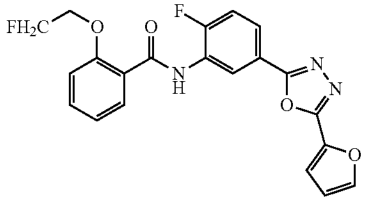

TABLE 2-continued
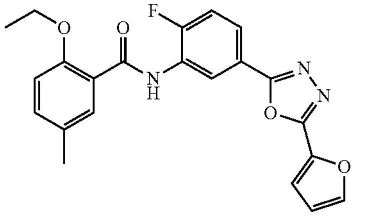 [SMILES: CCOc1ccc(C)cc1C(=O)Nc1cc(-c2nnc(-c3ccco3)o2)ccc1F]
Compound 221
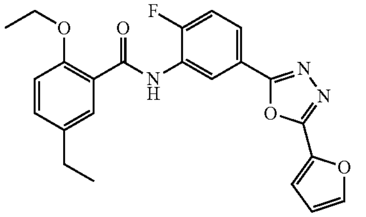 [SMILES: CCOc1ccc(CC)cc1C(=O)Nc1cc(-c2nnc(-c3ccco3)o2)ccc1F]
Compound 222
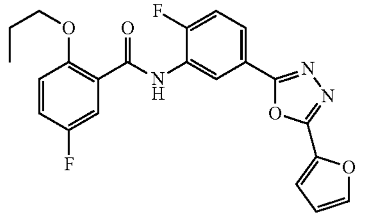 [SMILES: CCCOc1ccc(F)cc1C(=O)Nc1cc(-c2nnc(-c3ccco3)o2)ccc1F]
Compound 210
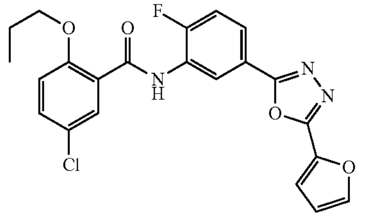
Compound 209
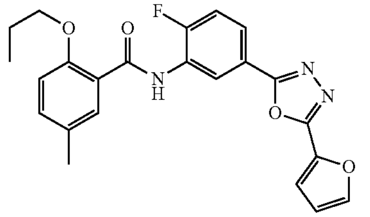 [SMILES: CCCOc1ccc(C)cc1C(=O)Nc1cc(-c2nnc(-c3ccco3)o2)ccc1F]
Compound 208
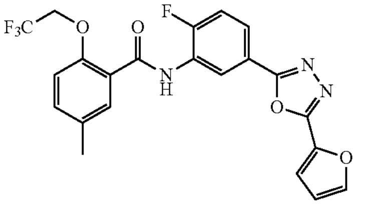 [SMILES: Cc1ccc(OCC(F)(F)F)c(C(=O)Nc2cc(-c3nnc(-c4ccco4)o3)ccc2F)c1]
Compound 322
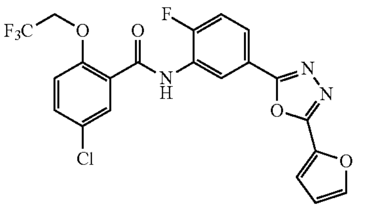 [SMILES: O=C(Nc1cc(-c2nnc(-c3ccco3)o2)ccc1F)c1cc(Cl)ccc1OCC(F)(F)F]
Compound 316
TABLE 2-continued
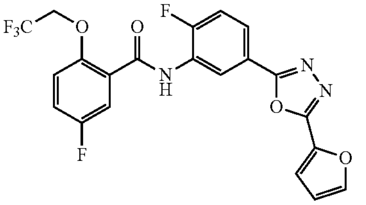 [SMILES: O=C(Nc1cc(-c2nnc(-c3ccco3)o2)ccc1F)c1cc(F)ccc1OCC(F)(F)F]
Compound 319
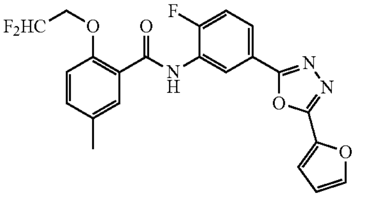 [SMILES: Cc1ccc(OCC(F)F)c(C(=O)Nc2cc(-c3nnc(-c4ccco4)o3)ccc2F)c1]
Compound 323
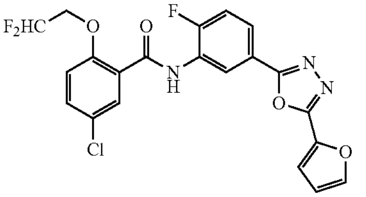
Compound 317
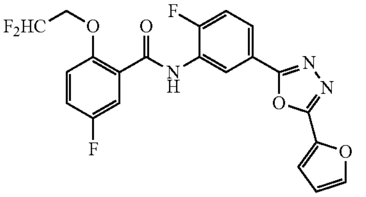
Compound 320
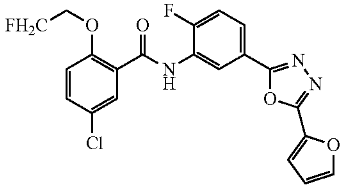
Compound 318
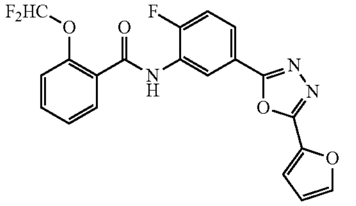
Compound 302
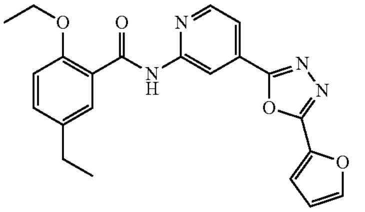 [SMILES: CCOc1ccc(CC)cc1C(=O)Nc1cc(-c2nnc(-c3ccco3)o2)ccn1]
Compound 373

TABLE 2-continued
Compound 281
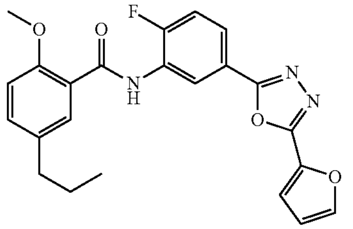 [SMILES: CCCc1ccc(OC)c(C(=O)Nc2cc(-c3nnc(-c4ccco4)o3)ccc2F)c1]
Compound 301
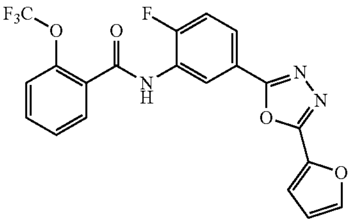 [SMILES: O=C(Nc1cc(-c2nnc(-c3ccco3)o2)ccc1F)c1ccccc1OC(F)(F)F]
Compound 304
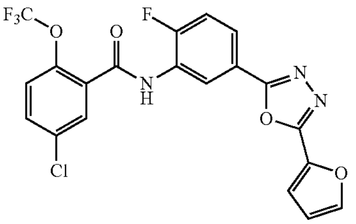 [SMILES: O=C(Nc1cc(-c2nnc(-c3ccco3)o2)ccc1F)c1cc(Cl)ccc1OC(F)(F)F]
Compound 305
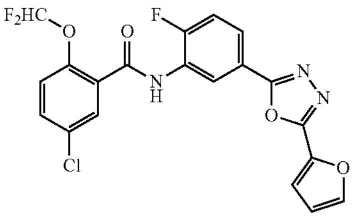
Compound 306
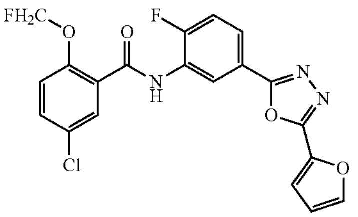
Compound 312
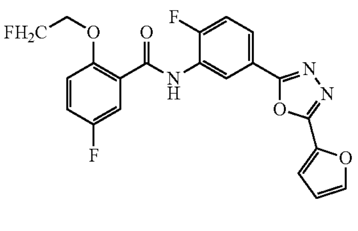
Compound 321
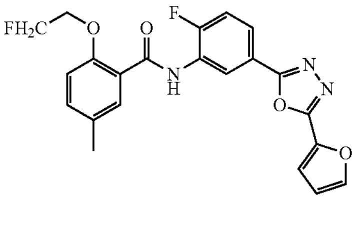
TABLE 2-continued
Compound 405
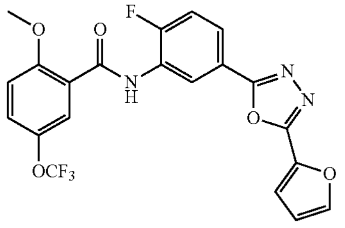 [SMILES: COc1ccc(OC(F)(F)F)cc1C(=O)Nc1cc(-c2nnc(-c3ccco3)o2)ccc1F]
Compound 396
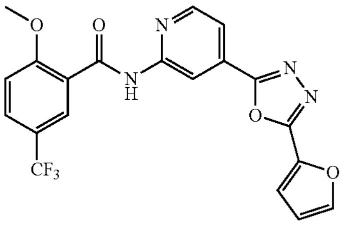 [SMILES: COc1ccc(C(F)(F)F)cc1C(=O)Nc1cc(-c2nnc(-c3ccco3)o2)ccn1]
Compound 400
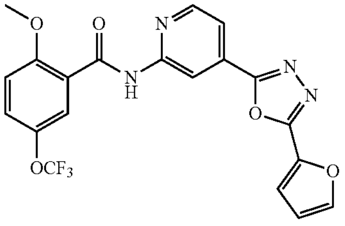 [SMILES: COc1ccc(OC(F)(F)F)cc1C(=O)Nc1cc(-c2nnc(-c3ccco3)o2)ccn1]
Compound 220
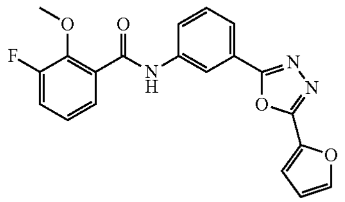 [SMILES: COc1c(F)cccc1C(=O)Nc1cccc(-c2nnc(-c3ccco3)o2)c1]
Compound 372
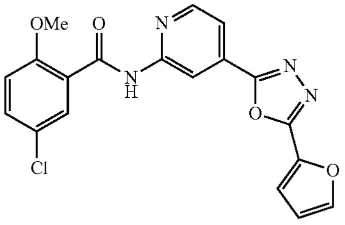 [SMILES: COc1ccc(Cl)cc1C(=O)Nc1cc(-c2nnc(-c3ccco3)o2)ccn1]
Compound 464
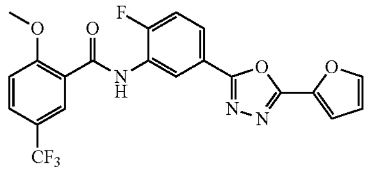 [SMILES: COc1ccc(C(F)(F)F)cc1C(=O)Nc1cc(-c2nnc(-c3ccco3)o2)ccc1F]
Compound 465
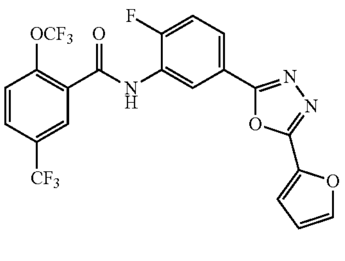 [SMILES: O=C(Nc1cc(-c2nnc(-c3ccco3)o2)ccc1F)c1cc(C(F)(F)F)ccc1OC(F)(F)F]

TABLE 2-continued
Compound 466
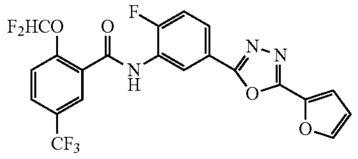 [SMILES: O=C(Nc1cc(-c2nnc(-c3ccco3)o2)ccc1F)c1cc(C(F)(F)F)ccc1OC(F)F]
Compound 467
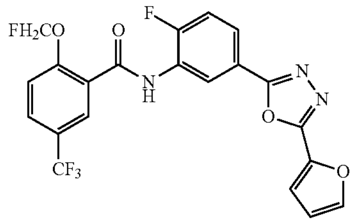
Compound 468
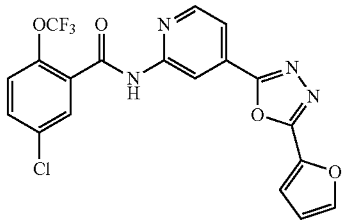 [SMILES: O=C(Nc1cc(-c2nnc(-c3ccco3)o2)ccn1)c1cc(Cl)ccc1OC(F)(F)F]
Compound 469
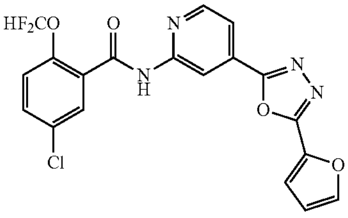
Compound 470
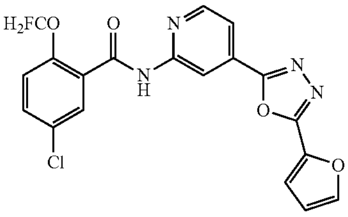
Compound 471
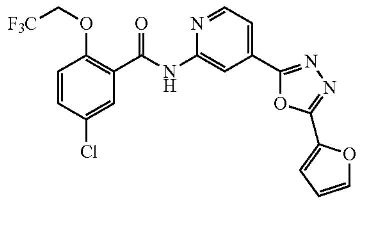 [SMILES: O=C(Nc1cc(-c2nnc(-c3ccco3)o2)ccn1)c1cc(Cl)ccc1OCC(F)(F)F]
Compound 472
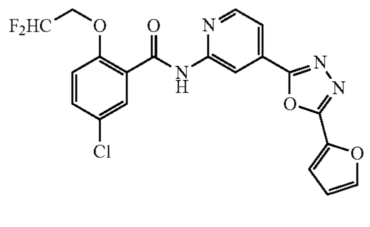 [SMILES: O=C(Nc1cc(-c2nnc(-c3ccco3)o2)ccn1)c1cc(Cl)ccc1OCC(F)F]
Compound 473
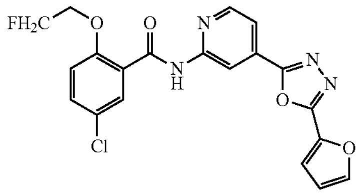
Compound 474
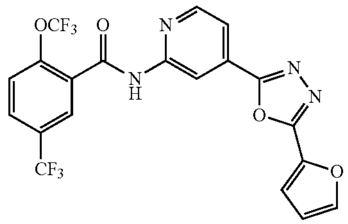
Compound 475
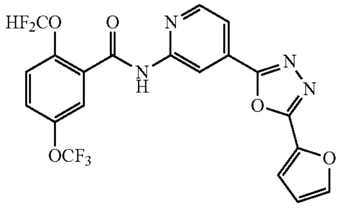
Compound 476
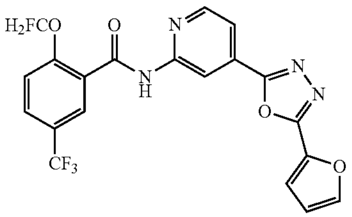
Compound 168
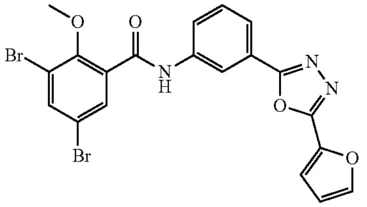 [SMILES: COc1c(Br)cc(Br)cc1C(=O)Nc1cccc(-c2nnc(-c3ccco3)o2)c1]
Compound 416
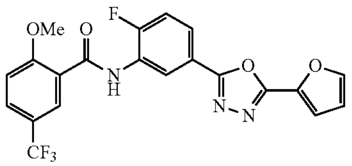 [SMILES: COc1ccc(C(F)(F)F)cc1C(=O)Nc1cc(-c2nnc(-c3ccco3)o2)ccc1F]
In some embodiments, the compound is selected from a compound in Table 3:
TABLE 3
Compound 118
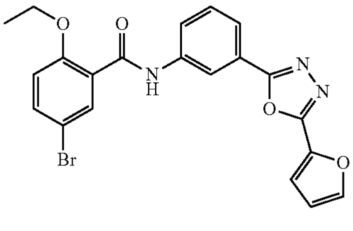

TABLE 3-continued
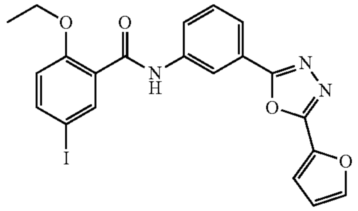 [SMILES: CCOc1ccc(I)cc1C(=O)Nc1cccc(-c2nnc(-c3ccco3)o2)c1]
Compound 200
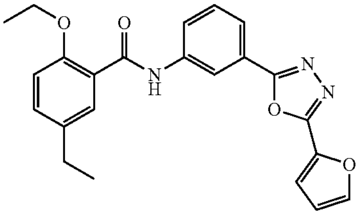 [SMILES: CCOc1ccc(CC)cc1C(=O)Nc1cccc(-c2nnc(-c3ccco3)o2)c1]
Compound 219
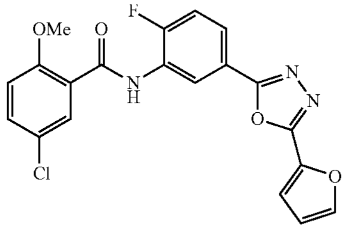 [SMILES: COc1ccc(Cl)cc1C(=O)Nc1cc(-c2nnc(-c3ccco3)o2)ccc1F]
Compound 184
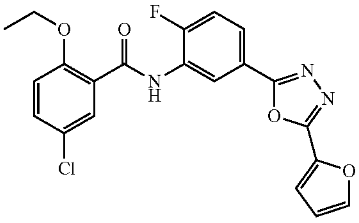 [SMILES: CCOc1ccc(Cl)cc1C(=O)Nc1cc(-c2nnc(-c3ccco3)o2)ccc1F]
Compound 216
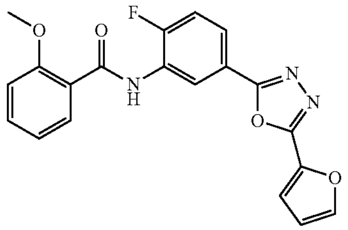 [SMILES: COc1ccccc1C(=O)Nc1cc(-c2nnc(-c3ccco3)o2)ccc1F]
Compound 128
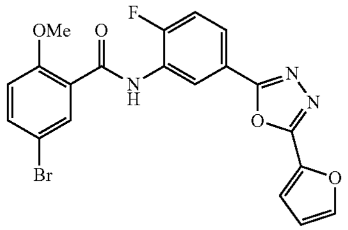
Compound 183
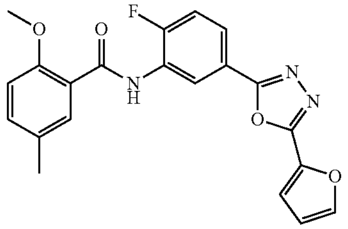 [SMILES: COc1ccc(C)cc1C(=O)Nc1cc(-c2nnc(-c3ccco3)o2)ccc1F]
Compound 300
TABLE 3-continued
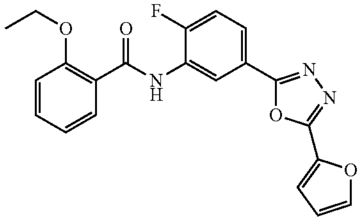
Compound 215
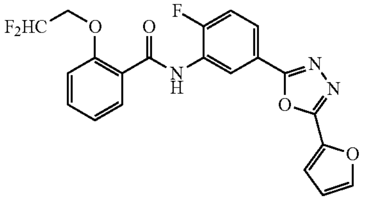 [SMILES: O=C(Nc1cc(-c2nnc(-c3ccco3)o2)ccc1F)c1ccccc1OCC(F)F]
Compound 314
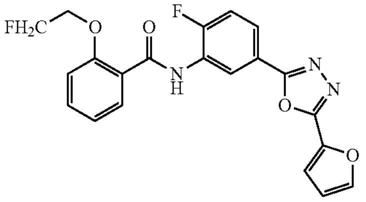
Compound 315
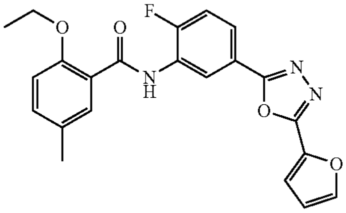 [SMILES: CCOc1ccc(C)cc1C(=O)Nc1cc(-c2nnc(-c3ccco3)o2)ccc1F]
Compound 221
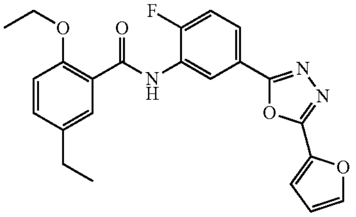 [SMILES: CCOc1ccc(CC)cc1C(=O)Nc1cc(-c2nnc(-c3ccco3)o2)ccc1F]
Compound 222
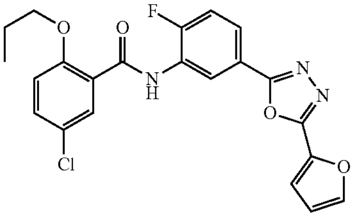
Compound 209
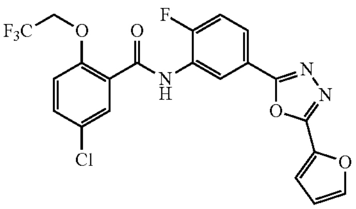
Compound 316

TABLE 3-continued

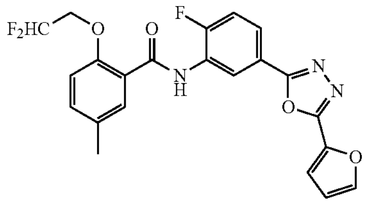 [SMILES: Cc1ccc(OCC(F)F)c(C(=O)Nc2cc(-c3nnc(-c4ccco4)o3)ccc2F)c1]

Compound 323

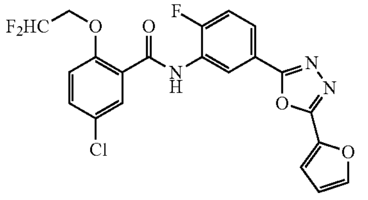

Compound 317

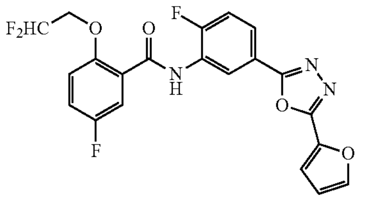

Compound 320

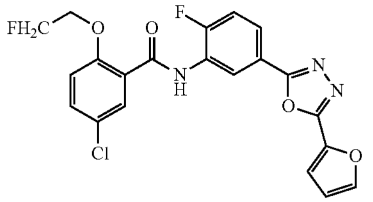

Compound 318

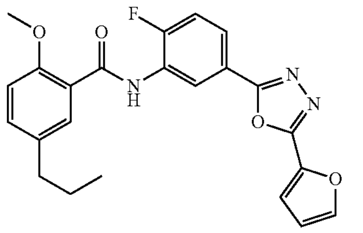 [SMILES: CCCc1ccc(OC)c(C(=O)Nc2cc(-c3nnc(-c4ccco4)o3)ccc2F)c1]

Compound 281

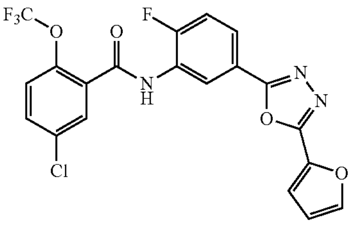 [SMILES: O=C(Nc1cc(-c2nnc(-c3ccco3)o2)ccc1F)c1cc(Cl)ccc1OC(F)(F)F]

Compound 304

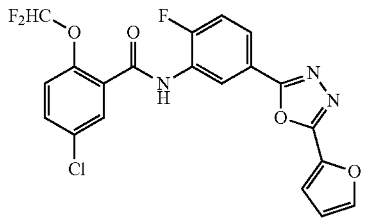

Compound 305

TABLE 3-continued

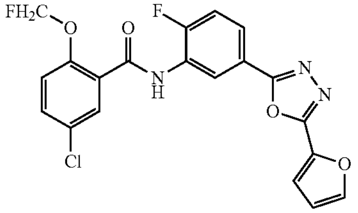 [SMILES: O=C(Nc1cc(-c2nnc(-c3ccco3)o2)ccc1F)c1cc(Cl)ccc1OC(F)F]

Compound 306

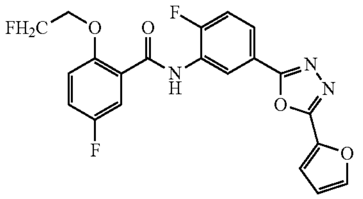

Compound 312

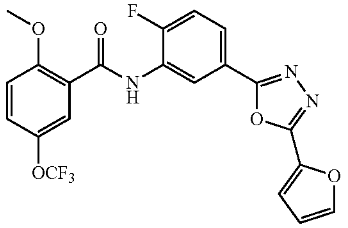 [SMILES: COc1ccc(OC(F)(F)F)cc1C(=O)Nc1cc(-c2nnc(-c3ccco3)o2)ccc1F]

Compound 405

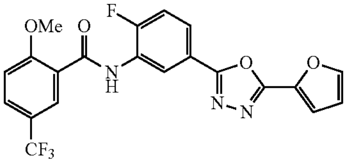 [SMILES: COc1ccc(C(F)(F)F)cc1C(=O)Nc1cc(-c2nnc(-c3ccco3)o2)ccc1F]

Compound 416

In some embodiments, the compound is:

Compound 222

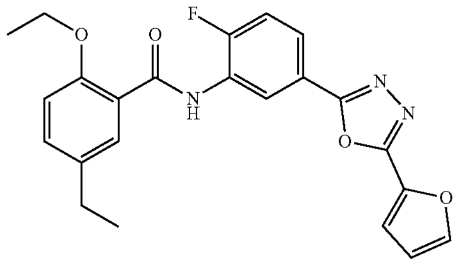

Chirality

In some embodiments, the compound may have one or more chiral centres.

The chiral centre, or each chiral centre, if more than one is present, is independently in the R-configuration or the S-configuration.

If no configuration is indicated, then both configurations are encompassed.

Substantially Purified Forms

One aspect of the present invention pertains to compounds, as described herein, in substantially purified form and/or in a form substantially free from contaminants.

In one embodiment, the substantially purified form is at least 50% by weight, e.g., at least 60% by weight, e.g., at least 70% by weight, e.g., at least 80% by weight, e.g., at least 90% by weight, e.g., at least 95% by weight, e.g., at least 97% by weight, e.g., at least 98% by weight, e.g., at least 99% by weight.

Unless specified, the substantially purified form refers to the compound in any stereoisomeric or enantiomeric form. For example, in one embodiment, the substantially purified form refers to a mixture of stereoisomers, i.e., purified with respect to other compounds. In one embodiment, the substantially purified form refers to one stereoisomer, e.g., optically pure stereoisomer. In one embodiment, the substantially purified form refers to a mixture of enantiomers. In one embodiment, the substantially purified form refers to an equimolar mixture of enantiomers (i.e., a racemic mixture, a racemate). In one embodiment, the substantially purified form refers to one enantiomer, e.g., optically pure enantiomer.

In one embodiment, the contaminants represent no more than 50% by weight, e.g., no more than 40% by weight, e.g., no more than 30% by weight, e.g., no more than 20% by weight, e.g., no more than 10% by weight, e.g., no more than 5% by weight, e.g., no more than 3% by weight, e.g., no more than 2% by weight, e.g., no more than 1% by weight.

Unless specified, the contaminants refer to other compounds, that is, other than stereoisomers or enantiomers. In one embodiment, the contaminants refer to other compounds and other stereoisomers. In one embodiment, the contaminants refer to other compounds and the other enantiomer.

In one embodiment, the substantially purified form is at least 60% optically pure (i.e., 60% of the compound, on a molar basis, is the desired stereoisomer or enantiomer, and 40% is the undesired stereoisomer or enantiomer), e.g., at least 70% optically pure, e.g., at least 80% optically pure, e.g., at least 90% optically pure, e.g., at least 95% optically pure, e.g., at least 97% optically pure, e.g., at least 98% optically pure, e.g., at least 99% optically pure.

Isomers

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, $—OCH_3$, is not to be construed as a reference to its structural isomer, a hydroxymethyl group, $—CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hydroxyazo, and nitro/aci-nitro.

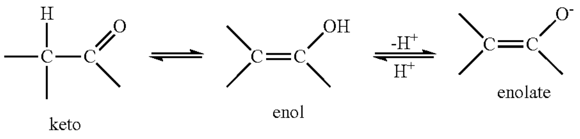

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; and the like.

Unless otherwise specified, a reference to a particular compound includes all such isomeric forms, including mixtures (e.g., racemic mixtures) thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Salts

It may be convenient or desirable to prepare, purify, and/or handle a corresponding salt of the compound, for example, a pharmaceutically-acceptable salt. Examples of pharmaceutically acceptable salts are discussed in Berge et al., 1977, "Pharmaceutically Acceptable Salts," *J. Pharm. Sci., Vol.* 66, pp. 1-19.

For example, if the compound is anionic, or has a functional group which may be anionic (e.g., —COOH may be $—COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperizine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

Unless otherwise specified, a reference to a particular compound also includes salt forms thereof.

Solvates and Hydrates

It may be convenient or desirable to prepare, purify, and/or handle a corresponding solvate of the compound. The term "solvate" is used herein in the conventional sense to refer to a complex of solute (e.g., compound, salt of compound) and solvent. If the solvent is water, the solvate may be conveniently referred to as a hydrate, for example, a mono-hydrate, a di-hydrate, a tri-hydrate, etc.

Unless otherwise specified, a reference to a particular compound also includes solvate and hydrate forms thereof.

Chemical Synthesis

Methods for the chemical synthesis of compounds of the present invention are described herein. These and/or other well-known methods may be modified and/or adapted in known ways in order to facilitate the synthesis of additional compounds of the present invention.

Compositions

One aspect of the present invention pertains to a composition (e.g., a pharmaceutical composition) comprising a compound, as described herein, and a pharmaceutically acceptable carrier, diluent, or excipient.

Another aspect of the present invention pertains to a method of preparing a composition (e.g., a pharmaceutical composition) comprising admixing a compound, as described herein, and a pharmaceutically acceptable carrier, diluent, or excipient.

Uses

The compounds described herein are believed to be effective inhibitors of ALCAT1.

Thus, the compounds described herein are believed to be useful in the treatment of aging and age-related diseases.

Thus, the compounds described herein are believed to be useful in the treatment of a disease characterised by one or more of oxidative stress, CL deficiency, enrichment of docosahexaenoic acid (DHA) in CL and mitochondrial dysfunction.

Thus, the compounds described herein are believed to be useful in the treatment of a disease or disorder associated with mitochondrial dysfunction.

Thus, the compounds described herein are believed to be useful in the treatment of a disease selected from obesity (such as diet-induced obesity), diabetes (such as type-2 diabetes), diabetic complications (such as neuropathy, cardiomyopathy, retinopathy and erectile dysfunction), fatty liver disease, cardiovascular disease, neurodegenerative disease, metabolic diseases, insulin resistance and cancer.

Thus, the compounds described herein are believed to be useful in the treatment of a disease selected from stroke, ischaemia, and reperfusion injury.

Thus, the compounds described herein are believed to be useful in the treatment of Barth syndrome.

Use in Methods of Inhibition

An aspect of the invention is a compound as described herein, for use in a method of inhibiting the expression, function or activity of ALCAT1 in vivo or in vitro.

An aspect of the invention is a compound as described herein, for use in a method of increasing the expression, function or activity of MFN2, for example as compared to a baseline control.

An aspect of the invention is a compound as described herein, for use in a method of decreasing oxidative stress as measured by reactive oxidative species (ROS), for example as compared to a baseline control.

An aspect of the invention is a compound as described herein, for use in a method of modulating cardiolipin (CL) structure, function, activity and/or expression.

Use in Methods of Therapy

An aspect of the invention is a compound as described herein, for use in the treatment of the human or animal body by therapy. For example, an aspect of the invention is a compound according to one of formulae (I), (IA) or (IB), for use in the treatment of the human or animal body by therapy.

An aspect of the invention is a compound according to Formula (I):

(I)

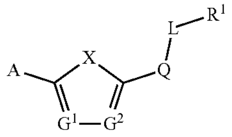

or a pharmaceutically acceptable salt, solvate or hydrate thereof, for use in the treatment of the human or animal body by therapy, wherein:

X is selected from O and S;

$G^1$ and $G^2$ are each independently selected from N and CH;

A is selected from

H, $C_{1-6}$ linear or branched alkyl or alkenyl optionally substituted with one or more groups $R^{A1}$, 5- or 6-membered heteroaryl groups containing 1 to 3 heteroatoms selected from N, O and S, optionally substituted with one or more groups $R^{B1}$, 4- to 6-membered heterocyclyl groups containing 1 to 3 heteroatoms selected from N, O and S, optionally substituted with one or more groups $R^{B2}$,

—CN,

—COOH, —$COOR^{C1}$, —$COR^{C2}$, —$CONH_2$, —$CONHR^{D1}$, —$CON(R^{D2})_2$,

—$NH_2$, —$NHR^{D4}$, —$N(R^{D3})_2$, —NHCOOH, —$NHCOOR^{C1}$, —NHCOH, —$NHCOR^{C2}$, —$NR^{D6}COOH$—$NR^{D7}COOR^{C1}$, —$NR^{D5}COR^{C2}$, and

—$SR^{E1}$;

L is a single bond, or is the group $L^A$, wherein $L^A$ is selected from

—$NR^LC(=O)$—*, —$C(=O)NR^L$—*,

—$NR^LC(=X^L)NR^L$—*,

—$SO_2$—$NR^L$—*, —$NR^L$—$SO_2$—*,

—OC(=O)—$NR^L$—*, and —$NR^L$—C(=O)O—*;

wherein the asterisk (*) indicates the point of attachment to $R^1$;

$X^L$ is selected from O and S;

$R^L$ is selected from

—H,

—C(=O)($C_{1-3}$alkyl),

—$P(=O)(OH)_2$, and

—$S(=O)_2NH_2$;

when L is a single bond, $R^1$ is $NH_2$;

when L is $L^A$, $R^1$ is $R^{1L}$, wherein $R^{1L}$ is selected from $C_{1-6}$ linear or branched unsubstituted alkyl;

phenyl, optionally substituted with one to three groups $R^{PH}$, 5 or 6-membered cycloalkyl, optionally substituted with one or more groups $R^{B3}$, 5 or 6-membered heteroaryl or heterocyclyl containing 1-3 heteroatoms selected from N, O and S, optionally substituted with one or more groups $R^{B4}$, and 8 to 10-membered bicyclyl, or heterobicyclyl containing 1-3 heteroatoms selected from N, O and S, optionally substituted with one or more groups $R^{B5}$;

wherein each $R^{PH}$ is independently selected from $C_{1-6}$ linear or branched alkyl, alkenyl or alkynyl optionally substituted with one or more groups $R^{A2}$, phenyl, optionally substituted with one or more groups $R^{A3}$, naphthyl, —F, —Cl, —Br, —I, —COOH, —$COOR^{C1}$, —$COR^{C2}$, —$CONH_2$, —$COONH_2$, —$CONHR^{D1}$, —$CON(R^{D2})_2$, —$NH_2$, —$NHR^{D4}$, —$NHR^{D8}$, —$N(R^{D3})_2$, —NHCOOH, —$NHCOOR^{C1}$, —NHCOH, —$NHCOR^{C2}$, —$NR^{D7}COOR^{C1}$, —$NR^{D5}COR^{C2}$, —$NHSO_2(C_{1-3}$alkyl),

—$SO_2NH_2$, —$SO_2NHR^{D1}$, —$SO_2N(R^{D2})_2$, —$SO_2R^{E2}$, —$SR^{E1}$,

—$NO_2$,

—CN,

—OH, and —$OR^{PH4}$;

wherein $R^{PH4}$ is selected from phenyl, benzyl, and $C_{1-6}$ linear or branched alkyl optionally substituted with one or more groups $R^{A5}$;

Q is selected from (Q1) and (Q2)

(Q1)

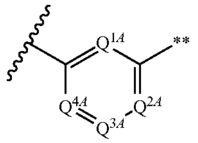

(Q2)

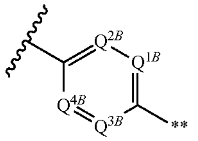

wherein the two asterisks (**) indicate the point of attachment to L;

two of $Q^{1A}$, $Q^{2A}$, $Q^{3A}$ and $Q^{4A}$ are CH;

the other two of $Q^{1A}$, $Q^{2A}$, $Q^{3A}$ and $Q^{4A}$ are independently selected from N, CH and $CR^{Q1}$;

two of $Q^{1B}$, $Q^{2B}$, $Q^{3B}$ and $Q^{4B}$ are CH;

the other two of $Q^{1B}$, $Q^{2B}$, $Q^{3B}$ and $Q^{4B}$ are independently selected from N, CH and $CR^{Q2}$;

each $R^{Q1}$ and each $R^{Q2}$ are independently selected from

—F, —Cl, —Br, —I, $C_{1-6}$ linear or branched unsubstituted alkyl,

—OH, —$O(C_{1-6}$alkyl),

—CN, and

—$N(R^{D3})_2$;

$R^{C1}$ and $R^{C2}$ are each independently selected from $C_{1-6}$ linear or branched alkyl, optionally substituted with one or more groups $R^{A6}$;

5-membered heteroaryl groups containing a single heteroatom selected from N, O and S, optionally substituted with one or two groups $R^{E3}$;

$R^{D1}$ to $R^{D7}$ are each independently selected from $C_{1-6}$ linear or branched alkyl, optionally substituted with one or more groups $R^{A7}$,

—COOH, —$COOR^{C1}$, —$COR^{C2}$,

—$C(=NH)NH_2$, or when two $R^{D2}$ or two $R^{D3}$ groups are attached to a single nitrogen atom they may, together with the nitrogen atom to which they are attached, form a 5 or 6-membered heterocyclic group containing 1-3 ring heteroatoms selected from N, O and S, optionally substituted with one or more groups $R^{D9}$;

wherein $R^{D9}$ is $C_{1-6}$ linear or branched alkyl, optionally substituted with one or more groups $R^{A8}$;

$R^{D8}$ is a $C_{5-6}$ heterocyclyl group containing one or two N atoms optionally substituted with one or more groups selected from —SH, and —$C(=O)OR^{D5A}$, wherein $R^{D5A}$ is a phenyl or benzyl group optionally substituted with an $NO_2$ group;

$R^{E1}$ and $R^{E2}$ are each independently selected from $C_{1-6}$ linear or branched unsubstituted alkyl, alkenyl or alkynyl;

$R^{E3}$ is independently selected from

—SH; and

—$C(=O)OR^{E4}$;

$R^{B1}$ to $R^{B5}$ are each independently selected from $C_{1-6}$ linear or branched alkyl optionally substituted with one or more groups $R^{A9}$, —F, —Cl, —Br, —OH, —$O(C_{1-3}$alkyl),

—CN,

—$NO_2$,

—COOH, —$COOR^{C1}$, —$COR^{C2}$, —$CONH_2$, —$CONHR^{D1}$, —$CON(R^{D2})_2$,

—$NH_2$, —$NHR^{D4}$, —$N(R^{D3})_2$, —NHCOOH, —$NHCOOR^{C1}$, —$NHCOR^{C2}$, —$NR^{D6}COOH$ —$NR^{D7}COOR^{C1}$, and —$NR^{D5}COR^{C2}$;

$R^{E4}$ is independently selected from phenyl or benzyl, optionally substituted with one or two groups $R^{A10}$;

$R^{A1}$ to $R^{A10}$ are each independently selected from

—F, —Cl, —Br,

—OH, —$OR^T$

—CN, —$NO_2$,

—$C(=O)R^T$, —COOH, —$COOR^T$, —$CON(R^G)_2$,

—$NH_2$, —$NHR^T$, —$N(R^T)_2$, —$NHC(=O)(R^F)$ and —$N(R^{D9})_2$;

$R^F$ is selected from $C_{1-6}$ linear or branched unsubstituted alkyl, and 5 to 6-membered heteroaryl including one to three heteroatoms selected from N, O and S;

the group —$N(R^G)_2$ is selected from azetidino, imidazolidino, pyrazolidino, pyrrolidino, piperidino, piperazino, N—$C_{1-4}$alkyl-piperazino, morpholino, azepino or diazepino, optionally substituted with one or more groups selected from linear or branched $C_{1-4}$alkyl, phenyl or benzyl;

$R^T$ is $C_{1-6}$ linear or branched unsubstituted alkyl; and the two $R^{D9}$ groups together with the nitrogen atom to which they are attached form a group selected from 5-membered heteroaryl group containing one or two nitrogen atoms; and 6-membered heterocyclic group containing one or two heteroatoms each independently selected from N, O and S.

In some embodiments, $R^L$ is selected from

—H, and —C(=O)($C_{1-3}$alkyl);

and in the group —N($R^{D9}$)$_2$, the two $R^{D9}$ groups together with the nitrogen atom to which they are attached form a 5-membered heteroaryl group containing one or two nitrogen atoms.

In some embodiments the invention provides a compound as described herein, for use in the treatment of aging or age-related diseases.

In some embodiments the invention provides a compound as described herein, for use in the treatment of a disease characterised by one or more of oxidative stress, CL deficiency, enrichment of docosahexaenoic acid (DHA) in CL and mitochondrial dysfunction.

In some embodiments the invention provides a compound as described herein, for use treating or preventing a disease or disorder associated with mitochondrial dysfunction.

In some embodiments the invention provides a compound as described herein, for use in the treatment of a disease selected from obesity (such as diet-induced obesity), diabetes (such as type-2 diabetes), diabetic complications (such as neuropathy, cardiomyopathy, retinopathy and erectile dysfunction), fatty liver disease, cardiovascular disease, neurodegenerative disease, metabolic diseases, insulin resistance and cancer.

In some embodiments the invention provides a compound as described herein, for use in the treatment of a disease selected from stroke, ischaemia, and reperfusion injury.

In some embodiments the invention provides a compound as described herein, for use in the prevention or treatment of Barth syndrome.

Use in the Manufacture of Medicaments

An aspect of the invention is the use of a compound as described herein in the manufacture of a medicament for the treatment of the human or animal body by therapy. For example, an aspect of the invention is the use of a compound according to one of formulae (I), (IA) or (IB) in the manufacture of a medicament for the treatment of the human or animal body by therapy.

An aspect of the invention is the use of a compound as described herein in the manufacture of a medicament for the treatment of aging and age-related diseases.

An aspect of the invention is the use of a compound as described herein in the manufacture of a medicament for the treatment of a disease characterised by one or more of oxidative stress, CL deficiency, enrichment of docosahexaenoic acid (DHA) in CL and mitochondrial dysfunction.

An aspect of the invention is the use of a compound as described herein in the manufacture of a medicament for the treatment of a disease or disorder associated with mitochondrial dysfunction.

In some embodiments the invention provides use of a compound as described herein, in the manufacture of a medicament for the treatment of a disease selected from obesity (such as diet-induced obesity), diabetes (such as type-2 diabetes), diabetic complications (such as neuropathy, cardiomyopathy, retinopathy and erectile dysfunction), fatty liver disease, cardiovascular disease, neurodegenerative disease, metabolic diseases, insulin resistance and cancer.

In some embodiments the invention provides use of a compound as described herein, in the manufacture of a medicament for the treatment of a disease selected from stroke, ischaemia, and reperfusion injury.

In some embodiments the invention provides use of a compound as described herein, in the manufacture of a medicament for the prevention or treatment of Barth syndrome.

Methods of Treatment

Another aspect of the invention is a method of treatment comprising administering to a patient in need of treatment a therapeutically effective amount of a compound, as described herein, preferably in the form of a pharmaceutical composition. For example, an aspect of the invention is a method of treatment comprising administering to a patient in need of treatment a therapeutically effective amount of a compound, according to one of formulae (I), (IA) or (IB), preferably in the form of a pharmaceutical composition.

An aspect of the invention is a method of treating or preventing mitochondrial dysfunction in vitro or in vivo, comprising administering to a cell or to a patient a therapeutically effective amount of a compound as described herein, and preventing or treating mitochondrial dysfunction in vitro or in vivo.

Diseases and Disorders

As explained above, it is known that ALCAT1 activity is associated with mitochondrial dysfunction in disease. As a result, as inhibitors of ALCAT1 the compounds described herein are useful in the treatment or prevention of a wide range of age-related diseases and disorders which are associated with mitochondrial dysfunction.

In some embodiments, the treatment is treatment of aging.

In some embodiments, the treatment is treatment of age-related diseases.

In some embodiments, the treatment is treatment of a disease characterised by one or more of oxidative stress, CL deficiency, enrichment of docosahexaenoic acid (DHA) in CL and mitochondrial dysfunction.

In some embodiments, the treatment is treatment of a disease or disorder associated with mitochondrial dysfunction.

In some embodiments, the treatment is treatment of obesity.

In some embodiments, the treatment is treatment of diabetes. In some embodiments, the treatment is treatment of type-2 diabetes.

In some embodiments, the treatment is treatment of diabetic complications. In some embodiments, the treatment is treatment of neuropathy. In some embodiments, the treatment is treatment of cardiomyopathy. In some embodiments, the treatment is treatment of retinopathy. In some embodiments, the treatment is treatment of erectile dysfunction.

In some embodiments, the treatment is treatment of fatty liver disease.

In some embodiments, the treatment is treatment of cardiovascular disease.

In some embodiments, the treatment is treatment of neurodegenerative disease. In some embodiments, the treatment is treatment of Alzheimer's disease.

In some embodiments, the treatment is treatment of a metabolic disease.

In some embodiments, the treatment is treatment of insulin resistance.

In some embodiments, the treatment is treatment of cancer. In some embodiments, the treatment is treatment of a tumour which over-expresses ALCAT1, or in which inhibition of ALCAT1 facilitates or improves the action of cytotoxic tumouricidal agents.

In some embodiments, the treatment is treatment of stroke, ischaemia, or reperfusion injury.

In some embodiments, the treatment is the prevention or treatment of Barth syndrome.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, alleviation of symptoms of the condition, amelioration of the condition, and cure of the condition. Treatment as a prophylactic measure (i.e., prophylaxis) is also included. For example, use with patients who have not yet developed the condition, but who are at risk of developing the condition, is encompassed by the term "treatment."

For example, use with patients who may not yet have a disorder or condition, but who are at risk of developing a disorder or condition, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

Kits

One aspect of the invention pertains to a kit comprising (a) a compound as described herein, or a composition comprising a compound as described herein, e.g., preferably provided in a suitable container and/or with suitable packaging; and (b) instructions for use, e.g., written instructions on how to administer the compound or composition.

The written instructions may also include a list of indications for which the compound is a suitable treatment.

Routes of Administration

The compound or pharmaceutical composition comprising the compound may be administered to a subject by any convenient route of administration, whether systemically/peripherally or topically (i.e., at the site of desired action).

Routes of administration include, but are not limited to, oral (e.g., by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

The Subject/Patient

The subject/patient may be a chordate, a vertebrate, a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutan, gibbon), or a human.

Furthermore, the subject/patient may be any of its forms of development, for example, a foetus.

In one preferred embodiment, the subject/patient is a human.

Formulations

While it is possible for the compound to be administered alone, it is preferable to present it as a pharmaceutical formulation (e.g., composition, preparation, medicament) comprising at least one compound, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one compound, as described herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 5th edition, 2005.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more compounds and optionally one or more other pharmaceutically acceptable ingredients, including, for example, penetration, permeation, and absorption enhancers. Formulations may also suitably be provided in the form of a depot or reservoir.

The compound may be dissolved in, suspended in, or admixed with one or more other pharmaceutically acceptable ingredients. The compound may be presented in a liposome or other microparticulate which is designed to target the compound, for example, to blood components or one or more organs.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the compound in a flavored basis, usually sucrose and acacia or tragacanth. Pastilles typically comprise the compound in an inert matrix, such as gelatin and glycerin, or sucrose and acacia. Mouthwashes typically comprise the compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the compound and a paraffinic or a water-miscible ointment base.

Creams are typically prepared from the compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the compound through the skin or other affected areas. Examples of such dermal penetration enhancers include dimethylsulfoxide and related analogues.

Emulsions are typically prepared from the compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulfate. The choice of suitable oils or fats for the formulation is based on achieving the desired cosmetic properties, since the solubility of the compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the compound is dissolved or suspended in a suitable carrier, especially an aqueous solvent for the compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/mL to about 100 μg/mL, for example from about 10 ng/mL to about 10 μg/mL, for example from about 10 ng/mL to about 1 μg/mL. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the compounds, and compositions comprising the compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Where the compound is a salt, an ester, an amide, a prodrug, or the like, the amount administered is calculated on the basis of the parent compound and so the actual weight to be used is increased proportionately.

Methods of Synthesis

Another aspect of the present invention is a method of synthesising a compound described herein.

In some embodiments, the method comprises the steps described in the general syntheses described herein.

EXAMPLES

General Synthetic Routes

Schemes 1 and 2 below show the general syntheses followed to prepare compounds according to the invention:

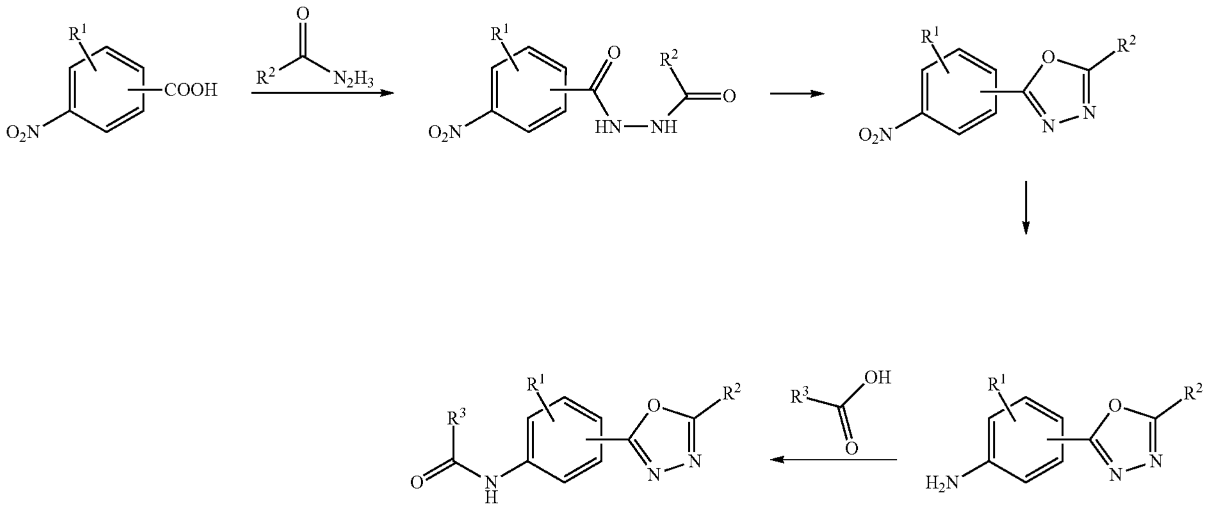

Scheme 2

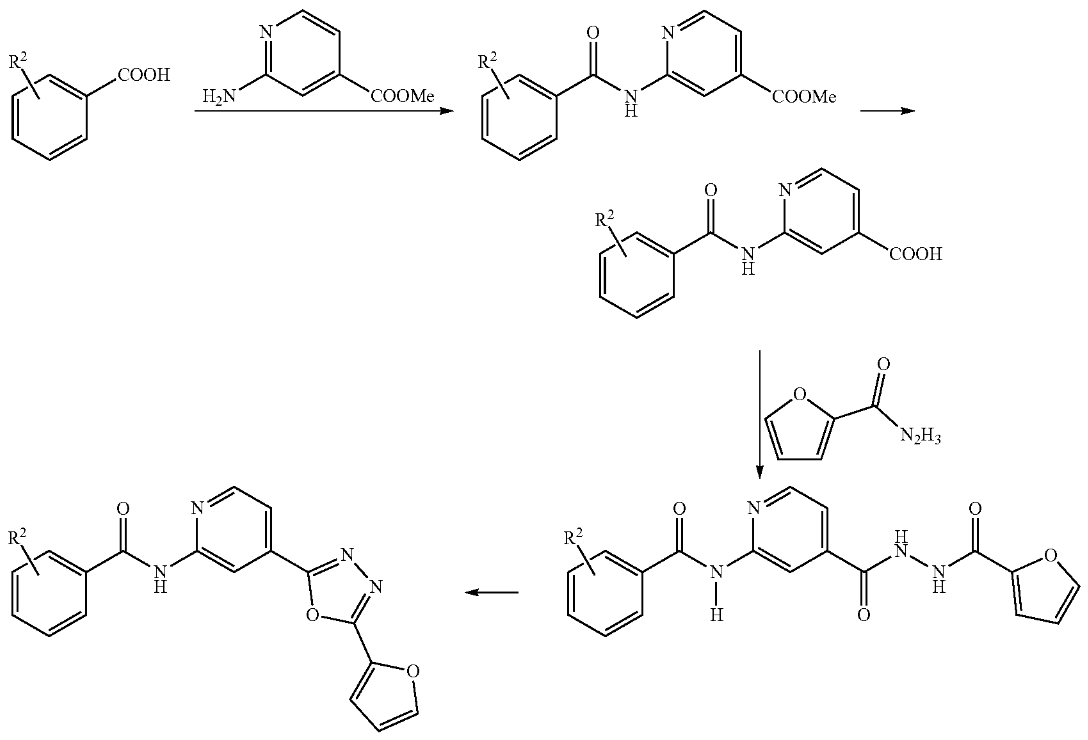

The syntheses of some specific compounds according to these reaction schemes are set out in the Examples below.

Example 1

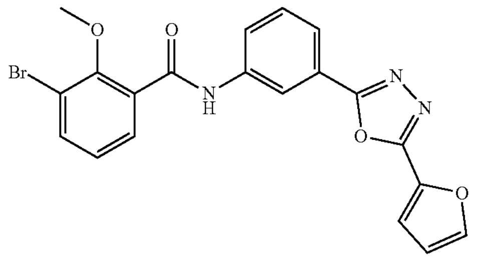 [SMILES: COc1c(Br)cccc1C(=O)Nc1cccc(-c2nnc(-c3ccco3)o2)c1]

3-Bromo-N-(3-(5-(furan-2-yl)-1,3,4-oxadiazol-2-yl)phenyl)-2-methoxybenzamide

Compound 192

According to the synthetic procedure depicted in Scheme 1, 3-bromo-N-(3-(5-(furan-2-yl)-1,3,4-oxadiazol-2-yl)phenyl)-2-methoxybenzamide can be prepares as follows:

a) N'-(3-nitrobenzoyl)furan-2-carbohydrazide: To a solution of 3-nitrobenzoic acid (10.0 g, 59.8 mmol) in dichloromethane (50 ml) were added N,N-dimethylformamide (0.1 ml) and oxalyl chloride (7.7 ml, 89.8 mmol), and the mixture was stirred at room temperature for 4 hr. The solvent was evaporated under reduced pressure to give acid chloride. This acid chloride was dissolved in tetrahydrofuran (50 ml) and added dropwise to a suspension of 2-furoic acid hydrazide (7.6 g, 60.4 mmol) and anhydrous sodium carbonate (6.3 g, 59.8 mmol) in tetrahydrofuran (50 mL) and water (50 mL) at 0° C. The mixture was stirred at 0° C. for 1 h, and at room temperature for 6 hr. A massive precipitation was observed. The product was harvested by filtration and washed with water, then finally dried in vacuo to afford 14.0 g (85.1% yield) of N'-(3-nitrobenzoyl)furan-2-carbohydrazide as a white solid.

b) 2-(Furan-2-yl)-5-(3-nitrophenyl)-1,3,4-oxadiazole: N'-(3-nitrobenzoyl)furan-2-carbohydrazide (14.0 g, 50.9 mmol) was dissolved in phosphorus oxychloride (70 ml) and the mixture was stirred with heating at 80° C. for 5 hr. Phosphorus oxychloride was evaporated under reduced pressure and water was added to the residue. The mixture was extracted with dichloromethane and the organic layer was washed with saturated aqueous solution of sodium hydrogencarbonate, dried over anhydrous sodium sulfate and concentrated under reduced pressure to afford 12.3 g (93.9% yield) of 2-(furan-2-yl)-5-(3-nitrophenyl)-1,3,4-oxadiazole as a yellow solid.

c) 3-(5-(Furan-2-yl)-1,3,4-oxadiazol-2-yl)aniline: A mixture of 2-(furan-2-yl)-5-(3-nitrophenyl)-1,3,4-oxadiazole (12.3 g, 47.8 mmol) and Raney-Ni (2.0 g) in methanol (100 ml) was stirred at 50° C. for 16 h under 2.0 Mpa hydrogen atmosphere. The mixture was filtered and the filtrate was concentrated under vacuum. The residue was purified by silica gel flash column chromatography (dichloromethane/methanol=50/1) gave 9.4 g (86.5% yield) of 3-(5-(furan-2-yl)-1,3,4-oxadiazol-2-yl)aniline as a white solid.

d) 3-Bromo-N-(3-(5-(furan-2-yl)-1,3,4-oxadiazol-2-yl) phenyl)-2-methoxybenzamide: A mixture of 3-bromo-2-methoxybenzoic acid (122.0 mg, 0.53 mmol) and N,N-dimethylformamide (0.01 ml) in thionyl chloride (0.5 ml) was stirred with refluxing for 1 hr. The excess thionyl chloride was evaporated under reduced pressure to give acid chloride. This acid chloride was dissolved in dichloromethane (5 ml) and added dropwise to a solution of 3-(5-(furan-2-yl)-1,3,4-oxadiazol-2-yl)aniline (100.0 mg, 0.44 mmol) and triethylamine (62.3 mg, 0.62 mmol) in dichloromethane (5 ml) at 0° C. The reaction mixture was allowed to warm slowly to room temperature and stirred for 12 h. The mixture was concentrated under vacuum, and the residue was purified by silica gel flash column chromatography (dichloromethane/methanol=100/1) to give the title compound (175.5 mg, 90.6% yield) as a white solid.

$^1$H NMR (400 MHz, DMSO): δ 10.73 (s, 1H), 8.59 (s, 1H), 8.10 (s, 1H), 7.92 (d, J=8.0 Hz, 1H), 7.83-7.80 (m, 2H), 7.63-7.59 (m, 2H), 7.44 (d, J=3.6 Hz, 1H), 7.22 (t, J=7.6 Hz, 1H), 6.85-6.84 (m, 1H), 3.84 (s, 3H);

LC-HRMS (ESI) calcd for [M+H, $C_{20}H_{15}BrN_3O_4]^+$: 440.0246, Found 440.0246.

Example 2

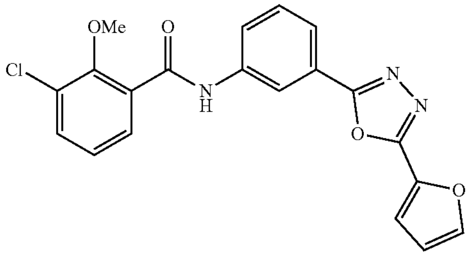 [SMILES: COc1c(Cl)cccc1C(=O)Nc1cccc(-c2nnc(-c3ccco3)o2)c1]

3-Chloro-N-(3-(5-(furan-2-yl)-1,3,4-oxadiazol-2-yl) phenyl)-2-methoxybenzamide

Compound 193

3-Chloro-N-(3-(5-(furan-2-yl)-1,3,4-oxadiazol-2-yl)phenyl)-2-methoxybenzamide can be prepared as in Example 1, but from 3-chloro-2-methoxybenzoic acid (98.5 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (163.0 mg, 93.6% yield) as a yellow solid.

$^1$H NMR (400 MHz, DMSO): δ 10.72 (s, 1H), 8.59 (s, 1H), 8.10 (d, J=1.2 Hz, 1H), 7.92 (d, J=8.0 Hz, 1H), 7.82 (d, J=7.6 Hz, 1H), 7.67 (dd, J=1.2, 8.0 Hz, 1H), 7.62 (t, J=8.0 Hz, 1H), 7.57-7.55 (m, 1H), 7.45 (d, J=3.6 Hz, 1H), 7.31-7.27 (m, 1H), 6.85-6.84 (m, 1H), 3.86 (s, 3H);

LC-HRMS (ESI) calcd for [M+H, $C_{20}H_{15}ClN_3O_4]^+$: 396.0751, Found 396.0756.

Example 3

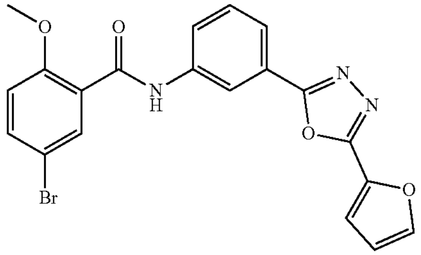 [SMILES: COc1ccc(Br)cc1C(=O)Nc1cccc(-c2nnc(-c3ccco3)o2)c1]

5-Bromo-N-(3-(5-(furan-2-yl)-1,3,4-oxadiazol-2-yl) phenyl)-2-methoxybenzamide

Compound 120

5-Bromo-N-(3-(5-(furan-2-yl)-1,3,4-oxadiazol-2-yl)phenyl)-2-methoxybenzamide can be prepared as in Example 1, but from 5-bromo-2-methoxybenzoic acid (122.0 mg, 0.53 mmol), 3-(5-(furan-2-yl)-1,3,4-oxadiazol-2-yl)aniline (100.0 mg, 0.44 mmol) and triethylamine (58.7 mg, 0.58 mmol). The crude product was purified by silica gel flash column chromatography (dichloromethane/methanol=100/1) to give the title compound (184.5 mg, 95.2% yield) as a white solid.

$^1$H NMR (400 MHz, DMSO): δ 10.50 (s, 1H), 8.56 (s, 1H), 8.10 (d, J=0.8 Hz, 1H), 7.91 (d, J=8.4 Hz, 1H), 7.80 (d, J=7.6 Hz, 1H), 7.74 (d, J=2.8 Hz, 1H), 7.68 (dd, J=2.8, 8.8 Hz, 1H), 7.60 (t, J=8.0 Hz, 1H), 7.48 (d, J=3.2 Hz, 1H), 7.17 (d, J=9.2 Hz, 1H), 6.85-6.83 (m, 1H), 3.89 (s, 3H);

LC-HRMS (ESI) calcd for [M+H, $C_{20}H_{15}BrN_3O_4]^+$: 440.0246, Found 440.0221.

Example 4

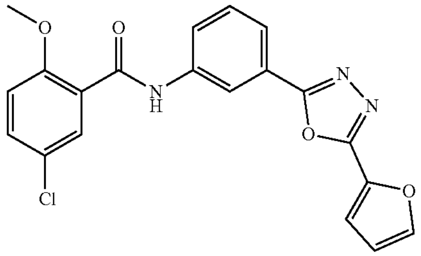 [SMILES: COc1ccc(Cl)cc1C(=O)Nc1cccc(-c2nnc(-c3ccco3)o2)c1]

5-Chloro-N-(3-(5-(furan-2-yl)-1,3,4-oxadiazol-2-yl) phenyl)-2-methoxybenzamide

Compound 124

5-Chloro-N-(3-(5-(furan-2-yl)-1,3,4-oxadiazol-2-yl)phenyl)-2-methoxybenzamide can be prepared as in Example 1, but from 5-chloro-2-methoxybenzoic acid (98.5 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (162.9 mg, 93.5% yield) as a white solid.

$^1$H NMR (400 MHz, DMSO): δ 10.50 (s, 1H), 8.57 (s, 1H), 8.10 (d, J=0.8 Hz, 1H), 7.91 (d, J=8.4 Hz, 1H), 7.80 (d, J=7.6 Hz, 1H), 7.64-7.55 (m, 3H), 7.44 (d, J=3.6 Hz, 1H), 7.23 (d, J=9.2 Hz, 1H), 6.85-6.83 (m, 1H), 3.90 (s, 3H);

LC-HRMS (ESI) calcd for [M+H, $C_{20}H_{15}ClN_3O_4]^+$: 396.0751, Found 396.0749.

Example 5

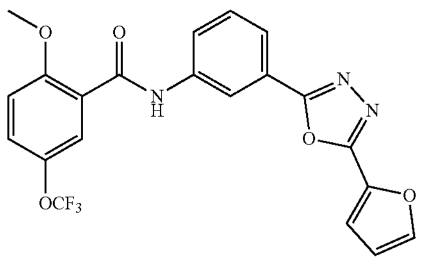

N-(3-(5-(Furan-2-yl)-1,3,4-oxadiazol-2-yl)phenyl)-2-methoxy-5-(trifluoromethoxy)benzamide Compound 279

N-(3-(5-(Furan-2-yl)-1,3,4-oxadiazol-2-yl)phenyl)-2-methoxy-5-(trifluoromethoxy)benzamide can be prepared as in Example 1, but from 2-methoxy-5-(trifluoromethoxy) benzoic acid (124.7 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (177.9 mg, 90.8% yield) as a white solid.

$^1$H NMR (400 MHz, DMSO): δ 10.53 (s, 1H), 8.57 (s, 1H), 8.11-8.10 (m, 1H), 7.93-7.91 (m, 1H), 7.82-7.80 (m, 1H), 7.63-7.53 (m, 3H), 7.45 (dd, J=0.4, 3.6 Hz, 1H), 7.31 (d, J=8.8 Hz, 1H), 6.85-6.84 (m, 1H), 3.93 (s, 3H);

LC-HRMS (ESI) calcd for [M+H, $C_{21}H_{15}F_3N_3O_5]^+$: 446.0964, Found 446.0960.

Example 6

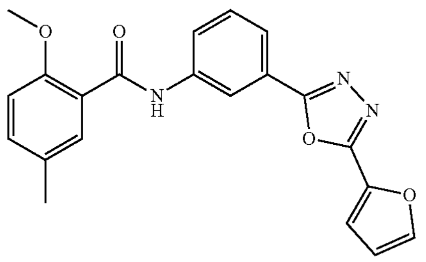 [SMILES: COc1ccc(C)cc1C(=O)Nc1cccc(-c2nnc(-c3ccco3)o2)c1]

N-(3-(5-(Furan-2-yl)-1,3,4-oxadiazol-2-yl)phenyl)-2-methoxy-5-methylbenzamide

Compound 197

N-(3-(5-(Furan-2-yl)-1,3,4-oxadiazol-2-yl)phenyl)-2-methoxy-5-methylbenzamide can be prepared as in Example 1, but from 2-methoxy-5-methylbenzoic acid (87.7 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (155.8 mg, 94.3% yield) as a white solid.

$^1$H NMR (400 MHz, DMSO): δ 10.39 (s, 1H), 8.60 (s, 1H), 8.10 (d, J=0.8 Hz, 1H), 7.92 (d, J=8.0 Hz, 1H), 7.79 (d, J=7.6 Hz, 1H), 7.59 (t, J=8.0 Hz, 1H), 7.47-7.44 (m, 2H), 7.33 (dd, J=2.0, 8.4 Hz, 1H), 7.09 (d, J=8.4 Hz, 1H), 6.85-6.84 (m, 1H), 3.88 (s, 3H), 2.30 (s, 3H);

LC-HRMS (ESI) calcd for [M+H, $C_{21}H_{18}N_3O_4]^+$: 376.1297, Found 376.1310.

Example 7

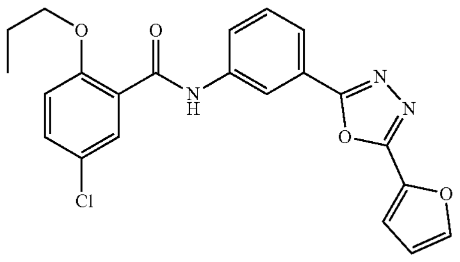

5-Chloro-N-(3-(5-(furan-2-yl)-1,3,4-oxadiazol-2-yl)phenyl)-2-propoxybenzamide

Compound 123

5-Chloro-N-(3-(5-(furan-2-yl)-1,3,4-oxadiazol-2-yl)phenyl)-2-propoxybenzamide can be prepared as in Example 1, but from 5-chloro-2-propoxybenzoic acid (113.3 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (171.8 mg, 92.1% yield) as a white solid.

$^1$H NMR (400 MHz, DMSO): δ 10.47 (s, 1H), 8.59 (s, 1H), 8.10 (d, J=0.8 Hz, 1H), 7.86 (d, J=8.0 Hz, 1H), 7.80 (d, J=8.0 Hz, 1H), 7.64 (d, J=2.8 Hz, 1H), 7.61 (t, J=8.0 Hz, 1H), 7.54 (dd, J=2.8, 8.8 Hz, 1H), 7.44 (d, J=3.6 Hz, 1H), 7.22 (d, J=8.8 Hz, 1H), 6.85-6.84 (m, 1H), 4.08 (t, J=6.4 Hz, 2H), 1.81-1.74 (m, 2H), 0.96 (t, J=7.4 Hz, 3H); LC-HRMS (ESI) calcd for [M+H, $C_{22}H_{19}ClN_3O_4]^+$: 424.1064, Found 424.1078.

Example 8

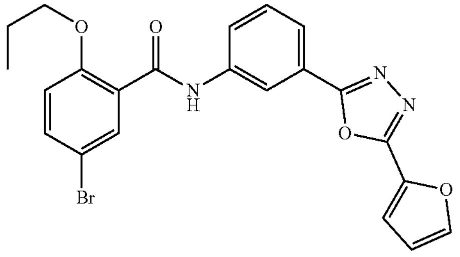 [SMILES: CCCOc1ccc(Cl)cc1C(=O)Nc1cccc(-c2nnc(-c3ccco3)o2)c1]

5-Bromo-N-(3-(5-(furan-2-yl)-1,3,4-oxadiazol-2-yl)phenyl)-2-propoxybenzamide

Compound 119

5-Bromo-N-(3-(5-(furan-2-yl)-1,3,4-oxadiazol-2-yl)phenyl)-2-propoxybenzamide can be prepared as in Example 1, but from 5-bromo-2-propoxybenzoic acid (136.8 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (191.4 mg, 92.9% yield) as a white solid.

$^1$H NMR (400 MHz, DMSO): δ 10.47 (s, 1H), 8.58 (s, 1H), 8.10 (d, J=1.2 Hz, 1H), 7.86 (d, J=8.4 Hz, 1H), 7.80 (d, J=7.6 Hz, 1H), 7.75 (d, J=2.4 Hz, 1H), 7.66 (dd, J=2.4, 8.8 Hz, 1H), 7.63-7.59 (m, 1H), 7.44 (d, J=3.2 Hz, 1H), 7.17 (d, J=9.2 Hz, 1H), 6.85-6.84 (m, 1H), 4.07 (t, J=6.4 Hz, 2H), 1.80-1.73 (m, 2H), 0.96 (t, J=7.4 Hz, 3H);

LC-HRMS (ESI) calcd for [M+H, $C_{22}H_{19}BrN_3O_4$]$^+$: 468.0559, Found 468.0568.

Example 9

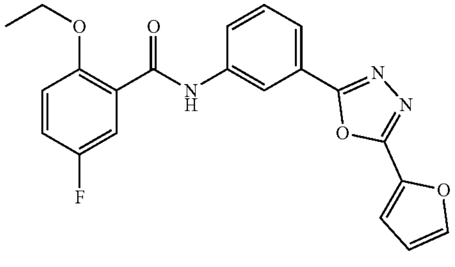

2-Ethoxy-5-fluoro-N-(3-(5-(furan-2-yl)-1,3,4-oxadiazol-2-yl)phenyl)benzamide

Compound 125

2-Ethoxy-5-fluoro-N-(3-(5-(furan-2-yl)-1,3,4-oxadiazol-2-yl)phenyl)benzamide can be prepared as in Example 1, but from 2-ethoxy-5-fluorobenzoic acid (97.2 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (159.4 mg, 92.1% yield) as a beige solid.

$^1$H NMR (400 MHz, DMSO): δ 10.49 (s, 1H), 8.61 (s, 1H), 8.11 (d, J=0.8 Hz, 1H), 7.88-7.85 (m, 1H), 7.81 (d, J=7.6 Hz, 1H), 7.63-7.59 (m, 1H), 7.50 (dd, J=3.2, 8.8 Hz, 1H), 7.45 (d, J=3.2 Hz, 1H), 7.40-7.34 (m, 1H), 7.22 (dd, J=4.4, 9.2 Hz, 1H), 6.85-6.84 (m, 1H), 4.17 (q, J=6.8 Hz, 2H), 1.39 (t, J=7.0 Hz, 3H);

LC-HRMS (ESI) calcd for [M+H, $C_{21}H_{17}FN_3O_4$]$^+$: 394.1203, Found 394.1200.

Example 10

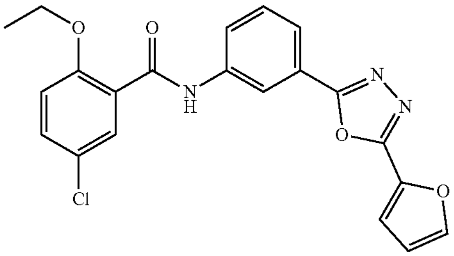 [SMILES: CCOc1ccc(F)cc1C(=O)Nc1cccc(-c2nnc(-c3ccco3)o2)c1]

5-Chloro-2-ethoxy-N-(3-(5-(furan-2-yl)-1,3,4-oxadiazol-2-yl)phenyl)benzamide

Compound 122

5-Chloro-2-ethoxy-N-(3-(5-(furan-2-yl)-1,3,4-oxadiazol-2-yl)phenyl)benzamide can be prepared as in Example 1, but from 5-chloro-2-ethoxybenzoic acid (105.9 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (170.6 mg, 94.6% yield) as a pale-yellow solid.

$^1$H NMR (400 MHz, DMSO): δ 10.48 (s, 1H), 8.59 (s, 1H), 8.11 (d, J=1.2 Hz, 1H), 7.87 (d, J=7.6 Hz, 1H), 7.81 (d, J=7.6 Hz, 1H), 7.66 (d, J=2.8 Hz, 1H), 7.61 (t, J=8.0 Hz, 1H), 7.57-7.54 (m, 1H), 7.44 (d, J=3.2 Hz, 1H), 7.22 (d, J=8.8 Hz, 1H), 6.85-6.84 (m, 1H), 4.18 (q, J=6.8 Hz, 2H), 1.38 (t, J=7.0 Hz, 3H);

LC-HRMS (ESI) calcd for [M+H, $C_{21}H_{17}ClN_3O_4$]$^+$: 410.0908, Found 410.0910.

Example 11

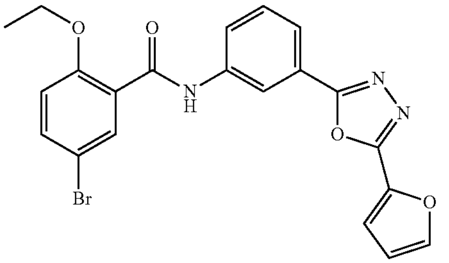 [SMILES: CCOc1ccc(Br)cc1C(=O)Nc1cccc(-c2nnc(-c3ccco3)o2)c1]

5-Bromo-2-ethoxy-N-(3-(5-(furan-2-yl)-1,3,4-oxadiazol-2-yl)phenyl)benzamide

Compound 118

5-Bromo-2-ethoxy-N-(3-(5-(furan-2-yl)-1,3,4-oxadiazol-2-yl)phenyl)benzamide can be prepared as in Example 1, but from 5-bromo-2-ethoxybenzoic acid (129.4 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (187.9 mg, 94.0% yield) as a white solid.

$^1$H NMR (400 MHz, DMSO): δ 10.47 (s, 1H), 8.59 (s, 1H), 8.10 (d, J=1.2 Hz, 1H), 7.87 (d, J=8.0 Hz, 1H), 7.81 (d, J=8.0 Hz, 1H), 7.77 (d, J=2.4 Hz, 1H), 7.67 (dd, J=2.8, 8.8 Hz, 1H), 7.61 (t, J=8.0 Hz, 1H), 7.44 (d, J=3.6 Hz, 1H), 7.17 (d, J=8.8 Hz, 1H), 6.85-6.84 (m, 1H), 4.17 (q, J=6.8 Hz, 2H), 1.38 (t, J=6.8 Hz, 3H);

LC-HRMS (ESI) calcd for [M+H, $C_{21}H_{17}BrN_3O_4$]$^+$: 454.0402, Found 454.0406.

Example 12

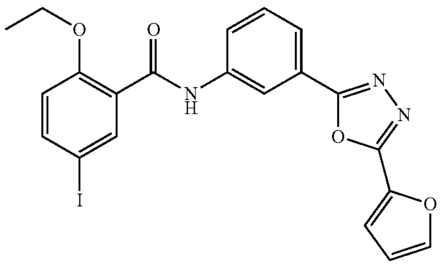 [SMILES: CCOc1ccc(I)cc1C(=O)Nc1cccc(-c2nnc(-c3ccco3)o2)c1]

2-Ethoxy-N-(3-(5-(furan-2-yl)-1,3,4-oxadiazol-2-yl)phenyl)-5-iodobenzamide

Compound 200

2-Ethoxy-N-(3-(5-(furan-2-yl)-1,3,4-oxadiazol-2-yl)phenyl)-5-iodobenzamide can be prepared as in Example 1, but from 2-ethoxy-5-iodobenzoic acid (154.2 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (197.6 mg, 89.6% yield) as a pale-yellow solid.

$^1$H NMR (400 MHz, DMSO): δ 10.44 (s, 1H), 8.58 (s, 1H), 8.10 (d, J=0.8 Hz, 1H), 7.90 (d, J=2.4 Hz, 1H), 7.86 (d, J=8.4 Hz, 1H), 7.82-7.79 (m, 2H), 7.62-7.58 (m, 1H), 7.44 (d, J=3.2 Hz, 1H), 7.04 (d, J=8.8 Hz, 1H), 6.85-6.84 (m, 1H), 4.17 (q, J=6.8 Hz, 2H), 1.38 (t, J=6.8 Hz, 3H);

LC-HRMS (ESI) calcd for [M+H, $C_{21}H_{17}IN_3O_4$]$^+$: 502.0264, Found 502.0264.

Example 13

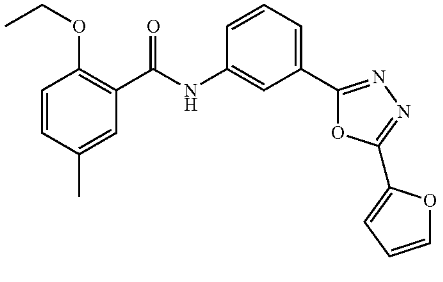 [SMILES: CCOc1ccc(C)cc1C(=O)Nc1cccc(-c2nnc(-c3ccco3)o2)c1]

2-Ethoxy-N-(3-(5-(furan-2-yl)-1,3,4-oxadiazol-2-yl)phenyl)-5-methylbenzamide

Compound 218

2-Ethoxy-N-(3-(5-(furan-2-yl)-1,3,4-oxadiazol-2-yl)phenyl)-5-methylbenzamide can be prepared as in Example 1, but from 2-ethoxy-5-methylbenzoic acid (95.1 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (160.4 mg, 93.6% yield) as a white solid.

$^1$H NMR (400 MHz, DMSO): δ 10.40 (s, 1H), 8.63 (s, 1H), 8.11 (d, J=1.2 Hz, 1H), 7.86 (d, J=8.0 Hz, 1H), 7.79 (d, J=8.0 Hz, 1H), 7.60 (t, J=8.0 Hz, 1H), 7.52 (d, J=2.0 Hz, 1H), 7.45 (d, J=2.8 Hz, 1H), 7.32 (dd, J=2.0, 8.4 Hz, 1H), 7.08 (d, J=8.4 Hz, 1H), 6.85-6.84 (m, 1H), 4.16 (q, J=6.8 Hz, 2H), 2.30 (s, 3H), 1.40 (t, J=6.8 Hz, 3H); LC-HRMS (ESI) calcd for [M+H, $C_{22}H_{20}N_3O_4$]$^+$: 390.1454, Found 390.1458.

Example 14

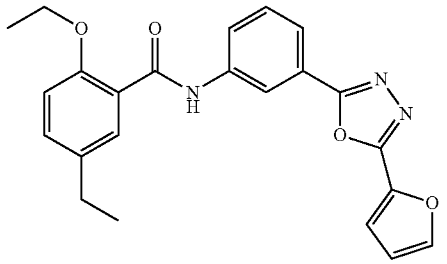 [SMILES: CCOc1ccc(CC)cc1C(=O)Nc1cccc(-c2nnc(-c3ccco3)o2)c1]

2-Ethoxy-5-ethyl-N-(3-(5-(furan-2-yl)-1,3,4-oxadiazol-2-yl)phenyl)benzamide

Compound 219

2-Ethoxy-5-ethyl-N-(3-(5-(furan-2-yl)-1,3,4-oxadiazol-2-yl)phenyl)benzamide can be prepared as in Example 1, but from 2-ethoxy-5-ethylbenzoic acid (102.6 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (170.6 mg, 96.1% yield) as a white solid.

$^1$H NMR (400 MHz, DMSO): δ 10.40 (s, 1H), 8.63 (s, 1H), 8.11 (d, J=1.2 Hz, 1H), 7.86 (d, J=8.0 Hz, 1H), 7.79 (d, J=8.0 Hz, 1H), 7.60 (t, J=8.0 Hz, 1H), 7.54 (d, J=2.0 Hz, 1H), 7.44 (d, J=3.6 Hz, 1H), 7.35-7.33 (m, 1H), 7.10 (d, J=8.4 Hz, 1H), 6.85-6.84 (m, 1H), 4.16 (q, J=6.8 Hz, 2H), 2.61 (q, J=7.6 Hz, 2H), 1.40 (t, J=6.8 Hz, 3H), 1.18 (t, J=7.6 Hz, 3H);

LC-HRMS (ESI) calcd for [M+H, $C_{23}H_{22}N_3O_4$]$^+$: 404.1610, Found 404.1607.

Example 15

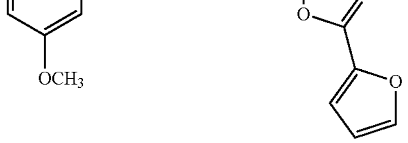

2-Fluoro-N-(3-(5-(furan-2-yl)-1,3,4-oxadiazol-2-yl)phenyl)-5-(trifluoromethoxy)benzamide Compound 211

2-Fluoro-N-(3-(5-(furan-2-yl)-1,3,4-oxadiazol-2-yl)phenyl)-5-(trifluoromethoxy)benzamide can be prepared as in Example 1, but from 2-fluoro-5-(trifluoromethoxy)benzoic acid (118.3 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (179.4 mg, 94.1% yield) as a white solid.

$^1$H NMR (400 MHz, DMSO): δ 10.87 (s, 1H), 8.53 (s, 1H), 8.10 (d, J=1.2 Hz, 1H), 7.94 (d, J=8.0 Hz, 1H), 7.84 (d, J=7.6 Hz, 1H), 7.78-7.76 (m, 1H), 7.68-7.61 (m, 2H), 7.58-7.54 (m, 1H), 7.45 (d, J=3.6 Hz, 1H), 6.85-6.84 (m, 1H);

LC-HRMS (ESI) calcd for [M+H, $C_{20}H_{12}F_4N_3O_4]^+$: 434.0764, Found 434.0765.

Example 16

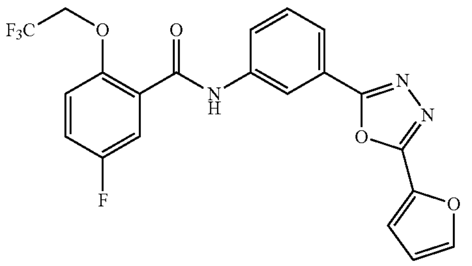 [SMILES: O=C(Nc1cccc(-c2nnc(-c3ccco3)o2)c1)c1cc(F)ccc1OCC(F)(F)F]

5-Fluoro-N-(3-(5-(furan-2-yl)-1,3,4-oxadiazol-2-yl)phenyl)-2-(2,2,2-trifluoroethoxy)benzamide Compound 228

5-Fluoro-N-(3-(5-(furan-2-yl)-1,3,4-oxadiazol-2-yl)phenyl)-2-(2,2,2-trifluoroethoxy)benzamide can be prepared as in Example 1, but from 5-fluoro-2-(2,2,2-trifluoroethoxy)benzoic acid (125.7 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (178.7 mg, 90.8% yield) as a white solid.

$^1$H NMR (400 MHz, DMSO): δ 10.54 (s, 1H), 8.56 (s, 1H), 8.11 (d, J=0.8 Hz, 1H), 7.87-7.84 (m, 1H), 7.81 (d, J=8.0 Hz, 1H), 7.61 (d, J=8.0 Hz, 1H), 7.49 (dd, J=3.2, 8.4 Hz, 1H), 7.45-7.41 (m, 2H), 7.36-7.32 (m, 1H), 6.85-6.84 (m, 1H), 4.86 (q, J=8.8 Hz, 2H); LC-HRMS (ESI) calcd for [M+H, $C_{21}H_{14}F_4N_3O_4]^+$: 448.0920, Found 448.0917.

Example 17

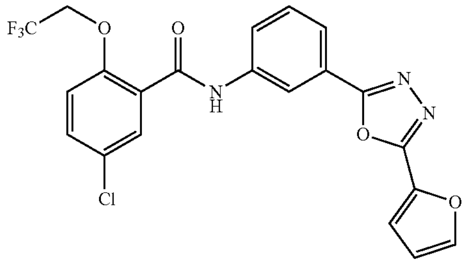 [SMILES: O=C(Nc1cccc(-c2nnc(-c3ccco3)o2)c1)c1cc(Cl)ccc1OCC(F)(F)F]

5-Chloro-N-(3-(5-(furan-2-yl)-1,3,4-oxadiazol-2-yl)phenyl)-2-(2,2,2-trifluoroethoxy)benzamide Compound 225

5-Chloro-N-(3-(5-(furan-2-yl)-1,3,4-oxadiazol-2-yl)phenyl)-2-(2,2,2-trifluoroethoxy)benzamide can be prepared as in Example 1, but from 5-chloro-2-(2,2,2-trifluoroethoxy)benzoic acid (134.4 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (189.6 mg, 92.9% yield) as a white solid.

$^1$H NMR (400 MHz, DMSO): δ 10.55 (s, 1H), 8.54 (s, 1H), 8.11-8.10 (m, 1H), 7.86 (d, J=8.4 Hz, 1H), 7.81 (d, J=7.6 Hz, 1H), 7.66-7.59 (m, 3H), 7.44 (d, J=3.6 Hz, 1H), 7.34 (d, J=8.8 Hz, 1H), 6.85-6.84 (m, 1H), 4.88 (q, J=8.8 Hz, 2H); LC-HRMS (ESI) calcd for [M+H, $C_{21}H_{14}ClF_3N_3O_4]^+$: 464.0625, Found 464.0627.

Example 18

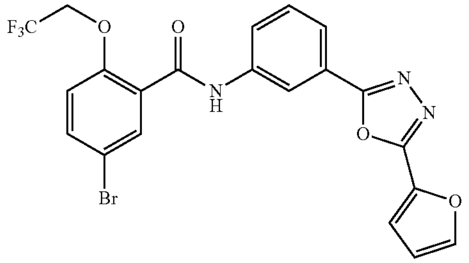 [SMILES: O=C(Nc1cccc(-c2nnc(-c3ccco3)o2)c1)c1cc(Br)ccc1OCC(F)(F)F]

5-Bromo-N-(3-(5-(furan-2-yl)-1,3,4-oxadiazol-2-yl)phenyl)-2-(2,2,2-trifluoroethoxy)benzamide Compound 226

5-Bromo-N-(3-(5-(furan-2-yl)-1,3,4-oxadiazol-2-yl)phenyl)-2-(2,2,2-trifluoroethoxy)benzamide can be prepared as in Example 1, but from 5-bromo-2-(2,2,2-trifluoroethoxy)benzoic acid (157.9 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (207.5 mg, 92.8% yield) as a white solid.

$^1$H NMR (400 MHz, DMSO): δ 10.55 (s, 1H), 8.54 (s, 1H), 8.13 (d, J=1.2 Hz, 1H), 7.85 (d, J=8.0 Hz, 1H), 7.81 (d,

J=7.6 Hz, 1H), 7.77-7.72 (m, 2H), 7.61 (t, J=8.0 Hz, 1H), 7.44 (d, J=3.2 Hz, 1H), 7.28 (d, J=8.4 Hz, 1H), 6.85-6.84 (m, 1H), 4.88 (q, J=8.8 Hz, 2H);

LC-HRMS (ESI) calcd for [M+H, $C_{21}H_{14}BrF_3N_3O_4]^+$: 508.0120, Found 508.0105.

Example 19

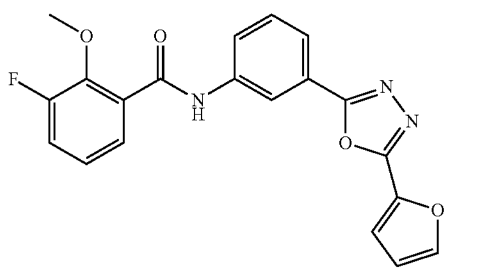 [SMILES: COc1c(F)cccc1C(=O)Nc1cccc(-c2nnc(-c3ccco3)o2)c1]

3-Fluoro-N-(2-fluoro-5-(5-(furan-2-yl)-1,3,4-oxadiazol-2-yl)phenyl)-2-methoxybenzamide Compound 220

3-Fluoro-N-(2-fluoro-5-(5-(furan-2-yl)-1,3,4-oxadiazol-2-yl)phenyl)-2-methoxybenzamide can be prepared as in Example 1, but from 3-fluoro-2-methoxybenzoic acid (89.8 mg, 0.53 mmol) and 3-(5-(furan-2-yl)-1,3,4-oxadiazol-2-yl) aniline (100.0 mg, 0.44 mmol). The crude product was purified by silica gel flash column chromatography (dichloromethane/methanol=100/1) to give the title compound (158.0 mg, 94.7% yield) as a off-white solid.

$^1$H NMR (400 MHz, DMSO): δ 10.66 (s, 1H), 8.59 (s, 1H), 8.11 (d, J=1.2 Hz, 1H), 7.92 (d, J=8.0 Hz, 1H), 7.81 (d, J=8.0 Hz, 1H), 7.61 (t, J=8.0 Hz, 1H), 7.48-7.39 (m, 3H), 7.27-7.22 (m, 1H), 6.85-6.83 (m, 1H), 3.94 (d, J=1.2 Hz, 3H);

LC-HRMS (ESI) calcd for [M+H, $C_{20}H_{15}FN_3O_4]^+$: 380.1047, Found 380.1048.

Example 20

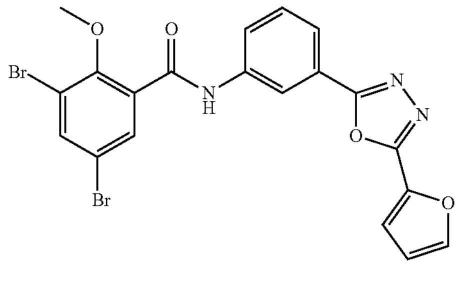

3,5-Dibromo-N-(3-(5-(furan-2-yl)-1,3,4-oxadiazol-2-yl)phenyl)-2-methoxybenzamide Compound 168

3,5-Dibromo-N-(3-(5-(furan-2-yl)-1,3,4-oxadiazol-2-yl) phenyl)-2-methoxybenzamide an be prepared as in Example 1, but from 3,5-dibromo-2-methoxybenzoic acid (163.6 mg, 0.53 mmol) and 3-(5-(furan-2-yl)-1,3,4-oxadiazol-2-yl)aniline (100.0 mg, 0.44 mmol). The crude product was purified by silica gel flash column chromatography (dichloromethane/methanol=100/1) to give the title compound (205.0 mg, 89.7% yield) as a white solid.

$^1$H NMR (400 MHz, DMSO): δ 10.80 (s, 1H), 8.55 (s, 1H), 8.10 (s, 1H), 8.06 (d, J=2.0 Hz, 1H), 7.90 (d, J=8.0 Hz, 1H), 7.84-7.82 (m, 2H), 7.62 (t, J=8.0 Hz, 1H), 7.44 (d, J=3.6 Hz, 1H), 6.85-6.83 (m, 1H), 3.84 (s, 3H); LC-HRMS (ESI) calcd for [M+H, $C_{20}H_{14}Br_2N_3O_4]^+$: 517.9351, Found 517.9350.

Example 21

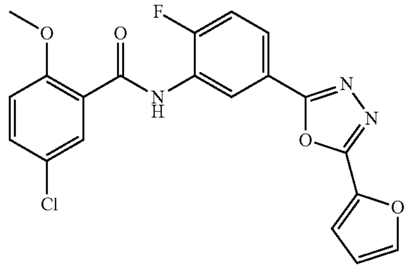

5-Chloro-N-(2-fluoro-5-(5-(furan-2-yl)-1,3,4-oxadiazol-2-yl)phenyl)-2-methoxybenzamide Compound 184

According to the synthetic procedure depicted in Scheme 1, 5-chloro-N-(2-fluoro-5-(5-(furan-2-yl)-1,3,4-oxadiazol-2-yl)phenyl)-2-methoxybenzamide can be prepares as follows:

a) N'-(4-fluoro-3-nitrobenzoyl)furan-2-carbohydrazide: To a solution of 4-fluoro-3-nitrobenzoic acid (10.0 g, 54.0 mmol) in dichloromethane (50 ml) were added N,N-dimethylformamide (0.1 ml) and oxalyl chloride (6.9 ml, 81.0 mmol), and the mixture was stirred at room temperature for 4 hr. The solvent was evaporated under reduced pressure to give acid chloride.

This acid chloride was dissolved in tetrahydrofuran (50 ml) and added dropwise to a suspension of 2-furoic acid hydrazide (6.9 g, 54.5 mmol) and anhydrous sodium carbonate (5.7 g, 54.0 mmol) in tetrahydrofuran (50 mL) and water (50 mL) at 0° C. The mixture was stirred at 0° C. for 1 h, and at room temperature for 6 hr. A massive precipitation was observed. The product was harvested by filtration and washed with water, then finally dried in vacuo to afford 14.4 g (91.0% yield) of N'-(4-fluoro-3-nitrobenzoyl)furan-2-carbohydrazide as a yellow solid.

b) 2-(4-Fluoro-3-nitrophenyl)-5-(furan-2-yl)-1,3,4-oxadiazole: N'-(4-fluoro-3-nitrobenzoyl)furan-2-carbohydrazide (14.4 g, 49.1 mmol) was dissolved in phosphorus oxychloride (70 ml) and the mixture was stirred with heating at 80° C. for 5 hr. Phosphorus oxychloride was evaporated under reduced pressure and water was added to the residue. The mixture was extracted with dichloromethane and the organic layer was washed with saturated aqueous solution of sodium hydrogencarbonate, dried over anhydrous sodium sulfate and concentrated under reduced pressure to afford 12.5 g (92.6% yield) of 2-(4-fluoro-3-nitrophenyl)-5-(furan-2-yl)-1,3,4-oxadiazole as a yellow solid.

c) 2-Fluoro-5-(5-(furan-2-yl)-1,3,4-oxadiazol-2-yl)aniline: A mixture of 2-(4-Fluoro-3-nitrophenyl)-5-(furan-2-yl)-1,3,4-oxadiazole (12.5 g, 45.4 mmol) and Raney Ni (2.0 g) in methanol (100 ml) was stirred at 50° C. for 16 h under 2.0 Mpa hydrogen atmosphere. The mixture was filtered and the filtrate was concentrated under vacuum. The residue was purified by silica gel flash column chromatography (dichloromethane/methanol=50/1) gave 9.3 g (83.6% yield) of 2-fluoro-5-(5-(furan-2-yl)-1,3,4-oxadiazol-2-yl)aniline as a white solid.

d) 5-Chloro-N-(2-fluoro-5-(5-(furan-2-yl)-1,3,4-oxadiazol-2-yl)phenyl)-2-methoxybenzamide: A mixture of 5-chloro-2-methoxybenzoic acid (91.3 mg, 0.49 mmol) and N,N-dimethylformamide (0.01 ml) in thionyl chloride (0.5 ml) was stirred with refluxing for 1 hr. The excess thionyl chloride was evaporated under reduced pressure to give acid chloride.

This acid chloride was dissolved in dichloromethane (5 ml) and added dropwise to a solution of 2-fluoro-5-(5-(furan-2-yl)-1,3,4-oxadiazol-2-yl)aniline (100.0 mg, 0.41 mmol) and triethylamine (57.8 mg, 0.57 mmol) in dichloromethane (5 ml) at 0° C. The reaction mixture was allowed to warm slowly to room temperature and stirred for 12 h. The mixture was concentrated under vacuum, and the residue was purified by silica gel flash column chromatography (dichloromethane/methanol=100/1) to give the title compound (154.9 mg, 91.8% yield) as a white solid.

$^1$H NMR (400 MHz, DMSO): δ 10.40 (s, 1H), 8.92-8.90 (m, 1H), 8.10 (d, J=1.2 Hz, 1H), 7.91-7.87 (m, 2H), 7.65-7.56 (m, 2H), 7.46 (d, J=3.6 Hz, 1H), 7.30 (d, J=8.8 Hz, 1H), 6.85-6.83 (m, 1H), 4.01 (s, 3H);

LC-HRMS (ESI) calcd for [M+H, $C_{20}H_{14}ClFN_3O_4]^+$: 414.0657, Found 414.0658.

Example 22

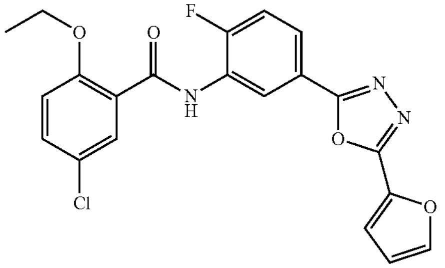 [SMILES: CCOc1ccc(Cl)cc1C(=O)Nc1cc(-c2nnc(-c3ccco3)o2)ccc1F]

5-chloro-2-ethoxy-N-(2-fluoro-5-(5-(furan-2-yl)-1,3,4-oxadiazol-2-yl)phenyl)benzamide Compound 216

5-Chloro-2-ethoxy-N-(2-fluoro-5-(5-(furan-2-yl)-1,3,4-oxadiazol-2-yl)phenyl)benzamide can be prepared as in Example 21, but from 5-chloro-2-ethoxybenzoic acid (98.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (159.6 mg, 91.5% yield) as a white solid.

$^1$H NMR (400 MHz, DMSO): δ 10.43 (s, 1H), 9.08 (d, J=9.6 Hz, 1H), 8.10 (s, 1H), 7.94 (d, J=2.8 Hz, 1H), 7.86-7.82 (m, 1H), 7.64-7.55 (m, 2H), 7.44 (d, J=3.6 Hz, 1H), 7.28 (d, J=9.2 Hz, 1H), 6.84-6.83 (m, 1H), 4.27 (q, J=6.8 Hz, 2H), 1.48 (t, J=6.8 Hz, 3H);

LC-HRMS (ESI) calcd for [M+H, $C_{21}H_{16}ClFN_3O_4]^+$: 428.0813, Found 428.0812.

Example 23

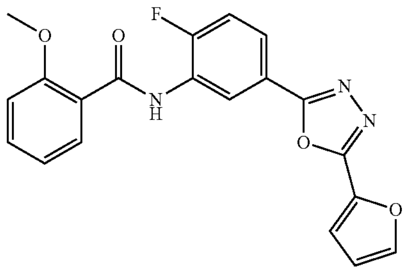

N-(2-Fluoro-5-(5-(furan-2-yl)-1,3,4-oxadiazol-2-yl)phenyl)-2-methoxybenzamide

Compound 128

N-(2-Fluoro-5-(5-(furan-2-yl)-1,3,4-oxadiazol-2-yl)phenyl)-2-methoxybenzamide can be prepared as in Example 21, but from 2-methoxybenzoic acid (74.5 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (140.8 mg, 91.0% yield) as a white solid.

$^1$H NMR (400 MHz, DMSO): δ 10.44 (s, 1H), 9.01 (d, J=6.0 Hz, 1H), 8.11 (d, J=1.2 Hz, 1H), 7.99 (d, J=6.4 Hz, 1H), 7.90-7.86 (m, 1H), 7.63-7.57 (m, 2H), 7.46 (d, J=3.2 Hz, 1H), 7.16 (t, J=7.6 Hz, 1H), 6.85-6.83 (m, 1H), 4.03 (s, 3H); LC-HRMS (ESI) calcd for [M+H, $C_{20}H_{15}FN_3O_4]^+$: 380.1047, Found 380.1052.

Example 24

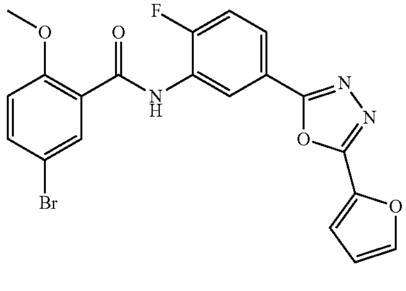

5-Bromo-N-(2-fluoro-5-(5-(furan-2-yl)-1,3,4-oxadiazol-2-yl)phenyl)-2-methoxybenzamide Compound 183

5-Bromo-N-(2-fluoro-5-(5-(furan-2-yl)-1,3,4-oxadiazol-2-yl)phenyl)-2-methoxybenzamide can be prepared as in Example 21, but from 5-bromo-2-methoxybenzoic acid (113.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (179.5 mg, 96.0% yield) as a white solid.

$^1$H NMR (400 MHz, DMSO): δ 10.40 (s, 1H), 8.92-8.90 (m, 1H), 8.11 (d, J=1.2 Hz, 1H), 8.00 (d, J=2.4 Hz, 1H), 7.93-7.89 (m, 1H), 7.77 (dd, J=2.4, 8.8 Hz, 1H), 7.60 (dd, J=8.8, 10.4 Hz, 1H), 7.47 (d, J=3.6 Hz, 1H), 7.26 (d, J=9.2 Hz, 1H), 6.85-6.84 (m, 1H), 4.01 (s, 3H);

LC-HRMS (ESI) calcd for [M+H, $C_{20}H_{14}BrFN_3O_4$]$^+$: 458.0152, Found 458.0159.

Example 25

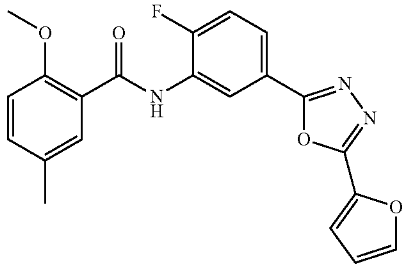 [SMILES: COc1ccc(C)cc1C(=O)Nc1cc(-c2nnc(-c3ccco3)o2)ccc1F]

N-(2-Fluoro-5-(5-(furan-2-yl)-1,3,4-oxadiazol-2-yl)phenyl)-2-methoxy-5-methylbenzamide Compound 300

N-(2-Fluoro-5-(5-(furan-2-yl)-1,3,4-oxadiazol-2-yl)phenyl)-2-methoxy-5-methylbenzamide can be prepared as in Example 21, but from 2-methoxy-5-methylbenzoic acid (81.4 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (154.4 mg, 96.2% yield) as a white solid.

$^1$H NMR (400 MHz, DMSO): δ 10.47 (s, 1H), 9.03 (d, J=5.6 Hz, 1H), 8.11 (d, J=1.2 Hz, 1H), 7.91-7.87 (m, 1H), 7.82 (s, 1H), 7.61 (dd, J=8.8, 10.4 Hz, 1H), 7.47 (d, J=3.2 Hz, 1H), 7.44-7.41 (m, 1H), 7.19 (d, J=8.4 Hz, 1H), 6.86-6.84 (m, 1H), 4.01 (s, 3H), 2.33 (s, 3H);

LC-HRMS (ESI) calcd for [M+H, $C_{21}H_{17}FN_3O_4$]$^+$: 394.1203, Found 394.1205.

Example 26

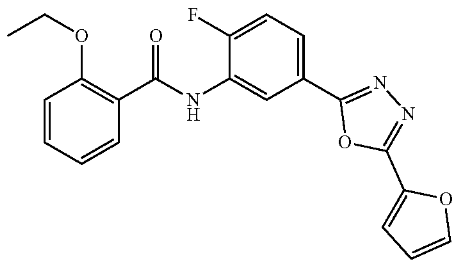 [SMILES: CCOc1ccccc1C(=O)Nc1cc(-c2nnc(-c3ccco3)o2)ccc1F]

2-Ethoxy-N-(2-fluoro-5-(5-(furan-2-yl)-1,3,4-oxadiazol-2-yl)phenyl)benzamide

Compound 215

2-Ethoxy-N-(2-fluoro-5-(5-(furan-2-yl)-1,3,4-oxadiazol-2-yl)phenyl)benzamide can be prepared as in Example 21, but from 2-methoxy-5-methylbenzoic acid (81.4 mg, 0.49 mmol) and 2-fluoro-5-(5-(furan-2-yl)-1,3,4-oxadiazol-2-yl) aniline (100.0 mg, 0.41 mmol). The crude product was purified by silica gel flash column chromatography (dichloromethane/methanol=100/1) to give the title compound (150.1 mg, 93.5% yield) as a white solid.

$^1$H NMR (400 MHz, DMSO): δ 10.47 (s, 1H), 9.19 (d, J=5.6 Hz, 1H), 8.11 (d, J=1.2 Hz, 1H), 8.09-8.06 (m, 1H), 7.88-7.84 (m, 1H), 7.63-7.59 (m, 2H), 7.46 (d, J=3.6 Hz, 1H), 7.28 (d, J=8.4 Hz, 1H), 7.18-7.14 (m, 1H), 6.85-6.84 (m, 1H), 4.31 (q, J=6.8 Hz, 2H), 1.51 (t, J=6.8 Hz, 3H);

LC-HRMS (ESI) calcd for [M+H, $C_{21}H_{17}FN_3O_4$]$^+$: 394.1203, Found 394.1228.

Example 27

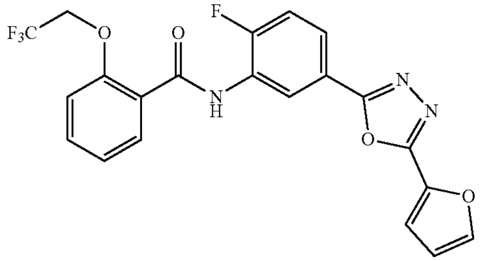

N-(2-Fluoro-5-(5-(furan-2-yl)-1,3,4-oxadiazol-2-yl)phenyl)-2-(2,2,2-trifluoroethoxy)benzamide Compound 313

N-(2-Fluoro-5-(5-(furan-2-yl)-1,3,4-oxadiazol-2-yl)phenyl)-2-(2,2,2-trifluoroethoxy)benzamide can be prepared as in Example 21, but from 2-(2,2,2-trifluoroethoxy)benzoic acid (107.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (160.0 mg, 87.7% yield) as a white solid.

$^1$H NMR (400 MHz, DMSO): δ 10.10 (s, 1H), 8.93 (d, J=1.6 Hz, 1H), 8.11 (d, J=1.2 Hz, 1H), 7.92-7.85 (m, 2H), 7.63-7.57 (m, 2H), 7.46 (d, J=3.2 Hz, 1H), 7.34 (d, J=8.4 Hz, 1H), 7.25-7.22 (m, 1H), 6.85-6.84 (m, 1H), 4.98 (q, J=8.8 Hz, 2H);

LC-HRMS (ESI) calcd for [M+H, $C_{21}H_{14}F_4N_3O_4$]$^+$: 448.0920, Found 448.0918.

Example 28

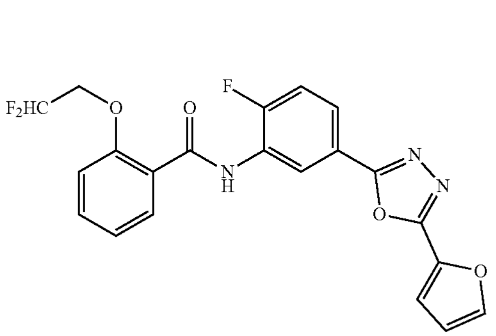 [SMILES: O=C(Nc1cc(-c2nnc(-c3ccco3)o2)ccc1F)c1ccccc1OCC(F)F]

2-(2,2-Difluoroethoxy)-N-(2-fluoro-5-(5-(furan-2-yl)-1,3,4-oxadiazol-2-yl)phenyl)benzamide Compound 314

2-(2,2-Difluoroethoxy)-N-(2-fluoro-5-(5-(furan-2-yl)-1,3,4-oxadiazol-2-yl)phenyl)benzamide can be prepared as in Example 21, but from 2-(2,2-difluoroethoxy)benzoic acid (99.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (156.8 mg, 89.5% yield) as a white solid.

$^1$H NMR (400 MHz, DMSO): δ 10.16 (s, 1H), 8.99 (d, J=6.0 Hz, 1H), 8.11 (d, J=0.8 Hz, 1H), 7.95 (d, J=6.4 Hz, H), 7.91-7.87 (m, 1H), 7.63-7.58 (m, 2H), 7.46 (d, J=3.2 Hz, 1H), 7.33 (d, J=8.4 Hz, 1H), 7.22 (t, J=7.6 Hz, 1H), 6.85-6.84 (m, 1H), 6.50 (tt, J=3.2, 54.6 Hz, 1H), 4.58 (dt, J=3.2, 14.4 Hz, 2H);

LC-HRMS (ESI) calcd for $[M+H, C_{21}H_{15}F_3N_3O_4]^+$: 430.1015, Found 430.1007.

Example 29

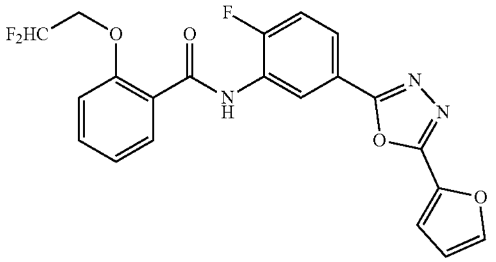 [SMILES: O=C(Nc1cc(-c2nnc(-c3ccco3)o2)ccc1F)c1ccccc1OCC(F)F]

N-(2-Fluoro-5-(5-(furan-2-yl)-1,3,4-oxadiazol-2-yl)phenyl)-2-(2-fluoroethoxy)benzamide Compound 315

N-(2-Fluoro-5-(5-(furan-2-yl)-1,3,4-oxadiazol-2-yl)phenyl)-2-(2-fluoroethoxy)benzamide can be prepared as in Example 21, but from 2-(2-fluoroethoxy)benzoic acid (90.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (155.8 mg, 92.8% yield) as a white solid.

$^1$H NMR (400 MHz, DMSO): δ 10.41 (s, 1H), 9.12 (d, J=5.6 Hz, 1H), 8.12 (s, 1H), 8.06 (d, J=6.8 Hz, H), 7.91-7.88 (m, 1H), 7.65-7.60 (m, 2H), 7.48 (d, J=3.6 Hz, 1H), 7.32 (d, J=8.4 Hz, 1H), 7.23-7.19 (m, 1H), 6.86-6.85 (m, 1H), 4.98-4.96 (m, 1H), 4.86-4.84 (m, 1H), 4.59-4.57 (m, 1H), 4.51-4.50 (m, 1H);

LC-HRMS (ESI) calcd for $[M+H, C_{21}H_{16}F_2N_3O_4]^+$: 412.1109, Found 412.1095.

Example 30

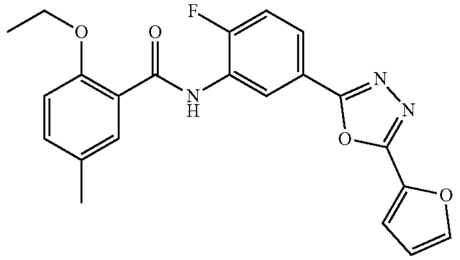 [SMILES: CCOc1ccc(C)cc1C(=O)Nc1cc(-c2nnc(-c3ccco3)o2)ccc1F]

2-Ethoxy-N-(2-fluoro-5-(5-(furan-2-yl)-1,3,4-oxadiazol-2-yl)phenyl)-5-methylbenzamide Compound 221

2-Ethoxy-N-(2-fluoro-5-(5-(furan-2-yl)-1,3,4-oxadiazol-2-yl)phenyl)-5-methylbenzamide can be prepared as in Example 21, but from 2-ethoxy-5-methylbenzoic acid (88.3 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (151.8 mg, 91.3% yield) as a yellow solid.

$^1$H NMR (400 MHz, DMSO): δ 10.49 (d, J=2.0 Hz, 1H), 9.16 (dd, J=1.6, 3.4 Hz, 1H), 8.10 (d, J=0.8 Hz, 1H), 7.85 (d, J=1.6 Hz, 1H), 7.82-7.78 (m, 1H), 7.58-7.53 (m, 1H), 7.43 (d, J=3.2 Hz, 1H), 7.37-7.35 (m, 1H), 7.12 (d, J=8.4 Hz, 1H), 6.84-6.83 (m, 1H), 4.24 (q, J=6.8 Hz, 2H), 2.92 (s, 3H), 1.48 (t, J=6.8 Hz, 1H); LC-HRMS (ESI) calcd for $[M+H, C_{22}H_{19}FN_3O_4]^+$: 408.1360, Found 408.1356.

Example 31

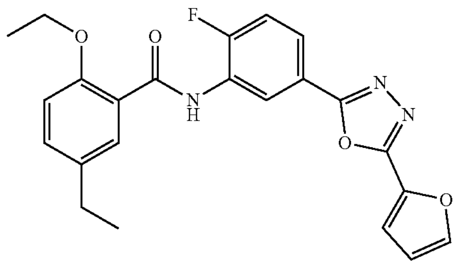 [SMILES: CCOc1ccc(CC)cc1C(=O)Nc1cc(-c2nnc(-c3ccco3)o2)ccc1F]

2-Ethoxy-5-ethyl-N-(2-fluoro-5-(5-(furan-2-yl)-1,3,4-oxadiazol-2-yl)phenyl)benzamide Compound 222

2-Ethoxy-5-ethyl-N-(2-fluoro-5-(5-(furan-2-yl)-1,3,4-oxadiazol-2-yl)phenyl)benzamide can be prepared as in Example 21, but from 2-ethoxy-5-ethylbenzoic acid (95.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (159.2 mg, 92.6% yield) as a white solid.

$^{1}$H NMR (400 MHz, DMSO): δ 10.55 (s, 1H), 9.19 (d, J=6.0 Hz, 1H), 8.11 (s, 1H), 7.90 (d, J=1.6 Hz, 1H), 7.85-7.82 (m, 1H), 7.62-7.57 (m, 1H), 7.46-7.41 (m, 2H), 7.18 (d, J=8.4 Hz, 1H), 6.85-6.84 (m, 1H), 4.27 (q, J=6.8 Hz, 2H), 2.62 (q, J=7.6 Hz, 2H), 1.49 (t, J=6.8 Hz, 3H), 1.19 (t, J=7.6 Hz, 3H);

LC-HRMS (ESI) calcd for $[M+H, C_{23}H_{21}FN_3O_4]^+$: 422.1516, Found 422.1520.

Example 32

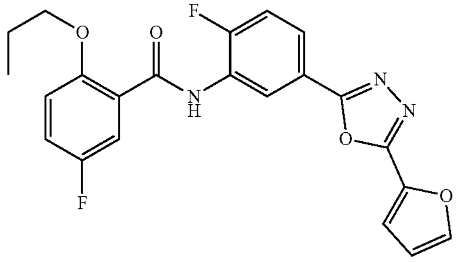 [SMILES: CCCOc1ccc(F)cc1C(=O)Nc1cc(-c2nnc(-c3ccco3)o2)ccc1F]

5-Fluoro-N-(2-fluoro-5-(5-(furan-2-yl)-1,3,4-oxadiazol-2-yl)phenyl)-2-propoxybenzamide Compound 210

5-Fluoro-N-(2-fluoro-5-(5-(furan-2-yl)-1,3,4-oxadiazol-2-yl)phenyl)-2-propoxybenzamide can be prepared as in Example 21, but from 5-fluoro-2-propoxybenzoic acid (97.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (171.0 mg, 98.5% yield) as a pale-yellow solid.

$^{1}$H NMR (400 MHz, DMSO): δ 10.47 (s, 1H), 9.11-9.09 (m, 1H), 8.10 (d, J=0.8 Hz, 1H), 7.87-7.83 (m, 1H), 7.74 (dd, J=3.6, 9.2 Hz, 1H), 7.61-7.56 (m, 1H), 7.46-7.41 (m, 2H), 7.31-7.28 (m, 1H), 6.84-6.83 (m, 1H), 4.18 (t, J=6.6 Hz, 2H), 1.91-1.85 (m, 2H), 1.02 (t, J=7.2 Hz, 3H);

LC-HRMS (ESI) calcd for $[M+H, C_{22}H_{13}F_2N_3O_4]^+$: 426.1265, Found 426.1273.

Example 33

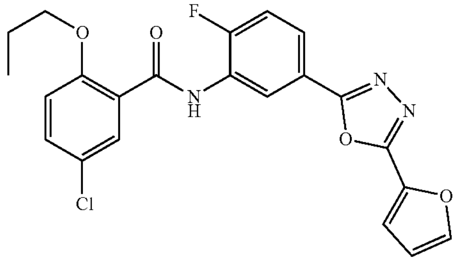 [SMILES: CCCOc1ccc(Cl)cc1C(=O)Nc1cc(-c2nnc(-c3ccco3)o2)ccc1F]

5-Chloro-N-(2-fluoro-5-(5-(furan-2-yl)-1,3,4-oxadiazol-2-yl)phenyl)-2-propoxybenzamide Compound 209

5-Chloro-N-(2-fluoro-5-(5-(furan-2-yl)-1,3,4-oxadiazol-2-yl)phenyl)-2-propoxybenzamide can be prepared as in Example 21, but from 5-chloro-2-propoxybenzoic acid (105.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (169.3 mg, 93.9% yield) as a pale-yellow solid.

$^{1}$H NMR (400 MHz, DMSO): δ 10.41 (d, J=1.6 Hz, 1H), 9.07 (dd, J=1.6, 7.2 Hz, 1H), 8.10 (d, J=1.2 Hz, 1H), 7.93 (d, J=2.8 Hz, 1H), 7.89-7.85 (m, 1H), 7.64-7.58 (m, 2H), 7.45 (d, J=3.2 Hz, 1H), 7.31 (d, J=8.8 Hz, 1H), 6.85-6.84 (m, 1H), 4.19 (t, J=6.4 Hz, 2H), 1.91-1.86 (m, 2H), 1.02 (t, J=7.2 Hz, 3H);

LC-HRMS (ESI) calcd for $[M+H, C_{22}H_{13}ClFN_3O_4]^+$: 442.0970, Found 442.0961.

Example 34

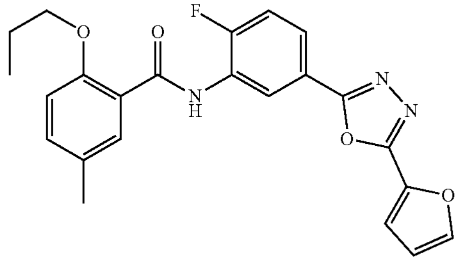 [SMILES: CCCOc1ccc(C)cc1C(=O)Nc1cc(-c2nnc(-c3ccco3)o2)ccc1F]

N-(2-Fluoro-5-(5-(furan-2-yl)-1,3,4-oxadiazol-2-yl)phenyl)-5-methyl-2-propoxybenzamide Compound 208

N-(2-Fluoro-5-(5-(furan-2-yl)-1,3,4-oxadiazol-2-yl)phenyl)-5-methyl-2-propoxybenzamide can be prepared as in Example 21, but from 5-methyl-2-propoxybenzoic acid (95.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (165.2 mg, 96.1% yield) as a yellow solid. $^{1}$H NMR (400 MHz, DMSO): δ 10.48 (d, J=1.6 Hz, 1H), 9.16 (d, J=6.4 Hz, 1H), 8.11 (s, 1H), 7.86-7.83 (m, 2H), 7.62-7.57 (m, 1H), 7.45 (d, J=3.2 Hz, 1H), 7.39 (d, J=8.0 Hz, 1H), 7.17 (d, J=8.4 Hz, 1H), 6.85-6.84 (m, 1H), 4.17 (t, J=6.4 Hz, 2H), 2.32 (s, 3H), 1.92-1.87 (m, 2H), 1.02 (t, J=7.4 Hz, 3H);

LC-HRMS (ESI) calcd for $[M+H, C_{23}H_{21}FN_3O_4]^+$: 422.1516, Found 422.1519.

Example 35

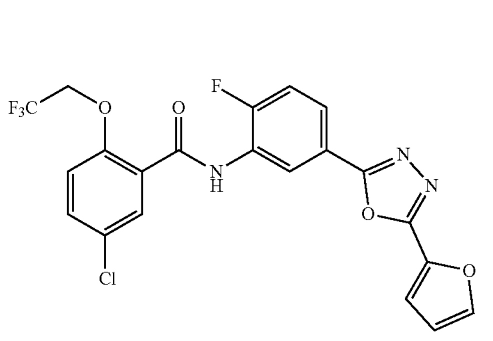

5-Chloro-N-(2-fluoro-5-(5-(furan-2-yl)-1,3,4-oxadiazol-2-yl)phenyl)-2-(2,2,2-trifluoroethoxy)benzamide Compound 316

5-Chloro-N-(2-fluoro-5-(5-(furan-2-yl)-1,3,4-oxadiazol-2-yl)phenyl)-2-(2,2,2-trifluoroethoxy)benzamide can be prepared as in Example 21, but from 5-chloro-2-(2,2,2-trifluoroethoxy)benzoic acid (124.7 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (191.0 mg, 97.2% yield) as a white solid.

$^1$H NMR (400 MHz, DMSO): δ 10.24 (s, 1H), 8.85 (d, J=6.0 Hz, 1H), 8.11 (s, 1H), 7.94-7.91 (m, 1H), 7.79 (d, J=2.4 Hz, 1H), 7.68-7.65 (m, 1H), 7.62-7.57 (m, 1H), 7.46 (d, J=3.2 Hz, 1H), 7.34 (d, J=8.8 Hz, 1H), 6.85-6.84 (m, 1H), 4.95 (q, J=8.8 Hz, 2H); LC-HRMS (ESI) calcd for [M+H, $C_{21}H_{13}ClF_4N_3O_4]^+$: 482.0531, Found 482.0518.

Example 36

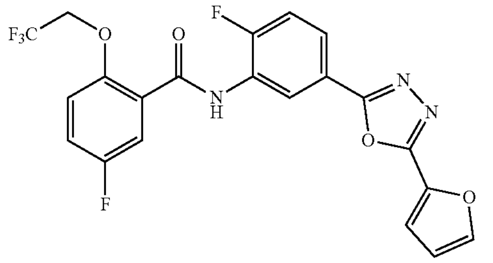

5-Fluoro-N-(2-fluoro-5-(5-(furan-2-yl)-1,3,4-oxadiazol-2-yl)phenyl)-2-(2,2,2-trifluoroethoxy)benzamide Compound 319

5-Fluoro-N-(2-fluoro-5-(5-(furan-2-yl)-1,3,4-oxadiazol-2-yl)phenyl)-2-(2,2,2-trifluoroethoxy)benzamide can be prepared as in Example 21, but from 5-fluoro-2-(2,2,2-trifluoroethoxy)benzoic acid (116.7 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (178.5 mg, 94.0% yield) as a white solid.

$^1$H NMR (400 MHz, DMSO): δ 10.22 (s, 1H), 8.88 (d, J=6.4 Hz, 1H), 8.11 (s, 1H), 7.94-7.91 (m, 1H), 7.63-7.58 (m, 2H), 7.50-7.45 (m, 2H), 7.39-7.36 (m, 1H), 6.85-6.84 (m, 1H), 4.94 (q, J=8.8 Hz, 2H);

LC-HRMS (ESI) calcd for [M+H, $C_{21}H_{13}F_5N_3O_4]^+$: 466.0826, Found 466.0812.

Example 37

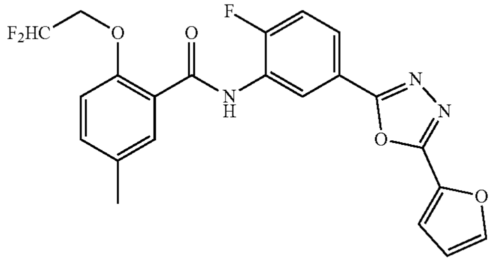 [SMILES: Cc1ccc(OCC(F)F)c(C(=O)Nc2cc(-c3nnc(-c4ccco4)o3)ccc2F)c1]

2-(2,2-Difluoroethoxy)-N-(2-fluoro-5-(5-(furan-2-yl)-1,3,4-oxadiazol-2-yl)phenyl)-5-methylbenzamide Compound 323

2-(2,2-Difluoroethoxy)-N-(2-fluoro-5-(5-(furan-2-yl)-1,3,4-oxadiazol-2-yl)phenyl)-5-methylbenzamide can be prepared as in Example 21, but from 2-(2,2-difluoroethoxy)-5-methylbenzoic acid (105.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (163.2 mg, 90.2% yield) as a white solid.

$^1$H NMR (400 MHz, DMSO): δ 10.15 (s, 1H), 9.00 (d, J=6.0 Hz, 1H), 8.11 (d, J=0.8 Hz, 1H), 7.91-7.87 (m, 1H), 7.77 (s, 1H), 7.63-7.58 (m, 1H), 7.46 (d, J=3.6 Hz, 1H), 7.42 (dd, J=1.6, 8.4 Hz, 1H), 7.23 (d, J=8.4 Hz, 1H), 6.85-6.84 (m, 1H), 6.49 (tt, J=3.2, 14.4 Hz, 1H), 4.54 (dt, J=2.8, 14.0 Hz, 2H), 2.34 (s, 3H);

LC-HRMS (ESI) calcd for [M+H, $C_{22}H_{17}F_3N_3O_4]^+$: 444.1171, Found 444.1170.

Example 38

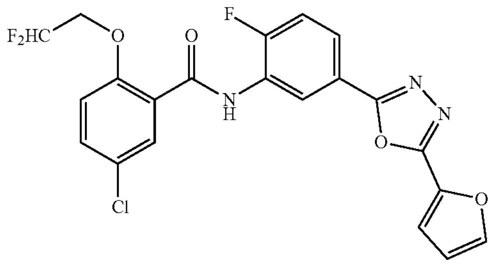

5-Chloro-2-(2,2-difluoroethoxy)-N-(2-fluoro-5-(5-(furan-2-yl)-1,3,4-oxadiazol-2-yl)phenyl)benzamide Compound 317

5-Chloro-2-(2,2-difluoroethoxy)-N-(2-fluoro-5-(5-(furan-2-yl)-1,3,4-oxadiazol-2-yl)phenyl)benzamide can be prepared as in Example 21, but from 5-chloro-2-(2,2-difluoroethoxy)benzoic acid (115.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (169.5 mg, 89.6% yield) as a white solid.

$^1$H NMR (400 MHz, DMSO): δ 10.22 (s, 1H), 8.93-8.90 (m, 1H), 8.11 (d, J=0.8 Hz, 1H), 7.93-7.90 (m, 1H), 7.86 (d, J=2.4 Hz, 1H), 7.66 (dd, J=2.8, 8.8 Hz, 1H), 7.61 (dd, J=8.8, 10.4 Hz, 1H), 7.46 (d, J=3.6 Hz, 1H), 7.36 (d, J=9.2 Hz, 1H), 6.85-6.84 (m, 1H), 6.47 (tt, J=3.2, 14.4 Hz, 1H), 4.56 (dt, J=3.2, 14.4 Hz, 2H);

LC-HRMS (ESI) calcd for [M+H, $C_{21}H_{14}ClF_3N_3O_4$]$^+$: 464.0625, Found 464.0632.

Example 39

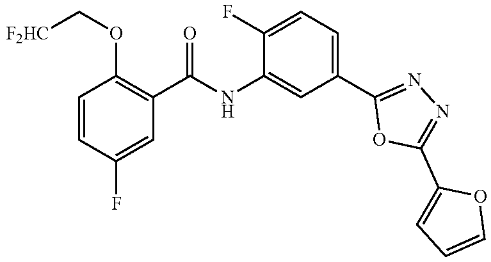

2-(2,2-Difluoroethoxy)-5-fluoro-N-(2-fluoro-5-(5-(furan-2-yl)-1,3,4-oxadiazol-2-yl)phenyl)benzamide Compound 320

2-(2,2-Difluoroethoxy)-5-fluoro-N-(2-fluoro-5-(5-(furan-2-yl)-1,3,4-oxadiazol-2-yl)phenyl)benzamide can be prepared as in Example 21, but from 2-(2,2-difluoroethoxy)-5-fluorobenzoic acid (107.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (172.5 mg, 94.5% yield) as a white solid.

$^1$H NMR (400 MHz, DMSO): δ 10.24 (s, 1H), 8.96-8.94 (m, 1H), 8.11 (d, J=0.8 Hz, 1H), 7.94-7.90 (m, 1H), 7.69 (d, J=3.2, 7.2 Hz, 1H), 7.64-7.59 (m, 1H), 7.51-7.46 (m, 2H), 7.39-7.36 (m, 1H), 6.85-6.84 (m, 1H), 6.47 (tt, J=3.2, 14.4 Hz, 1H), 4.56 (dt, J=3.2, 14.4 Hz, 2H);

LC-HRMS (ESI) calcd for [M+H, $C_{21}H_{14}F_4N_3O_4$]$^+$: 448.0920, Found 448.0915.

Example 40

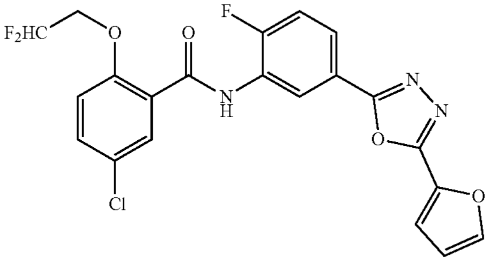

5-Chloro-N-(2-fluoro-5-(5-(furan-2-yl)-1,3,4-oxadiazol-2-yl)phenyl)-2-(2-fluoroethoxy)benzamide Compound 318

5-Chloro-N-(2-fluoro-5-(5-(furan-2-yl)-1,3,4-oxadiazol-2-yl)phenyl)-2-(2-fluoroethoxy)benzamide can be prepared as in Example 21, but from 5-chloro-2-(2-fluoroethoxy)benzoic acid (107.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (164.6 mg, 90.5% yield) as a white solid.

$^1$H NMR (400 MHz, DMSO): δ 10.37 (s, 1H), 9.04-9.01 (m, 1H), 8.11 (d, J=0.8 Hz, 1H), 7.94 (d, J=2.8 Hz, 1H), 7.92-7.89 (m, 1H), 7.67 (dd, J=2.8, 8.8 Hz, 1H), 7.62 (dd, J=8.8, 10.4 Hz, 1H), 7.46 (d, J=3.6 Hz, 1H), 7.35 (d, J=9.2 Hz, 1H), 6.85-6.84 (m, 1H), 4.94-4.92 (m, 1H), 4.82-4.80 (m, 1H), 4.57-4.55 (m, 1H), 4.49-4.76 (m, 1H); LC-HRMS (ESI) calcd for [M+H, $C_{21}H_{15}ClF_2N_3O_4$]$^+$: 446.0719, Found 446.0716.

Example 41

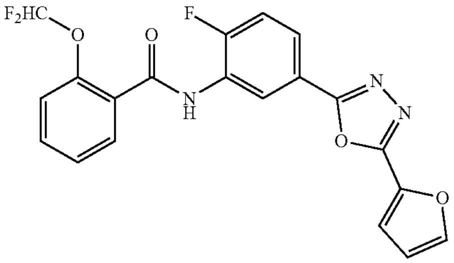 [SMILES: O=C(Nc1cc(-c2nnc(-c3ccco3)o2)ccc1F)c1ccccc1OC(F)F]

2-(Difluoromethoxy)-N-(2-fluoro-5-(5-(furan-2-yl)-1,3,4-oxadiazol-2-yl)phenyl)benzamide Compound 302

2-(Difluoromethoxy)-N-(2-fluoro-5-(5-(furan-2-yl)-1,3,4-oxadiazol-2-yl)phenyl)benzamide can be prepared as in Example 21, but from 2-(difluoromethoxy)benzoic acid (92.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (150.6 mg, 88.9% yield) as a white solid.

$^1$H NMR (400 MHz, DMSO): δ 10.41 (s, 1H), 8.72 (d, J=6.0 Hz, 1H), 8.11 (d, J=1.2 Hz, 1H), 7.95-7.91 (m, 1H), 7.76 (d, J=6.8 Hz, 1H), 7.65-7.56 (m, 2H), 7.46-7.39 (m, 1H), 7.33 (d, J=8.4 Hz, 1H), 7.26 (t, J=73.2 Hz, 1H), 6.84-6.83 (m, 1H); LC-HRMS (ESI) calcd for [M+H, $C_{20}H_{13}F_3N_3O_4]^+$: 416.0858, Found 416.0825.

Example 42

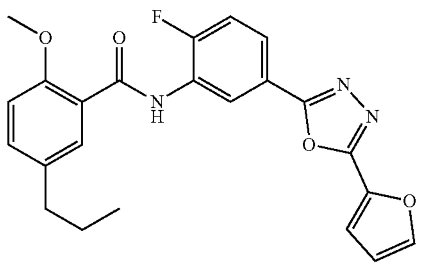 [SMILES: CCCc1ccc(OC)c(C(=O)Nc2cc(-c3nnc(-c4ccco4)o3)ccc2F)c1]

N-(2-Fluoro-5-(5-(furan-2-yl)-1,3,4-oxadiazol-2-yl)phenyl)-2-methoxy-5-propylbenzamide Compound 281

N-(2-Fluoro-5-(5-(furan-2-yl)-1,3,4-oxadiazol-2-yl)phenyl)-2-methoxy-5-propylbenzamide can be prepared as in Example 21, but from 2-methoxy-5-propylbenzoic acid (95.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (146.7 mg, 85.3% yield) as a white solid.

$^1$H NMR (400 MHz, DMSO): δ 10.46 (d, J=1.2 Hz, 1H), 9.03 (d, J=5.6 Hz, 1H), 8.11 (d, J=1.2 Hz, 1H), 7.89-7.86 (m, 1H), 7.82 (d, J=1.6 Hz, 1H), 7.62-7.57 (m, 1H), 7.46 (d, J=3.6 Hz, 1H), 7.43 (dd, J=2.0, 8.4 Hz, 1H), 7.20 (d, J=8.4 Hz, 1H), 6.85-6.84 (m, 1H), 4.01 (s, 3H), 2.58 (t, J=7.6 Hz, 2H), 1.64-1.55 (m, 2H), 0.90 (t, J=7.2 Hz, 3H);

LC-HRMS (ESI) calcd for [M+H, $C_{23}H_{21}FN_3O_4]^+$: 422.1516, Found 422.1518.

Example 43

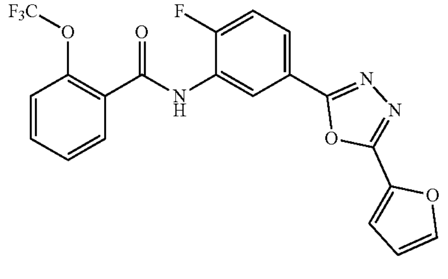 [SMILES: O=C(Nc1cc(-c2nnc(-c3ccco3)o2)ccc1F)c1ccccc1OC(F)(F)F]

N-(2-Fluoro-5-(5-(furan-2-yl)-1,3,4-oxadiazol-2-yl)phenyl)-2-(trifluoromethoxy)benzamide Compound 301

N-(2-Fluoro-5-(5-(furan-2-yl)-1,3,4-oxadiazol-2-yl)phenyl)-2-(trifluoromethoxy)benzamide can be prepared as in Example 21, but from 2-(trifluoromethoxy)benzoic acid (101.0 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (160.5 mg, 90.8% yield) as a white solid.

$^1$H NMR (400 MHz, DMSO): δ 10.61 (s, 1H), 8.57 (d, J=6.0 Hz, 1H), 8.11 (d, J=1.2 Hz, 1H), 7.98-7.94 (m, 1H), 7.81-7.79 (m, 1H), 7.71-7.67 (m, 1H), 7.62-7.55 (m, 3H), 7.46 (d, J=3.2 Hz, 1H), 6.85-6.84 (m, 1H);

LC-HRMS (ESI) calcd for [M+H, $C_{20}H_{12}F_4N_3O_4]^+$: 434.0764, Found 434.0748.

Example 44

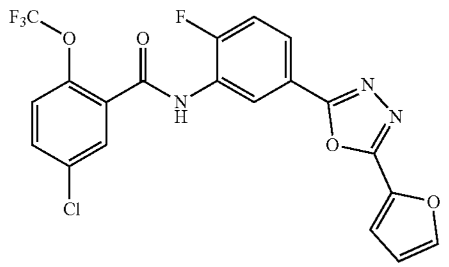 [SMILES: O=C(Nc1cc(-c2nnc(-c3ccco3)o2)ccc1F)c1cc(Cl)ccc1OC(F)(F)F]

5-Chloro-N-(2-fluoro-5-(5-(furan-2-yl)-1,3,4-oxadiazol-2-yl)phenyl)-2-(trifluoromethoxy)benzamide Compound 304

5-Chloro-N-(2-fluoro-5-(5-(furan-2-yl)-1,3,4-oxadiazol-2-yl)phenyl)-2-(trifluoromethoxy)benzamide can be prepared as in Example 21, but from 2-(trifluoromethoxy)benzoic acid (117.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (180.7 mg, 94.7% yield) as a white solid.

$^1$H NMR (400 MHz, DMSO): δ 10.73 (s, 1H), 8.60 (d, J=5.2 Hz, 1H), 8.11 (s, 1H), 7.99-7.95 (m, 1H), 7.92 (d, J=3.2 Hz, 1H), 7.77-7.75 (m, 1H), 7.62-7.58 (m, 2H), 7.46 (d, J=3.2 Hz, 1H), 6.85-6.84 (m, 1H);

LC-HRMS (ESI) calcd for [M+H, $C_{20}H_{11}ClF_4N_3O_4]^+$: 468.0374, Found 468.0402.

Example 45

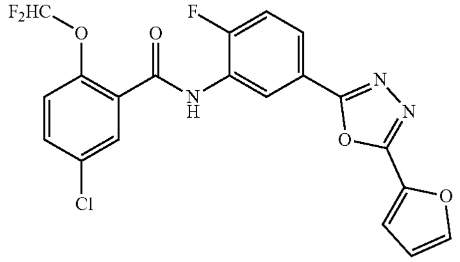 [SMILES: O=C(Nc1cc(-c2nnc(-c3ccco3)o2)ccc1F)c1cc(Cl)ccc1OC(F)F]

5-Chloro-2-(difluoromethoxy)-N-(2-fluoro-5-(5-(furan-2-yl)-1,3,4-oxadiazol-2-yl)phenyl)benzamide Compound 305

5-Chloro-2-(difluoromethoxy)-N-(2-fluoro-5-(5-(furan-2-yl)-1,3,4-oxadiazol-2-yl)phenyl)benzamide can be prepared as in Example 21, but from 5-chloro-2-(difluoromethoxy)benzoic acid (109.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (170.4 mg, 92.9% yield) as a pale-yellow solid.

$^1$H NMR (400 MHz, DMSO): δ 10.55 (s, 1H), 8.73-8.70 (m, 1H), 8.11 (d, J=0.8 Hz, 1H), 7.96-7.92 (m, 1H), 7.82 (d, J=2.4 Hz, 1H), 7.69 (dd, J=2.8, 8.8 Hz, 1H), 7.62-7.57 (m, 1H), 7.46 (d, J=3.6 Hz, 1H), 7.37 (d, J=8.8 Hz, 1H), 7.26 (t, J=73.2 Hz, 1H), 6.85-6.84 (m, 1H);

LC-HRMS (ESI) calcd for $[M+H, C_{20}H_{12}ClF_3N_3O_4]^+$: 450.0468, Found 450.0468.

Example 46

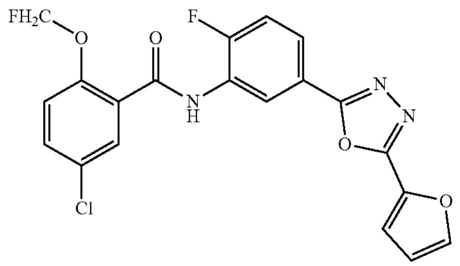

5-Chloro-N-(2-fluoro-5-(5-(furan-2-yl)-1,3,4-oxadiazol-2-yl)phenyl)-2-(fluoromethoxy)benzamide Compound 306

5-Chloro-N-(2-fluoro-5-(5-(furan-2-yl)-1,3,4-oxadiazol-2-yl)phenyl)-2-(fluoromethoxy)benzamide can be prepared as in Example 21, but from 5-chloro-2-(fluoromethoxy) benzoic acid (100.2 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (155.6 mg, 88.3% yield) as a yellow solid.

$^1$H NMR (400 MHz, DMSO): δ 10.41 (s, 1H), 8.75-8.73 (m, 1H), 8.11 (d, J=1.2 Hz, 1H), 7.96-7.92 (m, 1H), 7.78 (d, J=2.4 Hz, 1H), 7.66 (dd, J=2.8, 8.8 Hz, 1H), 7.61-7.57 (m, 1H), 7.47 (d, J=3.6 Hz, 1H), 7.37 (d, J=8.8 Hz, 1H), 6.85-6.84 (m, 1H), 6.04 (s, 1H), 5.90 (s, 1H);

LC-HRMS (ESI) calcd for $[M+H, C_{20}H_{13}ClF_2N_3O_4]^+$: 432.0563, Found 432.0555.

Example 47

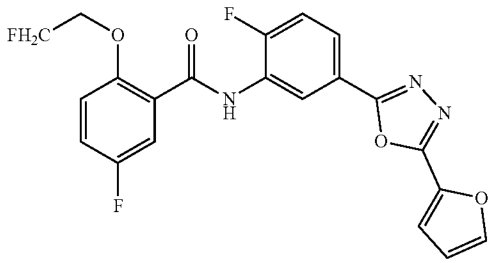

5-Fluoro-N-(2-fluoro-5-(5-(furan-2-yl)-1,3,4-oxadiazol-2-yl)phenyl)-2-(2-fluoroethoxy)benzamide Compound 312

5-Fluoro-N-(2-fluoro-5-(5-(furan-2-yl)-1,3,4-oxadiazol-2-yl)phenyl)-2-(2-fluoroethoxy)benzamide can be prepared as in Example 21, but from 5-fluoro-2-(2-fluoroethoxy) benzoic acid (99.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (168.4 mg, 96.2% yield) as a white solid.

$^1$H NMR (400 MHz, DMSO): δ 10.43 (s, 1H), 9.06 (d, J=5.6 Hz, 1H), 8.11 (s, 1H), 7.91-7.87 (m, 1H), 7.76 (dd, J=2.4, 9.2 Hz, 1H), 7.64-7.59 (m, 1H), 7.52-7.46 (m, 2H), 7.37-7.33 (m, 1H), 6.85-6.84 (m, 1H), 4.94-4.92 (m, 1H), 4.82-4.80 (m, 1H), 4.56-4.54 (m, 1H), 4.49-4.47 (m, 1H);

LC-HRMS (ESI) calcd for $[M+H, C_{21}H_{15}F_3N_3O_4]^+$: 430.1015, Found 430.1017.

Example 48

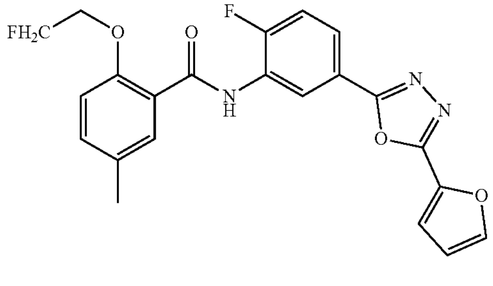

N-(2-Fluoro-5-(5-(furan-2-yl)-1,3,4-oxadiazol-2-yl)phenyl)-2-(2-fluoroethoxy)-5-methylbenzamide Compound 321

N-(2-Fluoro-5-(5-(furan-2-yl)-1,3,4-oxadiazol-2-yl)phenyl)-2-(2-fluoroethoxy)-5-methylbenzamide can be prepared as in Example 21, but from 2-(2-fluoroethoxy)-5-methylbenzoic acid (97.1 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (170.2 mg, 98.1% yield) as a white solid.

$^1$H NMR (400 MHz, DMSO): δ 10.40 (s, 1H), 9.12 (d, J=5.6 Hz, 1H), 8.11 (d, J=0.8 Hz, 1H), 7.88-7.86 (m, 2H), 7.60 (dd, J=8.8, 10.4 Hz, 1H), 7.46 (d, J=3.6 Hz, 1H), 7.42 (dd, J=2.0, 8.4 Hz, 1H), 7.20 (d, J=8.4 Hz, 1H), 6.85-6.84 (m, 1H), 4.95-4.93 (m, 1H), 4.83-4.81 (m, 1H), 4.55-4.53 (m, 1H), 4.47-4.45 (m, 1H), 2.33 (s, 3H);

LC-HRMS (ESI) calcd for [M+H, $C_{22}H_{18}F_2N_3O_4$]$^+$: 426.1265, Found 426.1277.

Example 49

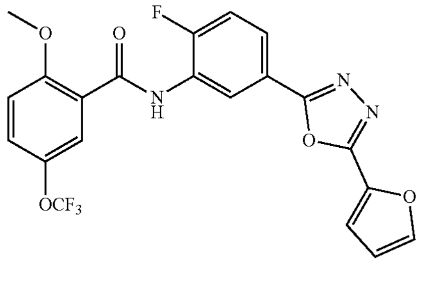

N-(2-Fluoro-5-(5-(furan-2-yl)-1,3,4-oxadiazol-2-yl)phenyl)-2-methoxy-5-(trifluoromethoxy)benzamide Compound 405

N-(2-Fluoro-5-(5-(furan-2-yl)-1,3,4-oxadiazol-2-yl)phenyl)-2-methoxy-5-(trifluoromethoxy)benzamide can be prepared as in Example 20, but from 2-methoxy-5-(trifluoromethoxy)benzoic acid (115.7 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (170.3 mg, 90.1% yield) as a white solid.

$^1$H NMR (400 MHz, DMSO): δ 10.45 (s, 1H), 8.93 (d, J=6.8 Hz, 1H), 8.11 (s, 1H), 7.94-7.91 (m, 1H), 7.84 (s, 1H), 7.67-7.59 (m, 2H), 7.47 (d, J=3.6 Hz, 1H), 7.40 (d, J=9.2 Hz, 1H), 6.85-6.84 (m, 1H), 4.04 (s, 3H); LC-HRMS (ESI) calcd for [M+H, $C_{21}H_{14}F_4N_3O_5$]$^+$: 464.0870, Found 464.0865.

Example 50

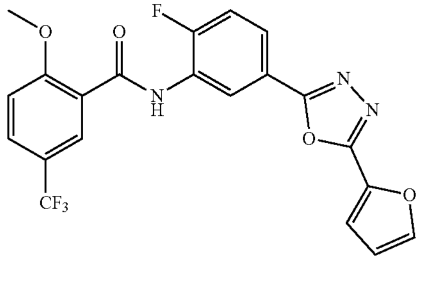 [SMILES: COc1ccc(C(F)(F)F)cc1C(=O)Nc1cc(-c2nnc(-c3ccco3)o2)ccc1F]

N-(2-Fluoro-5-(5-(furan-2-yl)-1,3,4-oxadiazol-2-yl)phenyl)-2-methoxy-5-(trifluoromethyl)benzamide Compound 416

N-(2-Fluoro-5-(5-(furan-2-yl)-1,3,4-oxadiazol-2-yl)phenyl)-2-methoxy-5-(trifluoromethyl)benzamide can be prepared as in Example 21, but from 2-methoxy-5-(trifluoromethyl)benzoic acid (107.9 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (179.1 mg, 98.1% yield) as a white solid.

$^1$H NMR (400 MHz, DMSO): δ 10.43 (s, 1H), 8.89 (d, J=5.6 Hz, 1H), 8.15 (s, 1H), 8.11 (s, 1H), 7.97-7.91 (m, 2H), 7.63-7.59 (m, 1H), 7.48-7.46 (m, 2H), 6.85-6.84 (m, 1H), 4.07 (s, 3H);

LC-HRMS (ESI) calcd for [M+H, $C_{21}H_{14}F_4N_3O_4$]$^+$: 448.0920, Found 448.0913.

Example 51

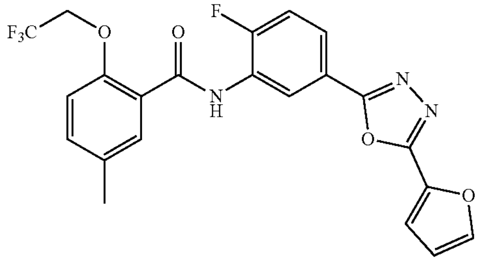 [SMILES: Cc1ccc(OCC(F)(F)F)c(C(=O)Nc2cc(-c3nnc(-c4ccco4)o3)ccc2F)c1]

N-(2-fluoro-5-(5-(furan-2-yl)-1,3,4-oxadiazol-2-yl)phenyl)-5-methyl-2-(2,2,2-trifluoroethoxy)benzamide Compound 322

N-(2-Fluoro-5-(5-(furan-2-yl)-1,3,4-oxadiazol-2-yl)phenyl)-2-methoxy-5-(trifluoromethyl)benzamide can be prepared as in Example 21, but from 5-methyl-2-(2,2,2-trifluoroethoxy)benzoic acid (114.6 mg, 0.49 mmol) and 2-fluoro-5-(5-(furan-2-yl)-1,3,4-oxadiazol-2-yl)aniline (100.0 mg, 0.41 mmol). The crude product was purified by silica gel flash column chromatography (dichloromethane/methanol=100/1) to give the title compound (173.7 mg, 92.3% yield) as a white solid.

1H NMR (400 MHz, DMSO): δ 10.07 (s, 1H), 8.93 (d, J=5.6 Hz, 1H), 8.10 (d, J=1.2 Hz, 1H), 7.91-7.87 (m, 2H), 7.68 (s, 1H), 7.61-7.56 (m, 1H), 7.45 (d, J=3.6 Hz, 1H), 7.42-7.40 (m, 1H), 7.24 (d, J=8.4 Hz, 1H), 6.85-6.84 (m, 1H), 4.94 (q, J=8.8 Hz, 1H), 2.34 (s, 3H); LC-HRMS (ESI) calcd for [M+H, C22H16F4N3O4]$^+$: 462.1077, Found 462.1070.

Example 52

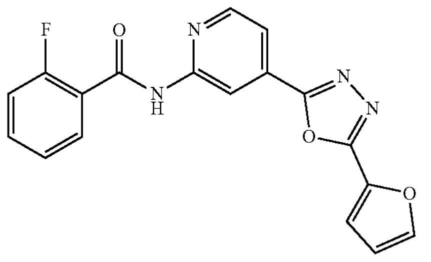 [SMILES: O=C(Nc1cc(-c2nnc(-c3ccco3)o2)ccn1)c1ccccc1F]

2-Fluoro-N-(4-(5-(furan-2-yl)-1,3,4-oxadiazol-2-yl) pyridin-2-yl)benzamide

Compound 39

According to the synthetic procedure depicted in Scheme 2, 2-fluoro-N-(4-(5-(furan-2-yl)-1,3,4-oxadiazol-2-yl)pyridin-2-yl)benzamide can be prepares as follows:

a) Methyl 2-(2-fluorobenzamido)isonicotinate: To a stirred solution of methyl 2-aminoisonicotinate (1.0 g, 6.6 mmol), 2-fluorobenzoic acid (1.0 g, 7.3 mmol) and N,N-diisopropylethylamine (2.5 g, 19.7 mmol) in dichloromethane (50 ml) was added benzotriazol-1-yl-oxytripyrrolidinophosphonium hexafluorophosphate (PyBop, 6.8 g, 13.1 mmol). The solution was stirred at room temperature for 12 hr. The solvent was evaporated under reduced pressure and the residue was purified by silica gel flash column chromatography (n-hexane/ethyl acetate=4/1) to 256.4 mg (14.2% yield) of methyl 2-(2-fluorobenzamido)isonicotinate as a white solid.

b) 2-(2-Fluorobenzamido)isonicotinic acid: To a solution of methyl 2-(2-fluorobenzamido)isonicotinate (256.4 mg, 0.93 mmol) in tetrahydrofuran (5 mL) was added 0.5 M lithium hydroxide solution (5 mL). The solution was stirred at room temperature for 12 hr. After concentration, the remained concentrated solution was acidified to pH 1 by adding 1 N hydrochloric acid. A massive precipitation was observed. The product was harvested by filtration and washed with water, then finally dried in vacuo to afford 180.5 mg (74.6% yield) of 2-(2-fluorobenzamido)isonicotinic acid as a white solid.

c) 2-Fluoro-N-(4-(2-(furan-2-carbonyl)hydrazinecarbonyl)pyridin-2-yl)benzamide: To a stirred solution of 2-(2-fluorobenzamido)isonicotinic acid (180.5 mg, 0.69 mmol), 2-furoic acid hydrazide (91.6 mg, 0.73 mmol) and N,N-diisopropylethylamine (267.5 mg, 2.07 mmol) in dichloromethane (10 ml) was added PyBop (468.4 mg, 0.90 mmol). The solution was stirred at room temperature for 12 hr. The solvent was evaporated under reduced pressure and the residue was purified by silica gel flash column chromatography (dichloromethane/methanol=100/1) to 206.8 mg (81.4% yield) of 2-fluoro-N-(4-(2-(furan-2-carbonyl) hydrazinecarbonyl)pyridin-2-yl)benzamide as a white solid.

d) 2-Fluoro-N-(4-(5-(furan-2-yl)-1,3,4-oxadiazol-2-yl) pyridin-2-yl)benzamide: 2-Fluoro-N-(4-(2-(furan-2-carbonyl)hydrazinecarbonyl)pyridin-2-yl)benzamide (206.8 mg, 0.56 mmol) was dissolved in phosphorus oxychloride (2 ml) and the mixture was stirred with heating at 80° C. for 5 hr. Phosphorus oxychloride was evaporated under reduced pressure and water was added to the residue. The mixture was extracted with dichloromethane and the organic layer was washed with saturated aqueous solution of sodium hydrogencarbonate, dried over anhydrous sodium sulfate and concentrated under reduced pressure. The residue was purified by silica gel flash column chromatography (dichloromethane/methanol=50/1) to give the title compound (82.5 mg, 42.1% yield) as a pale-yellow solid.

$^1H$ NMR (400 MHz, DMSO): δ 11.20 (s, 1H), 8.86 (s, 1H), 8.63 (d, J=5.2 Hz, 1H), 8.14 (s, 1H), 7.79 (d, J=4.8 Hz, 1H), 7.76-7.73 (m, 1H), 7.64-7.59 (m, 1H), 7.53 (d, J=3.6 Hz, 1H), 7.39-7.33 (m, 2H), 6.87-6.86 (m, 1H);

LC-HRMS (ESI) calcd for $[M+H, C_{13}H_{12}FN_4O_3]^+$: 351.0893, Found 351.0898.

Example 53

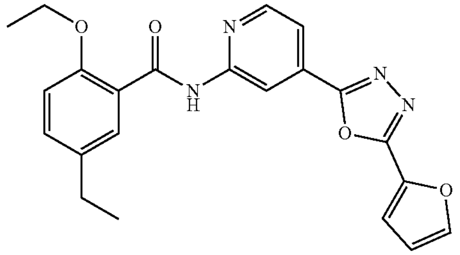 [SMILES: CCOc1ccc(CC)cc1C(=O)Nc1cc(-c2nnc(-c3ccco3)o2)ccn1]

2-Ethoxy-5-ethyl-N-(4-(5-(furan-2-yl)-1,3,4-oxadiazol-2-yl)pyridin-2-yl)benzamide Compound 373

According to the synthetic procedure depicted in Scheme 2, 2-fluoro-N-(4-(5-(furan-2-yl)-1,3,4-oxadiazol-2-yl)pyridin-2-yl)benzamide can be prepares as follows:

a) Methyl 2-(2-ethoxy-5-ethylbenzamido)isonicotinate: A mixture of 2-ethoxy-5-ethylbenzoic acid (1.4 g, 7.23 mmol) and N,N-dimethylformamide (0.01 ml) in thionyl chloride (5 ml) was stirred with refluxing for 2 hr. The excess thionyl chloride was evaporated under reduced pressure to give acid chloride.

This acid chloride was dissolved in dichloromethane (20 ml) and added dropwise to a solution of methyl 2-aminoisonicotinate (1.0 g, 6.6 mmol) and pyridine (0.69 ml, 8.54 mmol) in dichloromethane (50 ml) at 0° C. The reaction mixture was allowed to warm slowly to room temperature and stirred for 12 h. The mixture was concentrated under vacuum, and the residue was purified by silica gel flash column chromatography (n-hexane/ethyl acetate=4/1) to afford 1.96 g (90.5% yield) of methyl 2-(2-ethoxy-5-ethylbenzamido)isonicotinate as a pale-yellow solid.

b) 2-(2-Ethoxy-5-ethylbenzamido)isonicotinic acid: By the reaction in the same manner as in Example 52 using methyl 2-(2-ethoxy-5-ethylbenzamido)isonicotinate (1.96 g, 5.97 mmol), 1.38 g (73.5% yield) of 2-(2-ethoxy-5-ethylbenzamido)isonicotinic acid was obtained as a white solid.

c) 2-Ethoxy-5-ethyl-N-(4-(2-(furan-2-carbonyl)hydrazinecarbonyl)pyridin-2-yl)benzamide: By the reaction in the same manner as in Example 52 using 2-(2-ethoxy-5-ethylbenzamido)isonicotinic acid (1.38 g, 4.39 mmol), 2-furoic acid hydrazide (0.58 g, 4.61 mmol), N,N-diisopropylethylamine (1.7 g, 13.17 mmol) and PyBop (2.97 g, 5.71 mmol), 1.52 g (82.0% yield) of 2-ethoxy-5-ethyl-N-(4-(2-(furan-2-carbonyl)hydrazinecarbonyl)pyridin-2-yl)benzamide was obtained as a white solid.

d) 2-Ethoxy-5-ethyl-N-(4-(5-(furan-2-yl)-1,3,4-oxadiazol-2-yl)pyridin-2-yl)benzamide: By the reaction in the same manner as in Example 52 using 2-ethoxy-5-ethyl-N-(4-(2-(furan-2-carbonyl)hydrazinecarbonyl) pyridin-2-yl)benzamide (1.52 g, 3.60 mmol), 0.76 g (52.2% yield) of the title compound was obtained as a white solid.

$^1$H NMR (400 MHz, DMSO): δ 10.94 (s, 1H), 8.94 (s, 1H), 8.62 (d, J=5.2 Hz, 1H), 8.15 (s, 1H), 7.87 (s, 1H), 7.77 (d, J=5.6 Hz, 1H), 7.53 (d, J=3.2 Hz, 1H), 7.44 (d, J=7.6 Hz, 1H), 7.20 (d, J=8.4 Hz, 1H), 6.88-6.87 (m, 1H), 4.29 (q, J=6.8 Hz, 2H), 2.64 (q, J=7.6, Hz, 2H), 1.50 (t, J=6.8, 3H), 1.20 (t, J=7.6 Hz, 3H);

LC-HRMS (ESI) calcd for [M+H, $C_{22}H_{21}N_4O_4]^+$: 405.1563, Found 405.1545.

Example 54

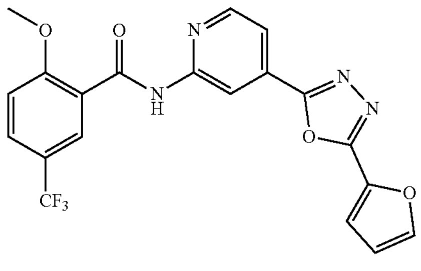 [SMILES: COc1ccc(C(F)(F)F)cc1C(=O)Nc1cc(-c2nnc(-c3ccco3)o2)ccn1]

N-(4-(5-(Furan-2-yl)-1,3,4-oxadiazol-2-yl)pyridin-2-yl)-2-methoxy-5-(trifluoromethyl)benzamide Compound 396

N-(4-(5-(Furan-2-yl)-1,3,4-oxadiazol-2-yl)pyridin-2-yl)-2-methoxy-5-(trifluoromethyl)benzamide can be prepared as in Example 53, but from methyl 2-aminoisonicotinate (0.20 g, 1.31 mmol) and 2-methoxy-5-(trifluoromethyl)benzoic acid (0.32 g, 1.44 mmol). 85.6 mg of the title compound was obtained as a white solid.

$^1$H NMR (400 MHz, DMSO): δ 10.92 (s, 1H), 8.89 (s, 1H), 8.63 (d, J=5.2 Hz, 1H), 8.14 (s, 1H), 8.07 (s, 1H), 7.93 (d, J=8.8 Hz, 1H), 7.80 (d, J=5.2 Hz, 1H), 7.53 (d, J=3.6 Hz, 1H), 7.44 (d, J=8.8 Hz, 1H), 6.87-6.86 (m, 1H), 4.03 (s, 3H); LC-HRMS (ESI) calcd for [M+H, $C_{20}H_{14}F_3N_4O_4]^+$: 431.0967, Found 431.0960.

Example 55

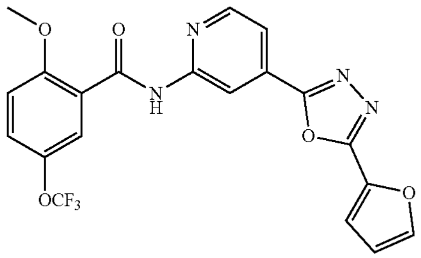 [SMILES: COc1ccc(OC(F)(F)F)cc1C(=O)Nc1cc(-c2nnc(-c3ccco3)o2)ccn1]

N-(4-(5-(Furan-2-yl)-1,3,4-oxadiazol-2-yl)pyridin-2-yl)-2-methoxy-5-(trifluoromethoxy)benzamide Compound 400

N-(4-(5-(Furan-2-yl)-1,3,4-oxadiazol-2-yl)pyridin-2-yl)-2-methoxy-5-(trifluoromethoxy)benzamide can be prepared as in Example 53, but from methyl 2-aminoisonicotinate (0.20 g, 1.31 mmol) and 2-methoxy-5-(trifluoromethoxy) benzoic acid (0.34 g, 1.44 mmol). 105.3 mg of the title compound was obtained as a white solid.

$^1$H NMR (400 MHz, DMSO): δ 10.89 (s, 1H), 8.89 (s, 1H), 8.63 (d, J=5.2 Hz, 1H), 8.15 (s, 1H), 7.81-7.77 (m, 2H), 7.63-7.60 (m, 1H), 7.54-7.53 (m, 1H), 7.37 (d, J=9.2 Hz, 1H), 6.88-6.87 (m, 1H), 4.01 (s, 3H);

LC-HRMS (ESI) calcd for [M+H, $C_{20}H_{14}F_3N_4O_5]^+$: 447.0916, Found 447.0911.

Example 56

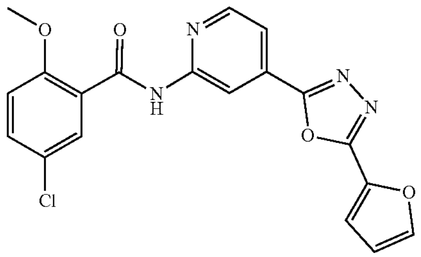 [SMILES: COc1ccc(Cl)cc1C(=O)Nc1cc(-c2nnc(-c3ccco3)o2)ccn1]

5-Chloro-N-(4-(5-(furan-2-yl)-1,3,4-oxadiazol-2-yl) pyridin-2-yl)-2-methoxybenzamide Compound 372

5-Chloro-N-(4-(5-(furan-2-yl)-1,3,4-oxadiazol-2-yl)pyridin-2-yl)-2-methoxybenzamide can be prepared as in Example 53, but from methyl 2-aminoisonicotinate (0.20 g, 1.31 mmol) and 5-chloro-2-methoxybenzoic acid (0.27 g, 1.44 mmol). 127.0 mg of the title compound was obtained as a pale-yellow solid;

$^1$H NMR (400 MHz, DMSO): δ 10.83 (s, 1H), 8.61 (d, J=0.8 Hz, 1H), 8.14 (s, 1H), 7.80-7.77 (m, 2H), 7.63-7.61 (m, 1H), 7.52 (d, J=2.8 Hz, 1H), 7.28 (d, J=9.2 Hz, 1H), 6.87-6.86 (m, 1H), 3.97 (s, 3H);

LC-HRMS (ESI) calcd for [M+H, $C_{19}H_{14}ClN_4O_4]^+$: 397.0704, Found 397.0689.

Example 63

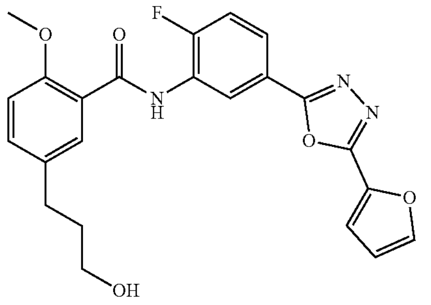 [SMILES: COc1ccc(CCCO)cc1C(=O)Nc1cc(-c2nnc(-c3ccco3)o2)ccc1F]

N-(2-fluoro-5-(5-(furan-2-yl)-1,3,4-oxadiazol-2-yl) phenyl)-5-(3-hydroxypropyl)-2-methoxybenzamide Compound 483

N-(2-fluoro-5-(5-(furan-2-yl)-1,3,4-oxadiazol-2-yl)phenyl)-5-(3-hydroxypropyl)-2-methoxybenzamide can be prepared as in example 1, but from 5-(3-hydroxypropyl)-2-methoxybenzoic acid (105.1 mg, 0.5 mmol) and 2-fluoro-5-(5-(furan-2-yl)-1,3,4-oxadiazol-2-yl) aniline (122.6 mg, 0.5 mmol). The crude product was purified by silica gel flash column chromatography (dichloromethane/methanol=100/1) to give the title compound (143.0 mg, 65.4% yield) as a yellow solid.

$^1$H NMR (400 MHz, DMSO) δ 10.47 (s, 1H), 9.04 (d, J=6.0 Hz, 1H), 8.12 (s, 1H), 7.92-7.86 (m, 1H), 7.84 (d, J=1.6 Hz, 1H), 7.66-7.56 (m, 1H), 7.47 (d, J=3.5 Hz, 1H), 7.44 (dd, J=8.5, 1.9 Hz, 1H), 7.21 (d, J=8.5 Hz, 1H), 6.85 (dd, J=3.4, 1.6 Hz, 1H), 4.49 (t, J=5.0 Hz, 1H), 4.02 (s, 3H), 3.43 (dd, J=11.3, 6.1 Hz, 2H), 2.70-2.59 (m, 2H), 1.78-1.67 (m, 2H);

LC-HRMS (ESI) calcd for [M+H, $C_{23}H_{21}FN_3O_5]^+$: 438.1460, Found 438.1461.

Example 64

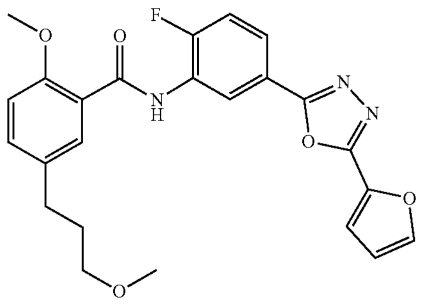

N-(2-fluoro-5-(5-(furan-2-yl)-1,3,4-oxadiazol-2-yl) phenyl)-2-methoxy-5-(3-methoxypropyl)benzamide Compound 484

N-(2-fluoro-5-(5-(furan-2-yl)-1,3,4-oxadiazol-2-yl)phenyl)-2-methoxy-5-(3-methoxypropyl)benzamide can be prepared as in example 1, but from 2-methoxy-5-(3-methoxypropyl)benzoic acid (112.1 mg, 0.5 mmol) and 2-fluoro-5-(5-(furan-2-yl)-1,3,4-oxadiazol-2-yl) aniline (122.6 mg, 0.5 mmol). The crude product was purified by silica gel flash column chromatography (dichloromethane/methanol=100/1) to give the title compound (167.4 mg, 74.2% yield) as a yellow solid.

$^1$H NMR (400 MHz, $CDCl_3$) δ 10.52 (d, J=3.0 Hz, 1H), 9.34 (dd, J=7.3, 2.1 Hz, 1H), 8.15 (d, J=2.3 Hz, 1H), 7.94 (ddd, J=8.5, 4.9, 2.2 Hz, 1H), 7.67 (d, J=1.1 Hz, 1H), 7.37 (dd, J=8.4, 2.4 Hz, 1H), 7.31-7.25 (m, 2H), 7.02 (d, J=8.5 Hz, 1H), 6.63 (dd, J=3.5, 1.7 Hz, 1H), 4.23 (t, J=6.2 Hz, 2H), 4.09 (s, 3H), 3.03 (s, 3H), 2.80 (t, J=7.5 Hz, 2H), 2.18-2.05 (m, 2H);

LC-HRMS (ESI) calcd for [M+H, $C_{24}H_{23}FN_3O_5]^+$: 452.1616, Found 452.1618.

Example 65

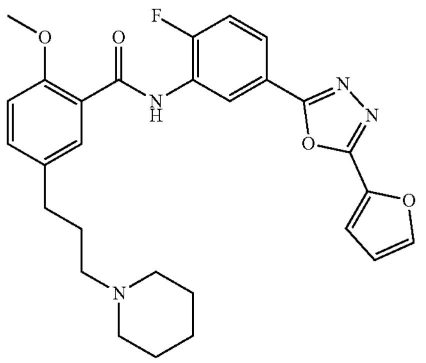 [SMILES: COc1ccc(CCCN2CCCCC2)cc1C(=O)Nc1cc(-c2nnc(-c3ccco3)o2)ccc1F]

N-(2-fluoro-5-(5-(furan-2-yl)-1,3,4-oxadiazol-2-yl) phenyl)-2-methoxy-5-(3-(piperidin-1-yl)propyl)benzamide Compound 495

N-(2-fluoro-5-(5-(furan-2-yl)-1,3,4-oxadiazol-2-yl)phenyl)-2-methoxy-5-(3-(piperidin-1-yl)propyl)benzamide can be prepared as in example 1, but from 2-methoxy-5-(3-(piperidin-1-yl)propyl) benzoic acid (138.7 mg, 0.5 mmol) and 2-fluoro-5-(5-(furan-2-yl)-1,3,4-oxadiazol-2-yl) aniline (122.6 mg, 0.5 mmol). The crude product was purified by silica gel flash column chromatography (dichloromethane/methanol=100/1) to give the title compound (68.6 mg, 27.2% yield) as a yellow solid.

$^1$H NMR (400 MHz, $CDCl_3$) δ 10.49 (d, J=3.0 Hz, 1H), 9.31 (dd, J=7.3, 1.8 Hz, 1H), 8.07 (d, J=2.1 Hz, 1H), 7.93-7.83 (m, 1H), 7.68 (d, J=0.7 Hz, 1H), 7.42 (dd, J=8.4, 2.1 Hz, 1H), 7.30-7.20 (m, 2H), 7.00 (d, J=8.5 Hz, 1H), 6.63 (dd, J=3.4, 1.7 Hz, 1H), 4.07 (s, 3H), 3.13-2.94 (m, 4H), 2.92-2.85 (m, 2H), 2.73 (t, J=7.4 Hz, 2H), 2.28-2.17 (m, 2H), 2.10-1.89 (m, 4H), 1.72-1.54 (m, 2H);

LC-HRMS (ESI) calcd for [M+H, $C_{23}H_{30}FN_4O_4]^+$: 505.2246, Found 505.2241.

Example 66

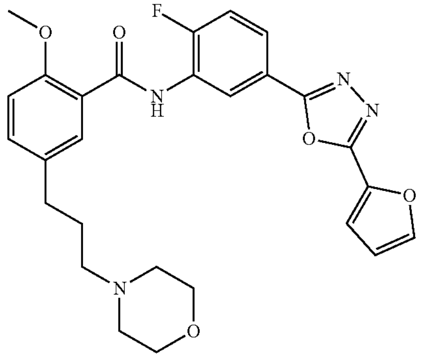 [SMILES: COc1ccc(CCCN2CCOCC2)cc1C(=O)Nc1cc(-c2nnc(-c3ccco3)o2)ccc1F]

N-(2-fluoro-5-(5-(furan-2-yl)-1,3,4-oxadiazol-2-yl) phenyl)-2-methoxy-5-(3-morpholinopropyl)benzamide Compound 496

N-(2-fluoro-5-(5-(furan-2-yl)-1,3,4-oxadiazol-2-yl)phenyl)-2-methoxy-5-(3-morpholinopropyl)benzamide can be prepared as in example 1, but from 2-methoxy-5-(3-morpholinopropyl)benzoic acid (139.6 mg, 0.5 mmol) and 2-fluoro-5-(5-(furan-2-yl)-1,3,4-oxadiazol-2-yl)aniline (122.6 mg, 0.5 mmol). The crude product was purified by silica gel flash column chromatography (dichloromethane/methanol=100/1) to give the title compound (105.8 mg, 41.8% yield) as a yellow solid.

$^1$H NMR (400 MHz, $CDCl_3$) δ 10.54 (s, 1H), 9.36 (d, J=5.4 Hz, 1H), 8.16 (d, J=2.1 Hz, 1H), 7.99-7.90 (m, 1H), 7.68 (s, 1H), 7.36 (dd, J=8.4, 2.2 Hz, 1H), 7.32-7.26 (m, 2H), 7.00 (d, J=8.5 Hz, 1H), 6.66-6.60 (m, 1H), 4.09 (s, 3H), 3.78-3.71 (m, 4H), 2.69 (t, J=7.6 Hz, 2H), 2.53-2.42 (m, 4H), 2.41-2.32 (m, 2H), 1.85 (dt, J=15.0, 7.6 Hz, 2H);

LC-HRMS (ESI) calcd for [M+H, $C_{27}H_{28}FN_4O_5]^+$: 507.2038, Found 507.2033.

Example 67

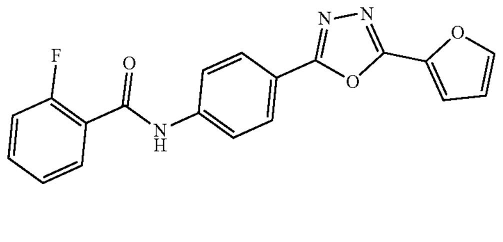 [SMILES: O=C(Nc1ccc(-c2nnc(-c3ccco3)o2)cc1)c1ccccc1F]

2-fluoro-N-(4-(5-(furan-2-yl)-1,3,4-oxadiazol-2-yl) phenyl)benzamide

Compound 35

2-fluoro-N-(4-(5-(furan-2-yl)-1,3,4-oxadiazol-2-yl)phenyl)benzamide can be prepared as in example 1, but from 2-fluorobenzoic acid (70.1 mg, 0.5 mmol) and 4-(5-(furan-2-yl)-1,3,4-oxadiazol-2-yl) aniline (113.6 mg, 0.5 mmol). The crude product was purified by silica gel flash column chromatography (dichloromethane/methanol=100/1) to give the title compound (113.2 mg, 64.8% yield) as a yellow solid.

$^1$H NMR (400 MHz, DMSO) δ 10.81 (s, 1H), 8.13-8.04 (m, 3H), 8.01-7.95 (m, 2H), 7.75-7.68 (m, 1H), 7.65-7.56 (m, 1H), 7.43 (d, J=3.5 Hz, 1H), 7.41-7.32 (m, 2H), 6.83 (dd, J=3.4, 1.7 Hz, 1H);

LC-HRMS (ESI) calcd for [M+H, $C_{19}H_{13}FN_3O_3]^+$: 350.0935, Found 350.0939.

Example 69

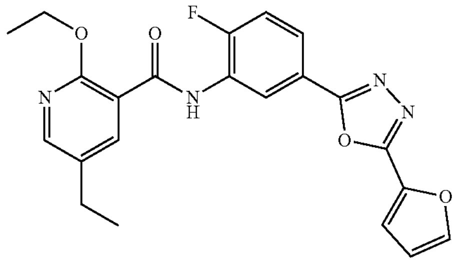 [SMILES: CCOc1ncc(CC)cc1C(=O)Nc1cc(-c2nnc(-c3ccco3)o2)ccc1F]

2-ethoxy-5-ethyl-N-(2-fluoro-5-(5-(furan-2-yl)-1,3,4-oxadiazol-2-yl)phenyl)nicotinamide Compound 485

2-ethoxy-5-ethyl-N-(2-fluoro-5-(5-(furan-2-yl)-1,3,4-oxadiazol-2-yl)phenyl)nicotinamide can be prepared as in example 1, but from 2-ethoxy-5-ethylnicotinic acid (97.6 mg, 0.5 mmol) and 2-fluoro-5-(5-(furan-2-yl)-1,3,4-oxadiazol-2-yl) aniline (122.6 mg, 0.5 mmol). The crude product was purified by silica gel flash column chromatography (dichloromethane/methanol=100/1) to give the title compound (137.2 mg, 65.0% yield) as a yellow solid.

$^1$H NMR (400 MHz, DMSO) δ 10.49 (s, 1H), 9.20-9.08 (m, 1H), 8.32-8.19 (m, 2H), 8.14-8.07 (m, 1H), 7.94-7.81 (m, 1H), 7.67-7.57 (m, 1H), 7.50-7.40 (m, 1H), 6.89-6.80 (m, 1H), 4.63-4.42 (m, 2H), 2.72-2.61 (m, 2H), 1.54-1.38 (m, 3H), 1.30-1.12 (m, 3H);

LC-HRMS (ESI) calcd for [M+H, $C_{22}H_{20}FN_4O_4]^+$: 423.1463, Found 423.1463.

Example 70

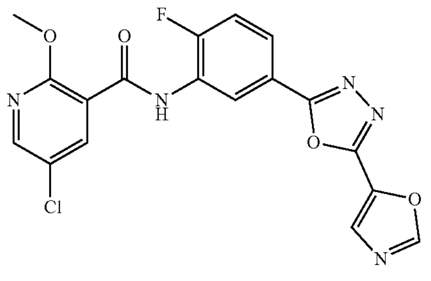 [SMILES: COc1ncc(Cl)cc1C(=O)Nc1cc(-c2nnc(-c3cnco3)o2)ccc1F]

5-chloro-N-(2-fluoro-5-(5-(oxazol-5-yl)-1,3,4-oxadiazol-2-yl)phenyl)-2-methoxynicotinamide Compound 486

5-chloro-N-(2-fluoro-5-(5-(oxazol-5-yl)-1,3,4-oxadiazol-2-yl)phenyl)-2-methoxynicotinamide can be prepared as in example 1, but from 5-chloro-2-methoxynicotinic acid (93.8 mg, 0.5 mmol) and 2-fluoro-5-(5-(oxazol-5-yl)-1,3,4-oxadiazol-2-yl) aniline (123.1 mg, 0.5 mmol). The crude product was purified by silica gel flash column chromatography (dichloromethane/methanol=100/1) to give the title compound (102.3 mg, 49.2% yield) as a yellow solid.

$^1$H NMR (400 MHz, $CDCl_3$) δ 10.42 (s, 1H), 9.31 (dd, J=7.3, 2.1 Hz, 1H), 8.59 (d, J=2.6 Hz, 1H), 8.31 (d, J=2.6 Hz, 1H), 8.13 (s, 1H), 8.02-7.96 (m, 1H), 7.93 (s, 1H), 7.33 (dd, J=10.3, 8.7 Hz, 1H), 4.23 (s, 3H);

LC-HRMS (ESI) calcd for $[M+H, C_{18}H_{12}ClFN_5O_4]^+$: 416.0556, Found 416.0557.

Example 71

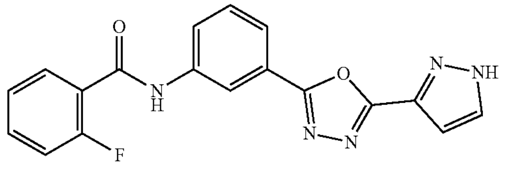 [SMILES: O=C(Nc1cccc(-c2nnc(-c3cc[nH]n3)o2)c1)c1ccccc1F]

N-(3-(5-(1H-pyrazol-3-yl)-1,3,4-oxadiazol-2-yl)phenyl)-2-fluorobenzamide

Compound 298

N-(3-(5-(1H-pyrazol-3-yl)-1,3,4-oxadiazol-2-yl)phenyl)-2-fluorobenzamide can be prepared as in example 1, but from 2-fluorobenzoic acid (70.0 mg, 0.5 mmol) and 3-(5-(1H-pyrazol-3-yl)-1,3,4-oxadiazol-2-yl) aniline (113.6 mg, 0.5 mmol). The crude product was purified by silica gel flash column chromatography (dichloromethane/methanol=100/1) to give the title compound (87.6 mg, 50.2% yield) as a yellow solid.

$^1$H NMR (400 MHz, DMSO) δ 13.69 (s, 1H), 10.75 (s, 1H), 8.58 (s, 1H), 8.05-8.02 (m, 1H), 7.95 (d, J=8.3 Hz, 1H), 7.83 (d, J=7.8 Hz, 1H), 7.72 (t, J=7.3 Hz, 1H), 7.65-7.58 (m, 2H), 7.43-7.32 (m, 2H), 6.98 (t, J=2.0 Hz, 1H);

LC-HRMS (ESI) calcd for $[M+H, C_{18}H_{13}FN_5O_2]^+$: 350.1048, Found 350.1042.

Example 72

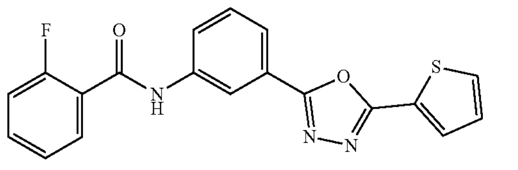 [SMILES: O=C(Nc1cccc(-c2nnc(-c3cccs3)o2)c1)c1ccccc1F]

2-fluoro-N-(3-(5-(thiophen-2-yl)-1,3,4-oxadiazol-2-yl)phenyl)benzamide

Compound 15

2-fluoro-N-(3-(5-(thiophen-2-yl)-1,3,4-oxadiazol-2-yl)phenyl)benzamide can be prepared as in example 1, but from 2-fluorobenzoic acid (70.0 mg, 0.5 mmol) and 3-(5-(thiophen-2-yl)-1,3,4-oxadiazol-2-yl) aniline (121.6 mg, 0.5 mmol). The crude product was purified by silica gel flash column chromatography (dichloromethane/methanol=100/1) to give the title compound (94.5 mg, 51.6% yield) as a yellow solid.

$^1$H NMR (400 MHz, DMSO) δ 10.74 (s, 1H), 8.56 (s, 1H), 8.01-7.94 (m, 2H), 7.92 (d, J=3.3 Hz, 1H), 7.83 (d, J=7.7 Hz, 1H), 7.73 (t, J=7.2 Hz, 1H), 7.66-7.56 (m, 2H), 7.43-7.30 (m, 3H);

LC-HRMS (ESI) calcd for $[M+H, C_{19}H_{13}FN_3O_2S]^+$: 366.0707, Found 366.0701.

Example 73

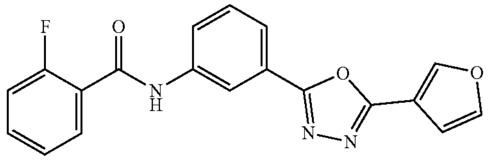 [SMILES: O=C(Nc1cccc(-c2nnc(-c3ccoc3)o2)c1)c1ccccc1F]

2-fluoro-N-(3-(5-(furan-3-yl)-1,3,4-oxadiazol-2-yl)phenyl)benzamide

Compound 20

2-fluoro-N-(3-(5-(furan-3-yl)-1,3,4-oxadiazol-2-yl)phenyl)benzamide can be prepared as in example 1, but from 2-fluorobenzoic acid (70.0 mg, 0.5 mmol) and 3-(5-(furan-3-yl)-1,3,4-oxadiazol-2-yl) aniline (113.6 mg, 0.5 mmol). The crude product was purified by silica gel flash column chromatography (dichloromethane/methanol=100/1) to give the title compound (123.1 mg, 70.5% yield) as a yellow solid.

$^1$H NMR (400 MHz, DMSO) δ 10.73 (s, 1H), 8.63 (s, 1H), 8.56 (s, 1H), 8.00-7.96 (m, 1H), 7.93 (d, J=8.1 Hz, 1H), 7.82 (d, J=7.8 Hz, 1H), 7.72 (t, J=7.4 Hz, 1H), 7.65-7.57 (m, 2H), 7.42-7.32 (m, 2H), 7.08 (d, J=1.0 Hz, 1H);

LC-HRMS (ESI) calcd for $[M+H, C_{19}H_{13}FN_3O_3]^+$: 350.0935, Found 350.0938.

Example 74

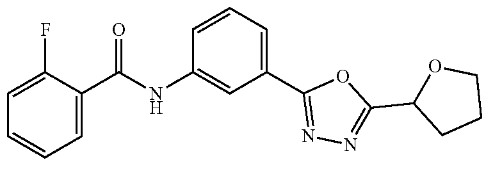 [SMILES: O=C(Nc1cccc(-c2nnc(C3CCCO3)o2)c1)c1ccccc1F]

2-fluoro-N-(3-(5-(tetrahydrofuran-2-yl)-1,3,4-oxadiazol-2-yl)phenyl)benzamide

Compound 22

2-fluoro-N-(3-(5-(tetrahydrofuran-2-yl)-1,3,4-oxadiazol-2-yl)phenyl)benzamide can be prepared as in example 1, but from 2-fluorobenzoic acid (70.0 mg, 0.5 mmol) and 3-(5-(tetrahydrofuran-2-yl)-1,3,4-oxadiazol-2-yl) aniline (115.6 mg, 0.5 mmol). The crude product was purified by silica gel flash column chromatography (dichloromethane/methanol=100/1) to give the title compound (108.5 mg, 61.2% yield) as a yellow solid.

$^1$H NMR (400 MHz, DMSO) δ 10.72 (s, 1H), 8.49 (s, 1H), 7.94 (d, J=8.1 Hz, 1H), 7.79-7.68 (m, 2H), 7.65-7.56 (m, 2H), 7.42-7.29 (m, 2H), 5.33-5.19 (m, 1H), 3.98-3.81 (m, 2H), 2.41-2.26 (m, 2H), 2.13-1.91 (m, 2H);

LC-HRMS (ESI) calcd for [M+H, $C_{19}H_{17}FN_3O_3$]$^+$: 354.1248, Found 354.1241.

Example 75

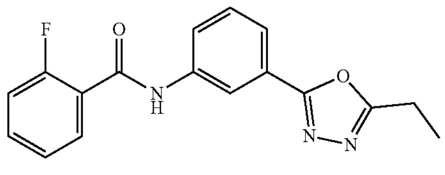 [SMILES: CCc1nnc(-c2cccc(NC(=O)c3ccccc3F)c2)o1]

N-(3-(5-ethyl-1,3,4-oxadiazol-2-yl)phenyl)-2-fluorobenzamide

Compound 289

N-(3-(5-ethyl-1,3,4-oxadiazol-2-yl)phenyl)-2-fluorobenzamide can be prepared as in example 1, but from 2-fluorobenzoic acid (70.0 mg, 0.5 mmol) and 3-(5-ethyl-1,3,4-oxadiazol-2-yl) aniline (94.6 mg, 0.5 mmol). The crude product was purified by silica gel flash column chromatography (dichloromethane/methanol=100/1) to give the title compound (65.3 mg, 42.0% yield) as a yellow solid.

$^1$H NMR (400 MHz, DMSO) δ 10.70 (s, 1H), 8.49 (s, 1H), 7.90 (d, J=8.1 Hz, 1H), 7.76-7.68 (m, 2H), 7.65-7.54 (m, 2H), 7.44-7.27 (m, 2H), 2.96 (q, J=7.5 Hz, 2H), 1.33 (t, J=7.5 Hz, 3H);

LC-HRMS (ESI) calcd for [M+H, $C_{17}H_{15}FN_3O_2$]$^+$: 312.1143, Found 312.1146.

Example 76

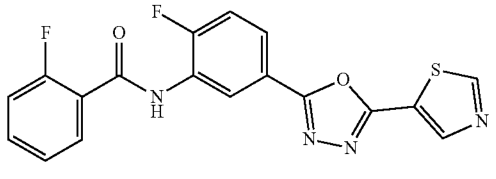 [SMILES: O=C(Nc1cc(-c2nnc(-c3cncs3)o2)ccc1F)c1ccccc1F]

2-fluoro-N-(2-fluoro-5-(5-(thiazol-5-yl)-1,3,4-oxadiazol-2-yl)phenyl)benzamide

Compound 290

2-fluoro-N-(2-fluoro-5-(5-(thiazol-5-yl)-1,3,4-oxadiazol-2-yl)phenyl)benzamide can be prepared as in example 1, but from 2-fluorobenzoic acid (70.0 mg, 0.5 mmol) and 2-fluoro-5-(5-(thiazol-5-yl)-1,3,4-oxadiazol-2-yl) aniline (131.1 mg, 0.5 mmol). The crude product was purified by silica gel flash column chromatography (dichloromethane/methanol=100/1) to give the title compound (125.7 mg, 65.4% yield) as a yellow solid.

$^1$H NMR (400 MHz, DMSO) δ 10.45 (s, 1H), 9.44 (s, 1H), 8.75 (d, J=0.5 Hz, 1H), 8.64 (d, J=6.0 Hz, 1H), 8.00 (ddd, J=8.5, 4.6, 2.2 Hz, 1H), 7.82-7.75 (m, 1H), 7.67-7.55 (m, 2H), 7.38 (dd, J=15.6, 8.0 Hz, 2H).

LC-HRMS (ESI) calcd for [M+H, $C_{18}H_{11}F_2N_4O_2S$]$^+$: 385.0565, Found 385.0565.

Example 77

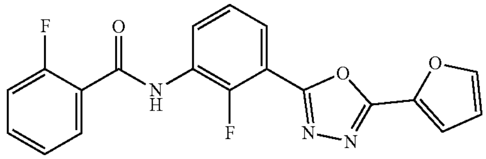 [SMILES: O=C(Nc1cccc(-c2nnc(-c3ccco3)o2)c1F)c1ccccc1F]

2-fluoro-N-(2-fluoro-3-(5-(furan-2-yl)-1,3,4-oxadiazol-2-yl)phenyl)benzamide

Compound 79

2-fluoro-N-(2-fluoro-3-(5-(furan-2-yl)-1,3,4-oxadiazol-2-yl)phenyl)benzamide can be prepared as in example 1, but from 2-fluorobenzoic acid (70.0 mg, 0.5 mmol) and 2-fluoro-3-(5-(furan-2-yl)-1,3,4-oxadiazol-2-yl) aniline (122.6 mg, 0.5 mmol). The crude product was purified by silica gel flash column chromatography (dichloromethane/methanol=100/1) to give the title compound (118.6 mg, 64.6% yield) as a yellow solid.

$^1$H NMR (400 MHz, DMSO) δ 10.43 (s, 1H), 8.12 (s, 1H), 8.06 (t, J=7.6 Hz, 1H), 7.94 (t, J=6.5 Hz, 1H), 7.77 (t, J=6.9 Hz, 1H), 7.63 (dd, J=13.4, 5.8 Hz, 1H), 7.52-7.44 (m, 2H), 7.43-7.29 (m, 2H), 6.85 (dd, J=3.5, 1.7 Hz, 1H).

LC-HRMS (ESI) calcd for [M+H, $C_{19}H_{12}F_2N_3O_3$]$^+$: 368.0841, Found 368.0849.

Scheme 3 below shows the general synthesis followed to prepare some compounds according to the invention:

Scheme 3

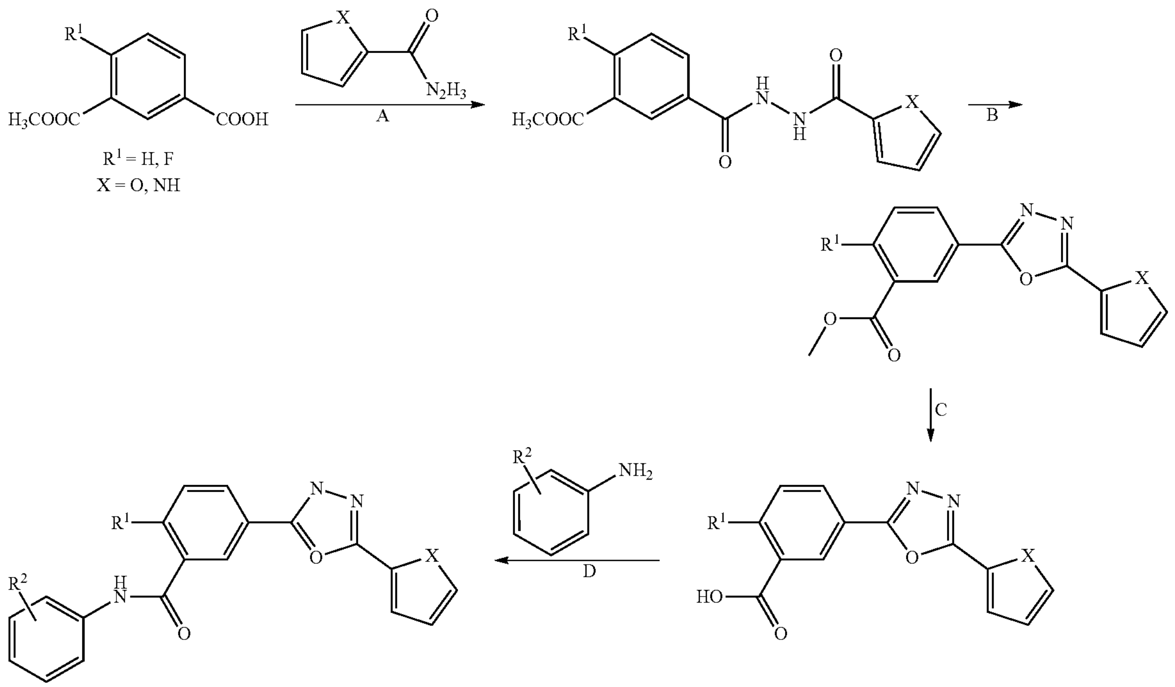

The following compounds were made according to this method:

Example 57

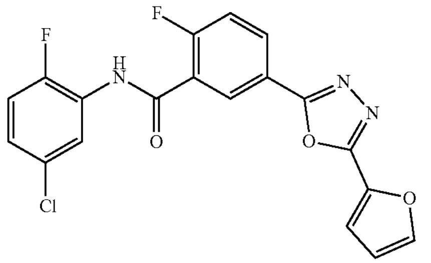 [SMILES: O=C(Nc1cc(Cl)ccc1F)c1cc(-c2nnc(-c3ccco3)o2)ccc1F]

N-(5-chloro-2-fluorophenyl)-2-fluoro-5-(5-(furan-2-yl)-1,3,4-oxadiazol-2-yl) benzamide Compound 479

According to the synthetic procedure depicted in Scheme 3, N-(5-chloro-2-fluorophenyl)-2-fluoro-5-(5-(furan-2-yl)-1,3,4-oxadiazol-2-yl) benzamide can be prepared as the following:

A:

Methyl 2-fluoro-5-(2-(furan-2-carbonyl)hydrazine-1-carbonyl)benzoate: To a solution of 4-fluoro-3-(methoxycarbonyl)benzoic acid (1.98 g, 10 mmol) in dichloromethane (20 ml) were added N,N-dimethylformamide (0.1 ml) and oxalyl chloride (1.3 ml, 15 mmol), and the mixture was stirred at room temperature for 4 hr. The solvent was evaporated under reduced pressure to give acid chloride. This acid chloride was dissolved in tetrahydrofuran (20 ml) and added dropwise to a suspension of furan-2-carbohydrazide (1.3 g, 10 mmol) and anhydrous sodium carbonate (1.1 g, 10 mmol) in tetrahydrofuran (10 mL) and water (10 mL) at 0° C. The mixture was stirred at 0° C. for 1 h, and at room temperature for 6 hr. A massive precipitation was observed. The product was harvested by filtration and washed with water, then finally dried in vacuo to afford 2.5 g (81.7% yield) of Methyl 2-fluoro-5-(2-(furan-2-carbonyl)hydrazine-1-carbonyl) benzoate as a white solid.

B:

Methyl 2-fluoro-5-(5-(furan-2-yl)-1,3,4-oxadiazol-2-yl) benzoate: Methyl 2-fluoro-5-(2-(furan-2-carbonyl) hydrazine-1-carbonyl)benzoate (2.5 g, 8.2 mmol) was dissolved in phosphorus oxychloride (40 ml) and the mixture was stirred with heating at 100° C. for 5 hr. Phosphorus oxychloride was evaporated under reduced pressure and water was added to the residue. A massive precipitation was observed. The product was harvested by filtration and washed with water, then dried in vacuo to afford 1.8 g (76.4% yield) of Methyl 2-fluoro-5-(5-(furan-2-yl)-1,3,4-oxadiazol-2-yl)benzoate.

C:

2-fluoro-5-(5-(furan-2-yl)-1,3,4-oxadiazol-2-yl)benzoic acid: Methyl 2-fluoro-5-(5-(furan-2-yl)-1,3,4-oxadiazol-2-yl)benzoate (1.8 g, 6.2 mmol) was dissolved in methanol (20 ml) and water (20 ml) were added LiOH (0.7 g, 31.2 mmol), and the mixture was stirred at room temperature for 8 hr. Thereafter, the reaction liquid was neutralized with 2N hydrochloric acid. The resulting white solid was filtered and washed with water, then finally dried in vacuo to afford 1.0 g (58.5% yield) of 2-fluoro-5-(5-(furan-2-yl)-1,3,4-oxadiazol-2-yl) benzoic acid.

D:

N-(5-chloro-2-fluorophenyl)-2-fluoro-5-(5-(furan-2-yl)-1,3,4-oxadiazol-2-yl)benzamide: 2-fluoro-5-(5-(furan-2-yl)-1,3,4-oxadiazol-2-yl)benzoic acid (137 mg, 0.5 mmol) in dichloromethane (10 ml) were added N,N-dimethylformamide (0.1 ml) and oxalyl chloride (1.3 ml, 15 mmol), and the mixture was stirred at room temperature for 4 hr. The solvent was evaporated under reduced pressure to give acid chloride. This acid chloride was dissolved in dichloromethane (5 ml) and added dropwise to a solution of 5-chloro-2-fluoroaniline (72.8 mg, 0.5 mmol) and triethylamine (101 mg, 1 mmol) in dichloromethane (5 ml) at 0° C. The reaction mixture was allowed to warm slowly to room temperature and stirred for 12 h. The mixture was concentrated under vacuum, and the residue was purified by silica gel flash column chromatography (dichloromethane/methanol=100/1) to give the title compound (106 mg, 52.8% yield) as a light yellow solid.

$^1$H NMR (400 MHz, DMSO) δ 10.61 (s, 1H), 8.52-8.36 (m, 1H), 8.33-8.22 (m, 1H), 8.12 (s, 1H), 8.08-7.95 (m, 1H), 7.66 (t, J=9.2 Hz, 1H), 7.51 (d, J=3.1 Hz, 1H), 7.46-7.25 (m, 2H), 6.91-6.80 (m, 1H);

LC-HRMS (ESI), calcd for [M+H, $C_{19}H_{11}ClF_2N_3O_3$]$^+$: 402.0452, Found 402.0456.

Example 58

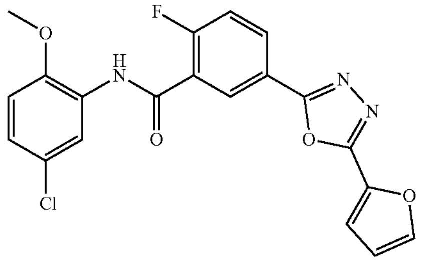 [SMILES: COc1ccc(Cl)cc1NC(=O)c1cc(-c2nnc(-c3ccco3)o2)ccc1F]

N-(5-chloro-2-methoxyphenyl)-2-fluoro-5-(5-(furan-2-yl)-1,3,4-oxadiazol-2-yl)benzamide Compound 480

N-(5-chloro-2-methoxyphenyl)-2-fluoro-5-(5-(furan-2-yl)-1,3,4-oxadiazol-2-yl) benzamide can be prepared as in example 57, but from 5-chloro-2-methoxyaniline (78.8 mg, 0.5 mmol) and 2-fluoro-5-(5-(furan-2-yl)-1,3,4-oxadiazol-2-yl)benzoic acid (137 mg, 0.5 mmol). The crude product was purified by silica gel flash column chromatography (dichloromethane/methanol=100/1) to give the title compound (103.0 mg, 49.8% yield) as a yellow solid.

$^1$H NMR (400 MHz, DMSO) δ 9.87 (d, J=5.7 Hz, 1H), 8.43 (d, J=5.1 Hz, 1H), 8.32-8.24 (m, 1H), 8.23-8.18 (m, 1H), 8.14-8.05 (m, 1H), 7.64 (t, J=9.6 Hz, 1H), 7.50 (d, J=3.4 Hz, 1H), 7.23 (dd, J=8.8, 2.5 Hz, 1H), 7.14 (d, J=8.8 Hz, 1H), 6.87-6.81 (m, 1H), 3.88 (s, 3H);

LC-HRMS (ESI) calcd for [M+H, $C_{20}H_{14}ClFN_3O_4$]$^+$: 414.0651, Found 414.0658.

Example 59

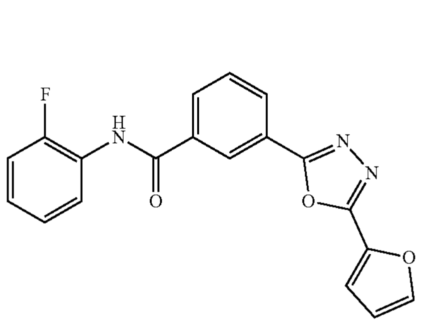 [SMILES: O=C(Nc1ccccc1F)c1cccc(-c2nnc(-c3ccco3)o2)c1]

N-(2-fluorophenyl)-3-(5-(furan-2-yl)-1,3,4-oxadiazol-2-yl)benzamide

Compound 44

N-(2-fluorophenyl)-3-(5-(furan-2-yl)-1,3,4-oxadiazol-2-yl)benzamide can be prepared as in example 57, but from 2-fluoroaniline (55.6 mg, 0.5 mmol) and 3-(5-(furan-2-yl)-1,3,4-oxadiazol-2-yl) benzoic acid (128.1 mg, 0.5 mmol). The crude product was purified by silica gel flash column chromatography (dichloromethane/methanol=100/1) to give the title compound (85.7 mg, 49.1% yield) as a yellow solid.

$^1$H NMR (400 MHz, DMSO) δ 10.45 (s, 1H), 8.65 (s, 1H), 8.30 (d, J=7.8 Hz, 1H), 8.24 (d, J=7.9 Hz, 1H), 8.11 (s, 1H), 7.80 (t, J=7.8 Hz, 1H), 7.63 (t, J=7.6 Hz, 1H), 7.50 (d, J=3.5 Hz, 1H), 7.38-7.19 (m, 3H), 6.85 (dd, J=3.4, 1.6 Hz, 1H);

LC-HRMS (ESI) calcd for [M+H, $C_{19}H_{13}FN_3O_3$]$^+$: 350.0935, Found 350.0938.

Example 60

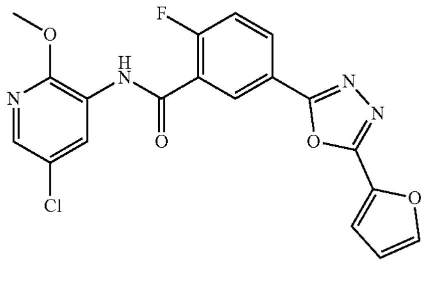 [SMILES: COc1ncc(Cl)cc1NC(=O)c1cc(-c2nnc(-c3ccco3)o2)ccc1F]

N-(5-chloro-2-methoxypyridin-3-yl)-2-fluoro-5-(5-(furan-2-yl)-1,3,4-oxadiazol-2-yl)benzamide Compound 481

N-(5-chloro-2-methoxypyridin-3-yl)-2-fluoro-5-(5-(furan-2-yl)-1,3,4-oxadiazol-2-yl)benzamide can be prepared as in example 57, but from 5-chloro-2-methoxypyridin-3-amine (79.3 mg, 0.5 mmol) and 3-(5-(furan-2-yl)-1,3,4-oxadiazol-2-yl)benzoic acid (128.1 mg, 0.5 mmol). The crude product was purified by silica gel flash column chromatography (dichloromethane/methanol=100/1) to give the title compound (110 mg, 53.0% yield) as a yellow solid.

$^1$H NMR (400 MHz, DMSO) δ 9.99 (d, J=9.1 Hz, 1H), 8.52 (dd, J=7.0, 2.2 Hz, 1H), 8.42 (d, J=2.6 Hz, 1H), 8.35-8.30 (m, 1H), 8.12 (s, 1H), 7.85 (d, J=2.7 Hz, 1H), 7.70 (dd, J=11.0, 8.8 Hz, 1H), 7.51 (d, J=3.4 Hz, 1H), 6.86 (dd, J=3.5, 1.7 Hz, 1H), 3.55 (s, 3H);

LC-HRMS (ESI) calcd for [M+H, $C_{19}H_{13}ClFN_4O_4$]$^+$: 415.0604, Found 415.0609.

Example 61

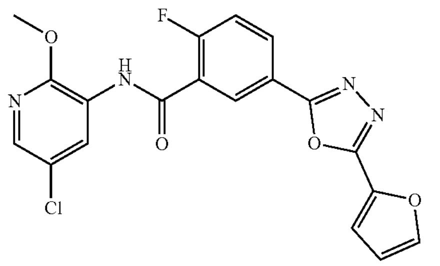 [SMILES: COc1ncc(Cl)cc1NC(=O)c1cc(-c2nnc(-c3ccco3)o2)ccc1F]

5-(5-(1H-pyrrol-2-yl)-1,3,4-oxadiazol-2-yl)-N-(5-chloro-2-methoxypyridin-3-yl)-2-fluorobenzamide Compound 482

5-(5-(1H-pyrrol-2-yl)-1,3,4-oxadiazol-2-yl)-N-(5-chloro-2-methoxypyridin-3-yl)-2-fluorobenzamide can be prepared as in example 57, but from 5-chloro-2-methoxypyridin-3-amine (79.3 mg, 0.5 mmol) and 5-(5-(1H-pyrrol-2-yl)-1,3,4-oxadiazol-2-yl)-2-fluorobenzoic acid (136.6 mg, 0.5 mmol). The crude product was purified by silica gel flash column chromatography (dichloromethane/methanol=100/1) to give the title compound (120 mg, 58.0% yield) as a yellow solid.

$^1H$ NMR (400 MHz, DMSO) δ 12.32 (s, 1H), 9.96 (d, J=8.5 Hz, 1H), 8.53 (d, J=5.9 Hz, 1H), 8.44-8.36 (m, 1H), 8.34-8.24 (m, 1H), 7.84 (s, 1H), 7.68 (t, J=9.8 Hz, 1H), 7.22-7.07 (m, 1H), 7.00-6.87 (m, 1H), 6.31 (s, 1H), 3.54 (s, 3H).

LC-HRMS (ESI) calcd for $[M+H, C_{19}H_{14}ClFN_5O_3]^+$: 414.0764, Found 414.0767.

Scheme 4 below shows the general synthesis followed to prepare some compounds according to the invention:

Scheme 4

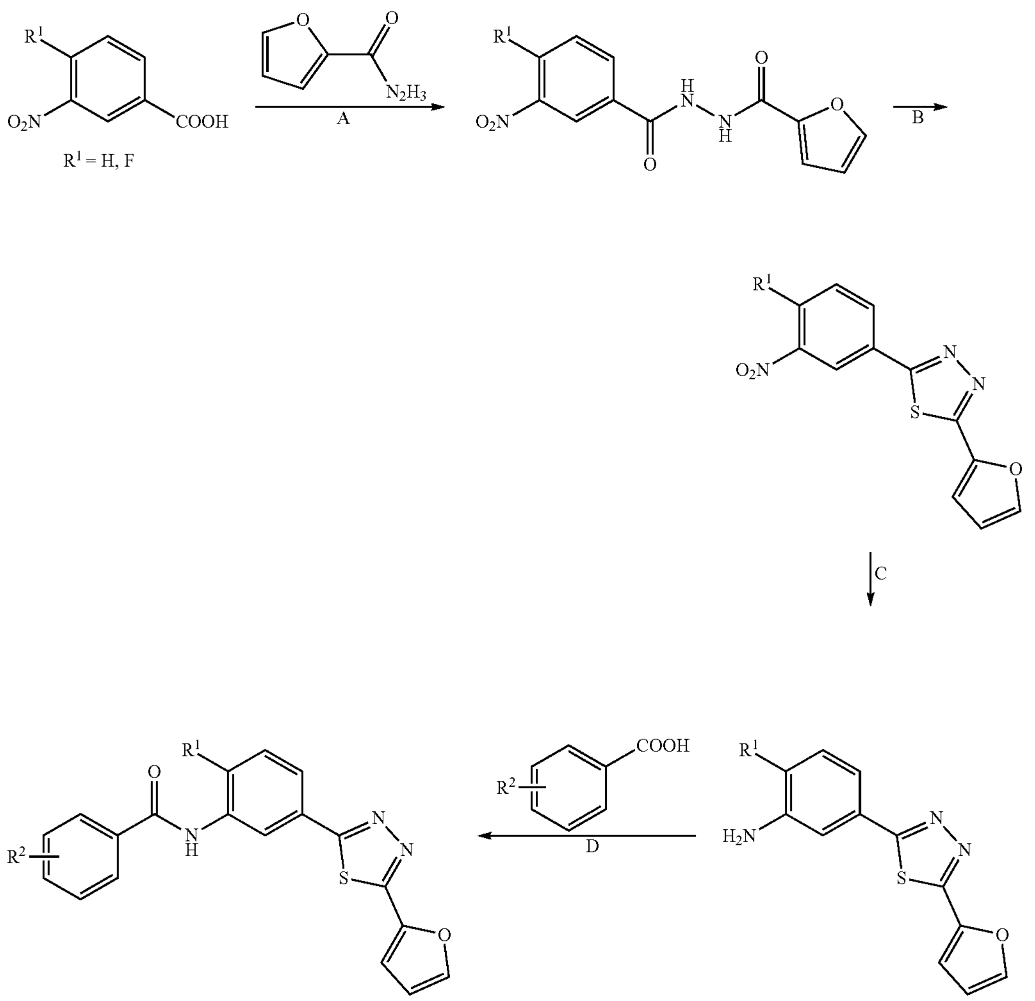

The following compounds were made according to this method:

Example 62

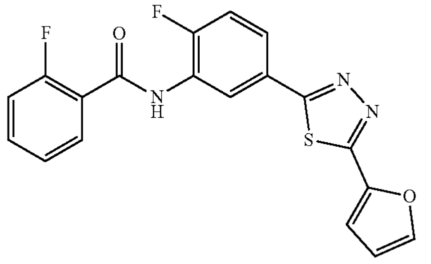 [SMILES: O=C(Nc1cc(-c2nnc(-c3ccco3)s2)ccc1F)c1ccccc1F]

2-fluoro-N-(3-(5-(furan-2-yl)-1,3,4-thiadiazol-2-yl) phenyl)benzamide

Compound 325

According to the synthetic procedure depicted in Scheme 4, 2-fluoro-N-(2-fluoro-5-(5-(furan-2-yl)-1,3,4-thiadiazol-2-yl)phenyl)benzamide can be prepared as the following:

A:

N'-(4-fluoro-3-nitrobenzoyl)furan-2-carbohydrazide: To a solution of 4-fluoro-3-nitrobenzoic acid (1.85 g, 10 mmol) in dichloromethane (20 ml) were added N,N-dimethylformamide (0.1 ml) and oxalyl chloride (1.3 ml, 15 mmol), and the mixture was stirred at room temperature for 4 hr. The solvent was evaporated under reduced pressure to give acid chloride. This acid chloride was dissolved in tetrahydrofuran (20 ml) and added dropwise to a suspension of 2-furoic acid hydrazide (1.3 g, 10 mmol) and sodium carbonate (1.1 g, 10 mmol) in tetrahydrofuran (10 mL) and water (10 mL) at 0° C. The mixture was stirred at 0° C. for 1 hr, and at room temperature for 6 hrs. A massive precipitation was observed. The product was harvested by filtration and washed with water, then finally dried in vacuo to afford 2.3 g (78.5% yield) of N'-(4-fluoro-3-nitrobenzoyl)furan-2-carbohydrazide as a white solid.

B:

2-(4-fluoro-3-nitrophenyl)-5-(furan-2-yl)-1,3,4-thiadiazole: N'-(4-fluoro-3-nitrobenzoyl) furan-2-carbohydrazide (2.3 g, 7.8 mmol), Lawesson's reagent (4.8 g, 11.8 mmol) was dissolved in toluene (40 ml) and the mixture was stirred at 110° C. for 12 hrs. The mixture was concentrated under vacuum, and the residue was purified by silica gel flash column chromatography (Hexane/Ethyl acetate=10/1) to give the title compound (1.4 g, 61.2% yield) as a yellow solid.

C:

2-fluoro-5-(5-(furan-2-yl)-1,3,4-thiadiazol-2-yl) aniline: A mixture of 2-(4-fluoro-3-nitrophenyl)-5-(furan-2-yl)-1,3,4-thiadiazole (1.4 g, 4.8 mmol) and Raney-Ni (0.3 g) in methanol (30 ml) was stirred at 50° C. for 16 hrs under 2.0 Mpa hydrogen atmosphere. The mixture was filtered and the filtrate was concentrated under vacuum. The residue was purified by silica gel flash column chromatography (dichloromethane/methanol=50/1) to give the title compound (1.0 g, 79.6% yield) as a yellow solid.

D:

2-fluoro-N-(2-fluoro-5-(5-(furan-2-yl)-1,3,4-thiadiazol-2-yl)phenyl)benzamide: 2-fluorobenzoic acid (140 mg, 1 mmol) in dichloromethane (10 ml) were added N,N-dimethylformamide (0.1 ml) and oxalyl chloride (2.6 ml, 30 mmol), and the mixture was stirred at room temperature for 4 hrs. The solvent was evaporated under reduced pressure to give acid chloride. This acid chloride was dissolved in dichloromethane (5 ml) and added dropwise to a solution of 2-fluoro-5-(5-(furan-2-yl)-1,3,4-thiadiazol-2-yl) aniline (261.2 mg, 1 mmol) and triethylamine (202 mg, 2 mmol) in dichloromethane (5 ml) at 0° C. The reaction mixture was allowed to warm up slowly to room temperature and stirred at this temperature for 12 hrs. The mixture was concentrated under vacuum, and the residue was purified by silica gel flash column chromatography (dichloromethane/methanol=100/1) to give the title compound (215 mg, 56.1% yield) as a light yellow solid.

$^1$H NMR (400 MHz, DMSO) δ 10.41 (s, 1H), 8.59 (d, J=5.8 Hz, 1H), 8.06 (s, 1H), 7.94-7.84 (m, 1H), 7.78 (t, J=7.1 Hz, 1H), 7.63 (dd, J=13.4, 6.2 Hz, 1H), 7.58-7.49 (m, 1H), 7.45-7.30 (m, 3H), 6.81 (d, J=1.6 Hz, 1H).

LC-HRMS (ESI) calcd for $[M+H, C_{19}H_{12}F_2N_3O_2S]^+$: 384.0613, Found 384.0610.

Scheme 5 below shows the general synthesis followed to prepare some compounds according to the invention:

Scheme 5

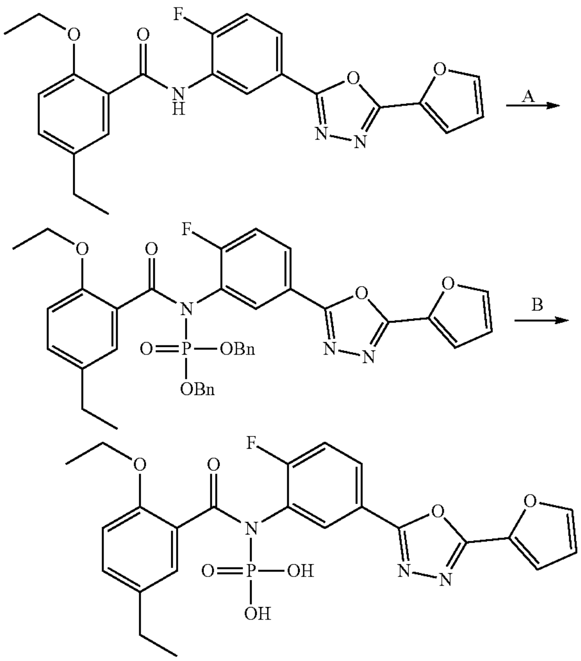

The following compounds were made according to this method:

Example 78

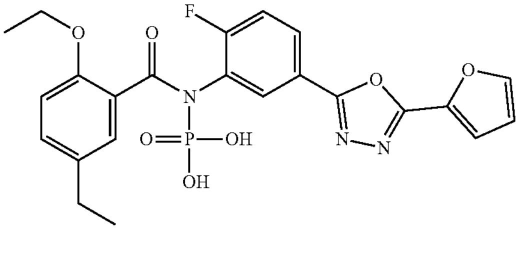 [SMILES: CCOc1ccc(CC)cc1C(=O)N(c1cc(-c2nnc(-c3ccco3)o2)ccc1F)P(=O)(O)O]

(2-ethoxy-5-ethylbenzoyl)(2-fluoro-5-(5-(furan-2-yl)-1,3,4-oxadiazol-2-yl)phenyl)phosphoramidic acid Compound 497

According to the synthetic procedures depicted in scheme 5, (2-ethoxy-5-ethylbenzoyl)(2-fluoro-5-(5-(furan-2-yl)-1,3,4-oxadiazol-2-yl)phenyl)phosphoramidic acid can be prepares as follows:

A:

Dibenzyl(2-ethoxy-5-ethylbenzoyl) (2-fluoro-5-(5-(furan-2-yl)-1,3,4-oxadiazol-2-yl)phenyl) phosphoramidate: To a solution of 2-ethoxy-5-ethyl-N-(2-fluoro-5-(5-(furan-2-yl)-1,3,4-oxadiazol-2-yl) phenyl) benzamide (FTEC-252) (0.42 g, 1 mmol) in N,N-dimethylformamide (10 ml) were added sodium hydride (60% dispersion in mineral oil) (48 mg, 1.2 mmol) and the mixture was stirred at 0° C. for 1 hr. Then dibenzyl phosphorochloridate (0.36 g, 1.2 mmol) was added to the mixture at 0° C. The reaction mixture was allowed to warm up slowly to room temperature and stirred at this temperature for 12 hrs. The mixture was concentrated under vacuum and the residue was purified by silica gel flash column chromatography (dichloromethane/methanol=100/1) to give the title compound (50 mg, 7.3% yield) as a yellow solid.

B:

(2-ethoxy-5-ethylbenzoyl)(2-fluoro-5-(5-(furan-2-yl)-1,3,4-oxadiazol-2-yl)phenyl)phosphoramidic acid: A mixture of dibenzyl (2-ethoxy-5-ethylbenzoyl)(2-fluoro-5-(5-(furan-2-yl)-1,3,4-oxadiazol-2-yl)phenyl) phosphoramidate (50 mg, 0.07 mmol), Et3N (0.3 g, 0.3 mmol) and Pd—C (5%) in ethanol (20 ml) was stirred at room temperature for 16 hrs under 2.0 Mpa hydrogen atmosphere. The mixture was filtered and the filtrate was concentrated under vacuum. The residue was purified by silica gel flash column chromatography (dichloromethane/methanol=50/1) to give the title compound (20 mg, 54.4% yield) as a solid 1H NMR (400 MHz, DMSO) δ 8.11-8.08 (m, 1H), 8.01-7.94 (m, 1H), 7.83-7.74 (m, 1H), 7.44-7.41 (m, 1H), 7.23-7.17 (m, 1H), 6.96 (s, 1H), 6.92 (d, J=8.5 Hz, 1H), 6.85-6.81 (m, 1H), 6.63-6.53 (m 1H), 3.86-3.73 (m, 2H), 2.46-2.38 (m, 2H), 1.36 (t, J=6.9 Hz, 3H), 1.05 (t, J=7.7 Hz, 3H).

LC-HRMS (ESI) calcd for [M+H, C23H22FN3O7]+: 502.1174, Found 502.1177.

Example 79

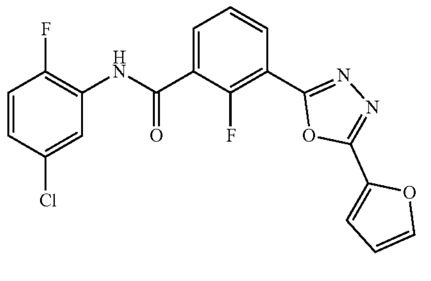 [SMILES: O=C(Nc1cc(Cl)ccc1F)c1cccc(-c2nnc(-c3ccco3)o2)c1F]

N-(5-chloro-2-fluorophenyl)-2-fluoro-3-(5-(furan-2-yl)-1,3,4-oxadiazol-2-yl)benzamide Compound 487

N-(5-chloro-2-fluorophenyl)-2-fluoro-3-(5-(furan-2-yl)-1,3,4-oxadiazol-2-yl)benzamide can be prepared as in example 57, but from 5-chloro-2-fluoroaniline (72.8 mg, 0.5 mmol) and 2-fluoro-3-(5-(furan-2-yl)-1,3,4-oxadiazol-2-yl) benzoic acid (137.1 mg, 0.5 mmol). The crude product was purified by silica gel flash column chromatography (dichloromethane/methanol=100/1) to give the title compound (105 mg, 52.3% yield) as a light yellow solid.

$^1$H NMR (400 MHz, $CDCl_3$) δ 8.78 (d, J=14.2 Hz, 1H), 8.59 (d, J=6.8 Hz, 1H), 8.42-8.30 (m, 2H), 7.73-7.70 (m, 1H), 7.53 (t, J=7.8 Hz, 1H), 7.31 (d, J=3.5 Hz, 1H), 7.11 (d, J=8.7 Hz, 2H), 6.66 (dd, J=3.5, 1.7 Hz, 1H).

LC-HRMS (ESI) calcd for [M+H, $C_{19}H_{11}ClF_2N_3O_3]^+$: 402.0452, Found 402.0457.

Example 80

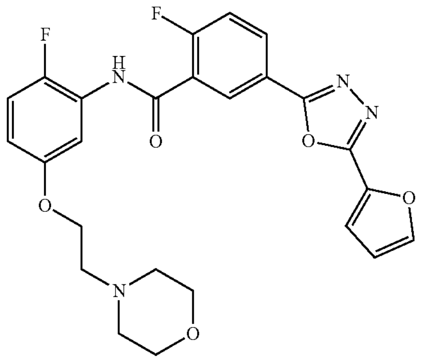 [SMILES: O=C(Nc1cc(OCCN2CCOCC2)ccc1F)c1cc(-c2nnc(-c3ccco3)o2)ccc1F]

2-Fluoro-N-(2-fluoro-5-(2-morpholinoethoxy)phenyl)-5-(5-(furan-2-yl)-1,3,4-oxadiazol-2-yl)benzamide Compound 488

2-Fluoro-N-(2-fluoro-5-(2-morpholinoethoxy)phenyl)-5-(5-(furan-2-yl)-1,3,4-oxadiazol-2-yl)benzamide can be prepared as in example 57, but from 2-fluoro-5-(2-morpholinoethoxy) aniline (120.1 mg, 0.5 mmol) and 2-fluoro-5-(5-(furan-2-yl)-1,3,4-oxadiazol-2-yl)benzoic acid (137.1 mg, 0.5 mmol). The crude product was purified by silica gel flash column chromatography (dichloromethane/methanol=100/1) to give the title compound (100 mg, 40.3% yield) as a light yellow solid.

$^1$H NMR (400 MHz, DMSO) δ 10.41 (s, 1H), 8.39-8.33 (m, 1H), 8.32-8.23 (m, 1H), 8.14-8.09 (m, 1H), 7.70-7.60 (m, 1H), 7.58-7.48 (m, 2H), 7.24 (t, J=9.2 Hz, 1H), 6.92-6.78 (m, 2H), 4.14-4.05 (m, 2H), 3.67-3.50 (m, 4H), 2.76-2.64 (m, 2H), 2.50-2.43 (m, 4H).

LC-HRMS (ESI) calcd for [M+H, $C_{25}H_{23}F_2N_4O_5]^+$: 497.1631, Found 497.1638.

Example 81

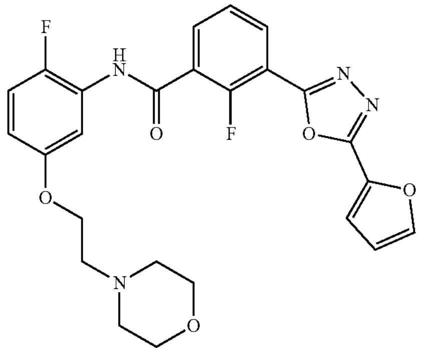 [SMILES: O=C(Nc1cc(OCCN2CCOCC2)ccc1F)c1cccc(-c2nnc(-c3ccco3)o2)c1F]

2-fluoro-N-(2-fluoro-5-(2-morpholinoethoxy)phenyl)-3-(5-(furan-2-yl)-1,3,4-oxadiazol-2-yl)benzamide Compound 489

2-fluoro-N-(2-fluoro-5-(2-morpholinoethoxy)phenyl)-3-(5-(furan-2-yl)-1,3,4-oxadiazol-2-yl)benzamide can be prepared as in example 1, but from 2-fluoro-5-(2-morpholinoethoxy)aniline (120.1 mg, 0.5 mmol) and 2-fluoro-3-(5-(furan-2-yl)-1,3,4-oxadiazol-2-yl)benzoic acid (137.1 mg, 0.5 mmol). The crude product was purified by silica gel flash column chromatography (dichloromethane/methanol=100/1) to give the title compound (155 mg, 62.4% yield) as a light yellow solid.

$^1$H NMR (400 MHz, DMSO) δ 10.44 (s, 1H), 8.26 (t, J=6.7 Hz, 1H), 8.13 (d, J=1.1 Hz, 1H), 7.95 (t, J=6.4 Hz, 1H), 7.57 (t, J=7.8 Hz, 1H), 7.54-7.50 (m, 1H), 7.49 (d, J=3.5 Hz, 1H), 7.23 (t, J=9.7 Hz, 1H), 6.86 (dd, J=3.5, 1.7 Hz, 1H), 6.82 (dt, J=8.9, 3.4 Hz, 1H), 4.08 (t, J=5.6 Hz, 2H), 3.70-3.44 (m, 4H), 2.69 (t, J=5.4 Hz, 2H), 2.49-2.43 (m, 4H).

LC-HRMS (ESI) calcd for [M+H, $C_{25}H_{23}F_2N_4O_5]^+$: 497.1631, Found 497.1638.

Example 82

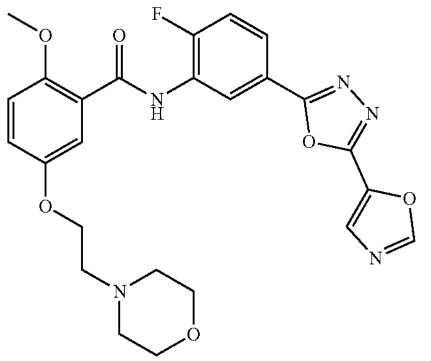

N-(2-fluoro-5-(5-(oxazol-5-yl)-1,3,4-oxadiazol-2-yl)phenyl)-2-methoxy-5-(2-morpholinoethoxy)benzamide Compound 490

N-(2-fluoro-5-(5-(oxazol-5-yl)-1,3,4-oxadiazol-2-yl)phenyl)-2-methoxy-5-(2-morpholinoethoxy)benzamide can be prepared as in example 1, but from 2-methoxy-5-(2-morpholinoethoxy)benzoic acid (140.7 mg, 0.5 mmol) and 2-fluoro-5-(5-(oxazol-5-yl)-1,3,4-oxadiazol-2-yl)aniline (123.1 mg, 0.5 mmol). The crude product was purified by silica gel flash column chromatography (dichloromethane/methanol=100/1) to give the title compound (115.3 mg, 45.3% yield) as a yellow solid.

$^1$H NMR (400 MHz, DMSO) δ 10.54 (d, J=2.0 Hz, 1H), 9.06 (d, J=5.6 Hz, 1H), 8.84 (s, 1H), 8.20 (s, 1H), 7.92-7.85 (m, 1H), 7.62 (dd, J=10.5, 8.8 Hz, 1H), 7.54 (d, J=2.4 Hz, 1H), 7.26-7.18 (m, 2H), 4.11 (t, J=5.7 Hz, 2H), 4.00 (s, 3H), 3.63-3.53 (m, 4H), 2.70 (t, J=5.7 Hz, 2H), 2.50-2.44 (m, 4H).

LC-HRMS (ESI) calcd for [M+H, $C_{25}H_{25}FN_5O_6]^+$: 510.1783, Found 510.1786.

Example 83

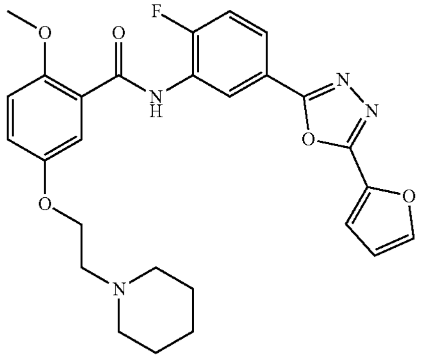

N-(2-fluoro-5-(5-(furan-2-yl)-1,3,4-oxadiazol-2-yl)phenyl)-2-methoxy-5-(2-(piperidin-1-yl)ethoxy)benzamide Compound 491

N-(2-fluoro-5-(5-(furan-2-yl)-1,3,4-oxadiazol-2-yl)phenyl)-2-methoxy-5-(2-(piperidin-1-yl)ethoxy)benzamide can be prepared as in example 1, but from 2-methoxy-5-(2-(piperidin-1-yl)ethoxy)benzoic acid (139.7 mg, 0.5 mmol) and 2-fluoro-5-(5-(furan-2-yl)-1,3,4-oxadiazol-2-yl)aniline (122.6 mg, 0.5 mmol). The crude product was purified by silica gel flash column chromatography (dichloromethane/methanol=100/1) to give the title compound (130.7 mg, 51.6% yield) as a yellow solid.

$^1$H NMR (400 MHz, $CDCl_3$) δ 10.60 (s, 1H), 9.33 (d, J=6.4 Hz, 1H), 8.00-7.90 (m, 1H), 7.88-7.79 (m, 1H), 7.72-7.62 (m, 1H), 7.33-7.26 (m, 2H), 7.18-7.08 (m, 1H), 7.06-6.98 (m, 1H), 6.68-6.59 (m, 1H), 4.66-4.42 (m, 2H), 4.06 (s, 3H), 3.36-3.24 (s, 2H), 3.23-2.70 (s, 4H), 2.04-1.77 (m, 4H), 1.74-1.46 (m, 2H).

LC-HRMS (ESI) calcd for [M+H, $C_{27}H_{28}FN_4O_5]^+$: 507.2038, Found 507.2039.

Example 84

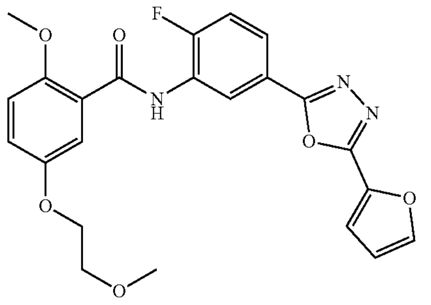 [SMILES: COCCOc1ccc(OC)c(C(=O)Nc2cc(-c3nnc(-c4ccco4)o3)ccc2F)c1]

N-(2-fluoro-5-(5-(furan-2-yl)-1,3,4-oxadiazol-2-yl) phenyl)-2-methoxy-5-(2-methoxyethoxy)benzamide Compound 492

N-(2-fluoro-5-(5-(furan-2-yl)-1,3,4-oxadiazol-2-yl)phenyl)-2-methoxy-5-(2-methoxyethoxy)benzamide can be prepared as in example 1, but from 2-methoxy-5-(2-methoxyethoxy)benzoic acid (113.1 mg, 0.5 mmol) and 2-fluoro-5-(5-(furan-2-yl)-1,3,4-oxadiazol-2-yl)aniline (122.6 mg, 0.5 mmol). The crude product was purified by silica gel flash column chromatography (dichloromethane/methanol=100/1) to give the title compound (152.3 mg, 67.2% yield) as a yellow solid.

$^1$H NMR (400 MHz, DMSO) δ 10.55 (s, 1H), 9.05 (d, J=5.8 Hz, 1H), 8.14-8.09 (m, 1H), 7.92-7.82 (m, 1H), 7.65-7.58 (m, 1H), 7.54 (d, J=2.5 Hz, 1H), 7.47 (d, J=3.5 Hz, 1H), 7.27-7.16 (m, 2H), 6.85 (dd, J=3.5, 1.7 Hz, 1H), 4.17-4.07 (m, 2H), 4.00 (s, 3H), 3.70-3.61 (m, 2H), 3.32 (s, 3H).

LC-HRMS (ESI) calcd for [M+H, $C_{23}H_{21}FN_3O_6$]$^+$: 454.1409, Found 454.1414.

Example 85

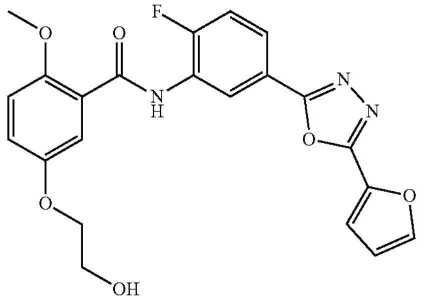 [SMILES: COc1ccc(OCCO)cc1C(=O)Nc1cc(-c2nnc(-c3ccco3)o2)ccc1F]

N-(2-fluoro-5-(5-(furan-2-yl)-1,3,4-oxadiazol-2-yl) phenyl)-5-(2-hydroxyethoxy)-2-methoxybenzamide Compound 493

N-(2-fluoro-5-(5-(furan-2-yl)-1,3,4-oxadiazol-2-yl)phenyl)-5-(2-hydroxyethoxy)-2-methoxybenzamide can be prepared as in example 1, but from 5-(2-hydroxyethoxy)-2-methoxybenzoic acid (106.1 mg, 0.5 mmol) and 2-fluoro-5-(5-(furan-2-yl)-1,3,4-oxadiazol-2-yl)aniline (122.6 mg, 0.5 mmol). The crude product was purified by silica gel flash column chromatography (dichloromethane/methanol=100/1) to give the title compound (108.5 mg, 49.4% yield) as a yellow solid.

$^1$H NMR (400 MHz, $CDCl_3$) δ 10.64 (s, 1H), 9.35 (d, J=5.5 Hz, 1H), 7.99-7.92 (m, 1H), 7.88 (d, J=3.1 Hz, 1H), 7.70-7.66 (m, 1H), 7.33-7.27 (m, 2H), 7.17-7.11 (m, 1H), 7.06-7.00 (m, 1H), 6.65-6.61 (m, 1H), 4.22-4.11 (m, 2H), 4.08 (s, 3H), 4.02-3.94 (m, 2H).

LC-HRMS (ESI) calcd for [M+H, $C_{22}H_{19}FN_3O_6$]$^+$: 440.1252, Found 440.1259.

Example 86

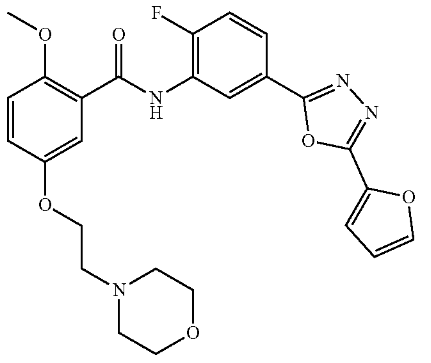

N-(2-fluoro-5-(5-(furan-2-yl)-1,3,4-oxadiazol-2-yl) phenyl)-2-methoxy-5-(2-morpholinoethoxy)benzamide Compound 494

N-(2-fluoro-5-(5-(furan-2-yl)-1,3,4-oxadiazol-2-yl)phenyl)-2-methoxy-5-(2-morpholinoethoxy)benzamide can be prepared as in example 1, but from 2-methoxy-5-(2-morpholinoethoxy)benzoic acid (140.7 mg, 0.5 mmol) and 2-fluoro-5-(5-(furan-2-yl)-1,3,4-oxadiazol-2-yl)aniline (122.6 mg, 0.5 mmol). The crude product was purified by silica gel flash column chromatography (dichloromethane/methanol=100/1) to give the title compound (145.5 mg, 57.2% yield) as a yellow solid.

$^1$H NMR (400 MHz, DMSO) δ 10.54 (s, 1H), 9.04 (d, J=5.4 Hz, 1H), 8.11 (d, J=1.1 Hz, 1H), 7.893-7.84 (m, 1H), 7.60 (dd, J=10.5, 8.7 Hz, 1H), 7.54 (d, J=2.4 Hz, 1H), 7.47 (d, J=3.5 Hz, 1H), 7.30-7.18 (m, 2H), 6.85 (dd, J=3.5, 1.7 Hz, 1H), 4.11 (t, J=5.7 Hz, 2H), 3.99 (s, 3H), 3.69-3.45 (m, 4H), 2.70 (t, J=5.7 Hz, 2H), 2.49-2.40 (m, 4H).

LC-HRMS (ESI) calcd for [M+H, $C_{26}H_{26}FN_4O_6$]$^+$: 509.1831, Found 509.1834.

Biological Methods

Expression of Human ALCAT1 in Insect Cells

The human ALCAT1 protein were expressed in *Spodoptera frugiperda* (Sf9) insect cells by using a Bac-to-Bac baculovirus expression system (Invitrogen) according to the manufacturer's instruction. High-titer recombinant baculovirus expressing the human ALCAT1 protein was generated by several rounds of viral amplification. The Sf9 cells were typically infected with recombinant baculovirus for 3 days, harvested in ice-cold phosphate-buffered saline (PBS), and homogenized in 20 mm NaCl by going through French press. The total cell lysates were centrifuged at 10,000×g for 1 hours at 4° C. to eliminate the nucleus fraction, followed by ultracentrifugation at 100,000×g to pallet the membrane fraction. The membrane fraction was resuspended in enzymatic buffer that contain 10% glycerol, quantified for protein concentration, aliquoted, and stored at −80° C.

In Vitro Acyltransferase Assays

ALCAT1 enzymatic activity was determined by measuring the conversion of monolysocardiolipin (MLCL) to cardiolipin or lysophosphatidylglycerol (LPG) to phosphatidylglycerol (PG) in an enzymatic reaction mixture that contained 50 mm Tris/HCl, pH 7.0, 100 μm lysophospholipids, 25 μm [$^{14}$C]acyl-CoA (50 mCi/mmol, American Radiolabeled Chemicals, Inc), and membrane fraction (0.5-2.5 μg) in a total volume of 200 μl. The reaction was incubated at room temperature for 30 min. The lipids were extracted will chloroform, dried, and separated by thin layer chromatography (TLC) with chloroform:hexane:methanol:acetic acid (50:30:10:5, v/v) or chloroform:methanol:water (65:25:4, v/v). After separation, TLC plates were exposed to a Phosphorlmager screen to visualize the radiolabeled products with a Molecular Dynamics Typhoon Scanner (Sunnyvale, CA). In some experiments, NBD-CoA was used at 100 μM to replace the [$^{14}$C]acyl-CoA in the enzymatic reaction. All quantitative data were expressed as mean±S.E. Statistical analyses for differences between two groups were carried out using a Student's t test.

Cell-Based Assay for ALCAT1 Inhibitor Compounds

The assay was performed on the H9C2 vector cell line and H9C2 with stable overexpression of ALCAT1. Materials used in the protocol were CoA, LPG, compounds, chloroform, methanol, 0.9% KCl, 6-well-plates, 1.5 mL tubes, DMEM, FBS, P/S and PBS.

Cells were seeded in 6-well-plates, 8×10$^5$ cells/well, and cultured at 37° C. in 5% $CO_2$ overnight. Cells were then pretreated with selected compounds (3 μM) for 1 hr and incubated with CoA (5 μM) and LPG (100 μM) with or w/o selected compound (3 μM) for a further 3 hrs.

Cells were washed once with ice-cold PBS, collected in ice-cold PBS and centrifuged at 5000 rpm for 5 min at 4° C. 200 μL of chloroform:methanol (2:1) was added to the cell pellet, which was vortexed to suspend the cells and incubated at RT for 1 hr.

40 μL of 0.9% KCl was added and the sample was vortexed before centrifugation at 10000 rpm for 5 min at RT. The aqueous phase (upper layer) was discarded and the organic phase (lower layer) was loaded to a TLC plate (10 cm×20 cm), 40 μL/sample.

The plates were developed in chloroform:methanol:water (65:25:4) for about 30 min and scanned using a Typhoon Scanner. The bands intensity was analysed using ImageJ and the inhibition activity of the tested compounds was calculated.

Assay for ALCAT1 Inhibitors

Compound inhibitors for ALCAT1 enzyme were analyzed by an in vitro enzymatic assay as detailed above. Compound inhibitors were added to the enzymatic mixture at 1-20 μM concentrations before the start of the acyltransferase reaction.

Results for compounds of the invention are shown in the Table below, with % inhibition provided for tests with 10 μM and 1 μM concentrations of compounds. Where multiple measurements were taken this is indicated by a "/" between multiple values.

| Compound | % inh @ 10 μM | % inh @ 1 μM | Compound | % inh @ 10 μM | % inh @ 1 μM |
|---|---|---|---|---|---|
| 1 | 48/49/79 | 59/63 | 3 | 48/89 | — |
| 5 | 39 | — | 7 | 3 | — |
| 9 | 87 | 47 | 10 | 2 | — |
| 11 | 9 | — | 15 | 69/20 | 20 |
| 16 | — | 58/85 | | | |
| 18 | 2 | — | 19 | 2 | — |
| 20 | 77/26 | 13 | 21 | 85 | — |
| 23 | 89 | — | 24 | 2 | — |
| 25 | 56 | — | 27 | 98 | — |
| 28 | 51 | — | 36 | 1 | — |
| 37 | 76/76/87 | — | 42 | 70 | 23 |
| 46 | 43/68/75 | 10/21 | 48 | 2/2/28 | — |
| 51 | — | 43/57 | 52 | — | 59 |
| 53 | 90 | 47 | 55 | 100 | 81 |
| 56 | 2 | — | 57 | 75/89/94 | — |
| 58 | 45 | — | 62 | 11 | 2 |
| 64 | 55 | 15 | 71 | 93 | 51 |
| 73 | 66 | 15 | 74 | 21 | 4 |
| 75 | 36 | 16 | 77 | 21 | 37 |
| 78 | — | 42/59 | 79 | — | 89 |
| 80 | — | 22 | 81 | — | 20/36 |
| 82 | 3 | 23 | 83 | 43 | 36 |
| 84 | — | 5 | 85 | 3 | 10 |
| 87 | 62 | 29 | | | |
| 98 | 2 | 11 | 100 | 7 | 3 |
| 113 | 94 | 96 | 114 | 48 | 36 |
| 115 | 53 | 51 | 118 | 100 | 95 |
| 477 | 68 | 63 | 119 | 95 | 92 |
| 120 | 100 | 94 | 122 | 100 | 100 |
| 478 | 62 | 57 | 123 | 100 | 90 |
| 124 | 100 | 92 | 125 | 97 | 92 |
| 126 | 100 | 83 | 127 | 100 | 85 |
| 128 | 100 | 100 | 130 | — | 50/57 |
| 132 | — | 26/39 | 133 | — | 19/17 |
| 135 | — | 56/62 | 136 | — | 28/23 |
| 137 | — | 37/48 | 139 | — | 50/48 |
| 140 | — | 29 | 141 | 67 | 65 |
| 143 | 17 | 13 | 144 | 92 | 73 |
| 145 | 38 | 9 | 150 | 92 | 72 |
| 168 | 100 | 100 | 169 | 93 | 74 |
| 170 | 27 | 20 | 171 | 100 | 79 |
| 172 | 26 | 6 | 174 | 100 | 96 |
| 175 | 100 | 90 | 176 | 100 | 73 |
| 177 | 1 | 3 | 178 | — | 27 |
| 179 | 41 | 17 | 181 | 68 | 34 |
| 182 | — | 33 | 183 | — | 100/100 |
| 184 | — | 100/100 | 186 | 100 | 92 |
| 188 | 100 | 93 | 189 | 100 | 92 |
| 190 | 100 | 80 | 191 | 100 | 82 |
| 192 | — | 89/93 | 193 | 90 | 92 |
| 195 | 88 | 70 | 196 | 97 | 68 |
| 197 | 97 | 80 | 200 | 100 | 98 |
| 207 | — | 86/87 | 208 | — | 97/98 |
| 209 | 100 | 100 | 210 | 97 | 97 |
| 211 | — | 95/97 | 212 | — | 26 |
| 213 | — | 56/64 | 214 | — | 67/76 |
| 215 | — | 100/100 | 216 | — | 100/100 |
| 217 | — | 69/68 | 218 | — | 99/98 |
| 219 | — | 99/98 | 220 | — | 96/94 |
| 221 | — | 100/100 | 222 | — | 100/97 |
| 223 | — | 94/90 | 224 | — | 91/97 |
| 225 | — | 92/97 | 226 | — | 100/99 |
| 227 | — | 85/89 | 228 | — | 100/99 |
| 229 | — | 97/97 | 230 | — | 94/89 |
| 232 | — | 61/61 | 233 | — | 68/65 |
| 234 | — | 46/42 | 235 | — | 12 |
| 236 | — | 7/8 | 237 | — | 35/46 |
| 238 | — | 23/23 | 240 | — | 12/6 |
| 248 | — | 30/50 | 271 | — | 83/84 |
| 273 | — | 97/96 | 274 | — | 77/82 |
| 275 | — | 98/99 | 277 | — | 23/23 |
| 278 | — | 97/100 | 280 | — | 94/100 |
| 287 | — | 5/33 | 288 | — | 48/59 |
| 289 | — | 6/38 | 290 | — | 24/31 |
| 292 | — | 14/12 | 293 | — | 13 |
| 295 | — | 37 | 296 | — | 55/73 |
| 297 | — | 75/83 | 304 | — | 98/96 |
| 305 | — | 100 | 306 | — | 100 |

-continued

| Compound | % inh @ 10 μM | % inh @ 1 μM | Compound | % inh @ 10 μM | % inh @ 1 μM |
|---|---|---|---|---|---|
| 312 | — | 98 | 321 | — | 94/92 |
| 331 | — | 12 | 332 | — | 30 |
| 333 | — | 18 | 334 | — | 35 |
| 336 | — | 66 | 337 | — | 66 |
| 338 | — | 65 | 340 | — | 72 |
| 341 | — | 73 | 342 | — | 41 |
| 343 | — | 35/100 | 344 | — | 33 |
| 345 | — | 24 | 346 | — | 86 |
| 347 | — | 94 | 279 | — | 97 |
| 300 | — | 96 | 313 | — | 94 |
| 314 | — | 95 | 315 | — | 93 |
| 316 | — | 94 | 319 | — | 96 |
| 323 | — | 96 | 317 | — | 96 |
| 320 | — | 96 | 318 | — | 98 |
| 302 | — | 97 | 281 | — | 100/97 |
| 405 | — | 98 | 416 | — | 98 |
| 322 | — | 94 | 39 | — | 92 |
| 373 | — | 98 | 396 | — | 96 |
| 400 | — | 96 | 480 | — | 96 |
| 44 | — | 26 | 325 | — | 63 |
| 35 | 5 | 16 | 298 | — | 15 |
| 22 | 8 | 20 | 497 | — | 90 |

Cell-Based Assay for ALCAT1 Inhibitors

Compound inhibitors for ALCAT1 enzyme were analyzed by an in vitro cell-based assay as detailed above. Results are provided in the Table below:

| Compound | % inh @ 3 μM | Compound | % inh @ 3 μM |
|---|---|---|---|
| 279 | 7 | 125 | 18/0 |
| 118 | 9 | 200 | 26/31 |
| 219 | 22 | 226 | 37/83/47 |
| 168 | 27 | 184 | 57 |
| 216 | 45 | 183 | 62 |
| 300 | 31 | 313 | 19 |
| 314 | 36 | 221 | 38 |
| 222 | 85 | 210 | 24 |
| 209 | 37 | 208 | 36 |
| 319 | 12 | 323 | 14 |
| 317 | 52 | 320 | 17 |
| 318 | 36 | 302 | 20 |
| 281 | 65 | 304 | 31 |
| 305 | 34 | 306 | 30 |
| 312 | 4 | 321 | 75 |
| 405 | 52 | 416 | 45 |
| 322 | 26 | 373 | 3 |
| 396 | 45 | 400 | 50 |
| 497 | 75 | | |

Some of the ALCAT1 inhibitors with high activity were also subject to $IC_{50}$ analysis. $IC_{50}$ is the drug concentration causing 50% inhibition of ALCAT1 enzyme activity. For the $IC_{50}$ analysis, chemical inhibitors of ALCAT1 enzyme were added at various concentrations, ranging from 100, 33, 10, 3.3, 0.1, 0.003, 0.001 μM, respectively. $IC_{50}$ values for each compound were analyzed in triplicates, and calculated by GraphPad software.

% inhibition and $IC_{50}$ values were determined for several compounds, as well as several reference compounds, using the assay described above. The results are summarised below.

The following compounds provided $IC_{50}$ values of ≤100 nM (≤0.1 μM):

192, 193, 120, 124, 279, 197, 123, 119, 125, 122, 118, 200, 218, 219, 211, 228, 225, 226, 184, 216, 128, 39, 183, 300, 215, 313, 314, 315, 221, 222, 210, 209, 208, 322, 316, 319, 323, 317, 320, 318, 302, 373, 281, 301, 304, 305, 306, 312, 321, 405, 396, 168, 27, 400, 416, 497.

The following compounds provided $IC_{50}$ values of <35 nM (<0.035 μM):

118,200,219, 184, 216, 128, 183, 300, 215, 314, 315, 221, 222, 209, 316, 323, 317, 320, 318, 281, 304, 305, 306, 312, 405 and 416.

The following compound provided an $IC_{50}$ value of <10 nM (<0.01 μM):

222.

The following Table shows the $IC_{50}$ results for some compounds of the invention:

| Compound | $IC_{50}$ (nM) | Compound | $IC_{50}$ (nM) | Compound | $IC_{50}$ (nM) |
|---|---|---|---|---|---|
| 1 | 210 | 3 | 890 | 5 | 4100 |
| 23 | 1800 | 27 | 47 | 37 | 3900 |
| 39 | 93 | 40 | 1700 | 44 | 990 |
| 46 | 3800 | | | 52 | 750 |
| 55 | 130 | 57 | 2800 | 58 | 2400 |
| 59 | 2000 | 79 | 110 | 113 | 110 |
| 118 | 31 | 119 | 90 | 120 | 38 |
| 122 | 39 | 123 | 87 | 124 | 62 |
| 125 | 67 | 126 | 110 | 127 | 210 |
| 128 | 29 | 144 | 130 | 150 | 410 |
| 168 | 48 | 169 | 470 | 171 | 350 |
| 174 | 110 | 175 | 150 | 176 | 220 |
| 183 | 24 | 184 | 18 | 186 | 390 |
| 188 | 640 | 189 | 320 | 190 | 290 |
| 191 | 330 | 192 | 92 | 193 | 67 |
| 195 | 360 | 196 | 340 | 197 | 79 |
| 200 | 33 | 203 | 1900 | 207 | 190 |
| 208 | 76 | 209 | 25 | 210 | 66 |
| 211 | 96 | 215 | 26 | 216 | 19 |
| 218 | 67 | 219 | 34 | 220 | 120 |
| 221 | 31 | 222 | 8 | 223 | 150 |
| 224 | 190 | 225 | 100 | 226 | 60 |
| 227 | 160 | 228 | 72 | 229 | 170 |
| 230 | 410 | 271 | 780 | 273 | 120 |
| 274 | 630 | 275 | 200 | 278 | 120 |
| 279 | 60 | 280 | 120 | 281 | 24 |
| 286 | 120 | 297 | 290 | 300 | 30 |
| 301 | 100 | 302 | 36 | 304 | 20 |
| 305 | 21 | 306 | 19 | 312 | 33 |
| 313 | 64 | 314 | 29 | 315 | 28 |
| 316 | 21 | 317 | 19 | 318 | 24 |
| 319 | 46 | 320 | 34 | 321 | 38 |
| 322 | 61 | 323 | 26 | 337 | 760 |
| 341 | 500 | 346 | 180 | 354 | 610 |
| 364 | 120 | 373 | 38 | 393 | 140 |
| 396 | 78 | 400 | 62 | 405 | 19 |
| 416 | 19 | 497 | 72 | | |

The disclosure of all references cited herein, inasmuch as it may be used by those skilled in the art to carry out the invention, is hereby specifically incorporated herein by cross-reference.

The invention claimed is:

1. A compound selected from the group consisting of:

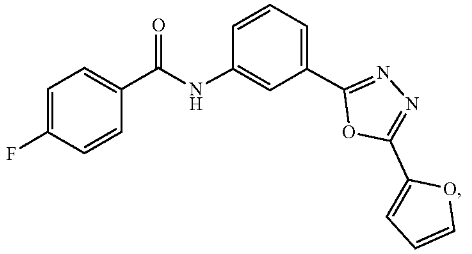

-continued
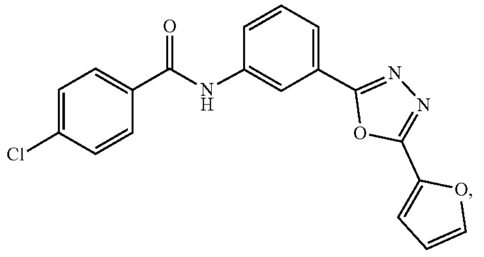
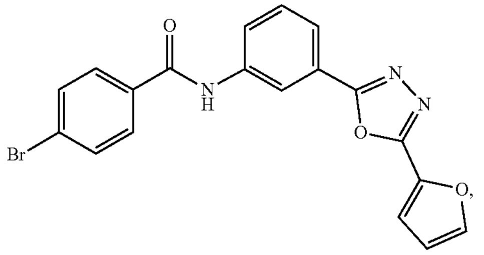
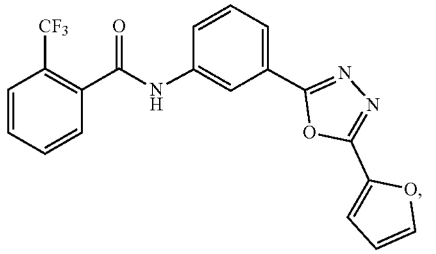
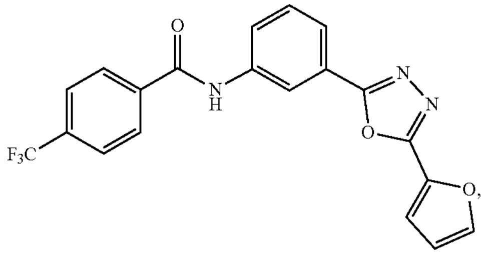
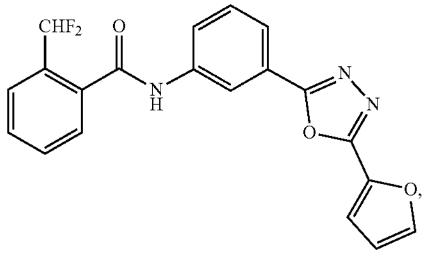
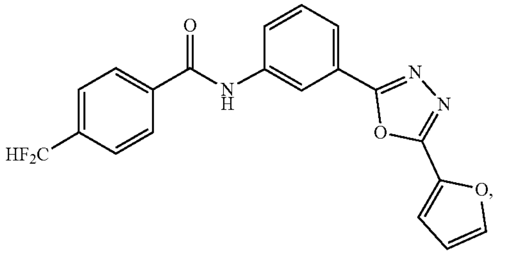
-continued
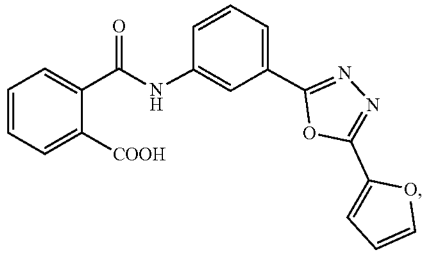
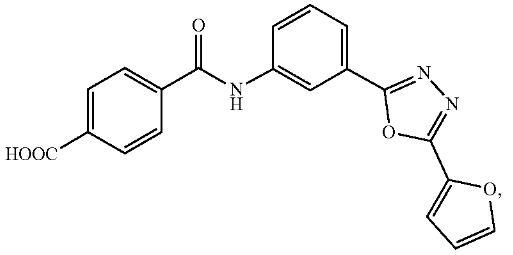
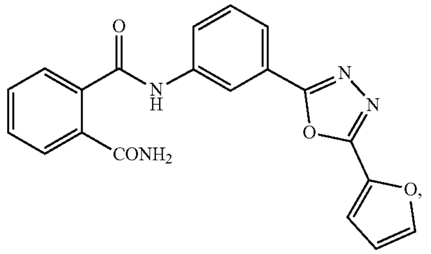
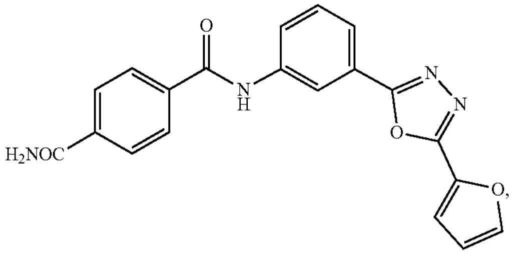
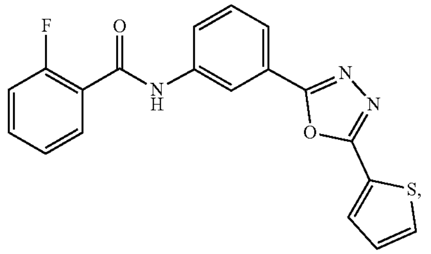
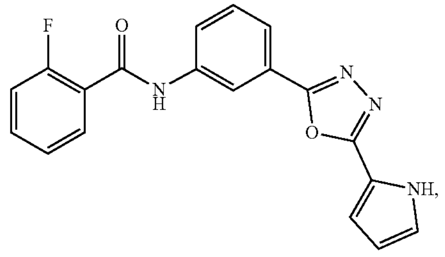

-continued
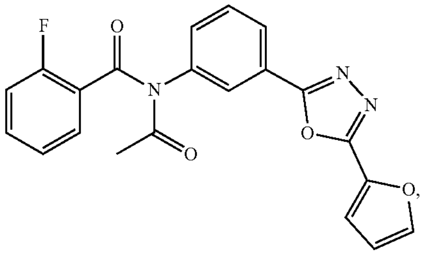
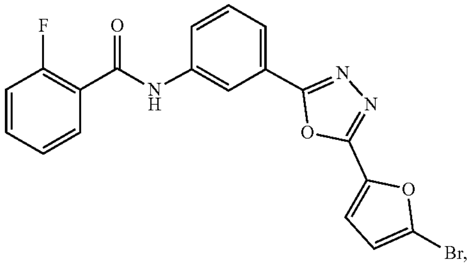
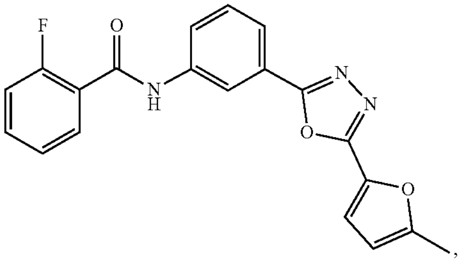
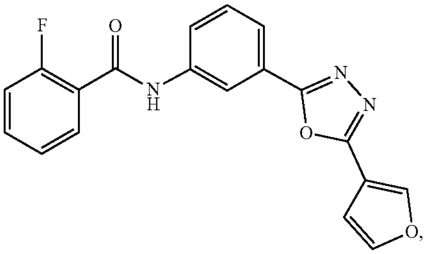
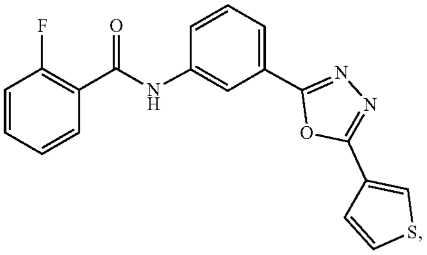
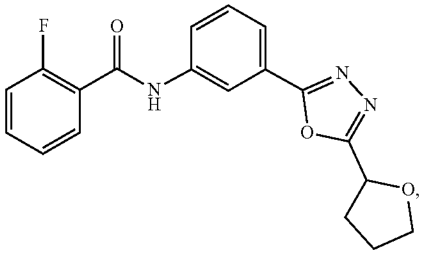
-continued
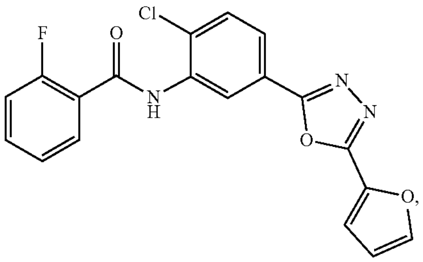
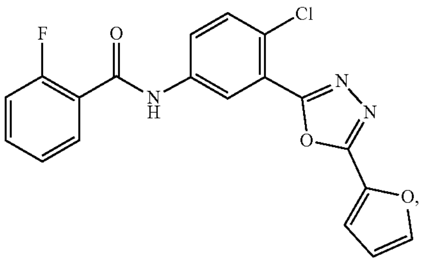
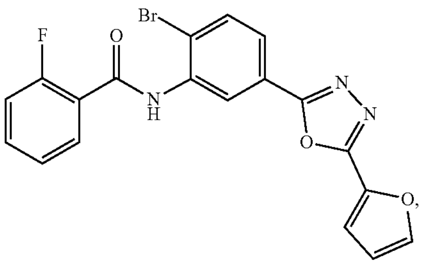
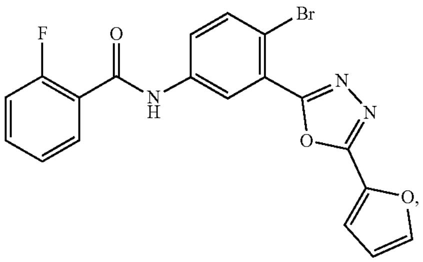
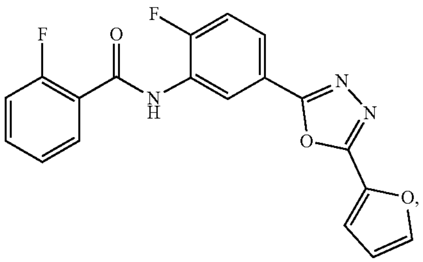
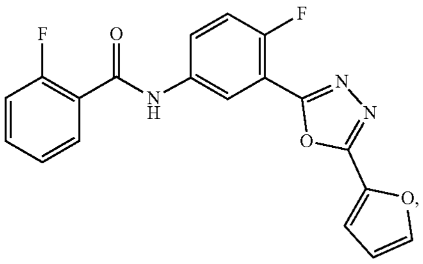

-continued
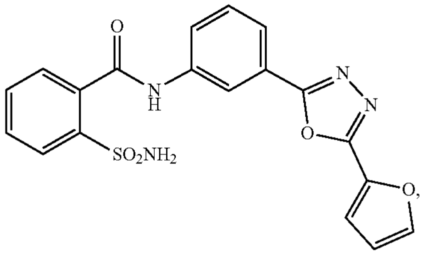
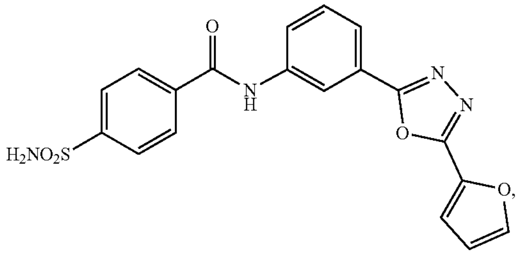
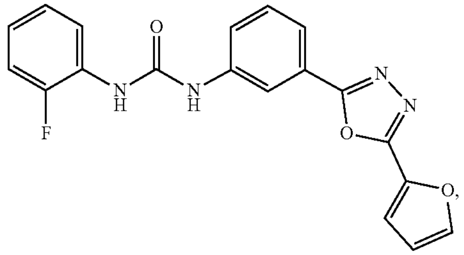
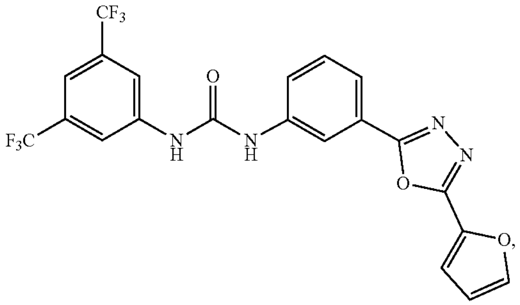
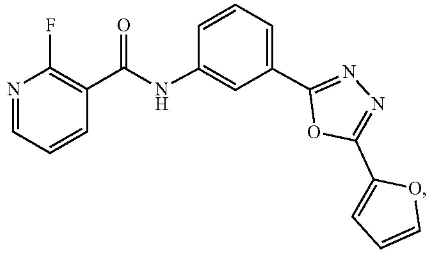
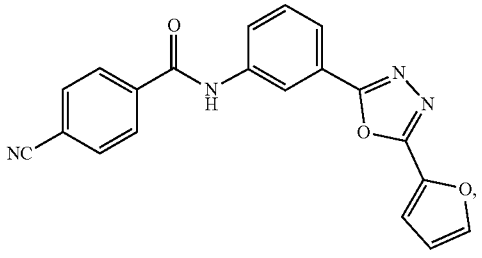
-continued
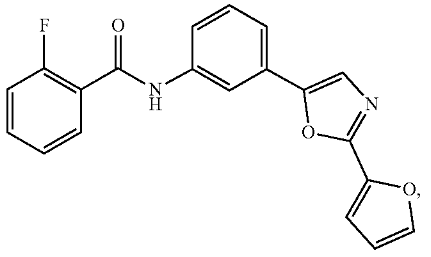
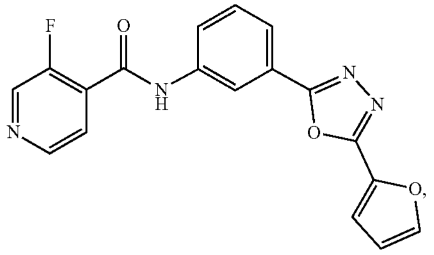
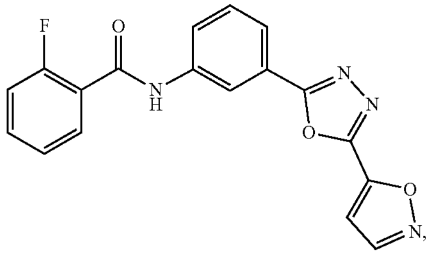
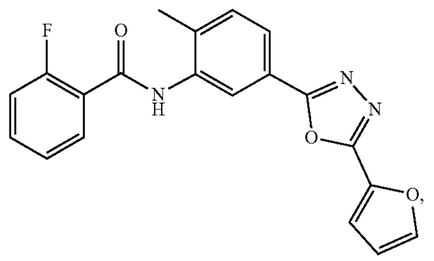
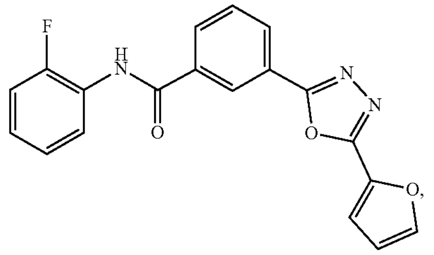
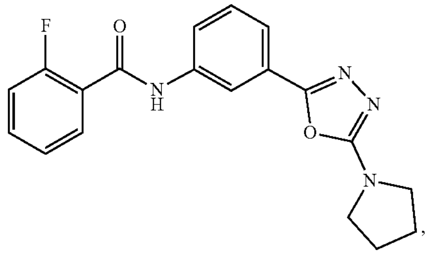

-continued
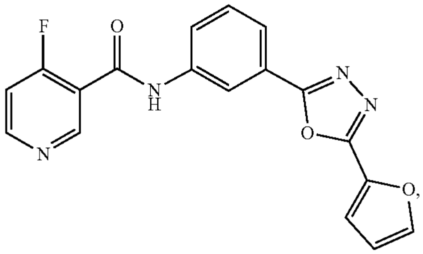
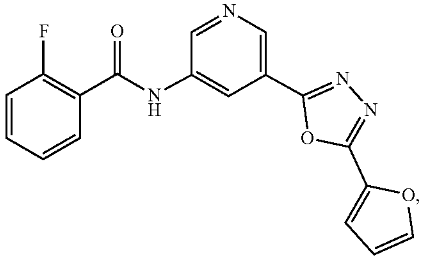
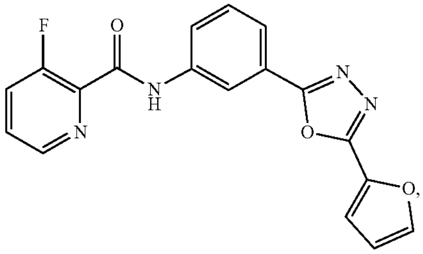
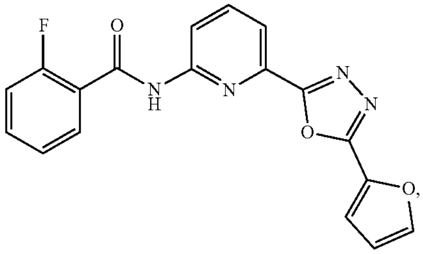
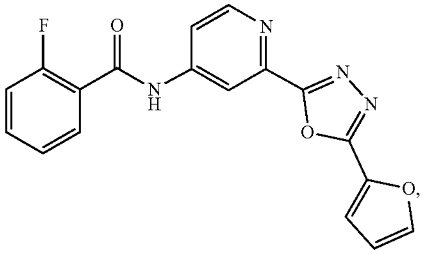
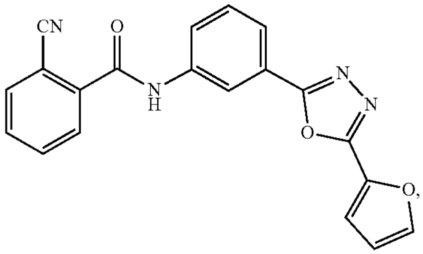
-continued
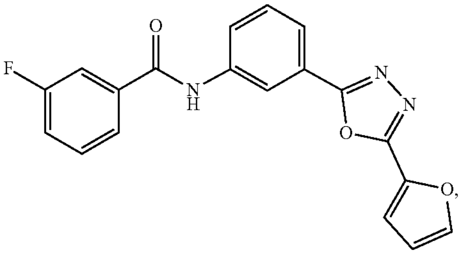
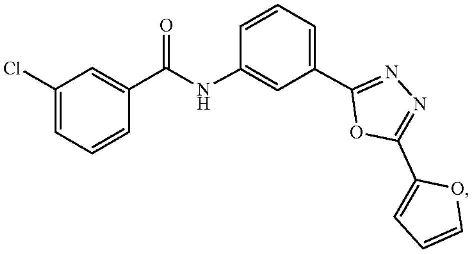
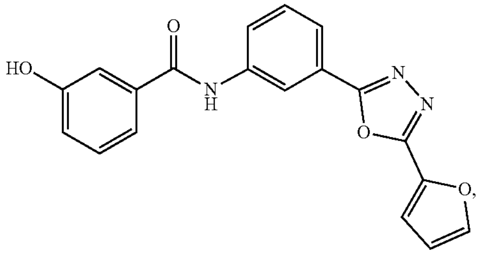
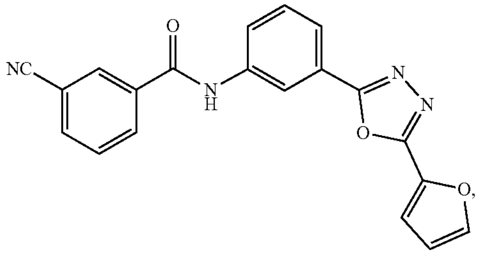
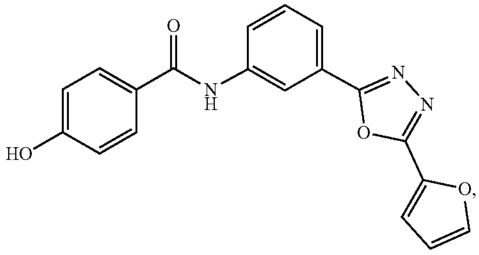
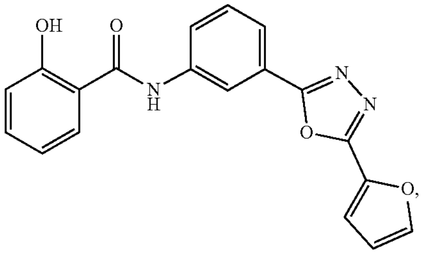

-continued
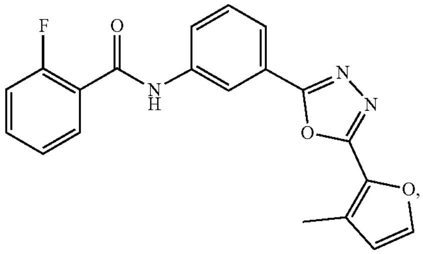
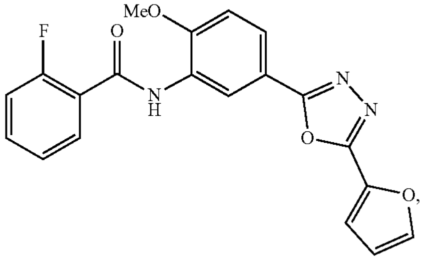
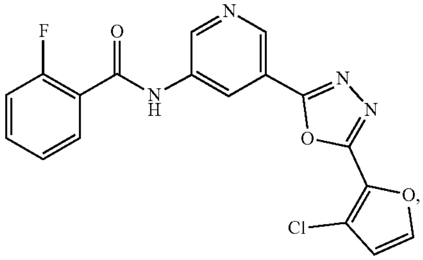
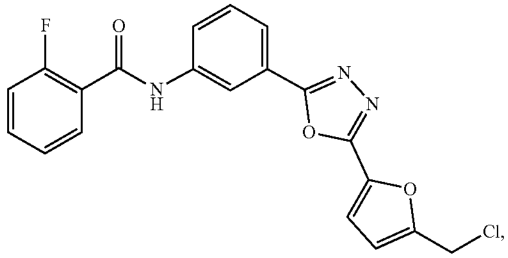
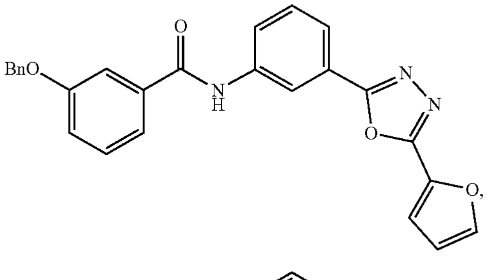
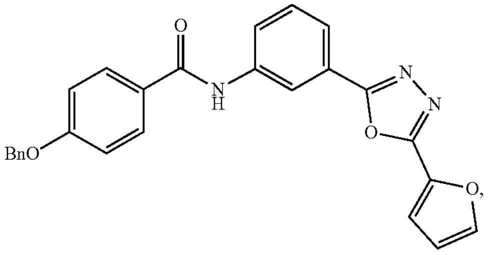
-continued
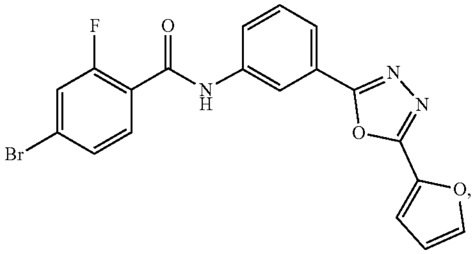
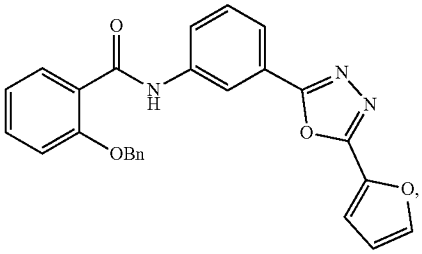
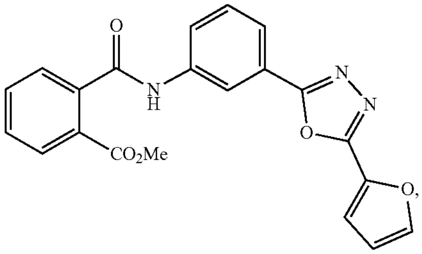
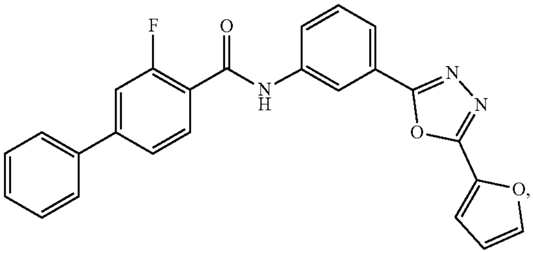
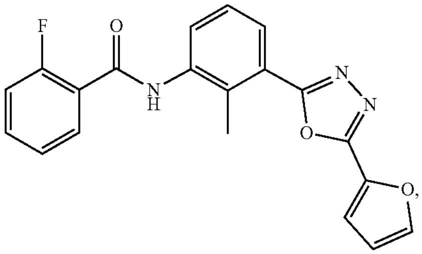
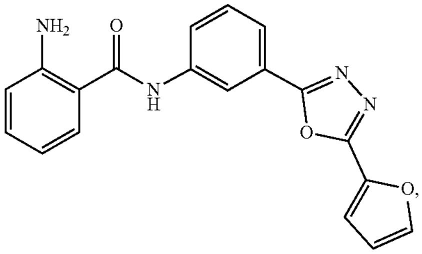

-continued
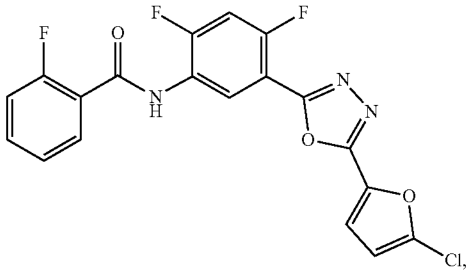
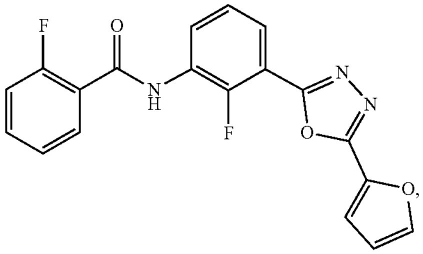
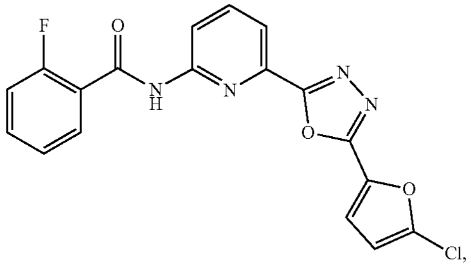
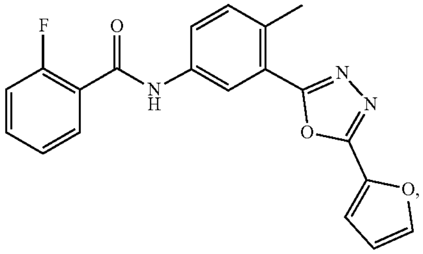
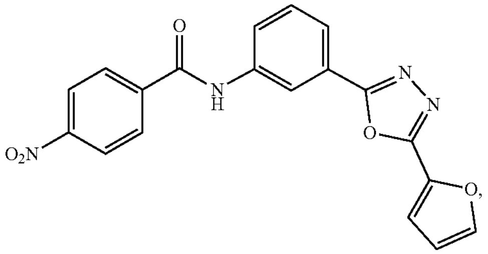
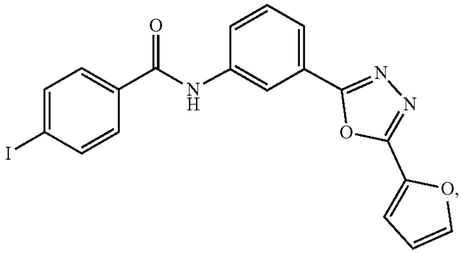
-continued
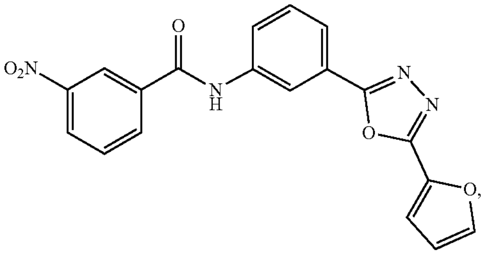
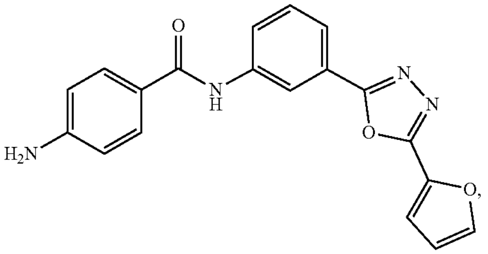
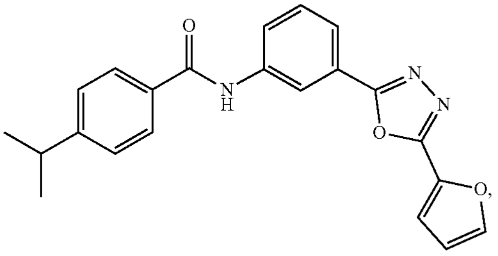
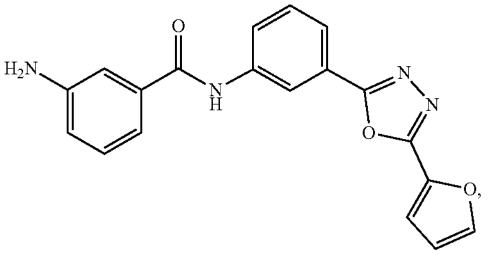
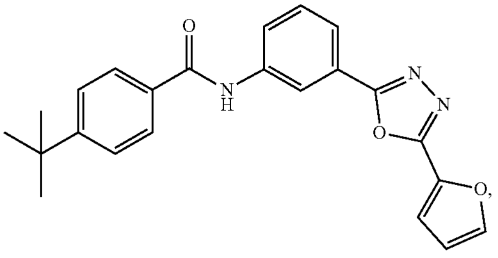
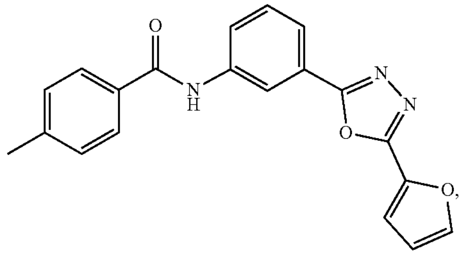

-continued
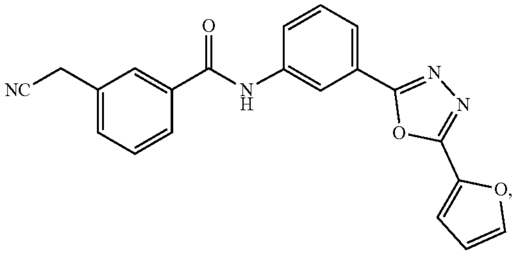
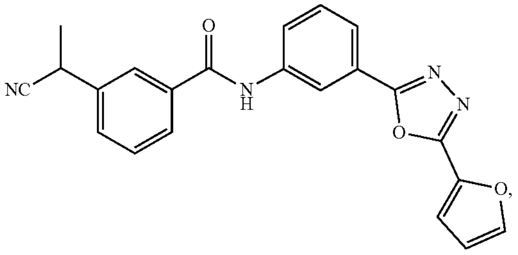
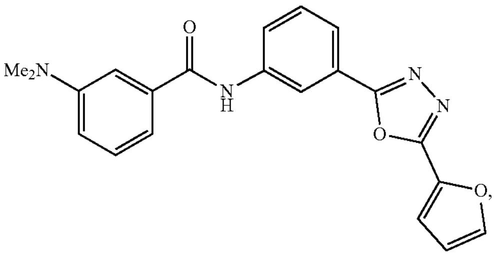
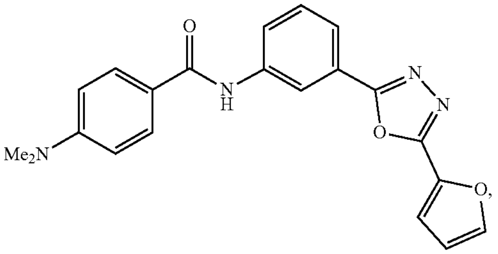
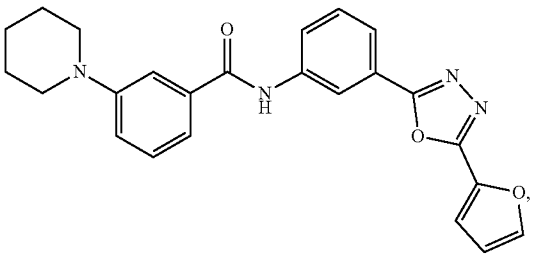
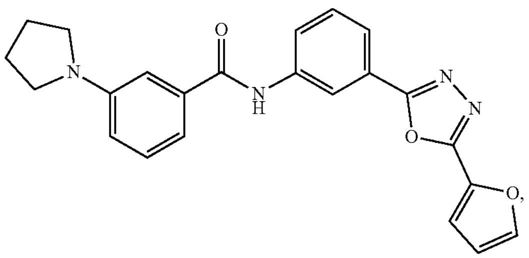
-continued
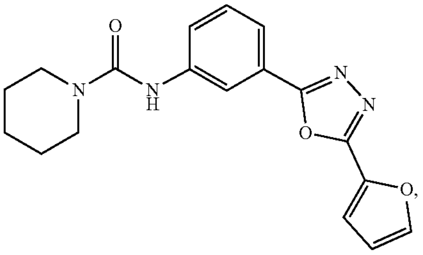
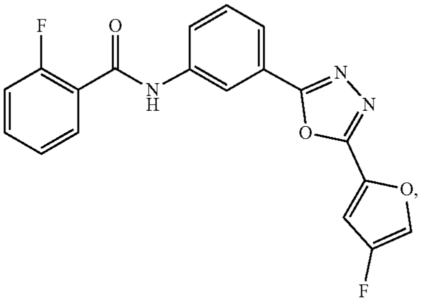
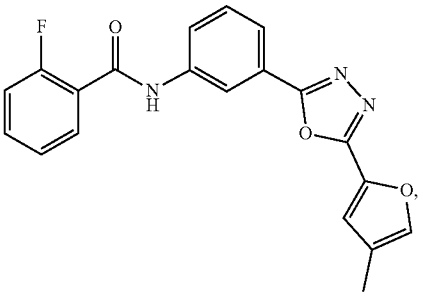
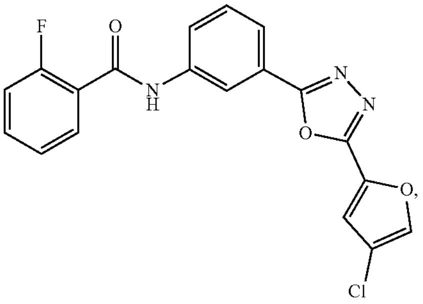
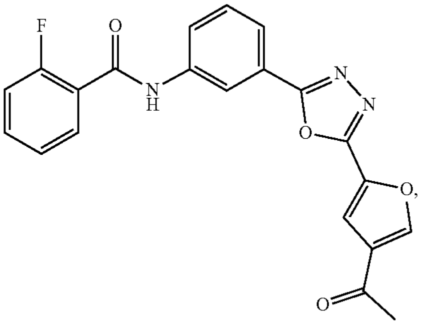

-continued
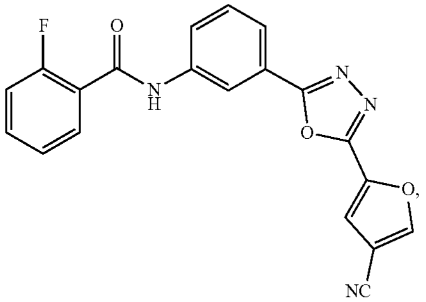
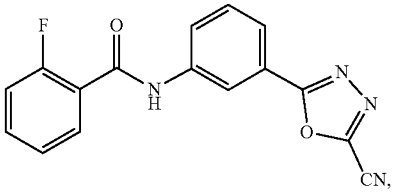
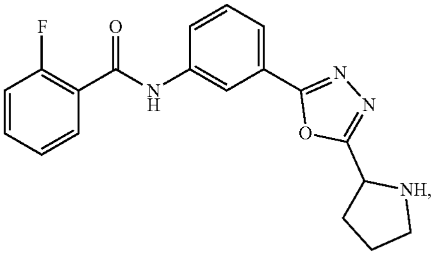
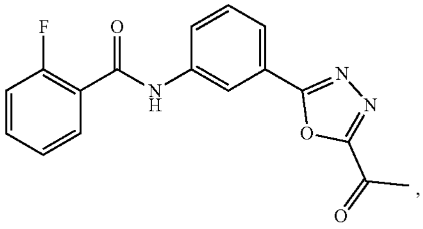
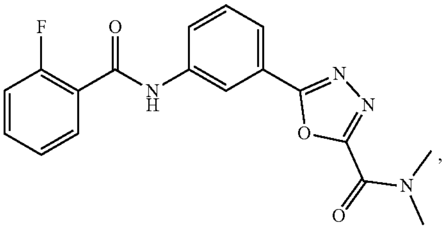
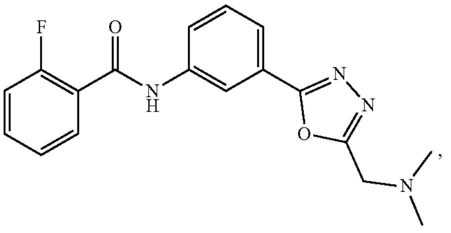
-continued
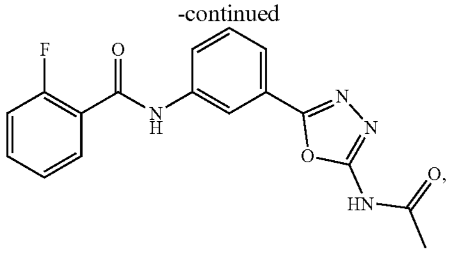
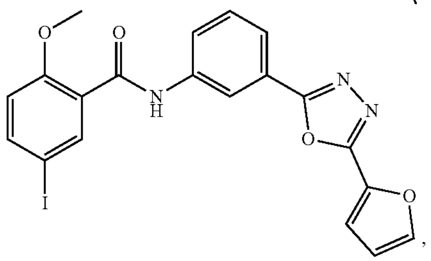
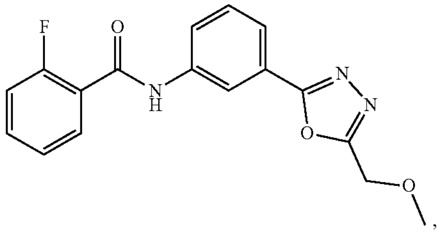
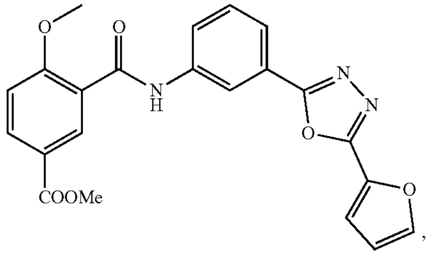
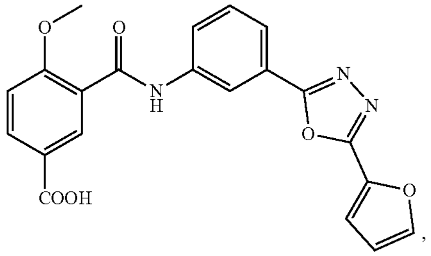
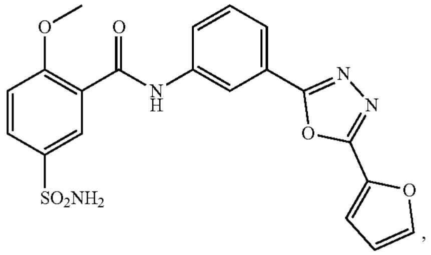
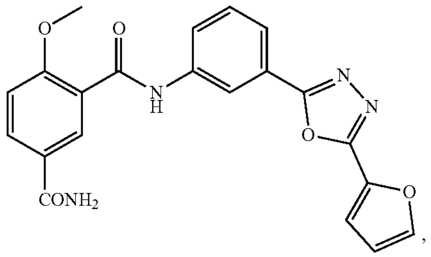

-continued
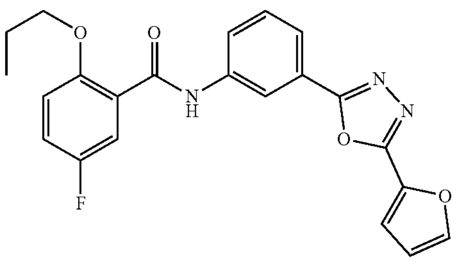
,
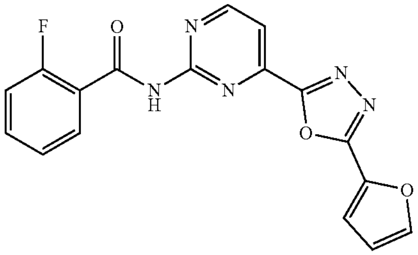
,
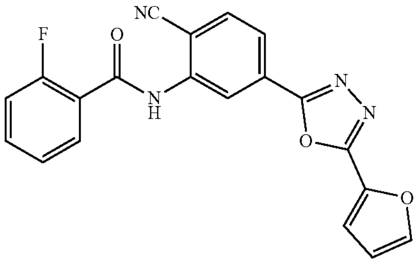
,
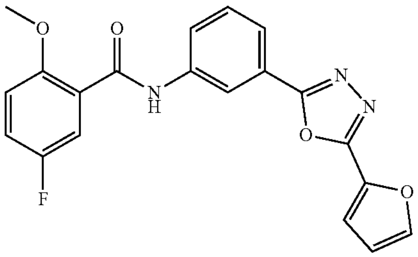
,
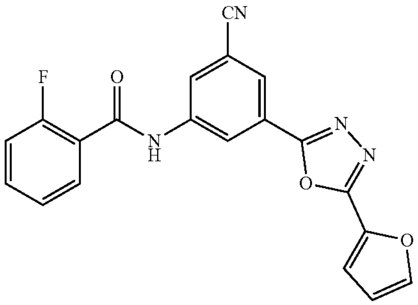
,
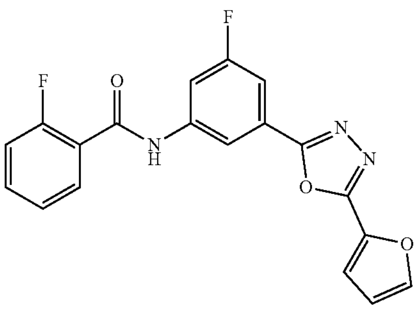
,
-continued
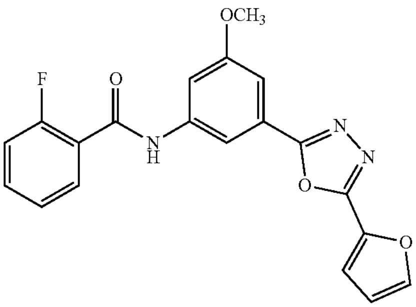
,
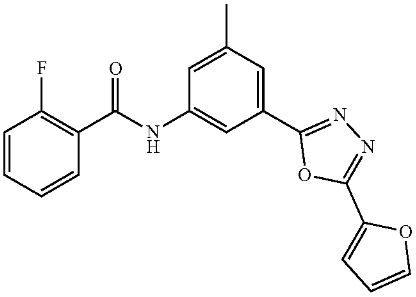
,
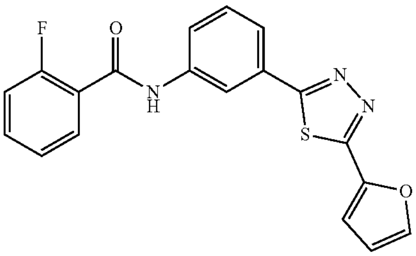
,
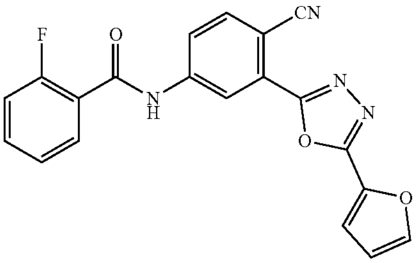
,
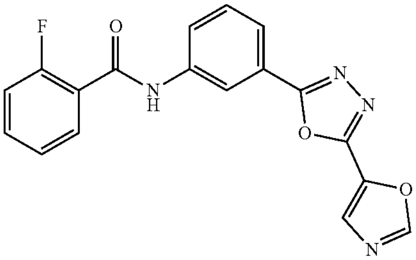
,
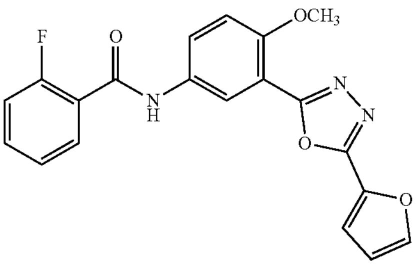
, -continued
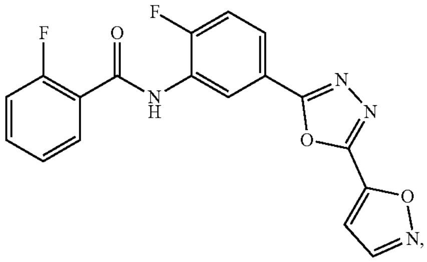,
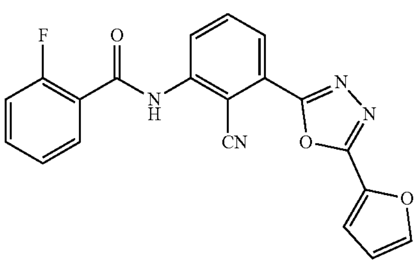,
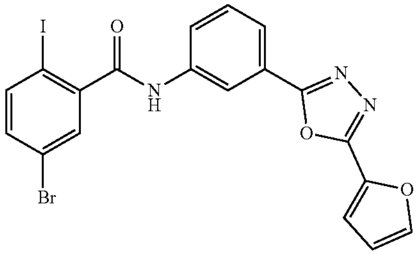,
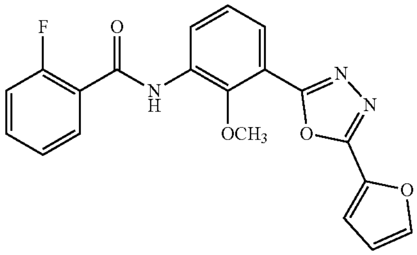,
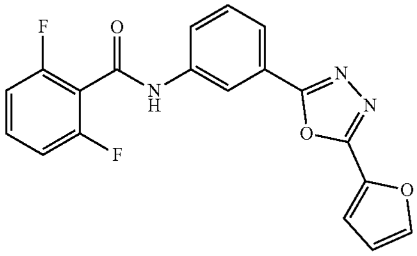,
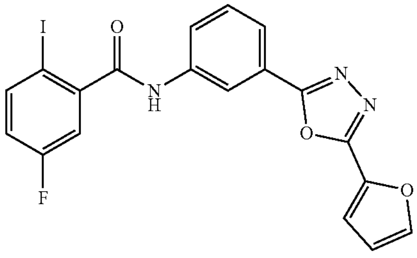,
-continued
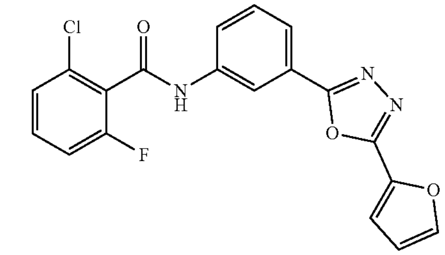,
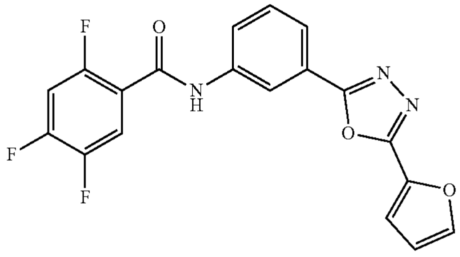,
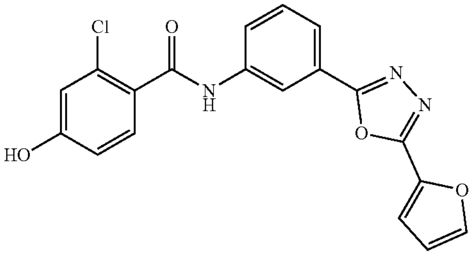,
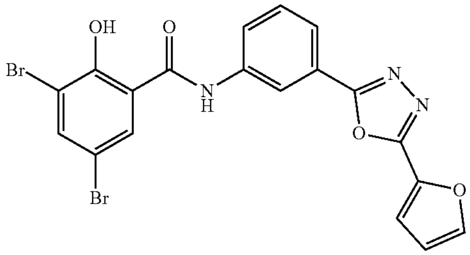,
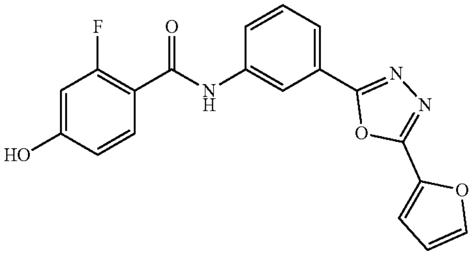,
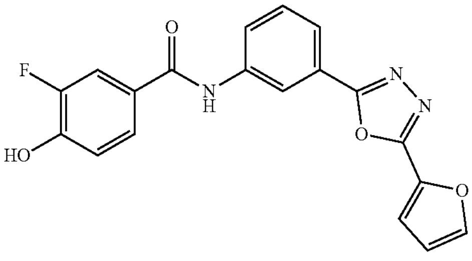, -continued
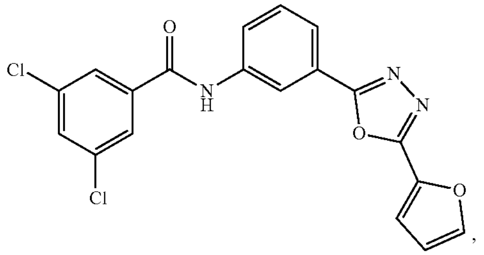
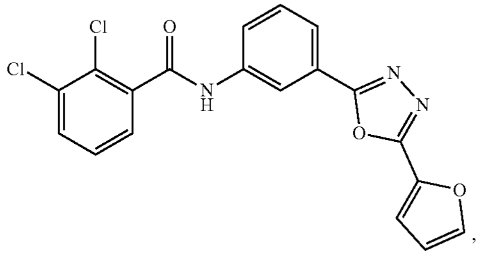
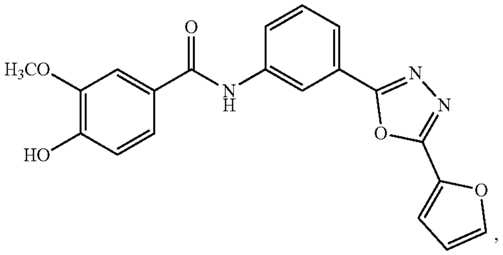
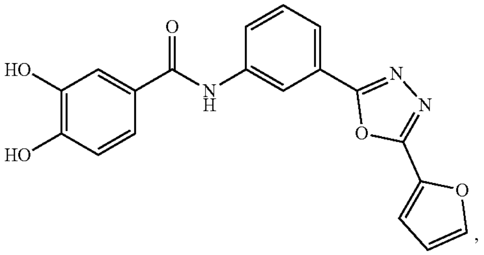
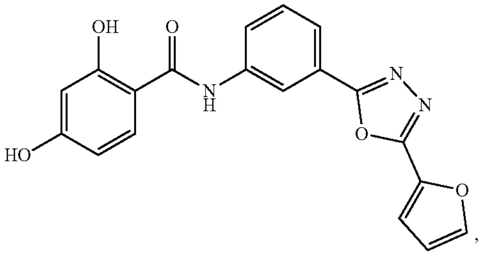
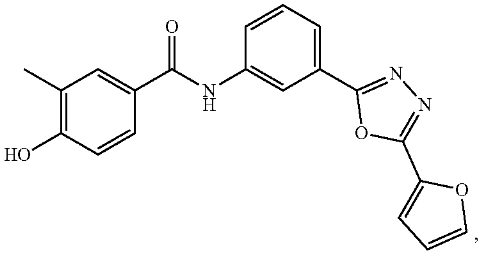
-continued
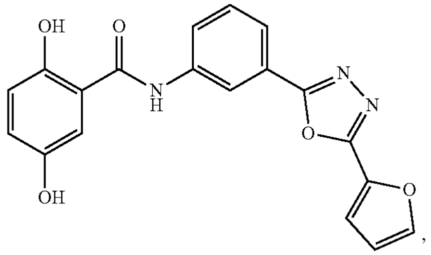
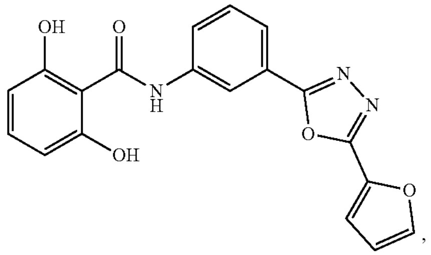
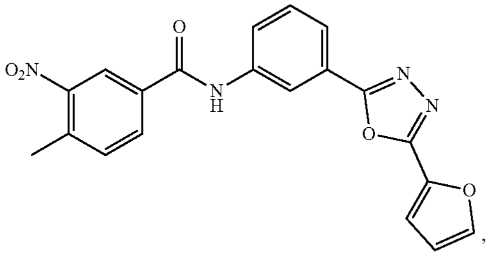
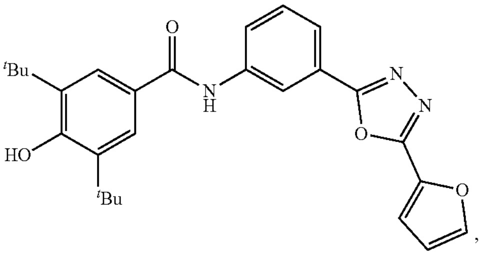
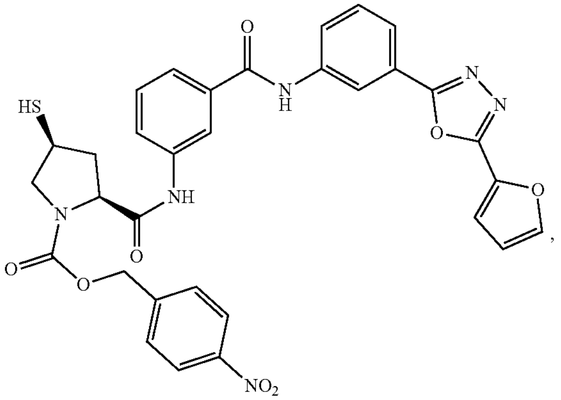
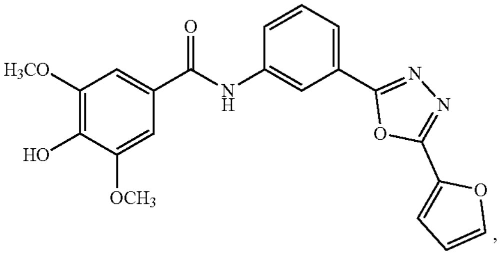

-continued
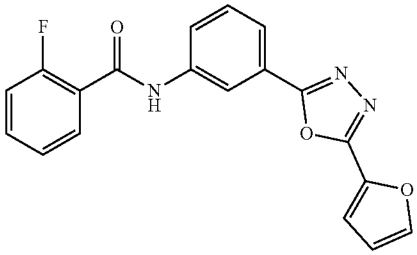
,
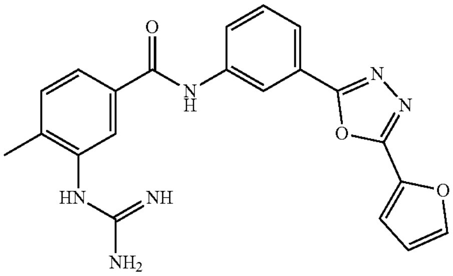
,
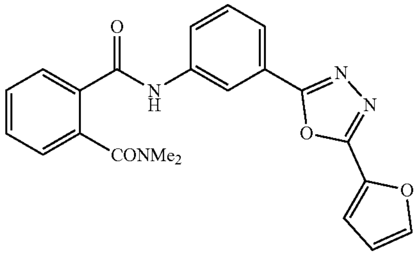
,
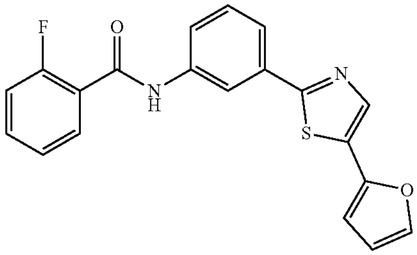
,
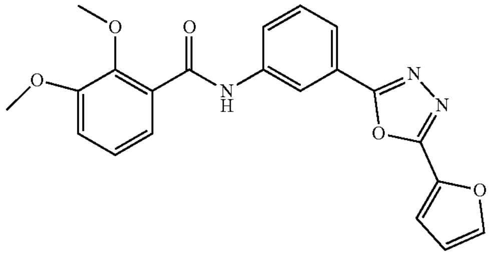
,
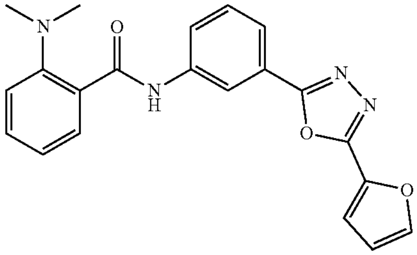
,
-continued
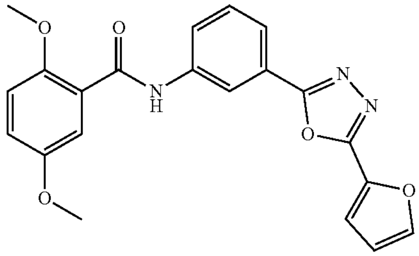
,
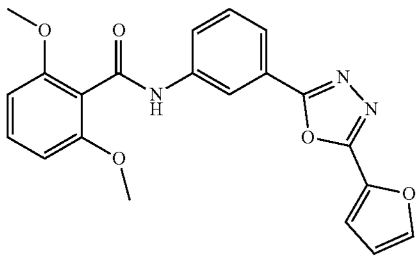
,
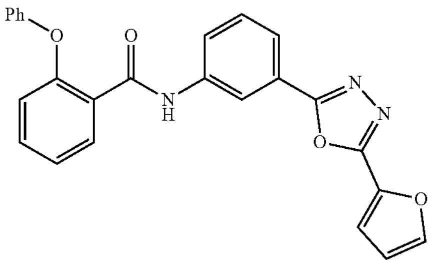
,
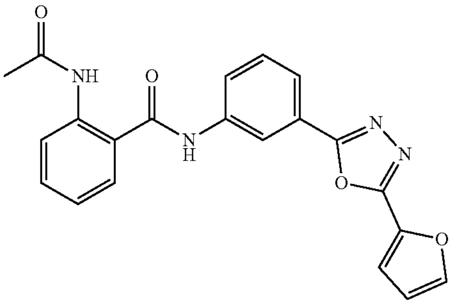
,
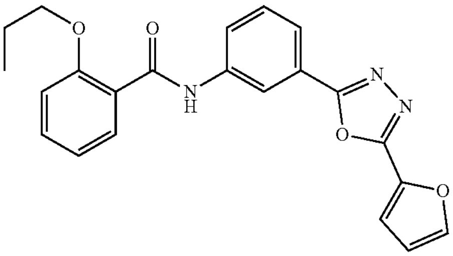
,
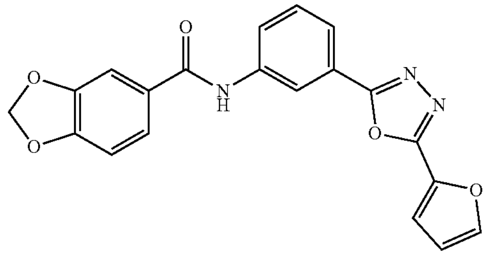
, -continued
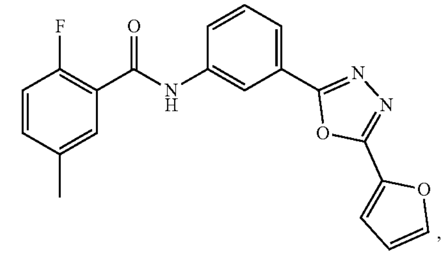,
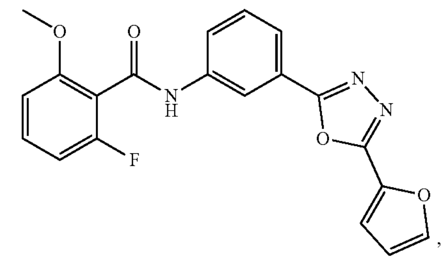,
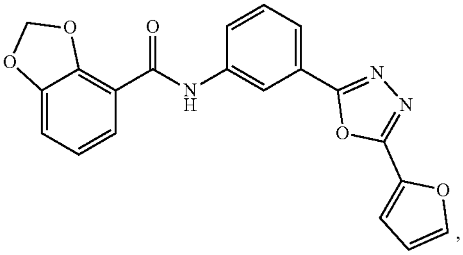,
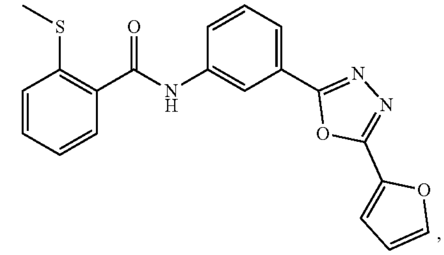,
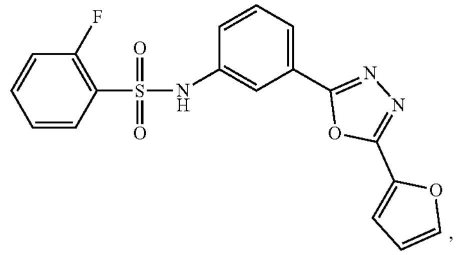,
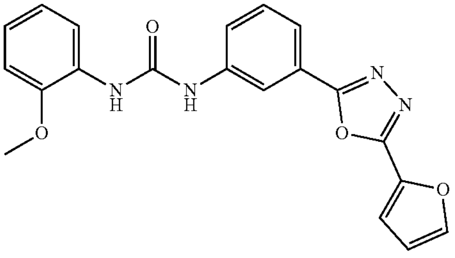,
-continued
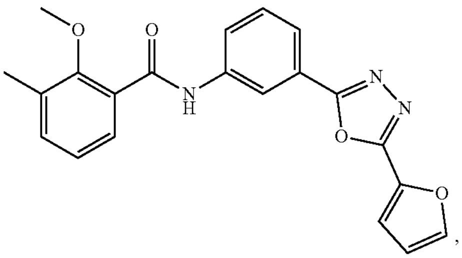,
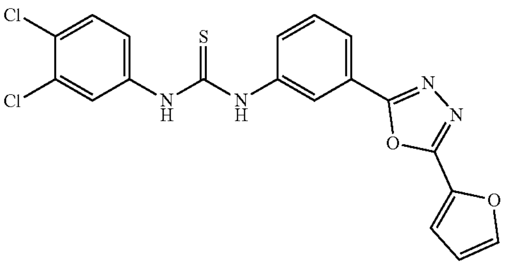,
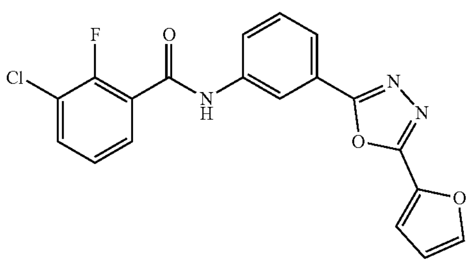,
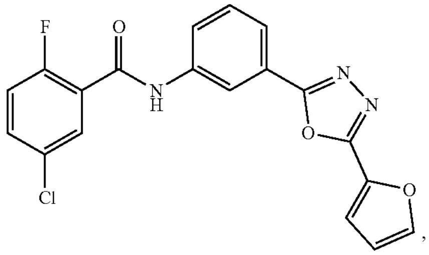,
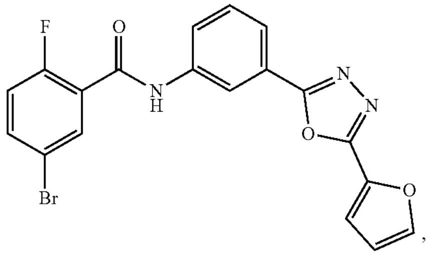,
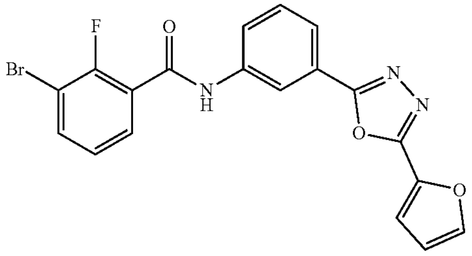, -continued
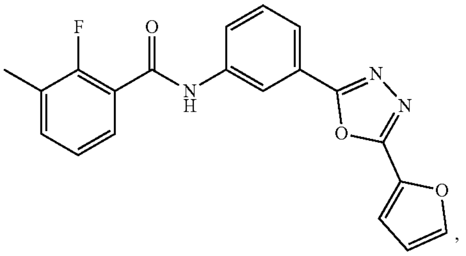
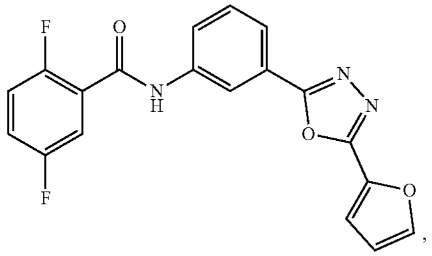
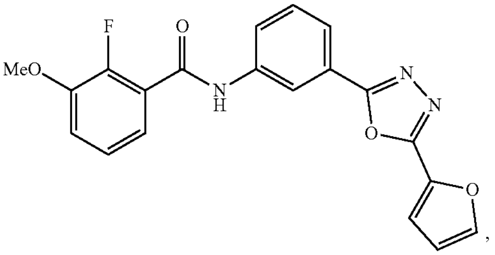
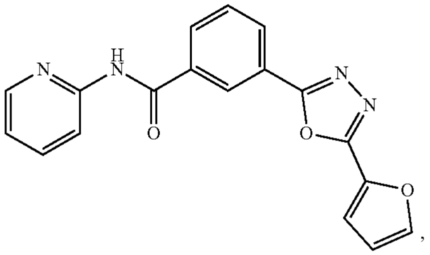
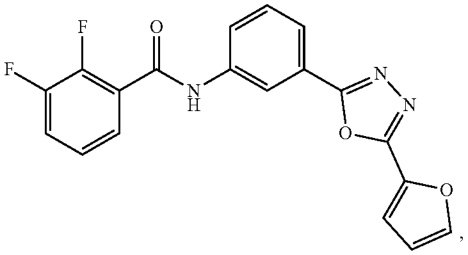
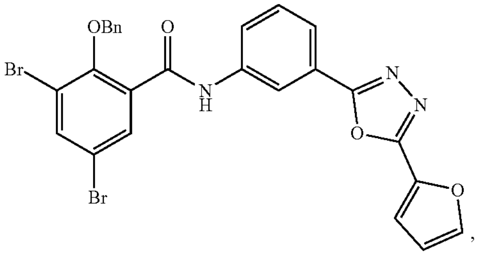
-continued
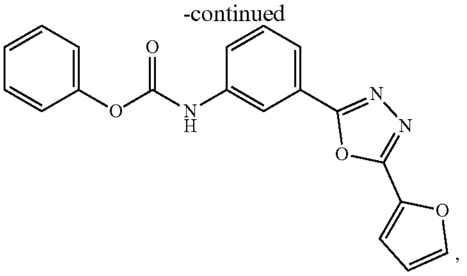
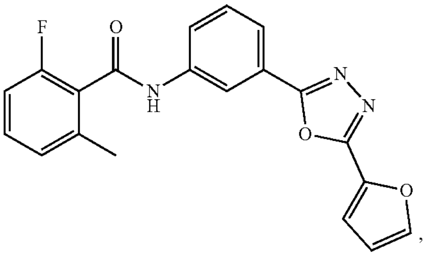
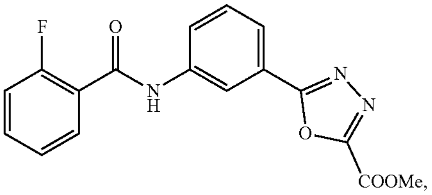
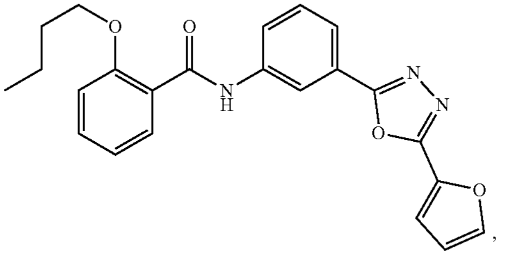
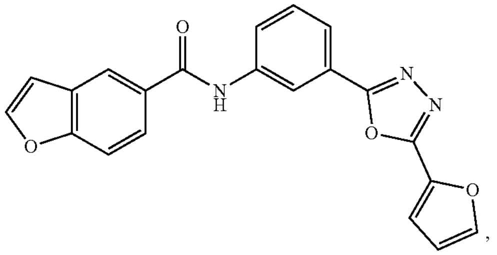
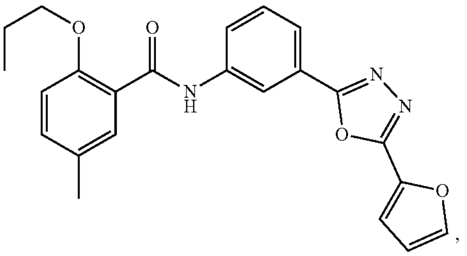
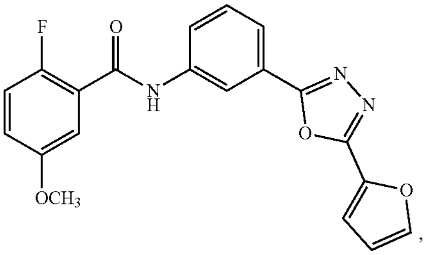

-continued
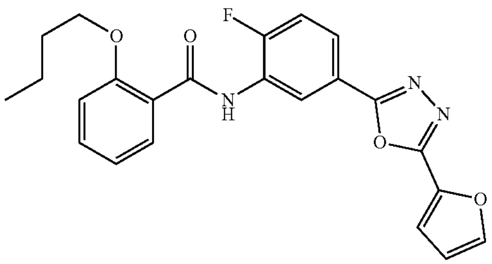,
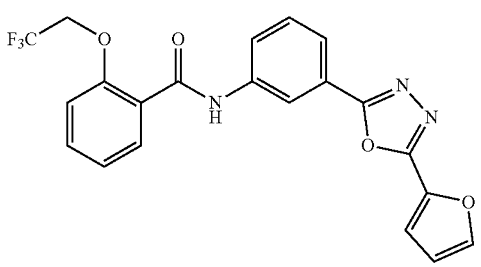,
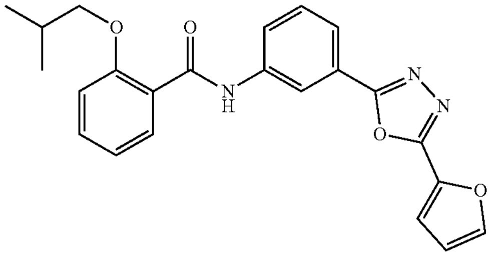,
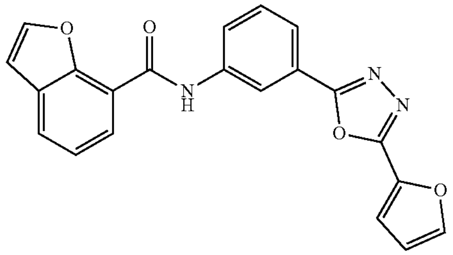,
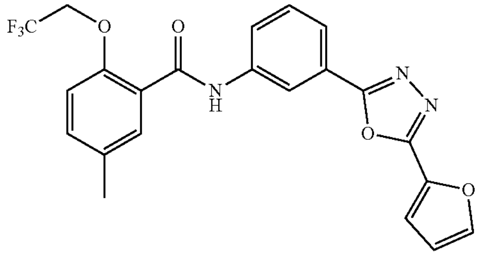,
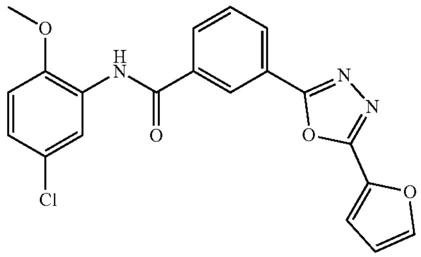,
-continued
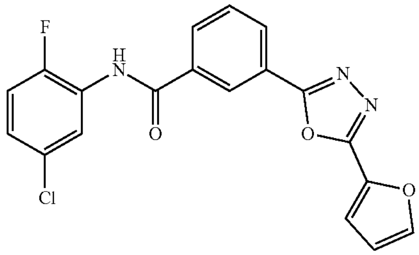,
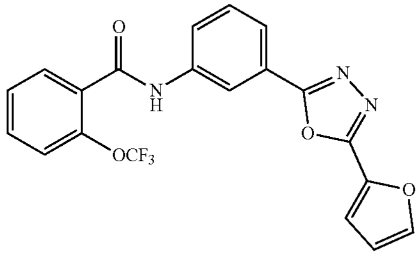,
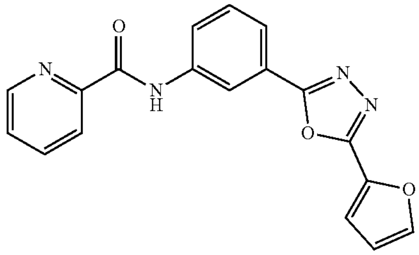,
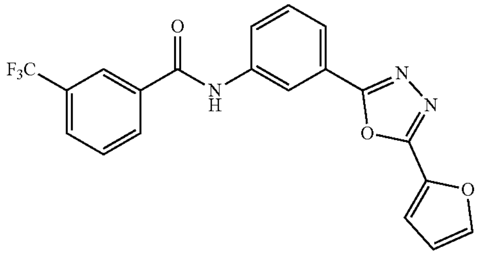,
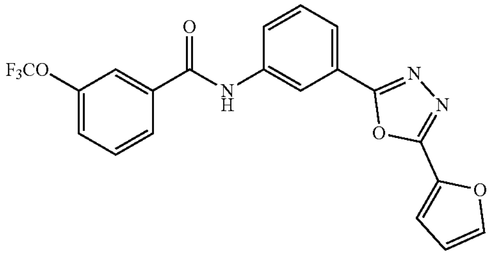,
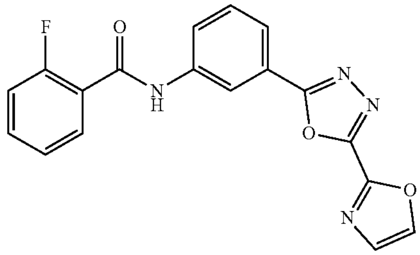, -continued
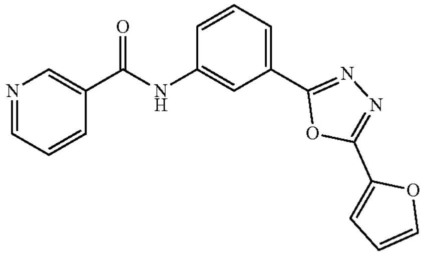
,
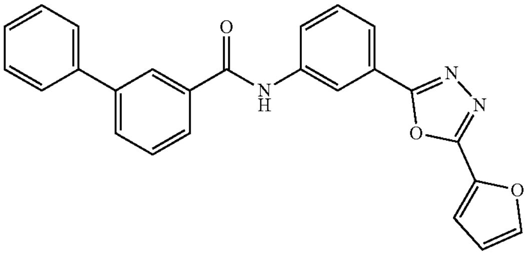
,
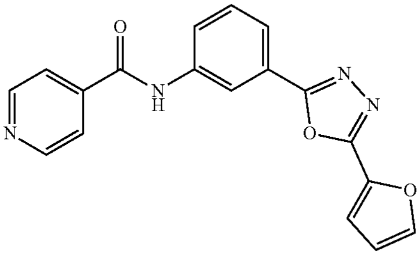
,
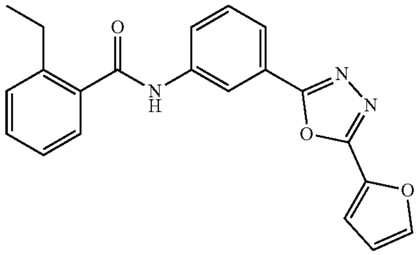
,
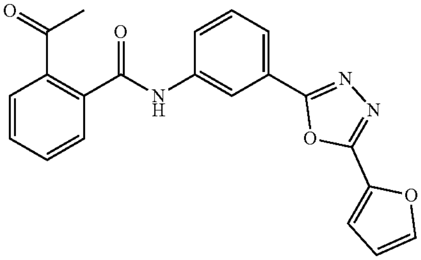
,
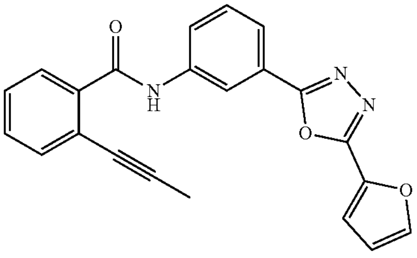
,
-continued
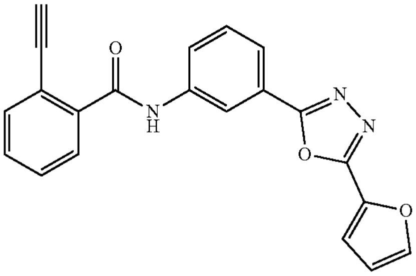
,
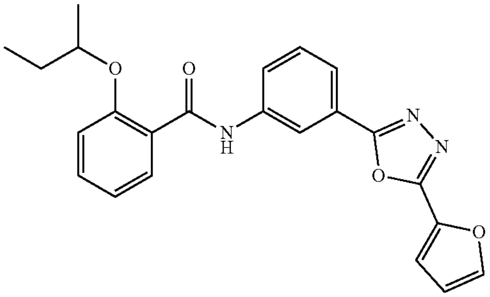
,
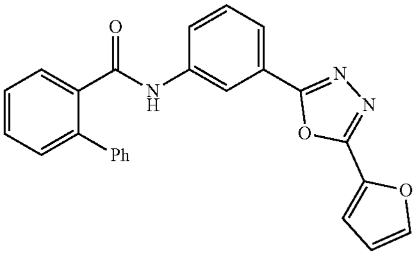
,
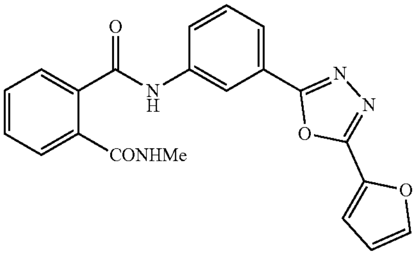
,
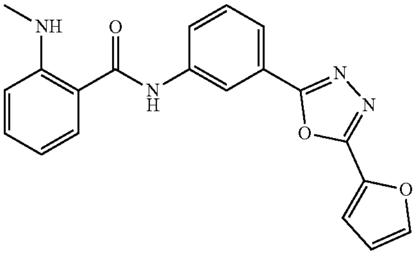
,
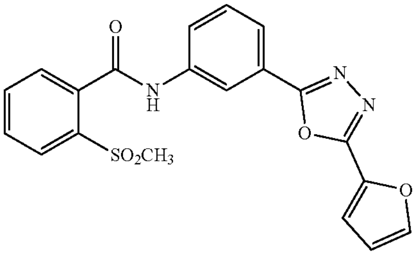
, -continued
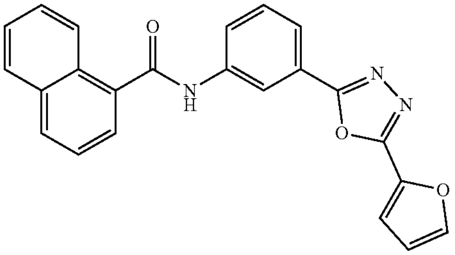
,
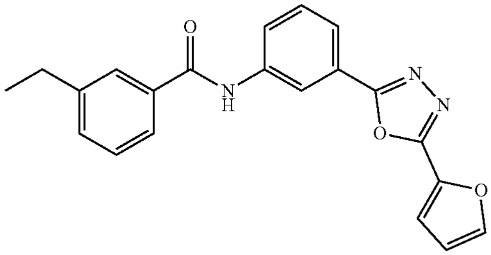
,
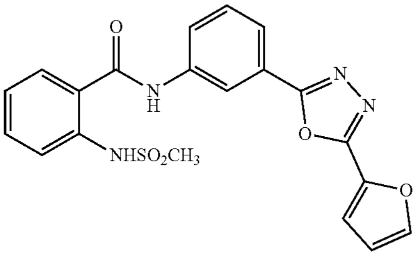
,
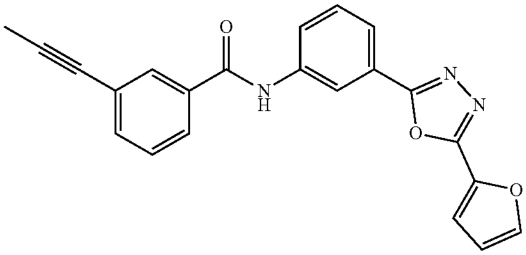
,
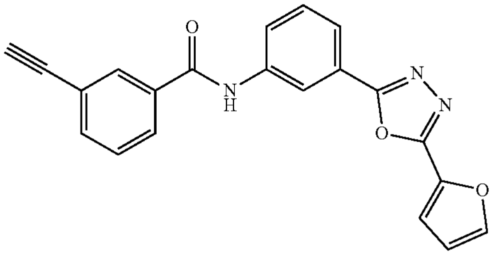
,
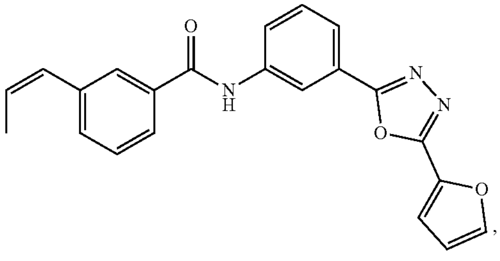
,
-continued
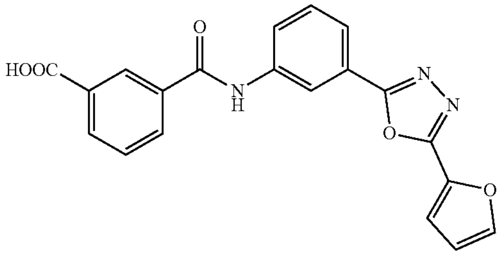
,
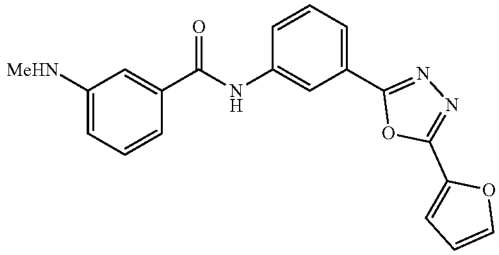
,
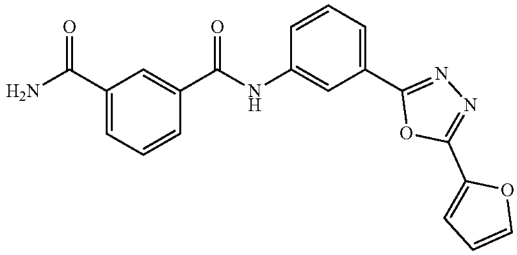
,
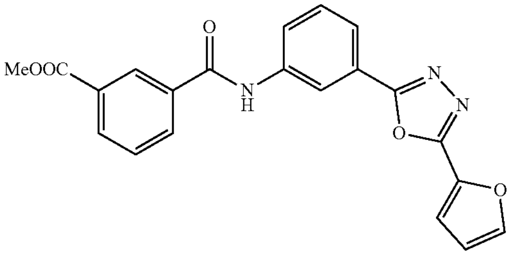
,
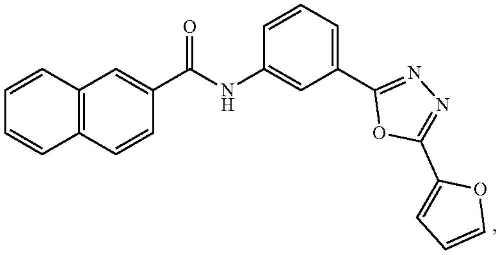
,
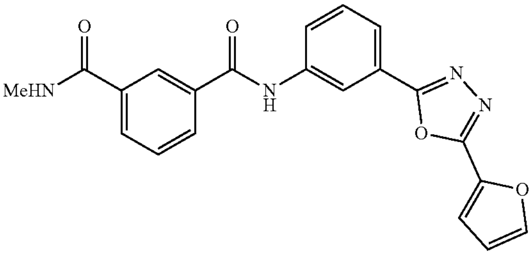
, -continued
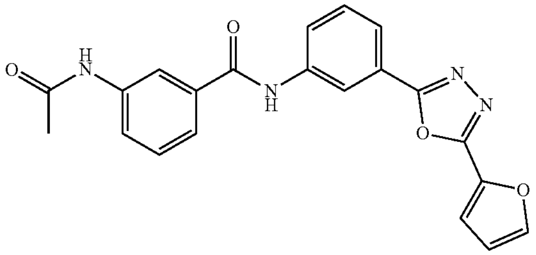,
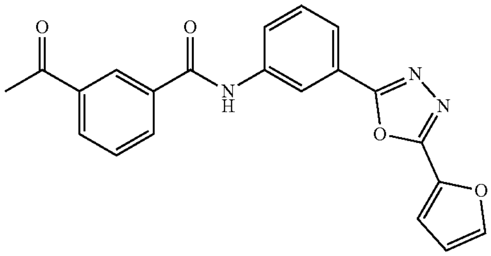,
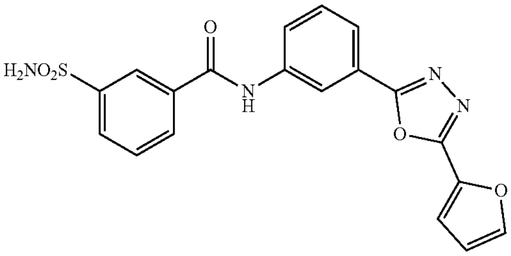,
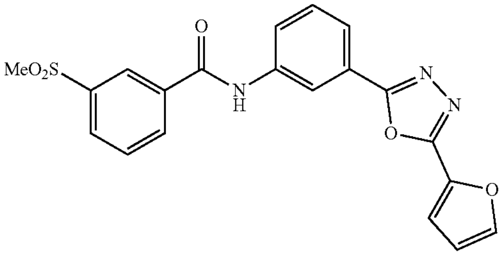,
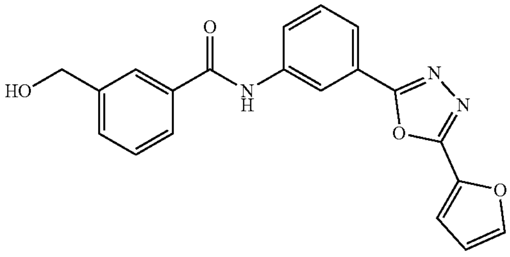,
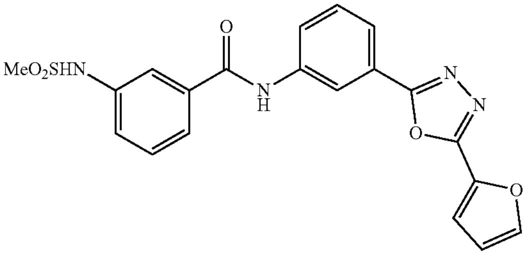,
-continued
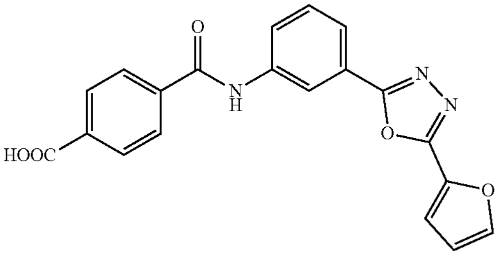,
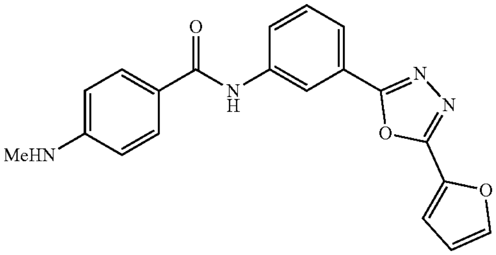,
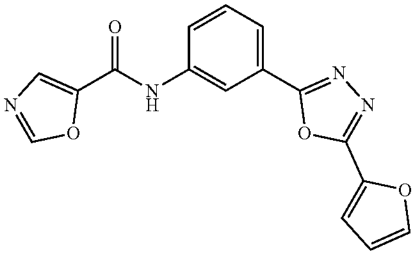,
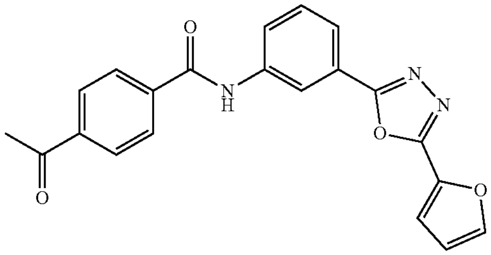,
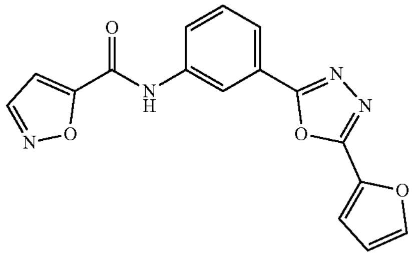,
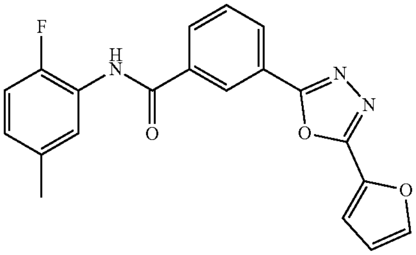, -continued
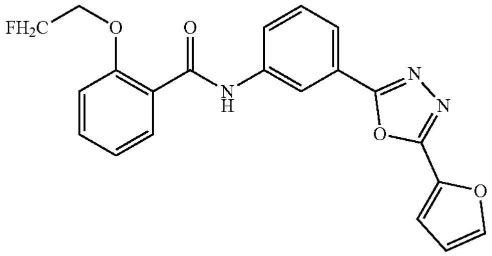
,
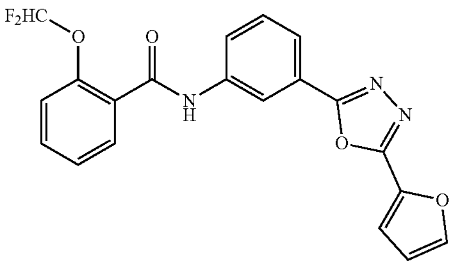
,
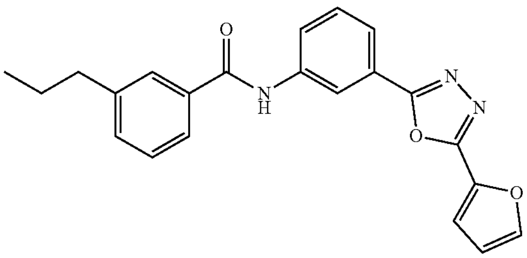
,
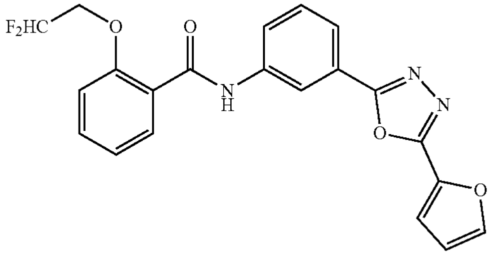
,
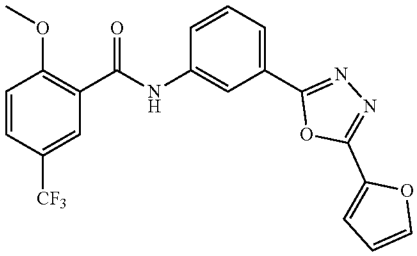
,
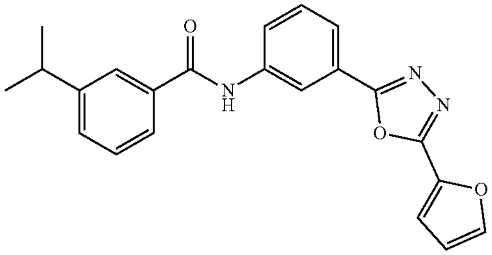
,
-continued
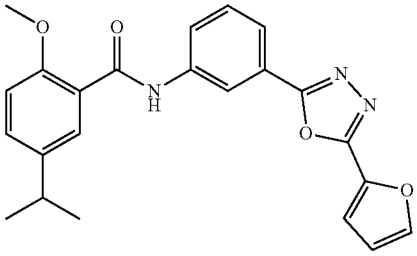
,
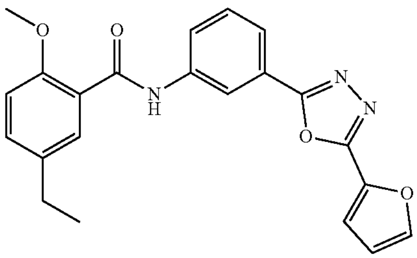
,
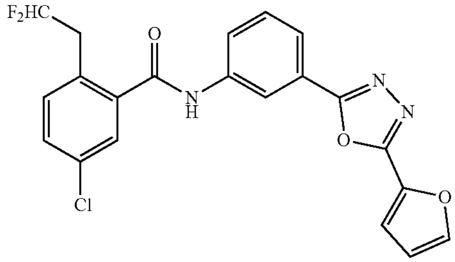
,
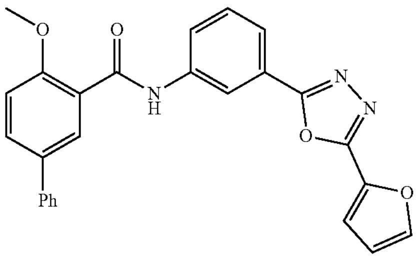
,
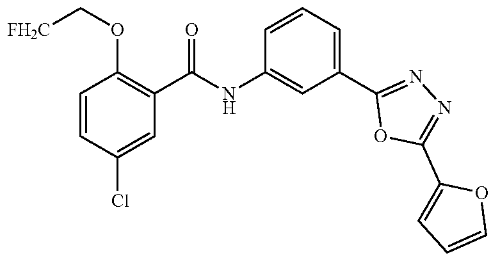
,
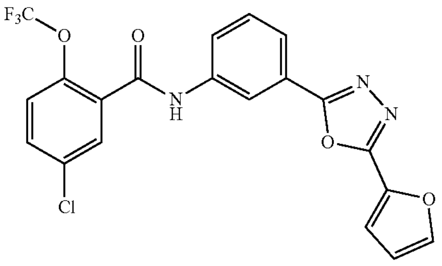
, -continued
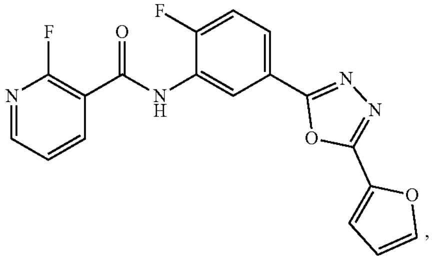
,
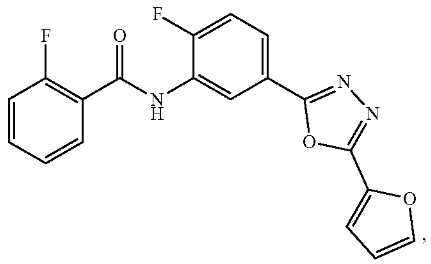
,
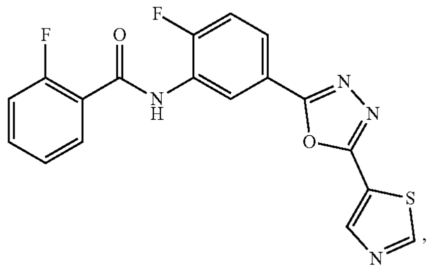
,
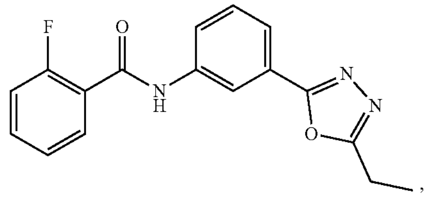
,
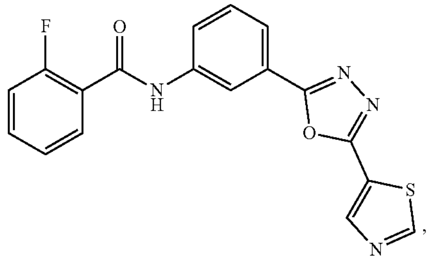
,
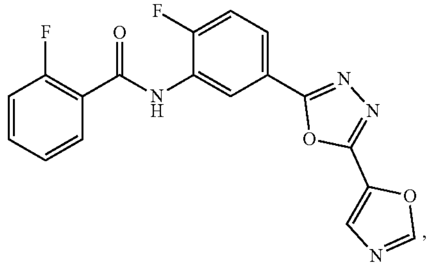
,
-continued
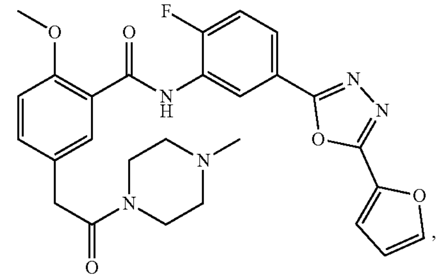
,
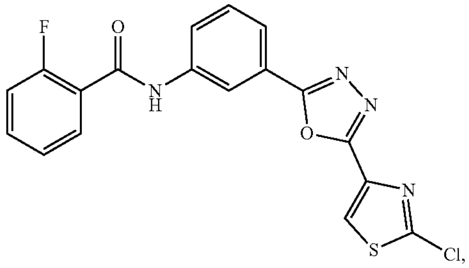
,
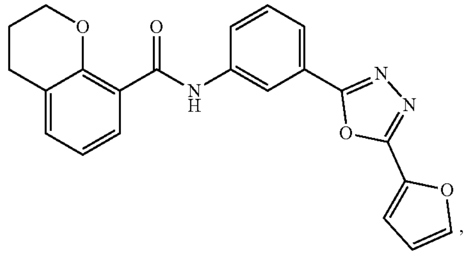
,
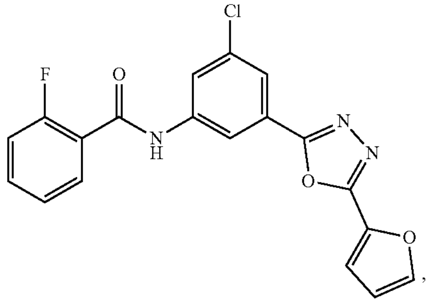
,
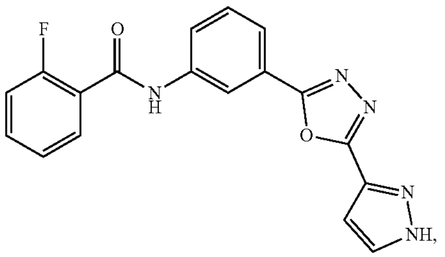
,
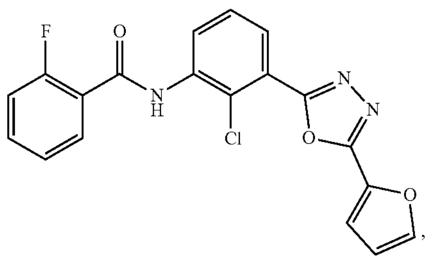
,

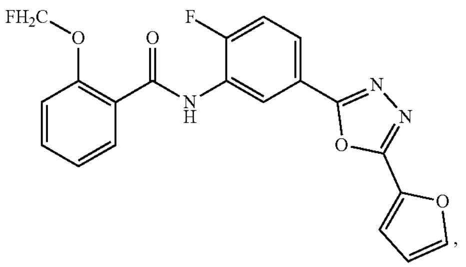
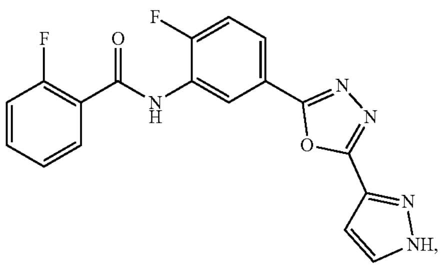
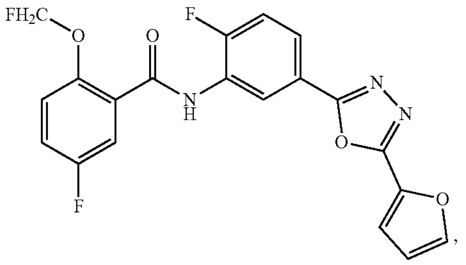
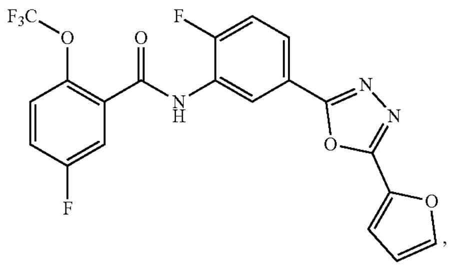
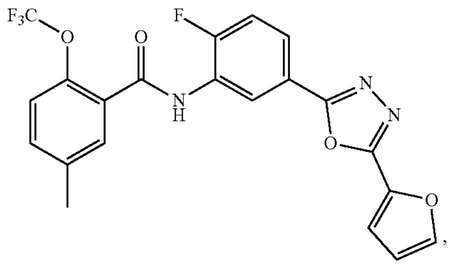
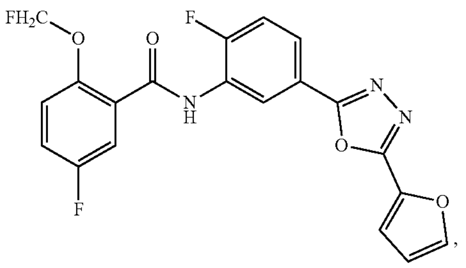
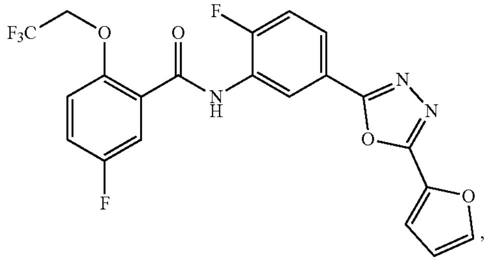
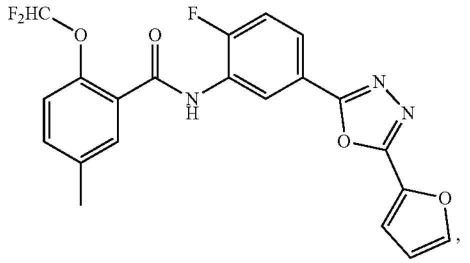
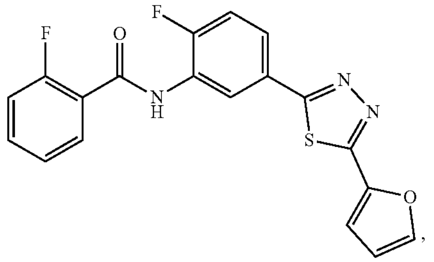
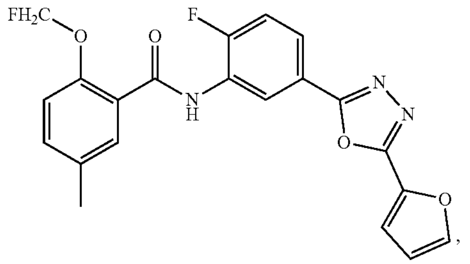
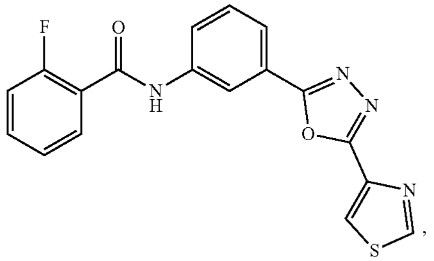
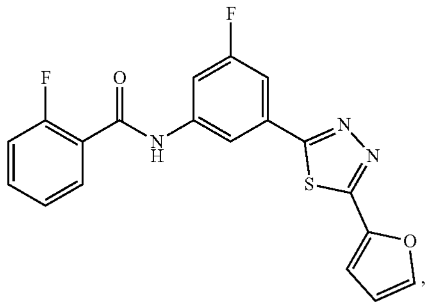

-continued
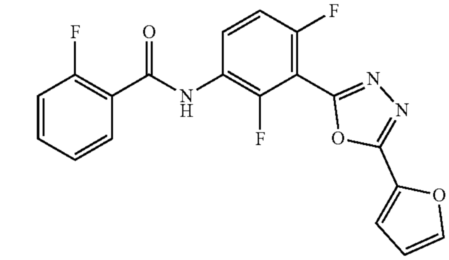,
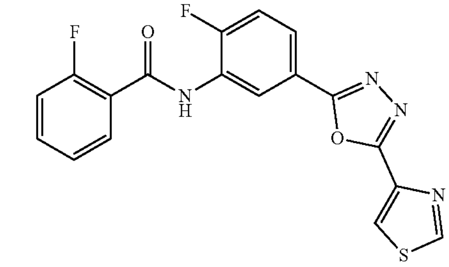,
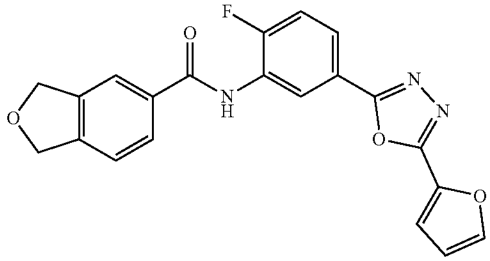,
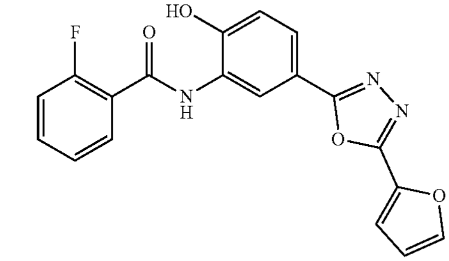,
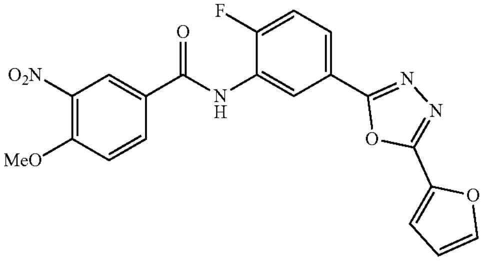,
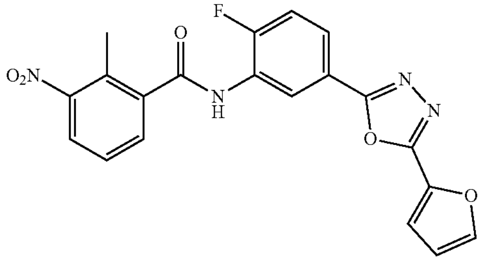,
-continued
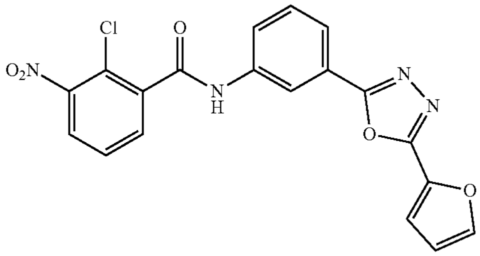,
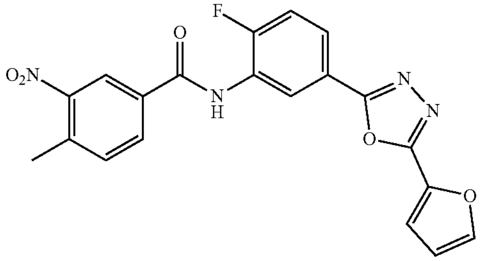,
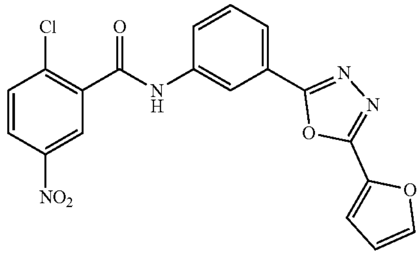,
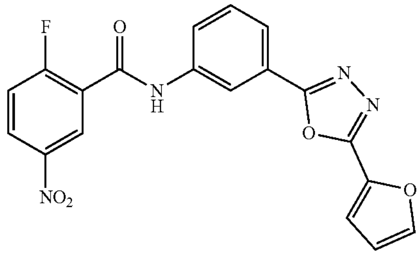,
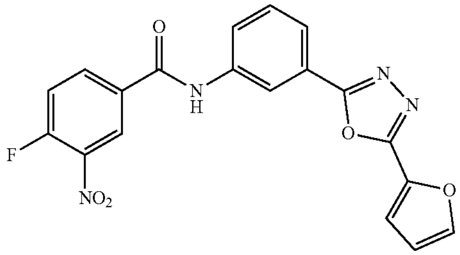,
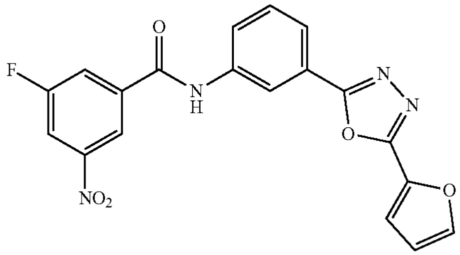, -continued
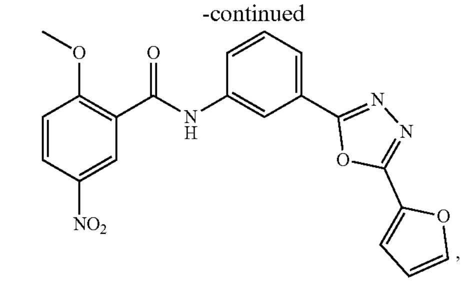
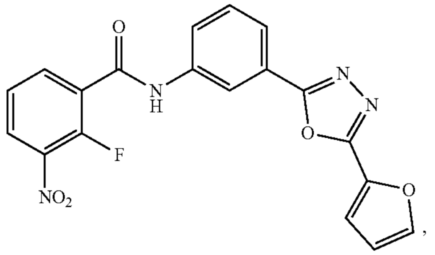
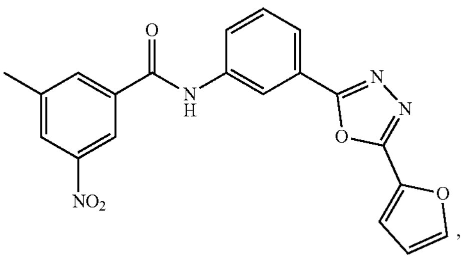
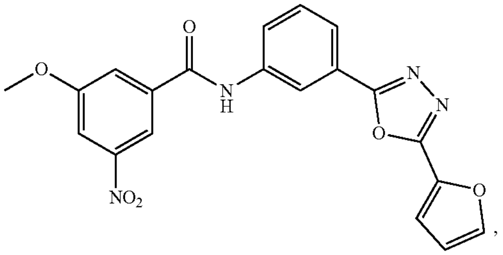
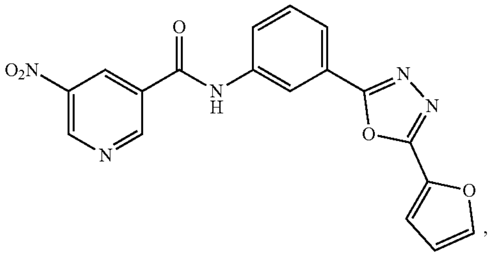
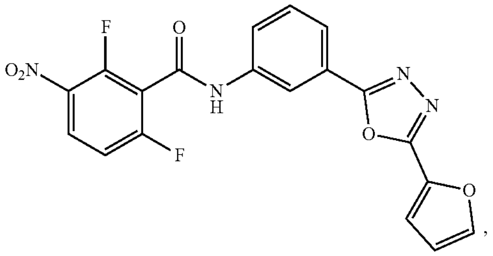
-continued
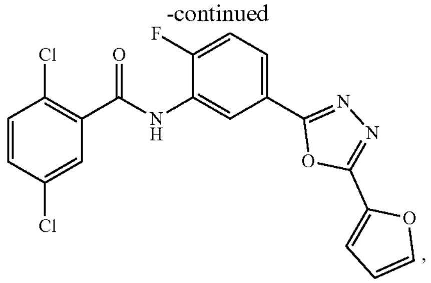
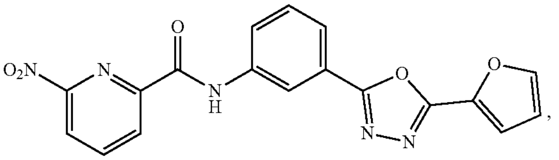
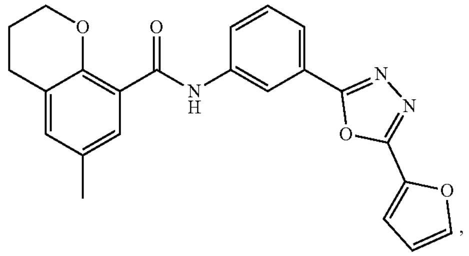
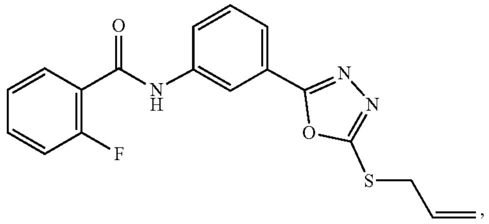
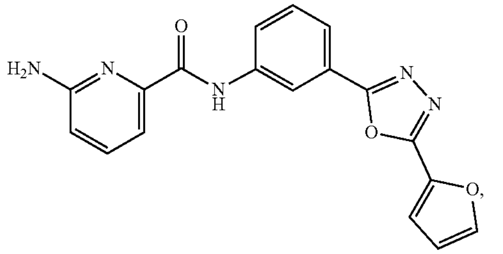
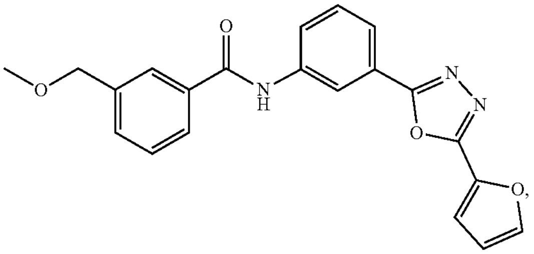

-continued
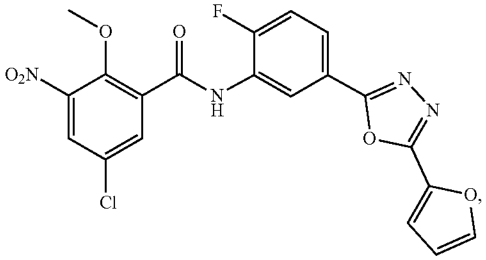
,
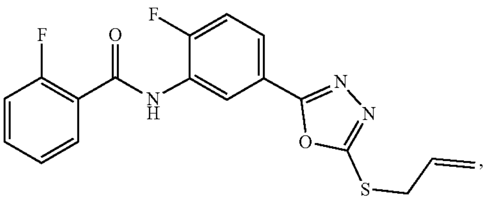
,
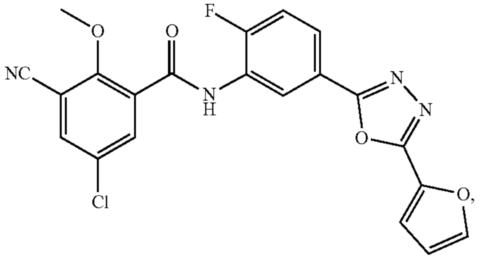
,
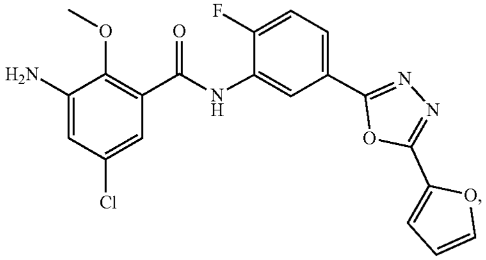
,
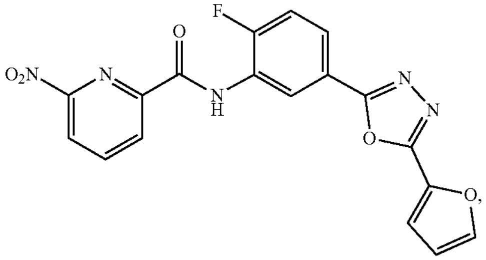
,
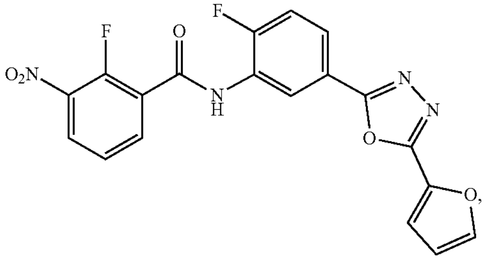
,
-continued
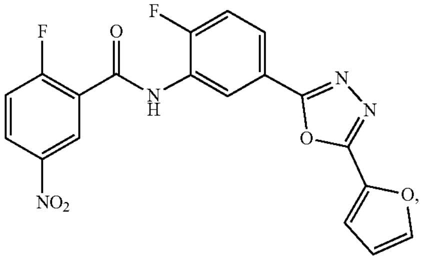
,
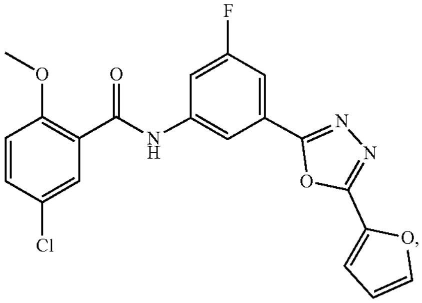
,
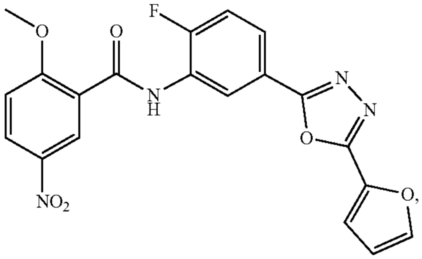
,
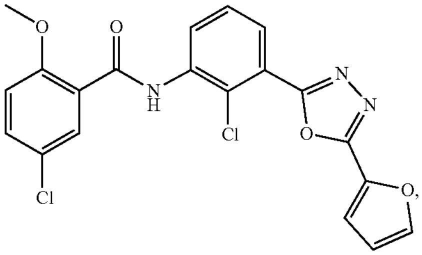
,
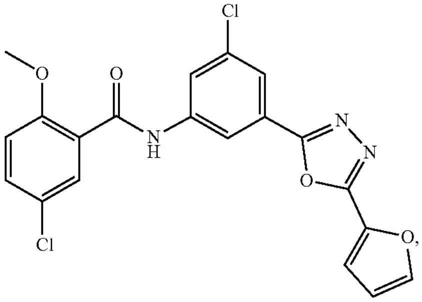
,
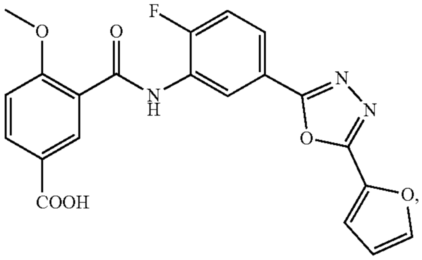
, -continued
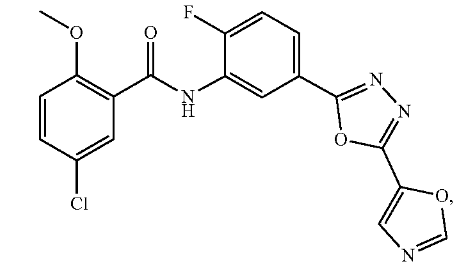
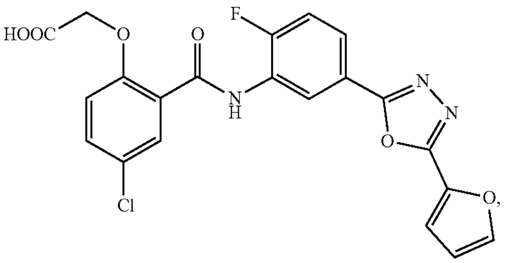
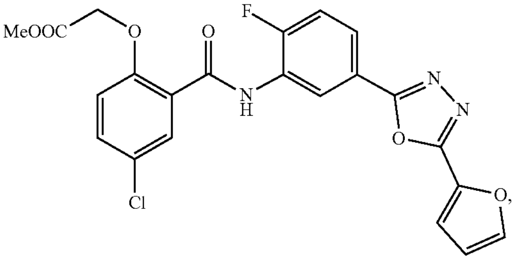
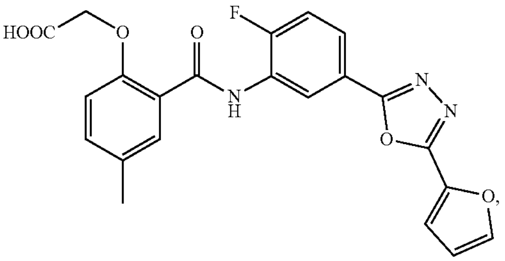
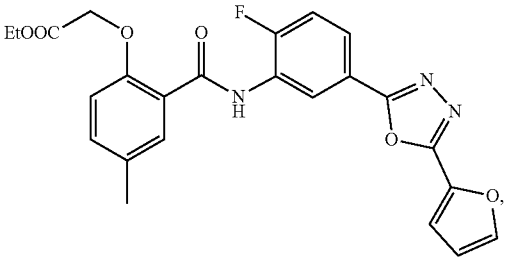
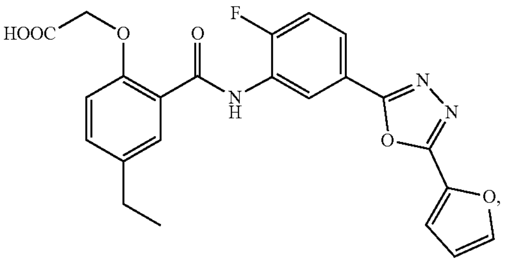
-continued
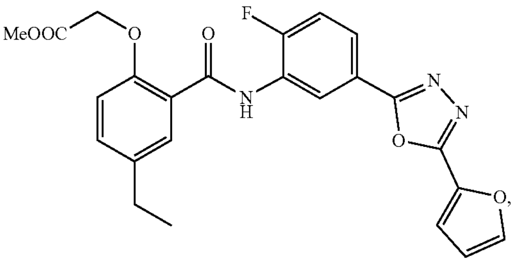
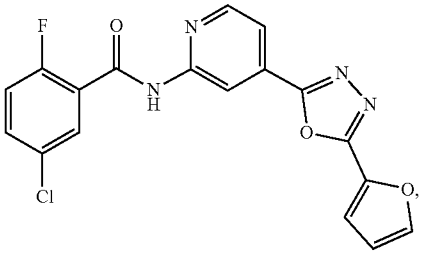
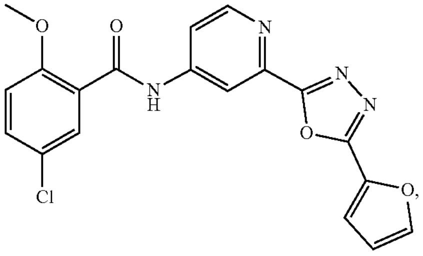
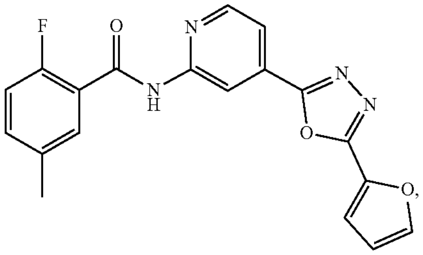
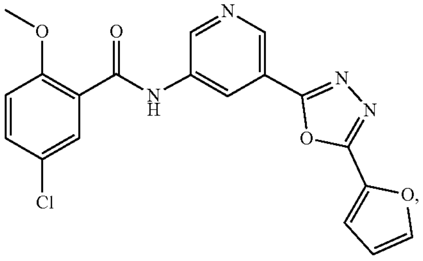
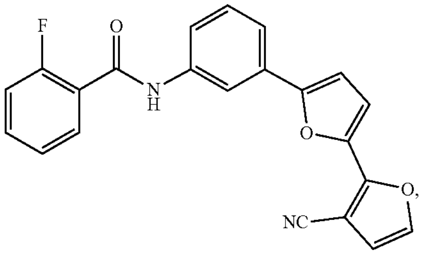

-continued
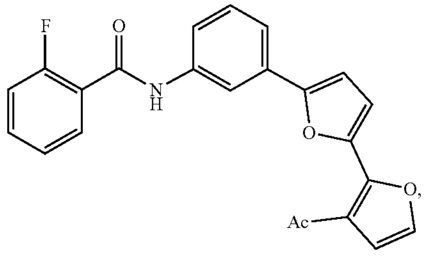
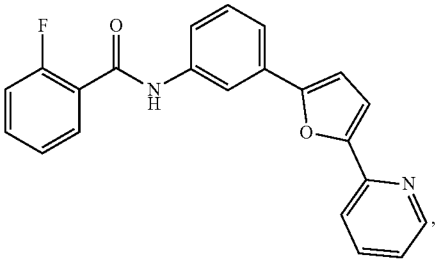
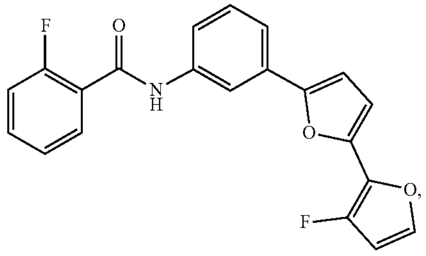
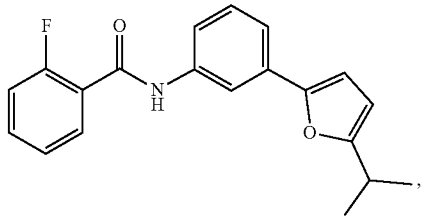
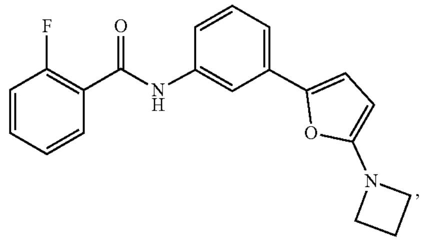
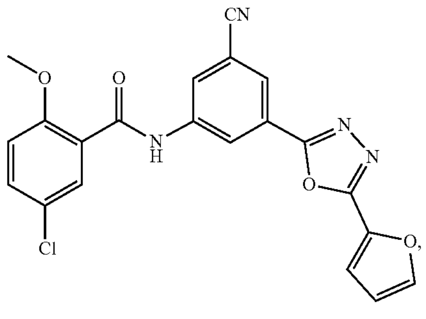
-continued
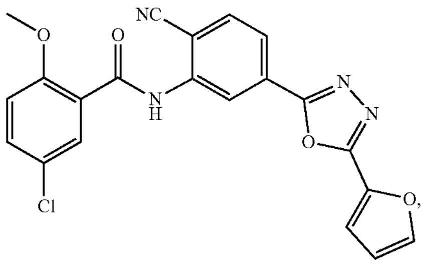
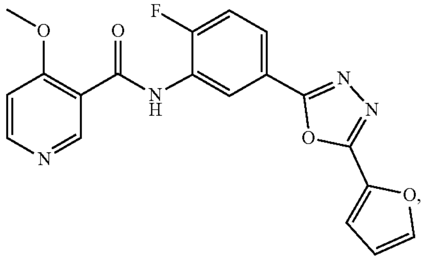
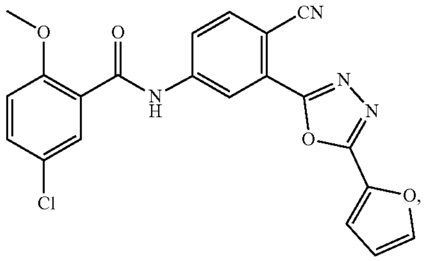
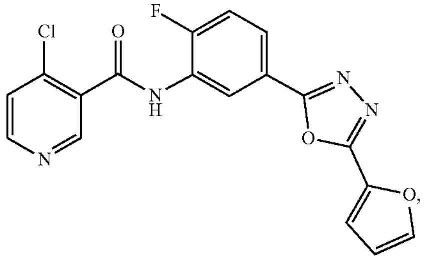
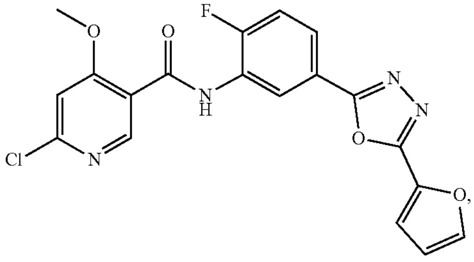
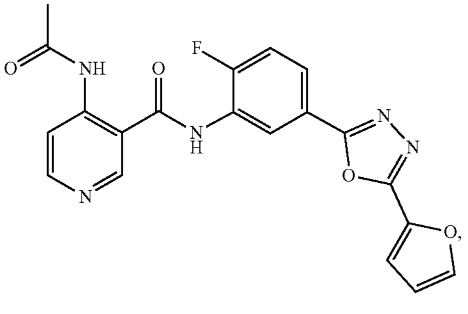

-continued
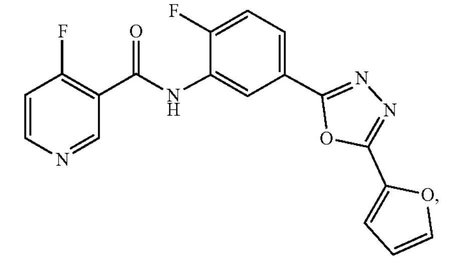
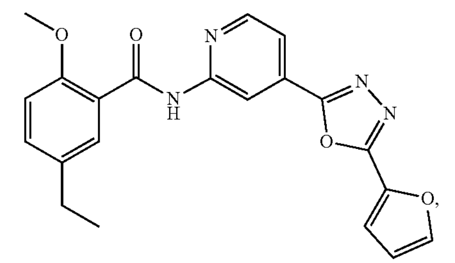
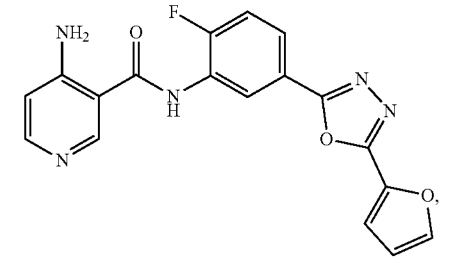
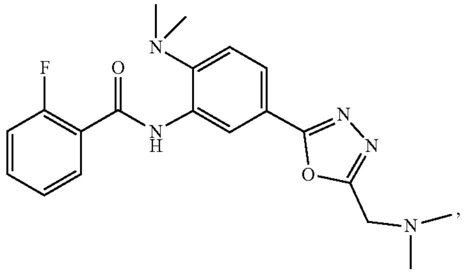
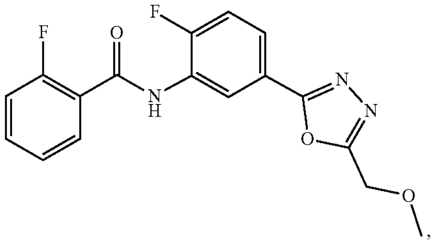
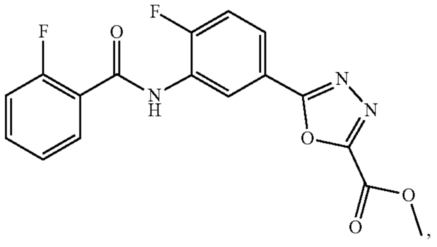
-continued
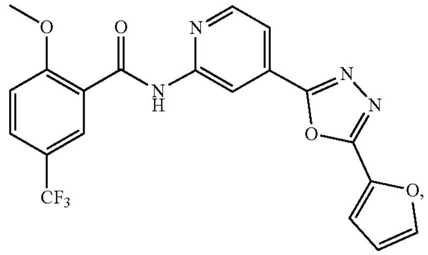
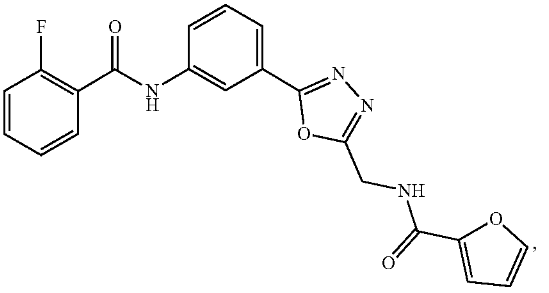
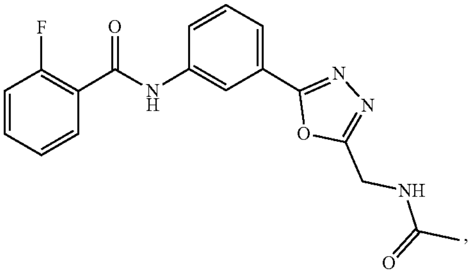
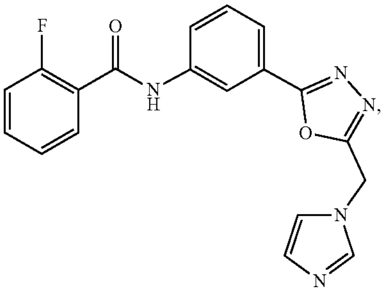
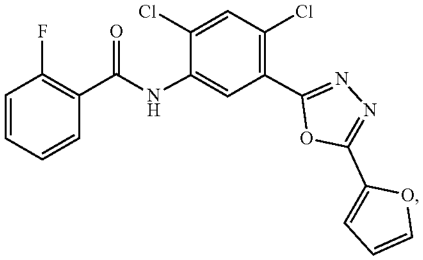
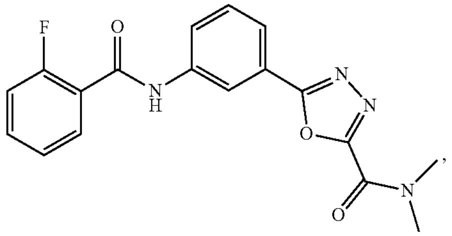

-continued
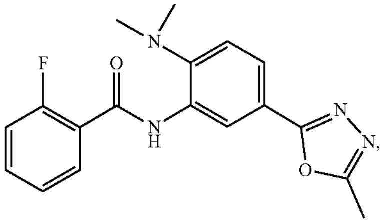
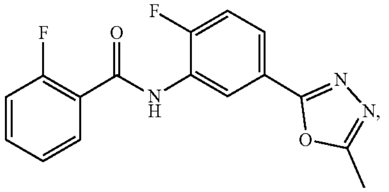
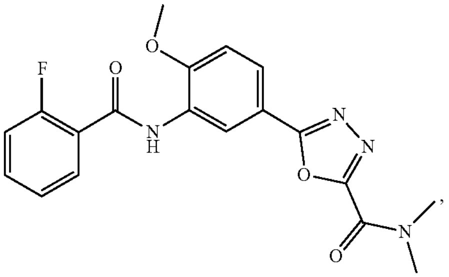
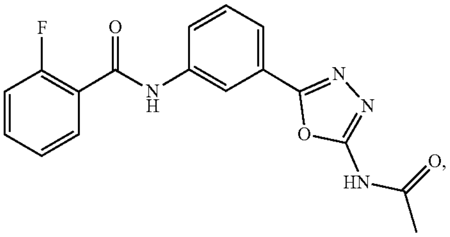
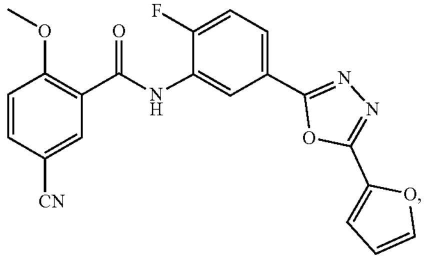
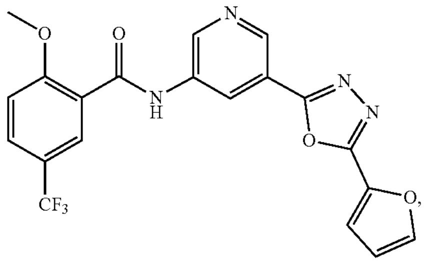
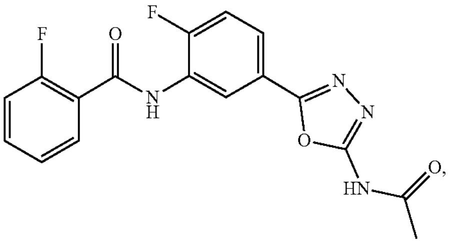
-continued
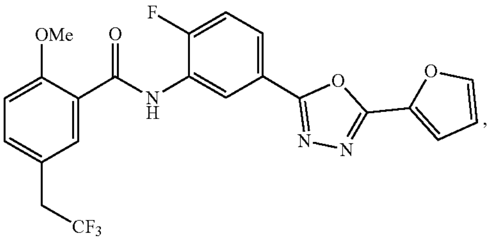
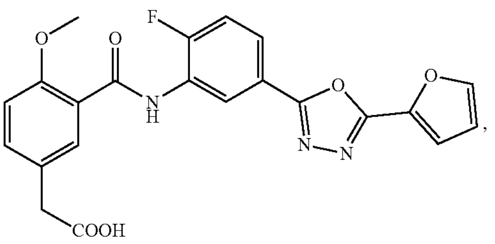
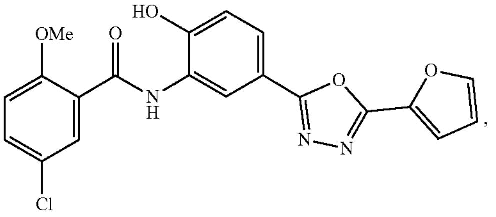
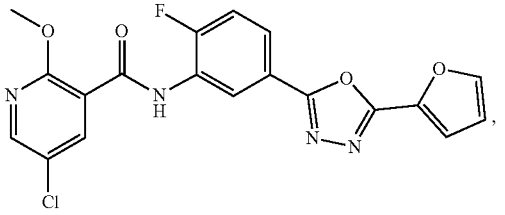
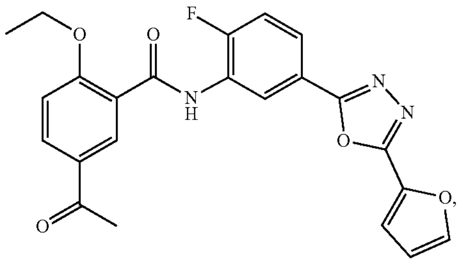
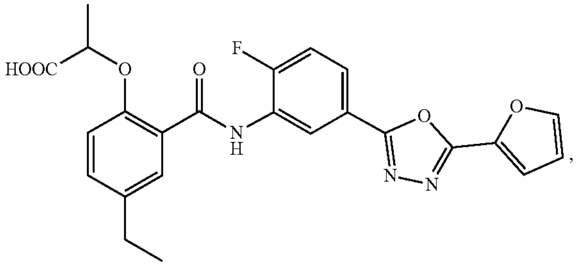
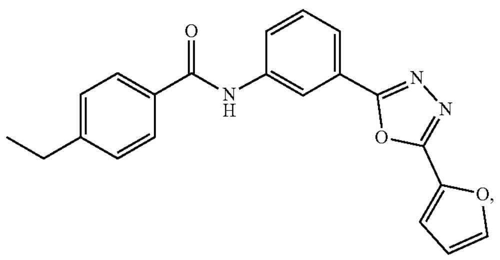

-continued
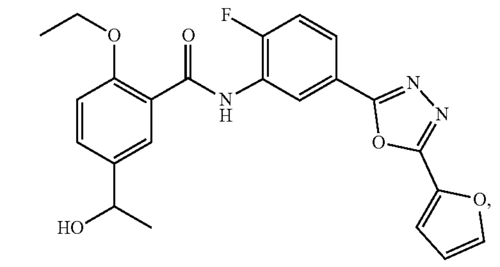
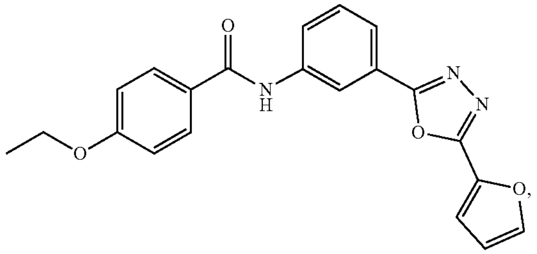
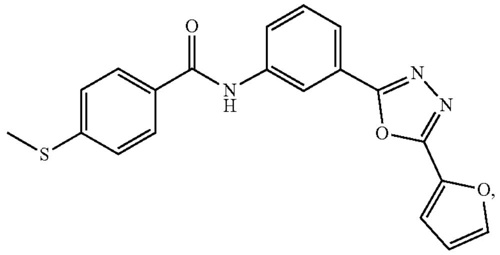
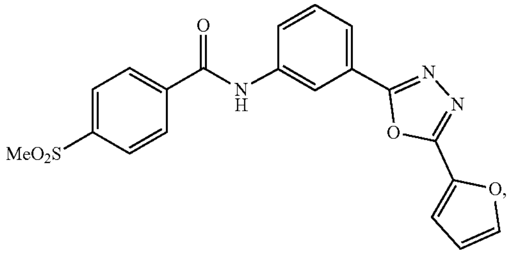
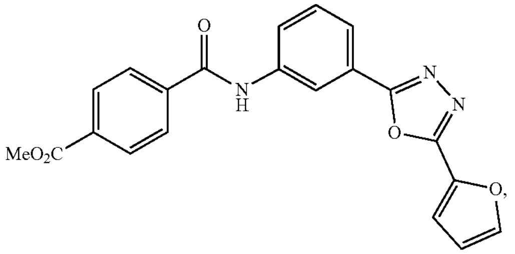
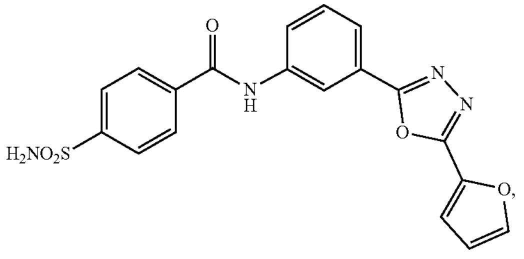
-continued
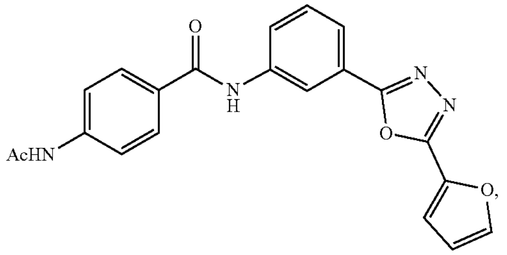
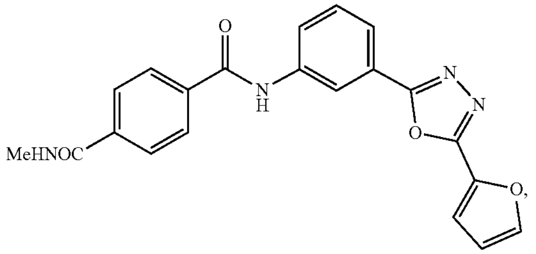
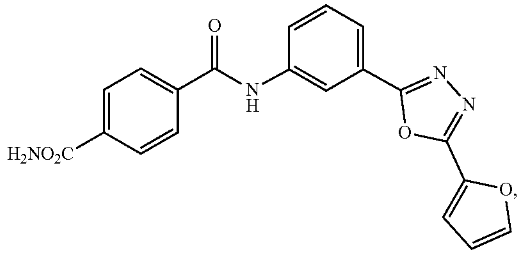
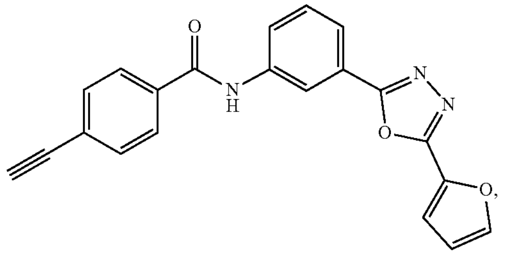
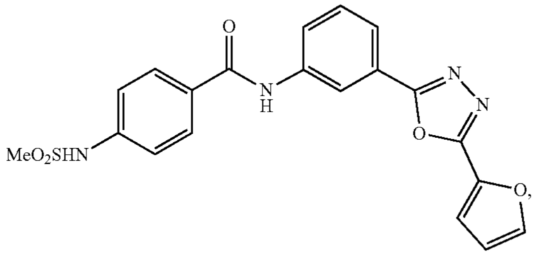
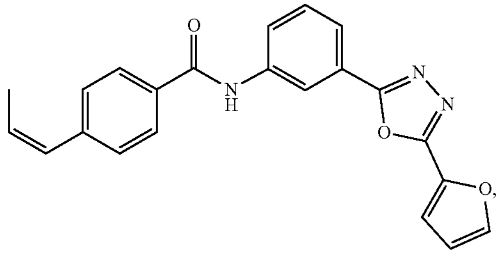

-continued
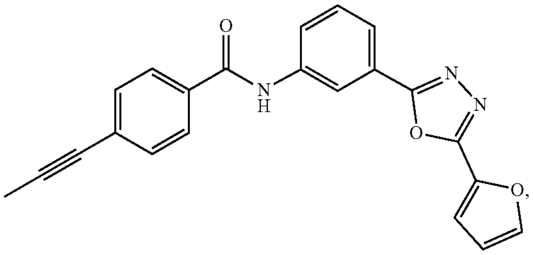
,
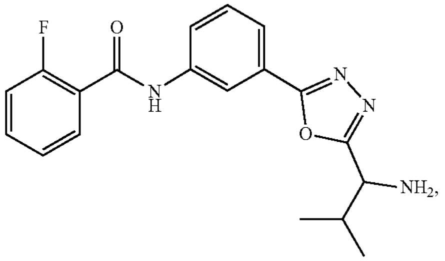
,
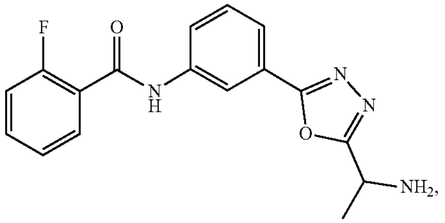
,
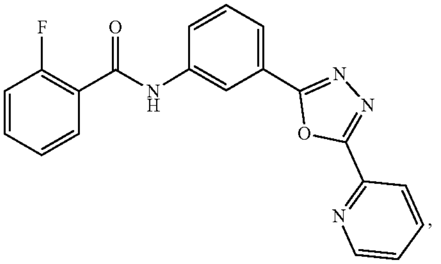
,
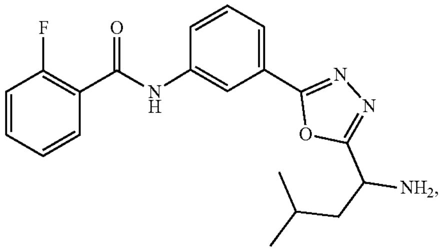
,
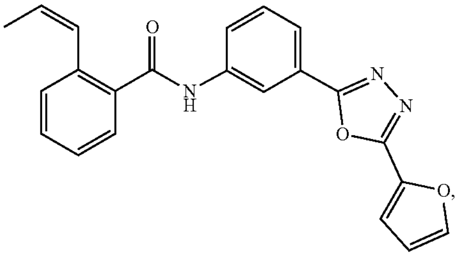
,
-continued
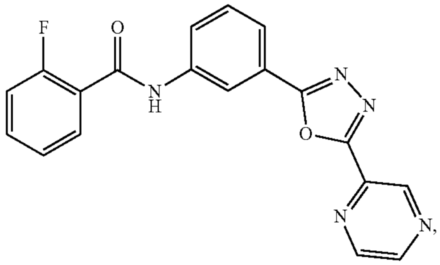
,
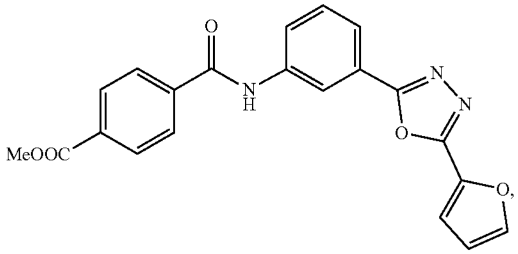
,
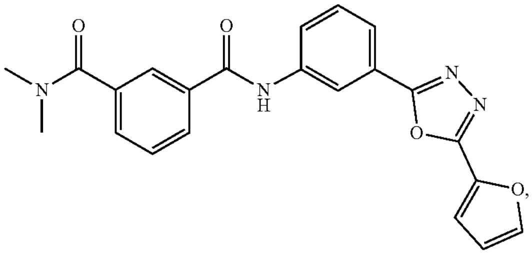
,
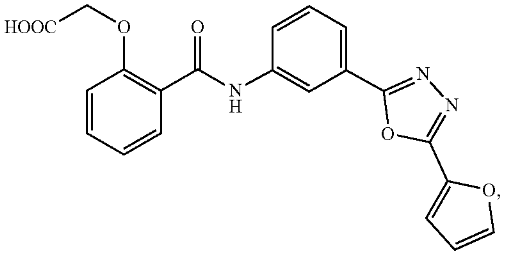
,
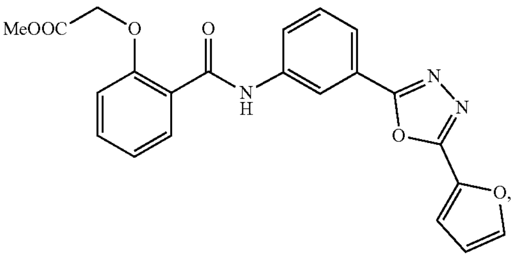
,
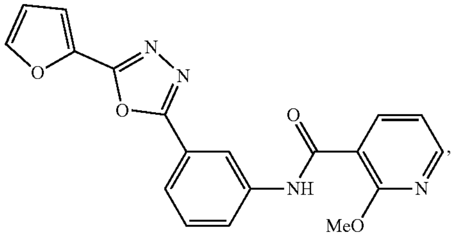
, -continued
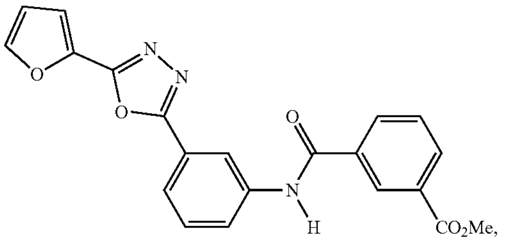
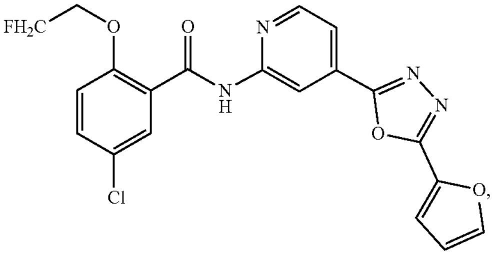
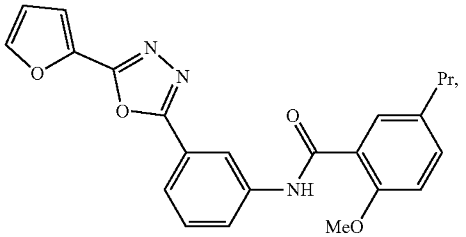
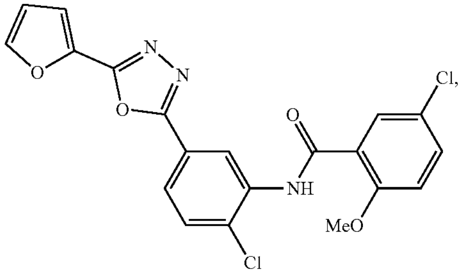
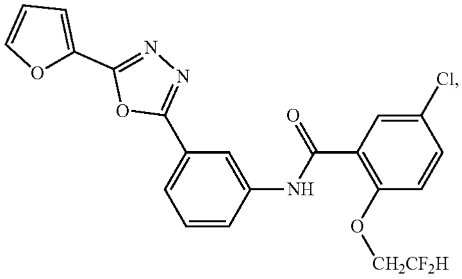
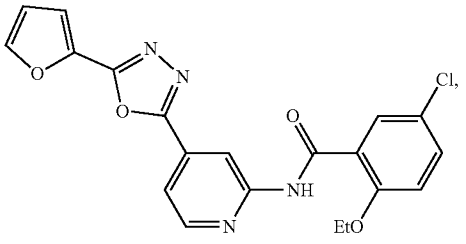
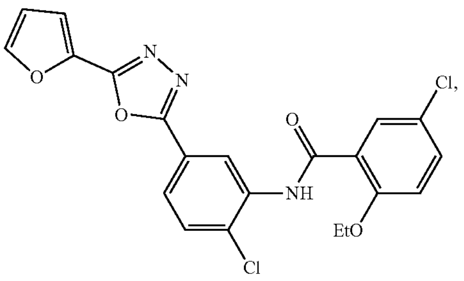
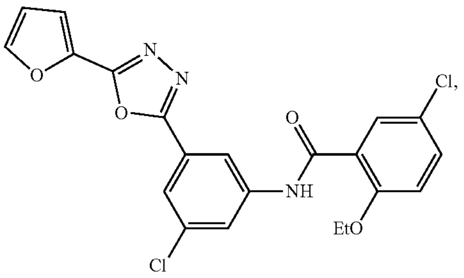
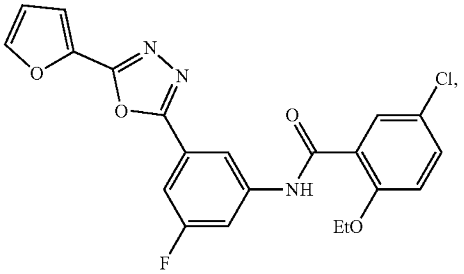
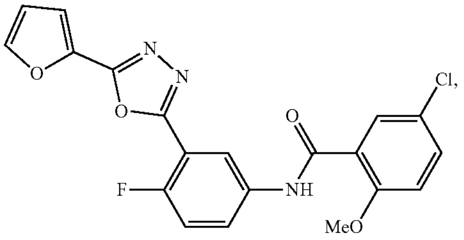
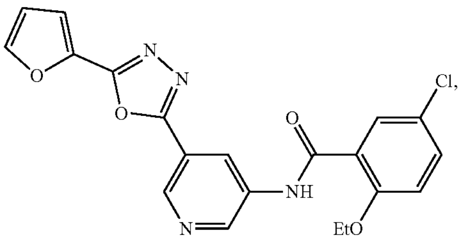
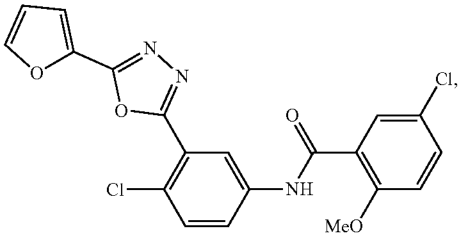

-continued
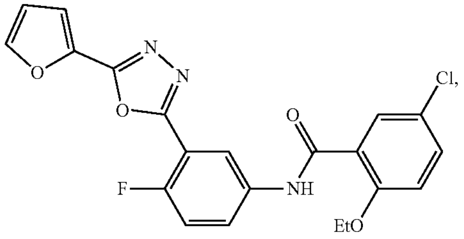
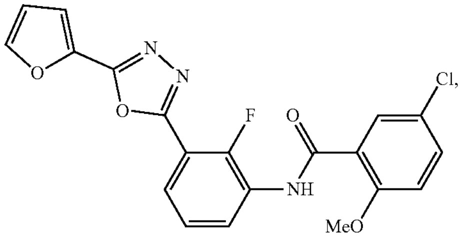
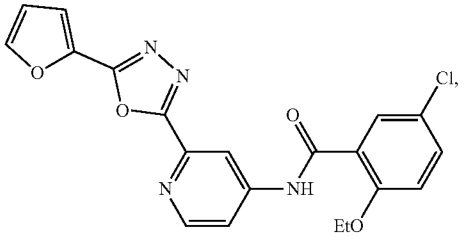
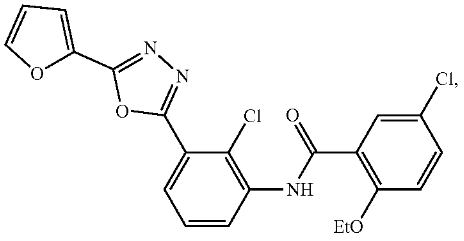
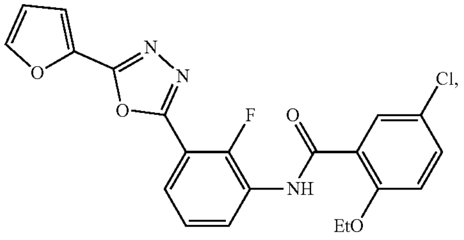
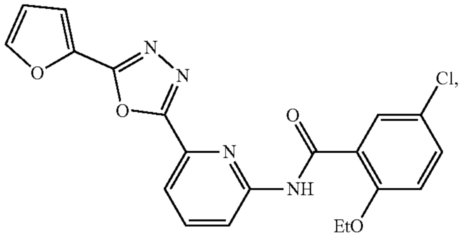
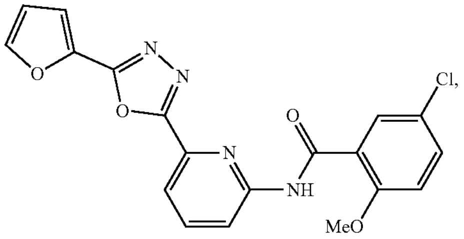
-continued
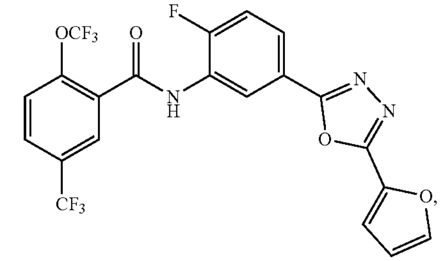
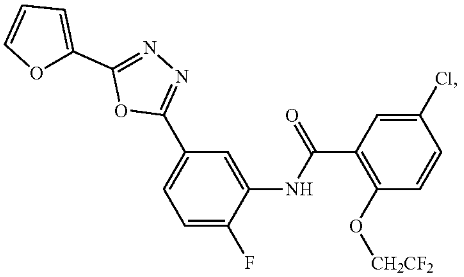
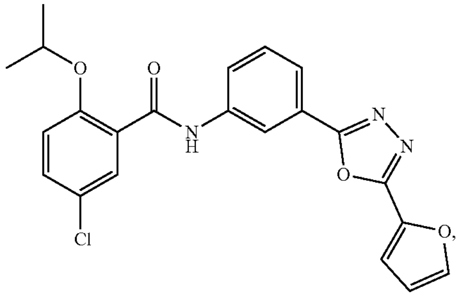
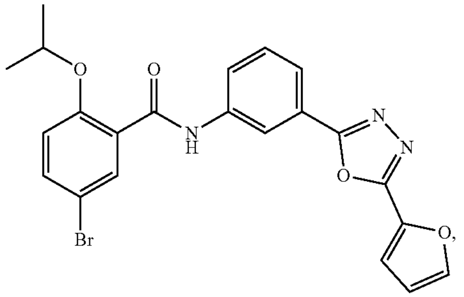
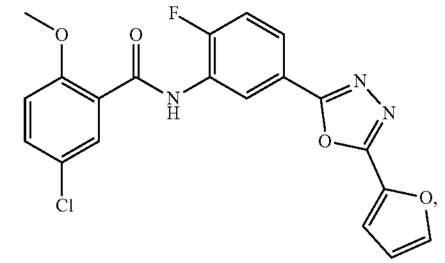
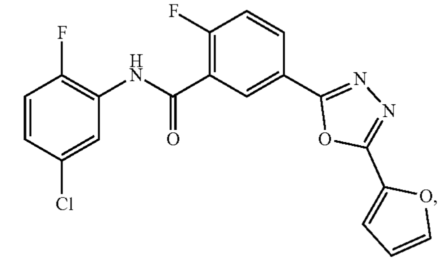

-continued
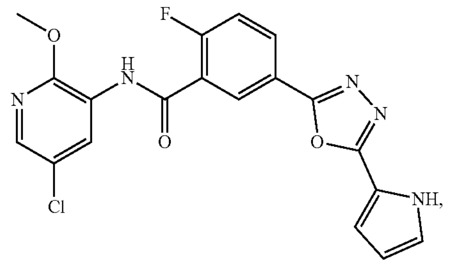
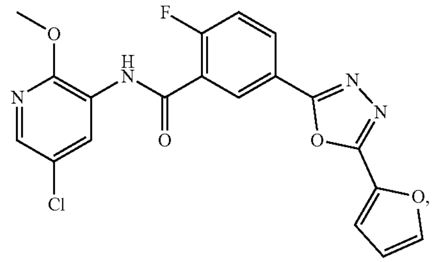
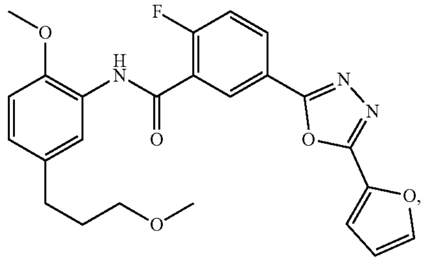
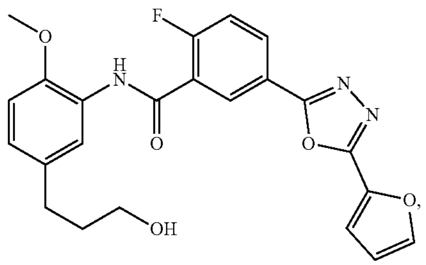
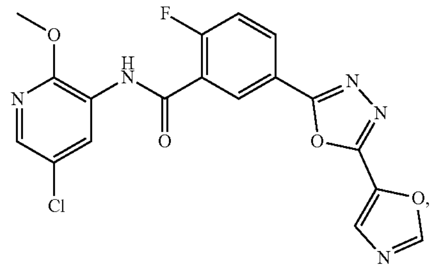
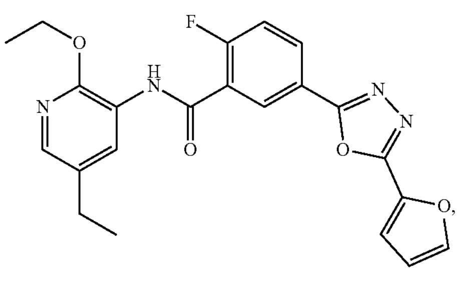
-continued
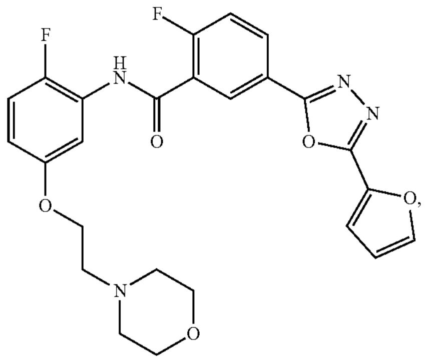
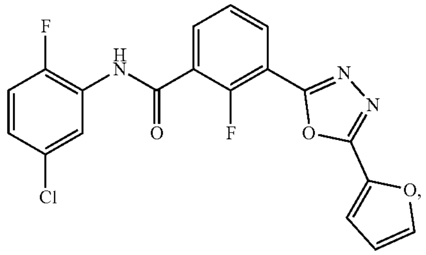
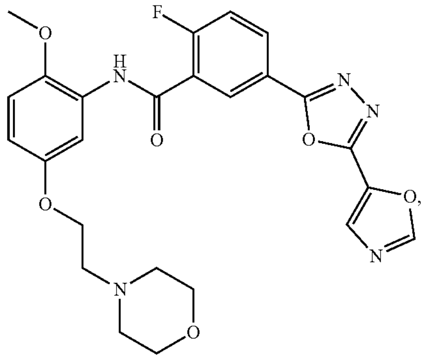
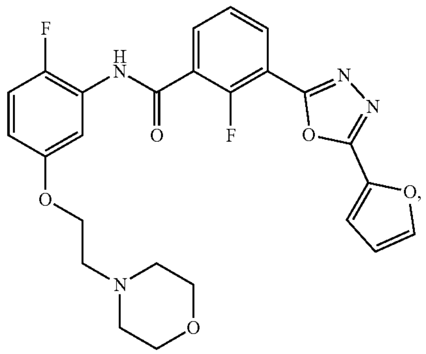
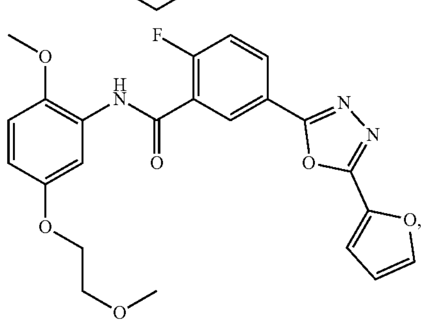

-continued

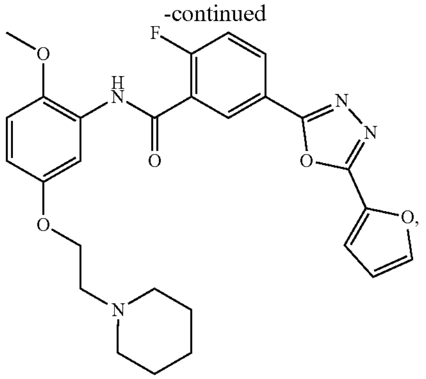

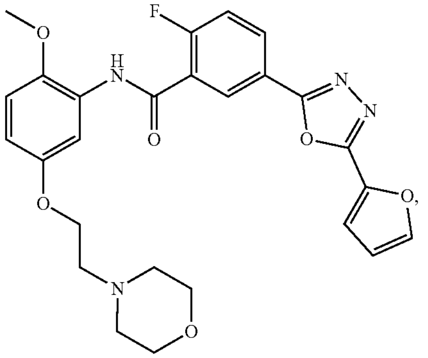

and

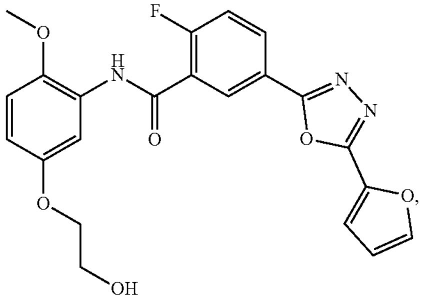

or a pharmaceutically acceptable salt thereof.

2. A composition comprising a compound according to claim 1, or a pharmaceutically acceptable salt thereof, and a pharmaceutically acceptable carrier, diluent or excipient.

3. A method of preparing a pharmaceutical composition comprising admixing a compound according to claim 1, or a pharmaceutically acceptable salt thereof, and a pharmaceutically acceptable carrier, diluent, or excipient.

4. A method of treating aging or age-related diseases comprising administering to a patient in need of treatment a therapeutically effective amount of a compound according to claim 1, or a pharmaceutically acceptable salt thereof.

5. A method of treating a disease selected from stroke, ischaemia, and reperfusion injury, comprising administering to a patient in need of treatment a therapeutically effective amount of a compound according claim 1, or a pharmaceutically acceptable salt thereof.

6. The compound according to claim 1, wherein the compound is

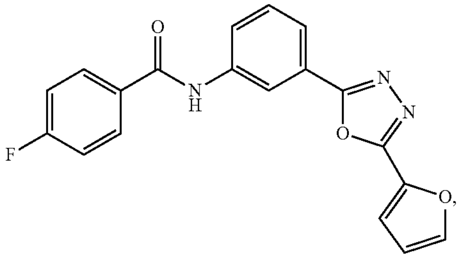 [SMILES: O=C(Nc1cccc(-c2nnc(-c3ccco3)o2)c1)c1ccc(F)cc1]

or a pharmaceutically acceptable salt thereof.

* * * * *